United States Patent
Janssen et al.

(10) Patent No.: US 11,932,702 B2
(45) Date of Patent: Mar. 19, 2024

(54) POLYPEPTIDES COMPRISING IMMUNOGLOBULIN SINGLE VARIABLE DOMAINS TARGETING GLYPICAN-3 AND T CELL RECEPTOR

(71) Applicants: Ablynx N.V., Zwijnaarde (BE); Sanofi, Paris (FR)

(72) Inventors: Daniel Janssen, Mortsel (BE); Carlo Boutton, Wielsbeke (BE); Evelyne Dombrecht, Zwijnaarde (BE); Bram Laukens, Zwijnaarde (BE); Paolo Meoni, Zwijnaarde (BE); Lily Pao, Bridgewater, NJ (US); Jan Pype, Herne (BE); Peter Schotte, De Pinte (BE); Benedikte Serruys, Sint-Michiels (BE); Ana Paula Vintem, Zwijnaarde (BE); Diane Van Hoorick, Laarne (BE)

(73) Assignees: Ablynx N.V., Zwijnaarde (BE); Sanofi, Paris (FR)

( * ) Notice: Subject to any disclaimer, the term of this patent is extended or adjusted under 35 U.S.C. 154(b) by 0 days.

(21) Appl. No.: 17/553,908

(22) Filed: Dec. 17, 2021

(65) Prior Publication Data
US 2022/0213215 A1    Jul. 7, 2022

Related U.S. Application Data

(60) Provisional application No. 63/127,224, filed on Dec. 18, 2020.

(30) Foreign Application Priority Data

Dec. 21, 2020  (EP) .................................. 20306633

(51) Int. Cl.
| | | |
|---|---|---|
| C07K 16/30 | (2006.01) | |
| A61P 35/00 | (2006.01) | |
| C07K 16/28 | (2006.01) | |
| A61K 39/00 | (2006.01) | |

(52) U.S. Cl.
CPC ............ C07K 16/303 (2013.01); A61P 35/00 (2018.01); C07K 16/2809 (2013.01); *A61K 2039/505* (2013.01); *C07K 2317/31* (2013.01); *C07K 2317/33* (2013.01); *C07K 2317/565* (2013.01); *C07K 2317/569* (2013.01); *C07K 2317/73* (2013.01); *C07K 2317/92* (2013.01); *C07K 2319/30* (2013.01)

(58) Field of Classification Search
CPC .............. C07K 16/303; C07K 16/2809; C07K 2317/569; A61P 35/00; A61K 2039/505
See application file for complete search history.

(56) References Cited

FOREIGN PATENT DOCUMENTS

| EP | 1674111 A1 | 6/2006 |
|---|---|---|
| EP | 2522724 A1 | 11/2012 |
| EP | 3199628 A1 | 8/2017 |
| EP | 3431102 A1 | 1/2019 |
| WO | WO 1994/004678 A1 | 3/1994 |
| WO | WO 1996/034103 A1 | 10/1996 |
| WO | WO 1999/023221 A2 | 5/1999 |
| WO | WO 2004/041865 A2 | 5/2004 |
| WO | WO 2006/122787 A1 | 11/2006 |
| WO | WO 2007/118670 A1 | 10/2007 |
| WO | WO 2008/020079 A1 | 2/2008 |
| WO | WO 2009/012394 A1 | 1/2009 |
| WO | WO 2012/175400 A1 | 12/2012 |
| WO | WO 2012/175741 A2 | 12/2012 |
| WO | WO 2015/173325 A2 | 11/2015 |
| WO | WO 2016/180969 A1 | 11/2016 |
| WO | WO 2017/080850 A1 | 5/2017 |
| WO | WO 2017/085172 A2 | 5/2017 |
| WO | WO 2018/091606 A1 | 5/2018 |
| WO | WO 2018/104444 A1 | 6/2018 |
| WO | WO 2018/134234 A1 | 7/2018 |
| WO | WO 2018/134235 A1 | 7/2018 |

OTHER PUBLICATIONS

Muyldermans S. Nanobodies: natural single-domain antibodies. Annu Rev Biochem. 2013;82:775-97. doi: 10.1146/annurev-biochem-063011-092449. Epub Mar. 13, 2013. (Year: 2013).*
Edwards et al. The remarkable flexibility of the human antibody repertoire;isolation of over one thousand different antibodies to a single protein,BLyS. J Mol Biol Nov. 14, 2003;334(1):103-18. (Year: 2003).*
Almagro JC, Fransson J. Humanization of antibodies. Front Biosci. Jan. 1, 2008;13:1619-33. (Year: 2008).*
Koenig et al. Mutational landscape of antibody variable domains reveals a switch modulating the interdomain conformational dynamics and antigen binding.PNAS Jan. 24, 2017 114(4)E486-E495;f irstpublished Jan. 5, 2017. (Year: 2017).*
Kussie et al. A single engineered amino acid substitution changes antibody fine specificity.J Immunol. Jan. 1, 1994;152(1):146-52. (Year: 1994).*
Wu et al. Humanization of a murine monoclonal antibody by simultaneous optimization of framework and CDR residues. J Mol Biol. Nov. 19, 1999;294(1):151-62. (Year: 1999).*
Chen et al. Enhancement and destruction of antibody function by somatic mutation: unequal occurrence is controlled by V gene combinatorial associations.EMBO J. Jun. 15, 1995; 14(12): 2784-94. (Year: 1995).*

(Continued)

*Primary Examiner* — Aurora M Fontainhas
*Assistant Examiner* — Jennifer A Benavides
(74) *Attorney, Agent, or Firm* — Wolf, Greenfield & Sacks, P.C.

(57) ABSTRACT

The present technology aims at providing a novel type of drug for treating a subject suffering from cancer. Specifically, the technology provides polypeptides comprising at least four immunoglobulin single variable domains (ISVDs), characterized in that one ISVD binds to TCR and at least two ISVDs bind to GPC3. The present technology also provides nucleic acids, vectors and compositions.

28 Claims, 24 Drawing Sheets

Figure 1A:
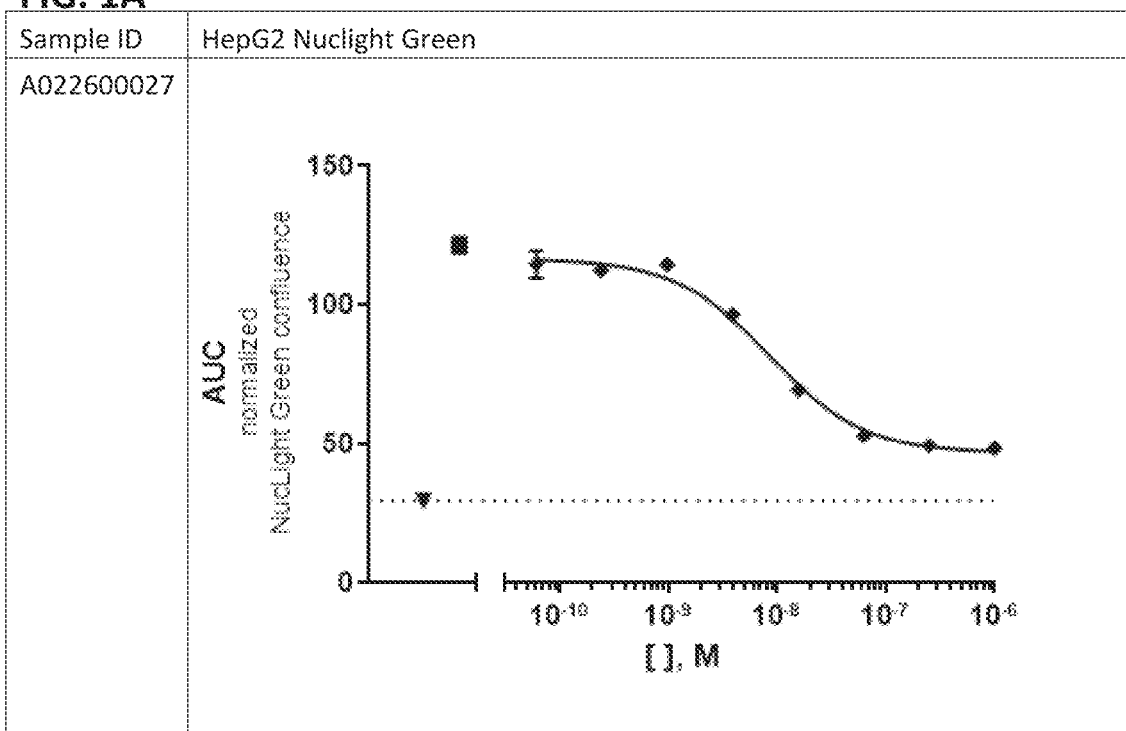

Specification includes a Sequence Listing.

(56) References Cited

OTHER PUBLICATIONS

Rudikoff S et al. Single amino acid substitution altering antigen-binding specificity. Proc Natl Acad Sci U S A. Mar. 1982;79(6):1979-83. (Year: 1982).*

Abdiche et al., Determining kinetics and affinities of protein interactions using a parallel real-time label-free biosensor, the Octet. Anal Biochem. Jun. 15, 2008;377(2):209-17. doi: 10.1016/j.ab.2008.03.035. Epub Mar. 25, 2008.

Blackwell et al., Impact of communication topology in particle swarm optimization. J Latex Class Files. Aug. 2015;14(8). 64 pages.

Call et al., Molecular mechanisms for the assembly of the T cell receptor-CD3 complex. Mol Immunol. Apr. 2004;40(18):1295-305. doi: 10.1016/j.molimm.2003.11.017.

Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.

Conrath et al., Camel single-domain antibodies as modular building units in bispecific and bivalent antibody constructs. J Biol Chem. Mar. 9, 2001;276(10):7346-50. doi: 10.1074/jbc.M007734200. Epub Oct. 25, 2000.

Davies et al., 'Camelising' human antibody fragments: NMR studies on VH domains. FEBS Lett. Feb. 21, 1994;339(3):285-90. doi: 10.1016/0014-5793(94)80432-x.

Davies et al., Single antibody domains as small recognition units: design and in vitro antigen selection of camelized, human VH domains with improved protein stability. Protein Eng. Jun. 1996;9(6):531-7. doi: 10.1093/protein/9.6.531.

Detre et al., A "quickscore" method for immunohistochemical semiquantitation: validation for oestrogen receptor in breast carcinomas. J Clin Pathol. Sep. 1995;48(9):876-8. doi: 10.1136/jcp.48.9.876.

Drake et al., Characterizing high-affinity antigen/antibody complexes by kinetic- and equilibrium-based methods. Anal Biochem. May 1, 2004;328(1):35-43. doi: 10.1016/j.ab.2003.12.025.

Feng et al., Therapeutically targeting glypican-3 via a conformation-specific single-domain antibody in hepatocellular carcinoma. Proc Natl Acad Sci U S A. Mar. 19, 2013;110(12):E1083-91. doi: 10.1073/pnas.1217868110. Epub Mar. 5, 2013.

Fleming et al., Engineered Anti-GPC3 Immunotoxin, HN3-ABD-T20, Produces Regression in Mouse Liver Cancer Xenografts Through Prolonged Serum Retention. Hepatology. May 2020;71(5):1696-1711. doi: 10.1002/hep.30949. Epub Jan. 27, 2020.

Fraley et al., The Gyrolab™ immunoassay system: a platform for automated bioanalysis and rapid sample turnaround. Bioanalysis. Jul. 2013;5(14):1765-74. doi: 10.4155/bio.13.145.

Glennie et al., Preparation and performance of bispecific F(ab' gamma)2 antibody containing thioether-linked Fab' gamma fragments. J Immunol. Oct. 1, 1987;139(7):2367-75.

Hamers-Casterman et al., Naturally occurring antibodies devoid of light chains. Nature. Jun. 3, 1993;363(6428):446-8. doi: 10.1038/363446a0.

Johnsson et al., Immobilization of proteins to a carboxymethyldextran-modified gold surface for biospecific interaction analysis in surface plasmon resonance sensors. Anal Biochem. Nov. 1, 1991;198(2):268-77. doi: 10.1016/0003-2697(91)90424-r.

Jonsson et al., Real-time biospecific interaction analysis using surface plasmon resonance and a sensor chip technology. Biotechniques. Nov. 1991;11(5):620-7.

Kabat et al., Sequences of Proteins of Immunological Interest. vol. I. 5th Ed. US Department of Health and Human Services. Public Health Service. National Institutes of Health. 1991. 11 pages.

Klein et al., Design and characterization of structured protein linkers with differing flexibilities. Protein Eng Des Sel. Oct. 2014;27(10):325-30. doi: 10.1093/protein/gzu043.

Martin, Chapter 3: Protein Sequence and Structure Analysis of Antibody Variable Domains. In Antibody Engineering vol. 2. Springer Lab Manuals. Springer, Berlin, Heidelberg. 2010:33-51. doi: 10.1007/978-3-642-01147-4_3.

Muyldermans et al., Single domain camel antibodies: current status. J Biotechnol. Jun. 2001;74(4):277-302. doi: 10.1016/s1389-0352(01)00021-6.

Ober et al., Differences in promiscuity for antibody-FcRn interactions across species: implications for therapeutic antibodies. Int Immunol. Dec. 2001;13(12):1551-9. doi: 10.1093/intimm/13.12.1551.

Van Der Linden et al., Induction of immune responses and molecular cloning of the heavy chain antibody repertoire of Lama glama. J Immunol Methods. Jun. 23, 2000;240(1-2):185-95. doi: 10.1016/s0022-1759(00)00188-5.

* cited by examiner

A022600096 (triangle symbol, dotted line)
A022600102 (square symbol, dotted line)
A022600103 (triangle symbol, solid line)
A022600104 (circle symbol, dotted line)
A022600105 (diamond symbol, solid line)

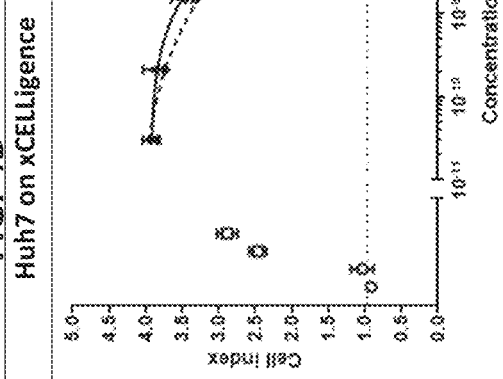
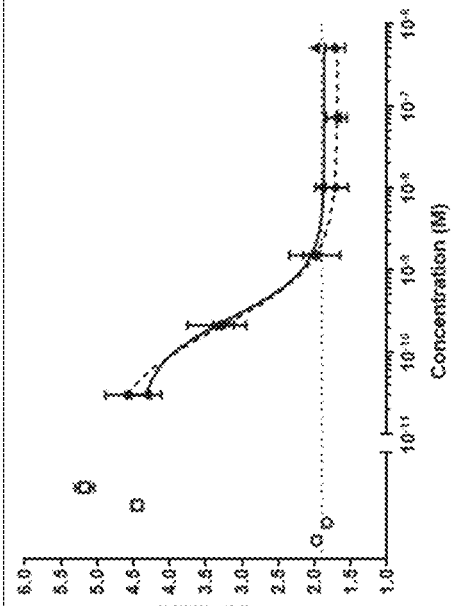
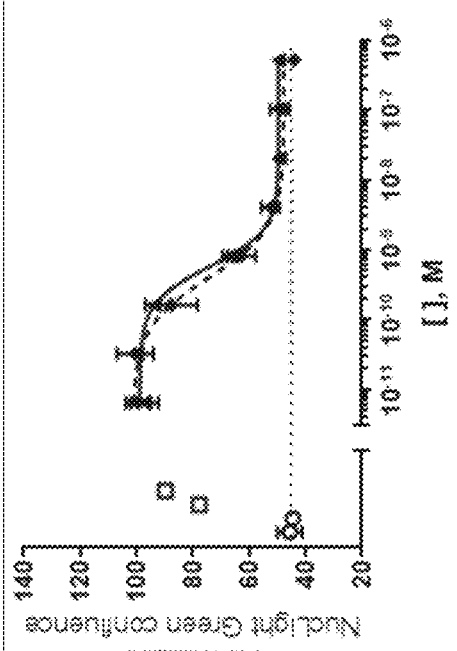
FIG. 4A
FIG. 4B

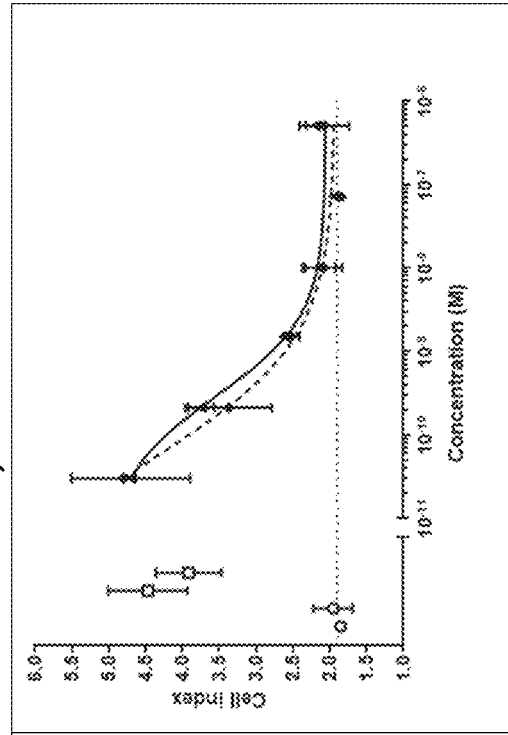
FIG. 4B, Cont.
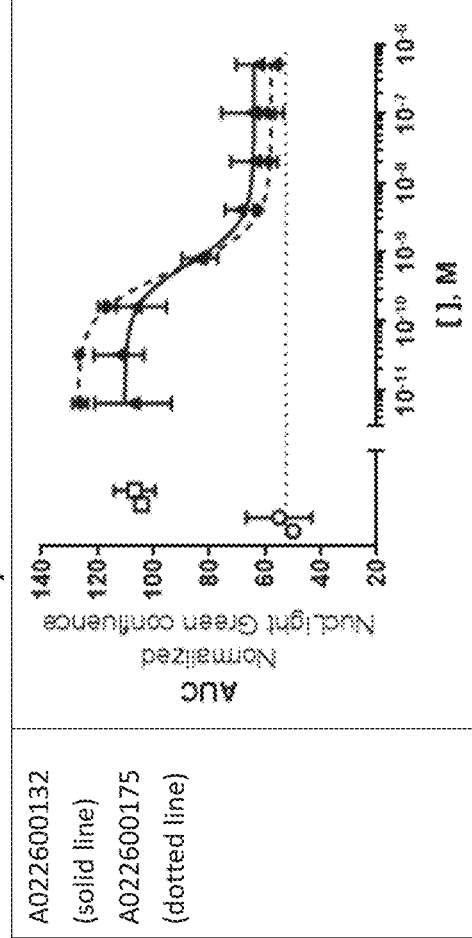
FIG. 4A, Cont.
A022600132 (solid line)
A022600175 (dotted line)

Figure 5A:
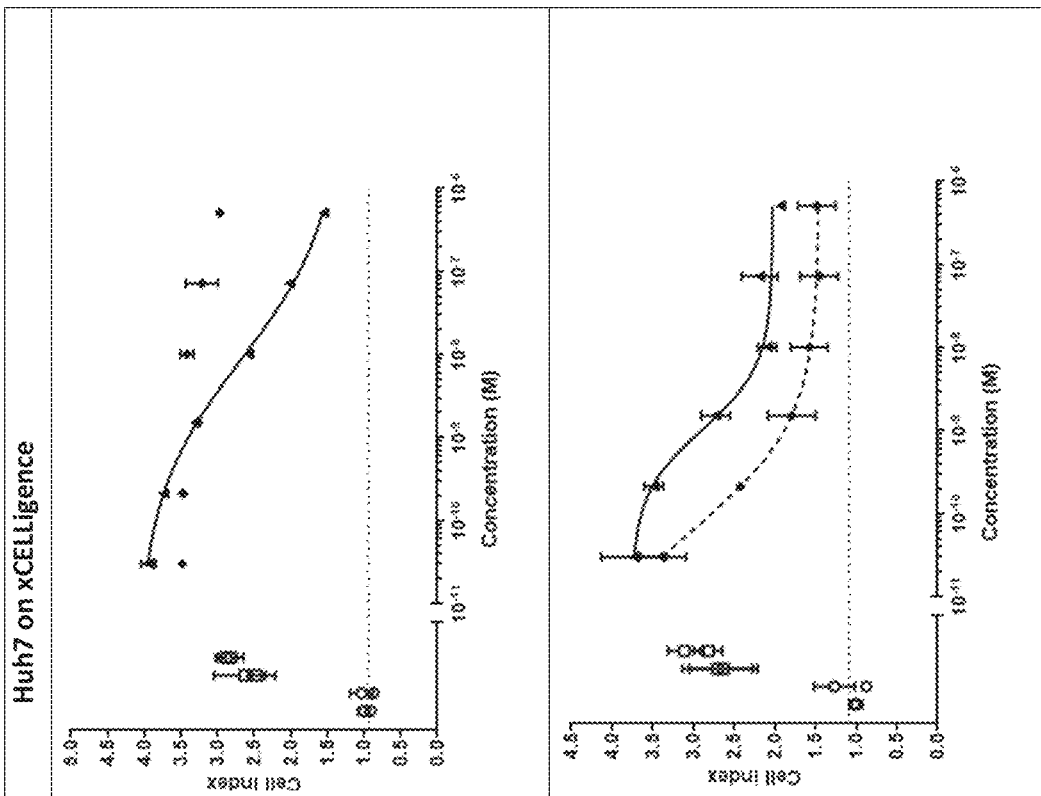
Figure 5B:
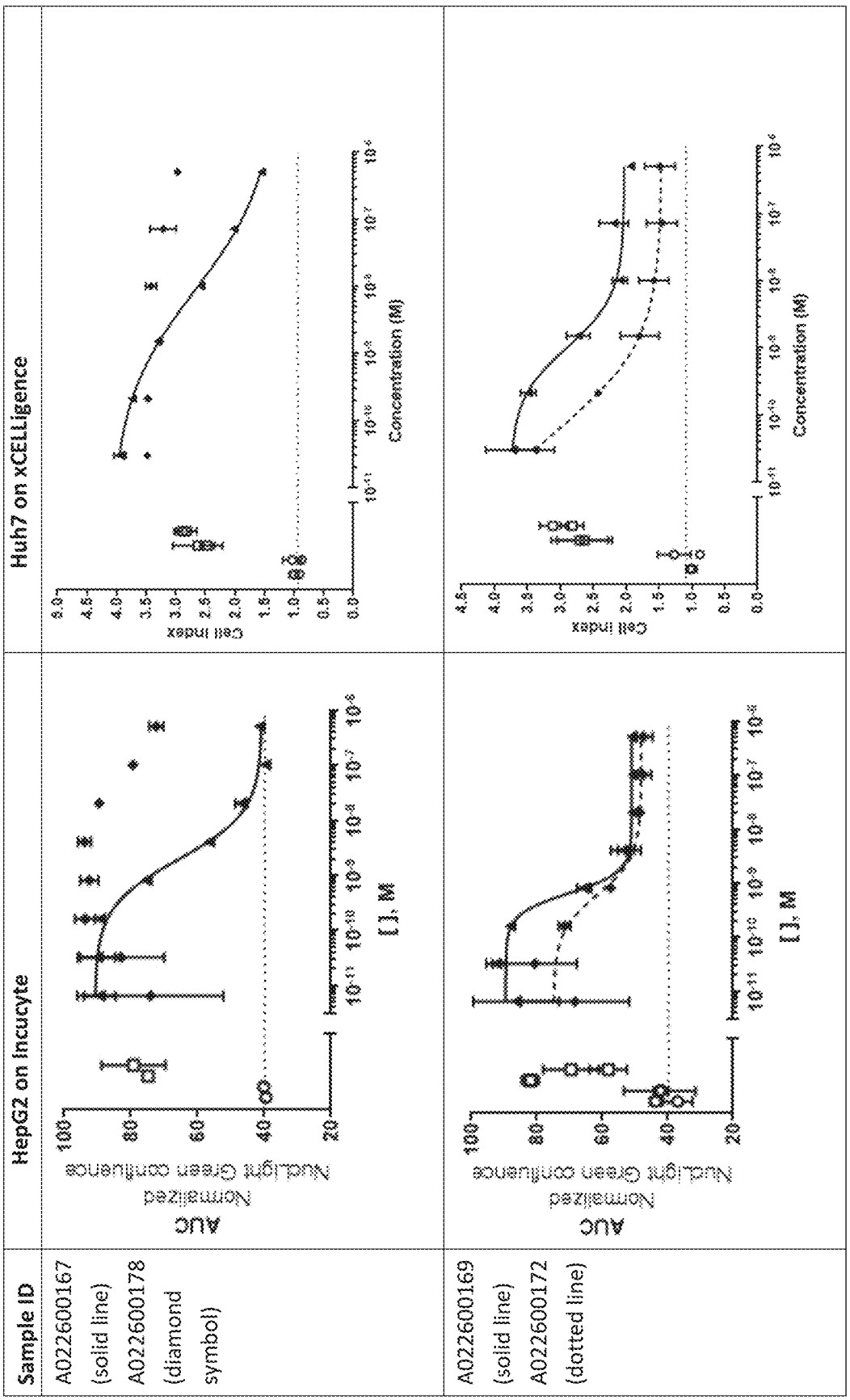

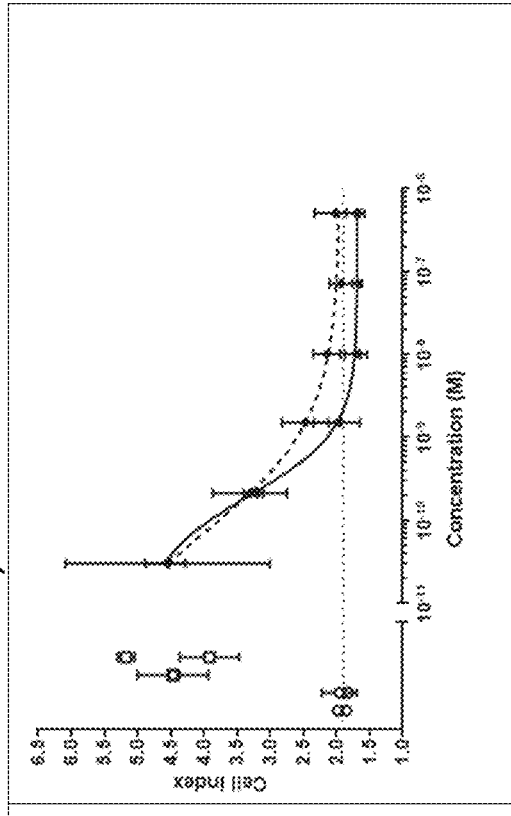
FIG. 5A, Cont.
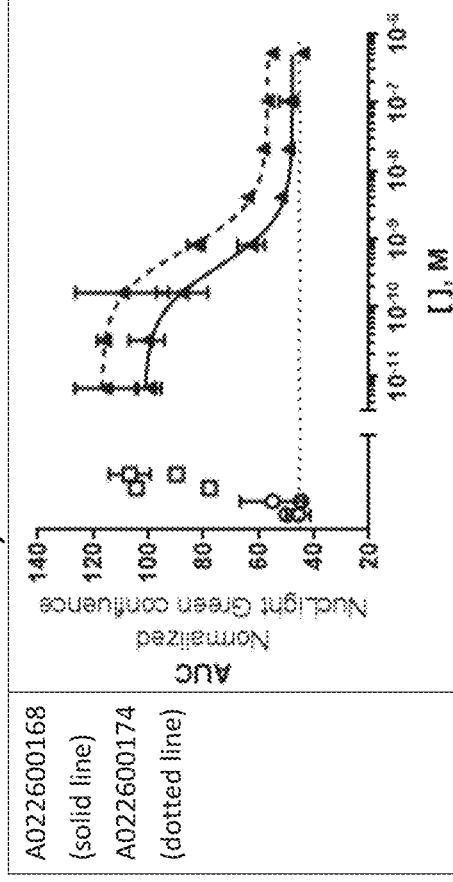
FIG. 5B, Cont.

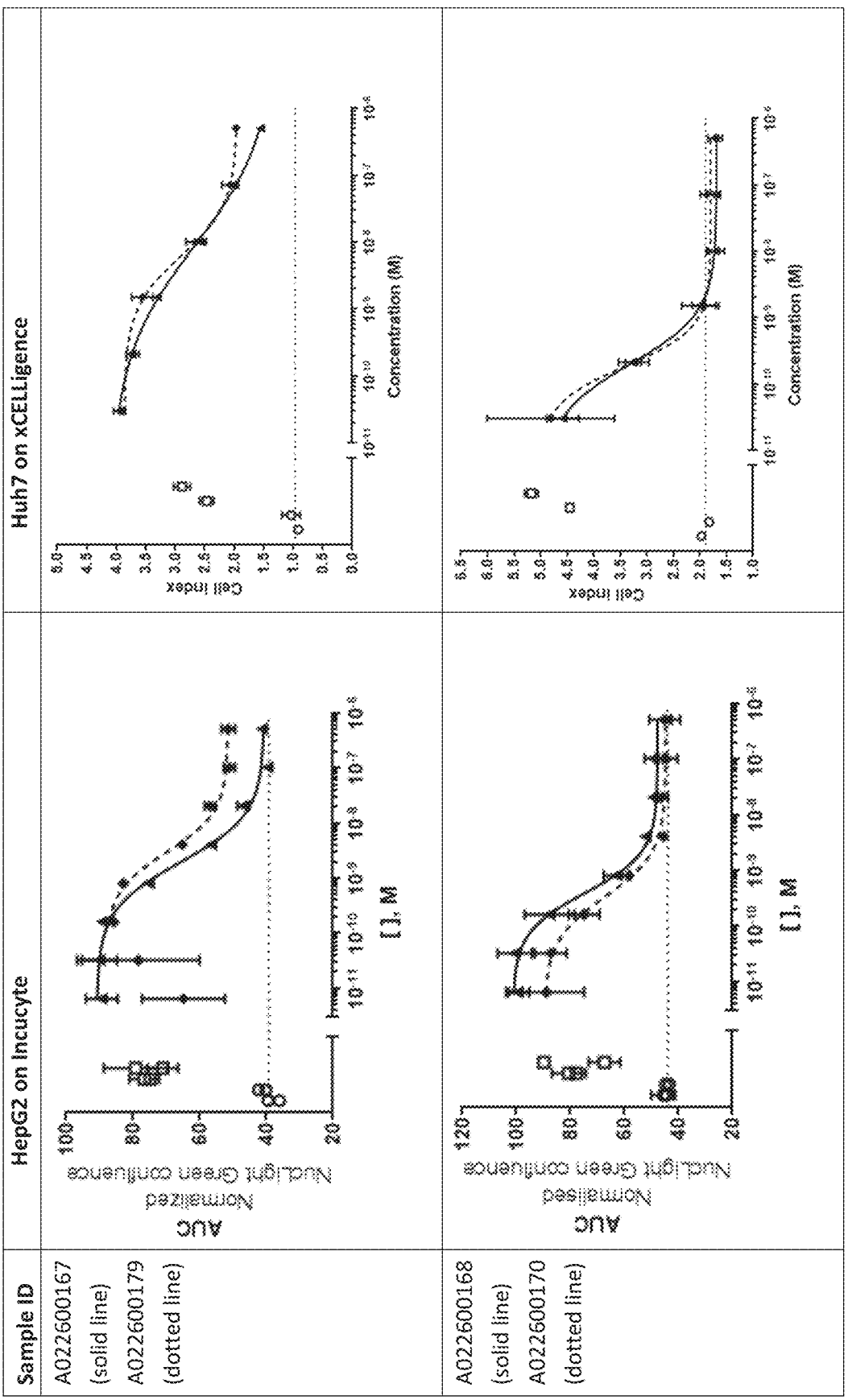

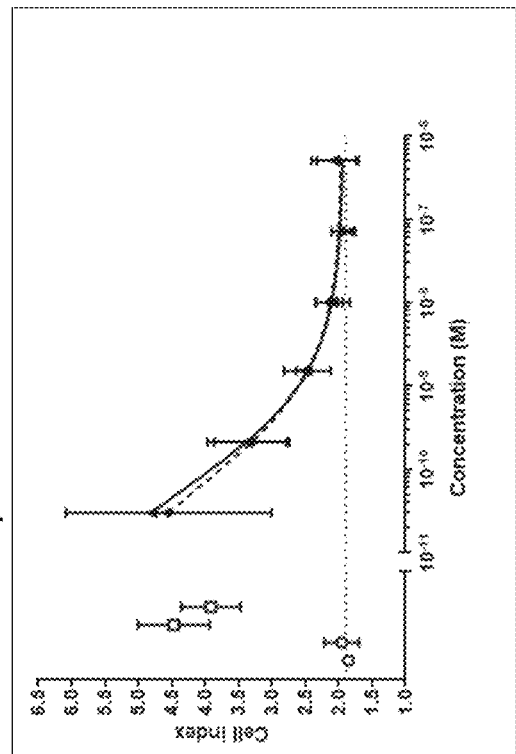
FIG. 6B, Cont.
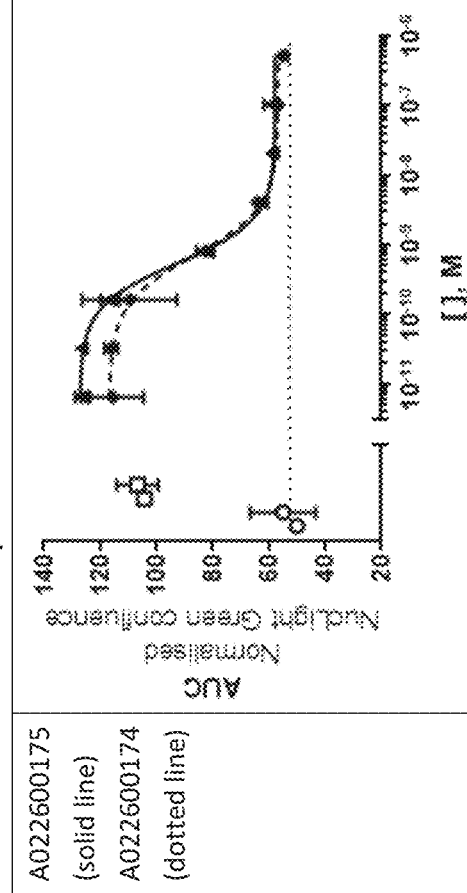
FIG. 6A, Cont.
A022600175 (solid line)
A022600174 (dotted line)

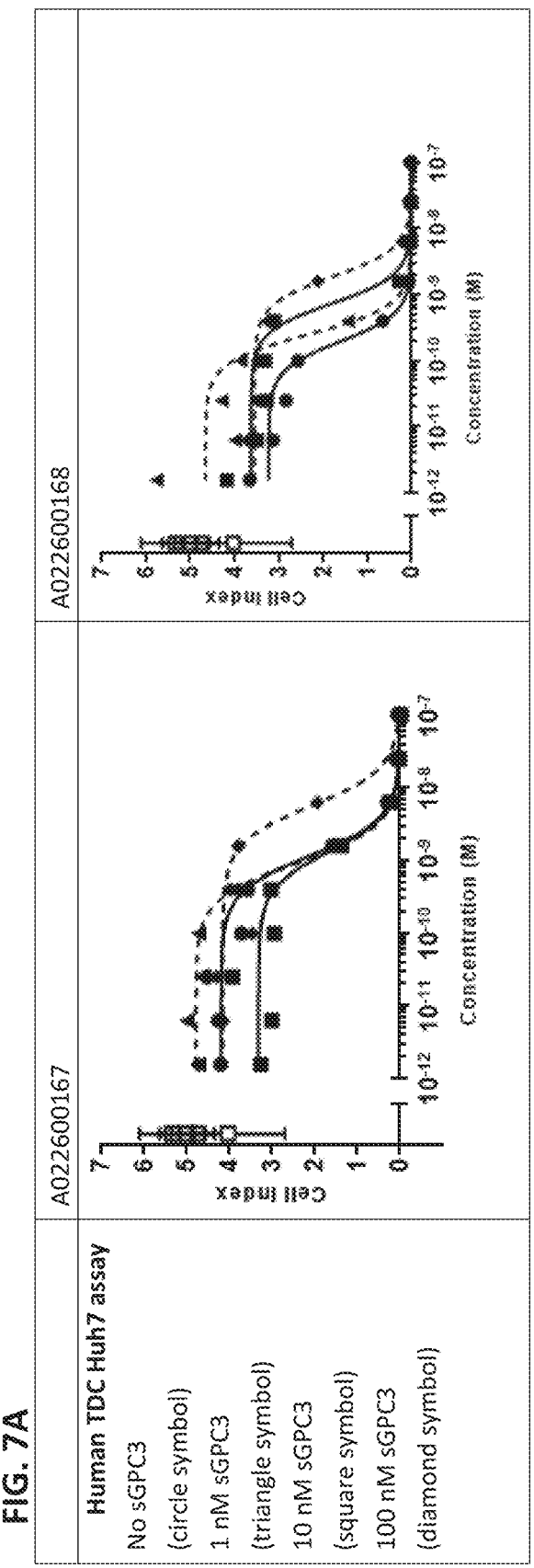

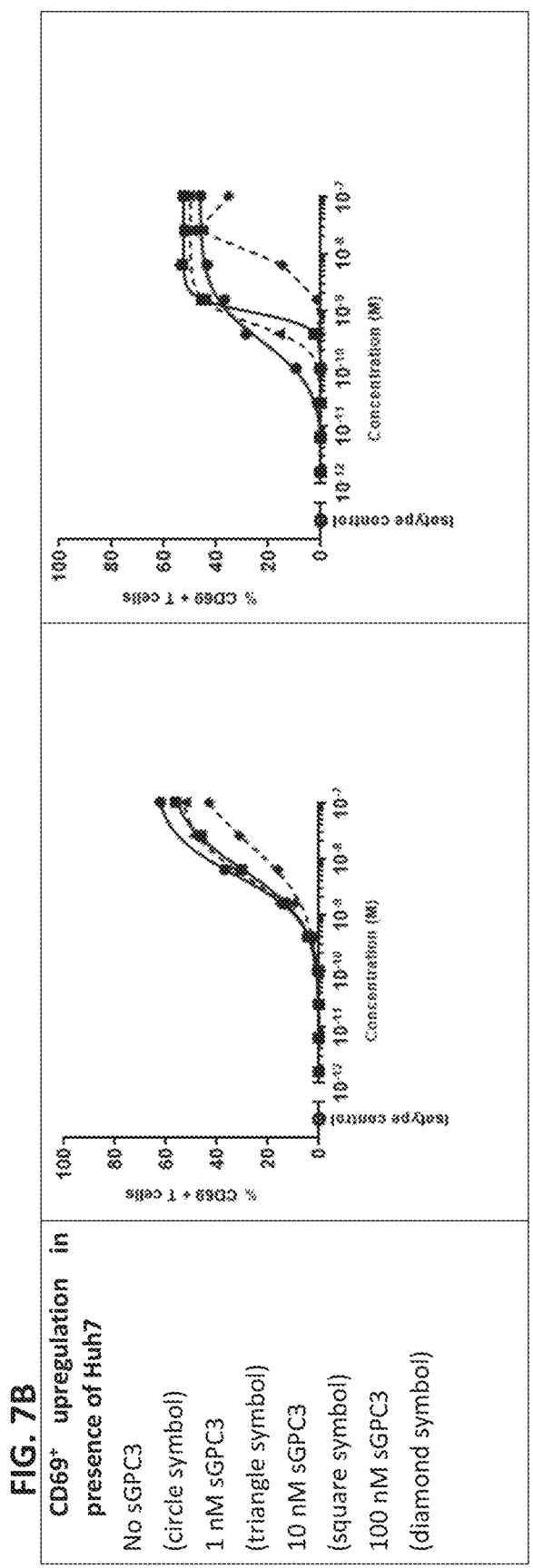

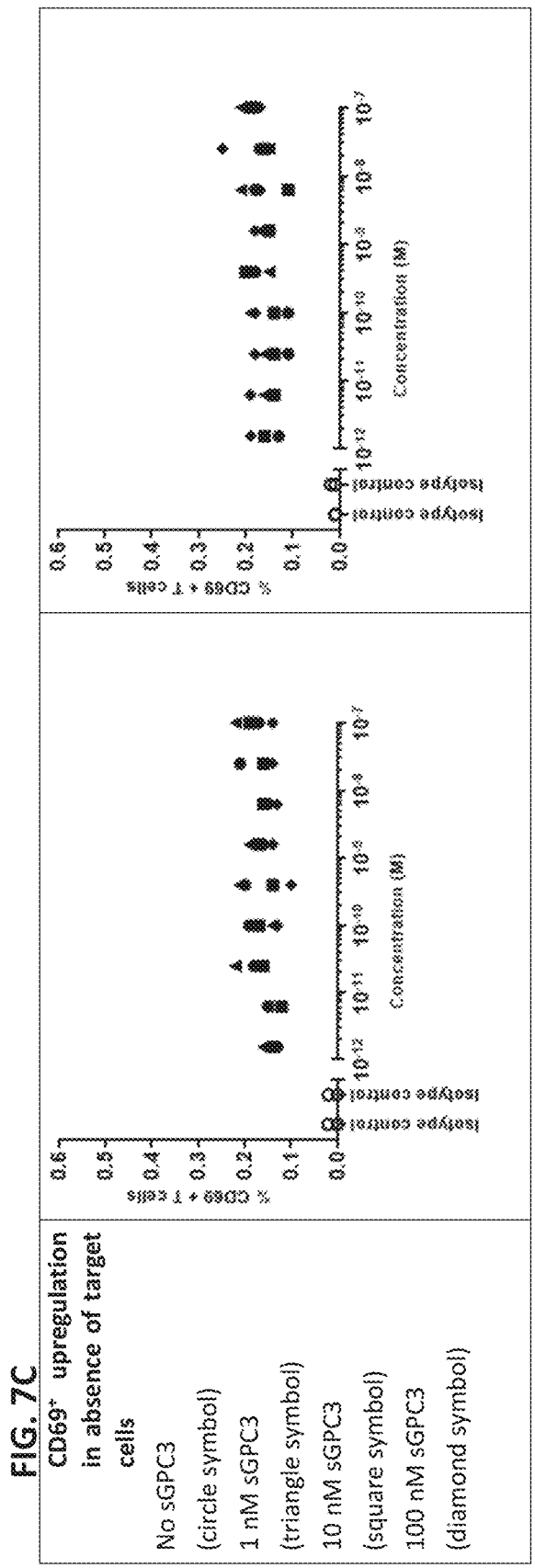

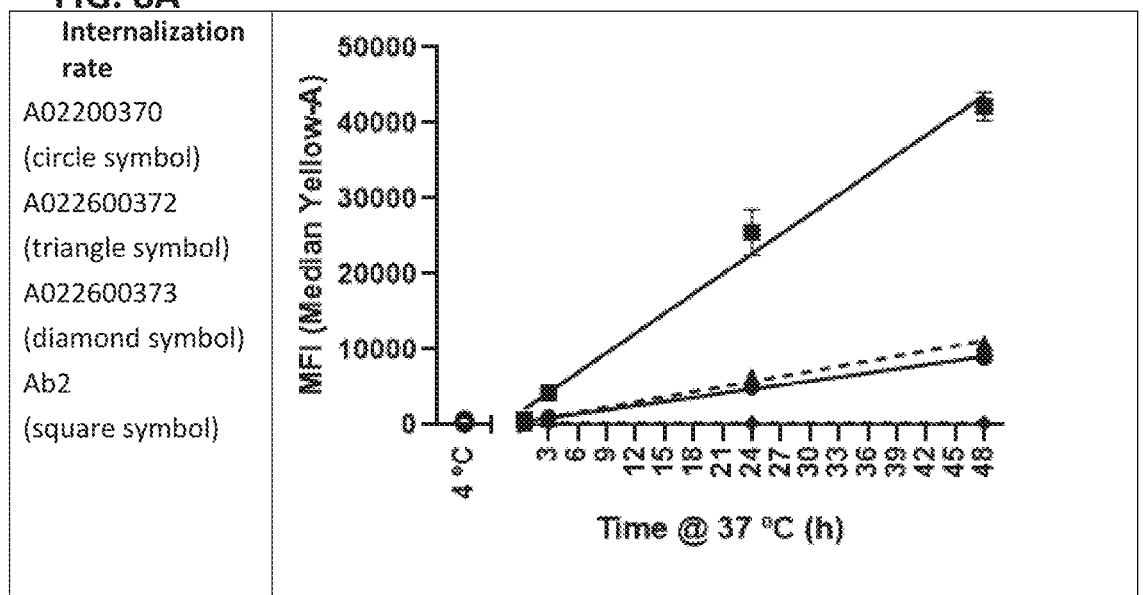

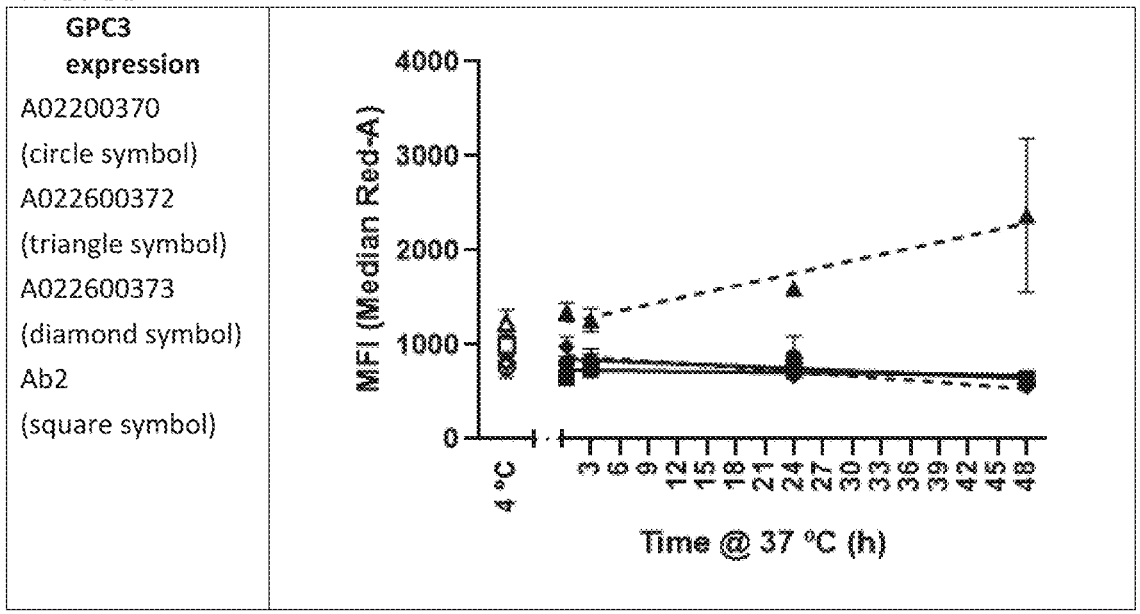

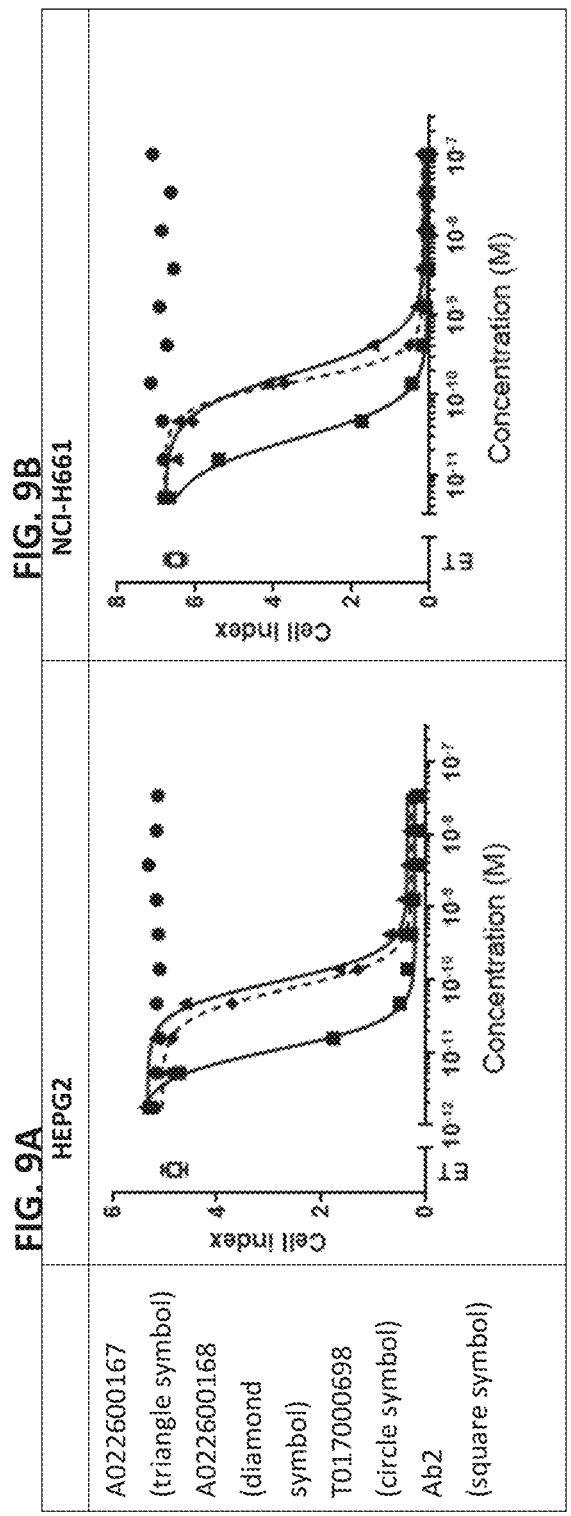

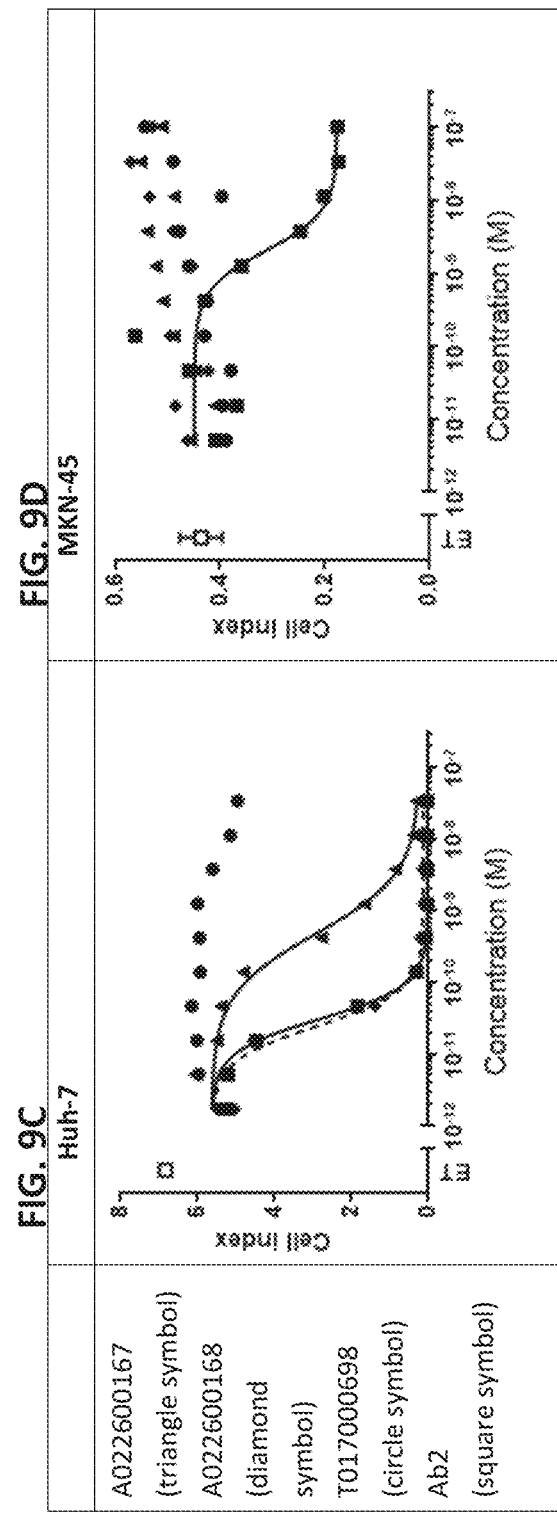

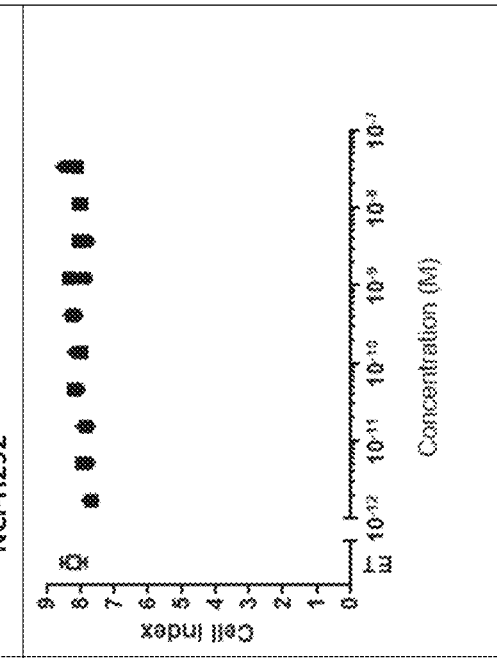
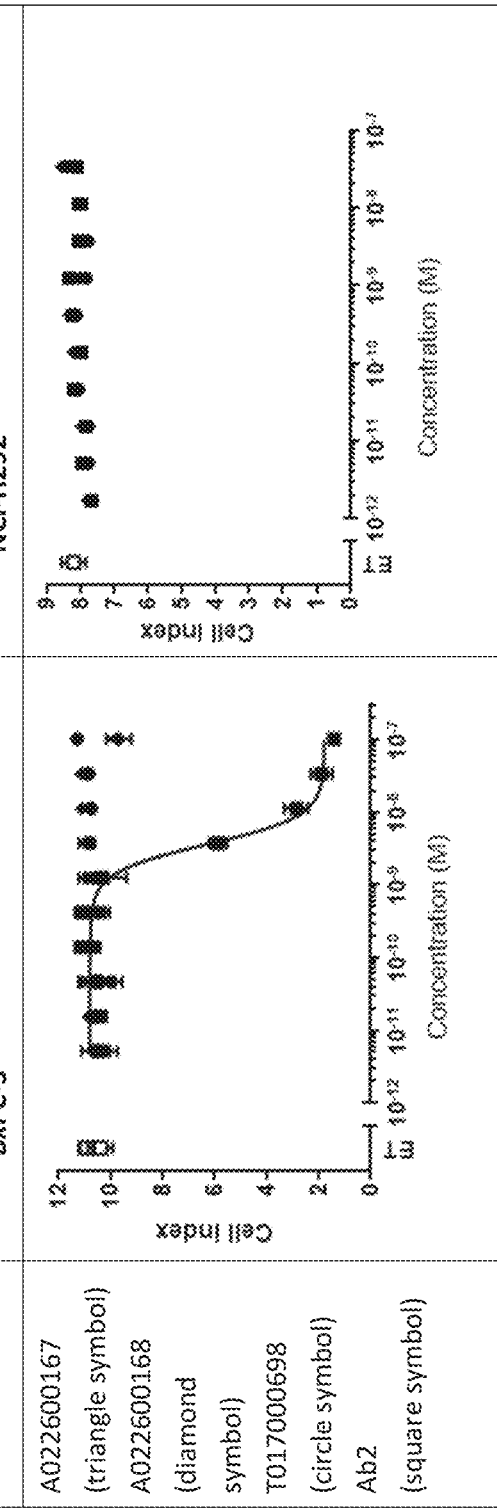
FIG. 9E BxPC-3
FIG. 9F NCI-H292

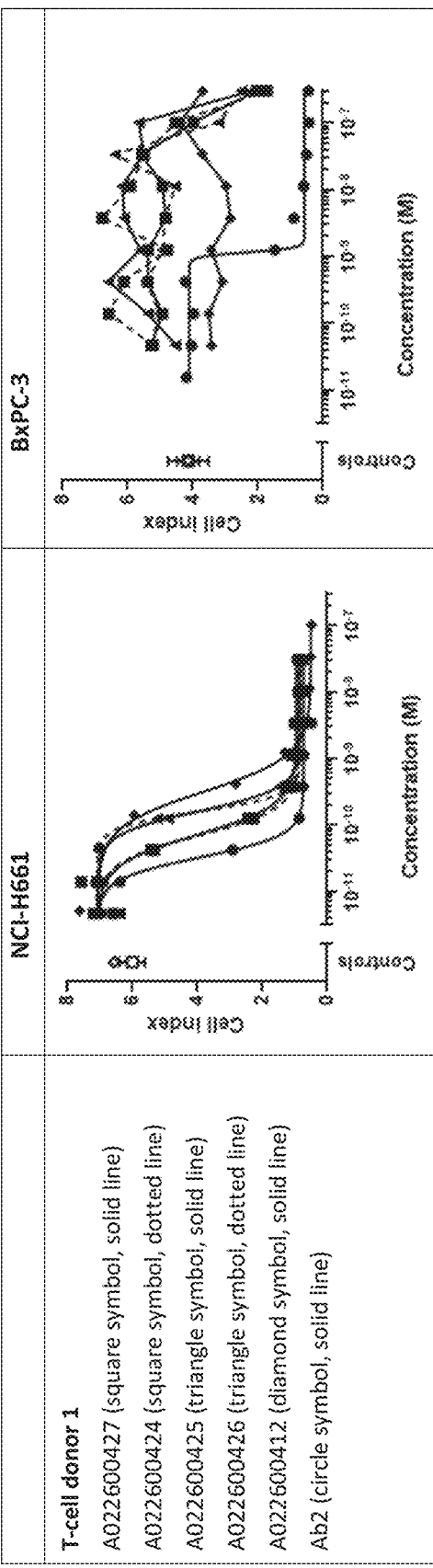
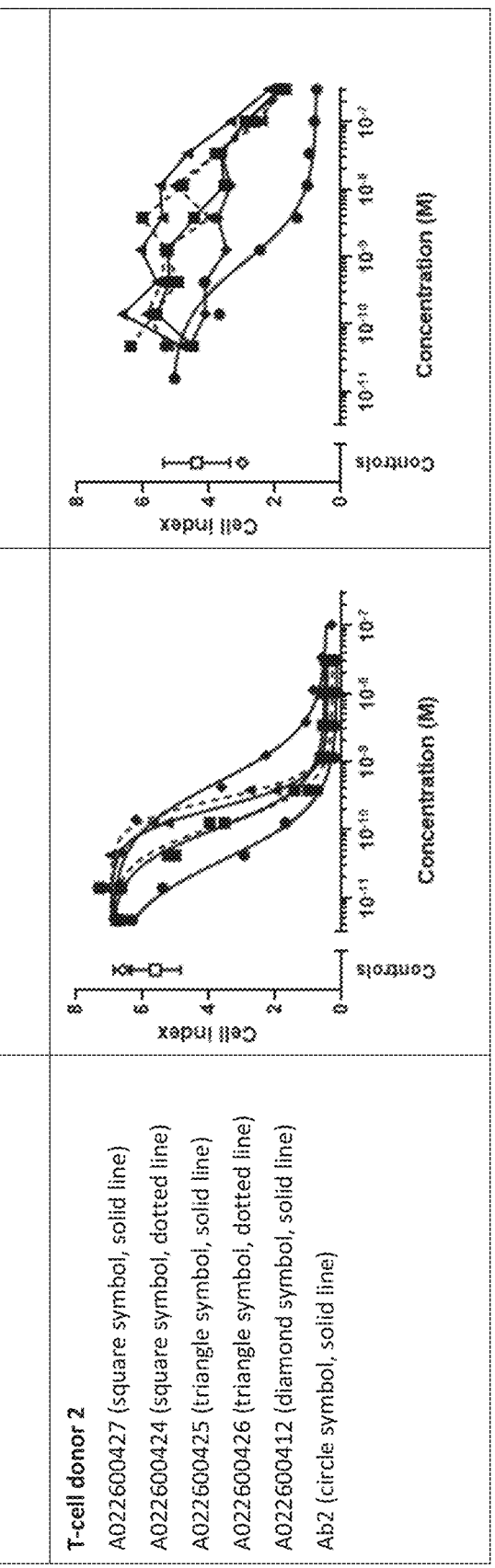

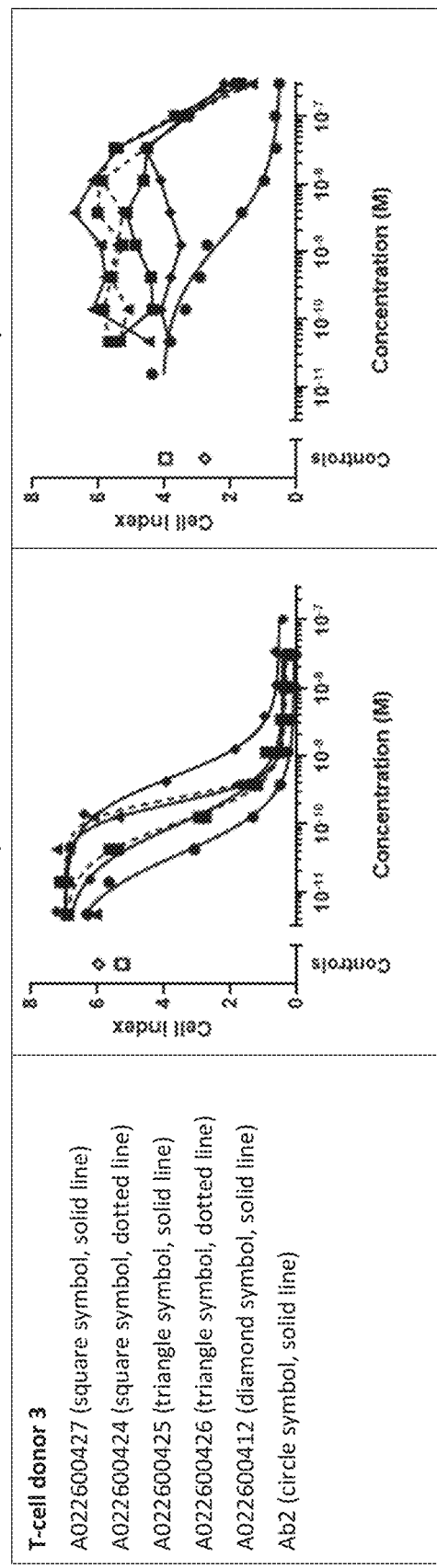
FIG. 10A, Cont.  FIG. 10B, Cont.

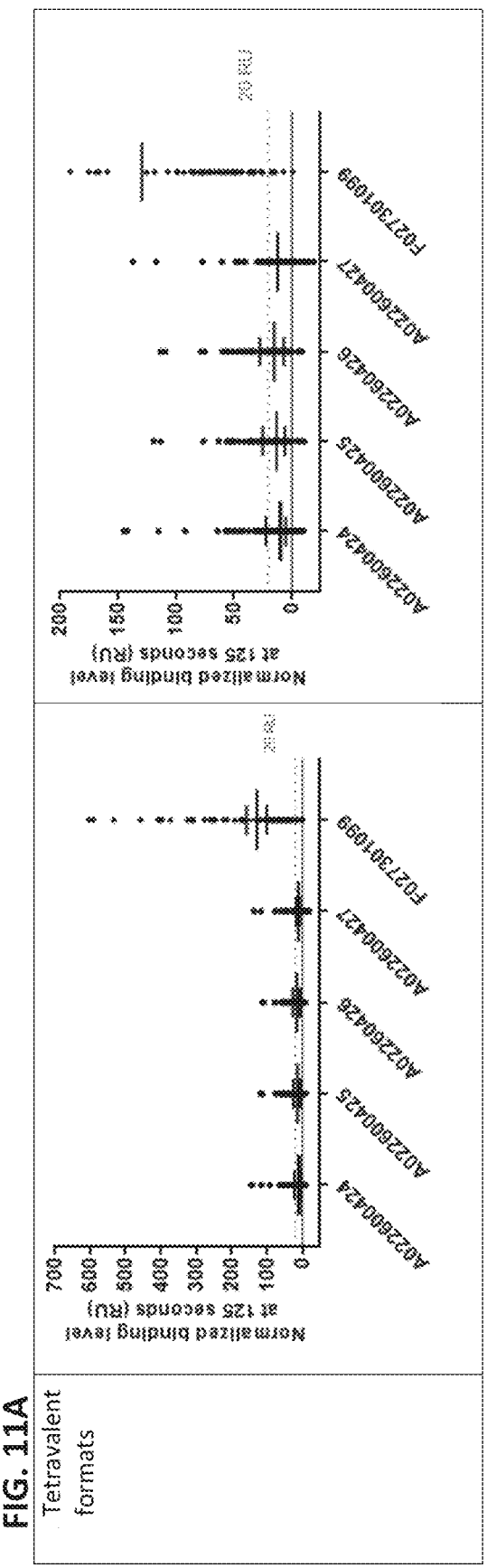

Trivalent formats

US 11,932,702 B2

SEQUENCE LISTING

<160> NUMBER OF SEQ ID NOS: 185

<210> SEQ ID NO 1
<211> LENGTH: 498
<212> TYPE: PRT
<213> ORGANISM: Artificial Sequence
<220> FEATURE:
<223> OTHER INFORMATION: Synthetic-A022600424

<400> SEQUENCE: 1

```
Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Gly Ser Glu Val Gln Leu Val Glu
        115                 120                 125

Ser Gly Gly Gly Val Val Gln Pro Gly Gly Ser Leu Arg Leu Ser Cys
    130                 135                 140

Ala Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Lys
                165                 170                 175

Gly Val Thr Ser Tyr Ala Asp Ser Val Lys Gly Arg Phe Thr Ile Ser
            180                 185                 190

Arg Asp Asn Ala Lys Asn Thr Leu Tyr Leu Gln Met Asn Ser Leu Arg
        195                 200                 205

Pro Glu Asp Thr Ala Leu Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Val Val Gln Pro Gly Gly Ser Leu
            260                 265                 270

Arg Leu Ser Cys Ala Ala Ser Gly Ser Ile Phe Arg Ser Val Phe Ser
        275                 280                 285

Ser Ser Thr Met Glu Trp Tyr Arg Gln Ala Pro Gly Lys Lys Arg Glu
    290                 295                 300

Leu Val Ala Arg Ile Ala Pro Gly Glu Gly Thr Tyr Tyr Gly Ala Leu
305                 310                 315                 320

Tyr Ala Asp Ser Val Lys Gly Arg Phe Thr Ile Ser Arg Asp Asn Ala
                325                 330                 335

Lys Asn Thr Val Tyr Leu Gln Met Asn Ser Leu Arg Pro Glu Asp Thr
            340                 345                 350

Ala Leu Tyr Tyr Cys Ala Ser Gly Val Ala Trp Gly Gln Gly Thr Leu
```

```
                     355                 360                 365
Val Thr Val Ser Ser Gly Gly Gly Ser Gly Gly Gly Ser Glu Val
            370                 375                 380
Gln Leu Val Glu Ser Gly Gly Val Val Gln Pro Gly Gly Ser Leu
385                 390                 395                 400
Arg Leu Ser Cys Ala Ala Ser Gly Phe Thr Phe Arg Ser Phe Gly Met
                405                 410                 415
Ser Trp Val Arg Gln Ala Pro Gly Lys Gly Pro Glu Trp Val Ser Ser
            420                 425                 430
Ile Ser Gly Ser Gly Ser Asp Thr Leu Tyr Ala Asp Ser Val Lys Gly
                435                 440                 445
Arg Phe Thr Ile Ser Arg Asp Asn Ser Lys Asn Thr Leu Tyr Leu Gln
        450                 455                 460
Met Asn Ser Leu Arg Pro Glu Asp Thr Ala Leu Tyr Tyr Cys Thr Ile
465                 470                 475                 480
Gly Gly Ser Leu Ser Arg Ser Ser Gln Gly Thr Leu Val Thr Val Ser
                485                 490                 495
Ser Ala

<210> SEQ ID NO 2
<211> LENGTH: 117
<212> TYPE: PRT
<213> ORGANISM: Artificial Sequence
<220> FEATURE:
<223> OTHER INFORMATION: Synthetic-TCE01

<400> SEQUENCE: 2

Asp Val Gln Leu Val Glu Ser Gly Gly Gly Val Val Gln Pro Gly Gly
1               5                   10                  15
Ser Leu Arg Leu Ser Cys Val Ala Ser Gly Tyr Val His Lys Ile Asn
            20                  25                  30
Phe Tyr Gly Trp Tyr Arg Gln Ala Pro Gly Lys Glu Arg Glu Lys Val
        35                  40                  45
Ala His Ile Ser Ile Gly Asp Gln Thr Asp Tyr Ala Asp Ser Ala Lys
    50                  55                  60
Gly Arg Phe Thr Ile Ser Arg Asp Glu Ser Lys Asn Thr Val Tyr Leu
65                  70                  75                  80
Gln Met Asn Ser Leu Arg Pro Glu Asp Thr Ala Ala Tyr Tyr Cys Arg
                85                  90                  95
Ala Leu Ser Arg Ile Trp Pro Tyr Asp Tyr Trp Gly Gln Gly Thr Leu
            100                 105                 110
Val Thr Val Ser Ser
        115

<210> SEQ ID NO 3
<211> LENGTH: 123
<212> TYPE: PRT
<213> ORGANISM: Artificial Sequence
<220> FEATURE:
<223> OTHER INFORMATION: Synthetic-A022600351

<400> SEQUENCE: 3

Glu Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser Phe
            20                  25                  30
Ala Met Thr Trp Val Arg Arg Pro Pro Gly Lys Gly Leu Glu Trp Val
```

```
            35                  40                  45
Ala Thr Ile Thr Asn Lys Gly Val Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Leu Tyr Ile Cys Ala
                 85                  90                  95

Asn Ala Arg Arg Thr Gly Pro Arg Ala Pro Thr Asp Ile Gly Ser Tyr
                100                 105                 110

Arg Gly Gln Gly Thr Leu Val Thr Val Ser Ser
            115                 120
```

<210> SEQ ID NO 4
<211> LENGTH: 119
<212> TYPE: PRT
<213> ORGANISM: Artificial Sequence
<220> FEATURE:
<223> OTHER INFORMATION: Synthetic-A022600314

<400> SEQUENCE: 4

```
Glu Val Gln Leu Val Glu Ser Gly Gly Gly Val Val Gln Pro Gly Gly
 1                   5                  10                  15

Ser Leu Arg Leu Ser Cys Ala Ala Ser Gly Ser Ile Phe Arg Ser Val
                 20                  25                  30

Phe Ser Ser Ser Thr Met Glu Trp Tyr Arg Gln Ala Pro Gly Lys Lys
                 35                  40                  45

Arg Glu Leu Val Ala Arg Ile Ala Pro Gly Gly Thr Tyr Tyr Gly
 50                  55                  60

Ala Leu Tyr Ala Asp Ser Val Lys Gly Arg Phe Thr Ile Ser Arg Asp
 65                  70                  75                  80

Asn Ala Lys Asn Thr Val Tyr Leu Gln Met Asn Ser Leu Arg Pro Glu
                 85                  90                  95

Asp Thr Ala Leu Tyr Tyr Cys Ala Ser Gly Val Ala Trp Gly Gln Gly
                100                 105                 110

Thr Leu Val Thr Val Ser Ser
            115
```

<210> SEQ ID NO 5
<211> LENGTH: 115
<212> TYPE: PRT
<213> ORGANISM: Artificial Sequence
<220> FEATURE:
<223> OTHER INFORMATION: Synthetic-ALB23002

<400> SEQUENCE: 5

```
Glu Val Gln Leu Val Glu Ser Gly Gly Gly Val Val Gln Pro Gly Gly
 1                   5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Pro Glu Trp Val
                 35                  40                  45

Ser Ser Ile Ser Gly Ser Gly Ser Asp Thr Leu Tyr Ala Asp Ser Val
                 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95
```

Thr Ile Gly Gly Ser Leu Ser Arg Ser Ser Gln Gly Thr Leu Val Thr
            100                 105                 110
Val Ser Ser
        115

<210> SEQ ID NO 6
<211> LENGTH: 10
<212> TYPE: PRT
<213> ORGANISM: Artificial Sequence
<220> FEATURE:
<223> OTHER INFORMATION: Synthetic-CDR1

<400> SEQUENCE: 6

Gly Tyr Val His Lys Ile Asn Phe Tyr Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic-CDR1

<400> SEQUENCE: 7

Gly Phe Thr Phe Ser Ser Phe Ala Met Thr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic-CDR1

<400> SEQUENCE: 8

Gly Ser Ile Phe Arg Ser Val Phe Ser Ser Thr Met Glu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic-CDR1

<400> SEQUENCE: 9

Gly Phe Thr Phe Arg Ser Phe Gly Met Ser
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic-CDR2

<400> SEQUENCE: 10

His Ile Ser Ile Gly Asp Gln Thr Asp
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic-CDR2

```
<400> SEQUENCE: 11

Thr Ile Thr Asn Lys Gly Val Thr Ser
1               5

<210> SEQ ID NO 12
<211> LENGTH: 13
<212> TYPE: PRT
<213> ORGANISM: Artificial Sequence
<220> FEATURE:
<223> OTHER INFORMATION: Synthetic-CDR2

<400> SEQUENCE: 12

Arg Ile Ala Pro Gly Glu Gly Thr Tyr Tyr Gly Ala Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic-CDR2

<400> SEQUENCE: 13

Ser Ile Ser Gly Ser Gly Ser Asp Thr Leu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic-CDR3

<400> SEQUENCE: 14

Leu Ser Arg Ile Trp Pro Tyr Asp Tyr
1               5

<210> SEQ ID NO 15
<211> LENGTH: 15
<212> TYPE: PRT
<213> ORGANISM: Artificial Sequence
<220> FEATURE:
<223> OTHER INFORMATION: Synthetic-CDR3

<400> SEQUENCE: 15

Ala Arg Arg Thr Gly Pro Arg Ala Pro Thr Asp Ile Gly Ser Tyr
1               5                   10                  15

<210> SEQ ID NO 16
<211> LENGTH: 3
<212> TYPE: PRT
<213> ORGANISM: Artificial Sequence
<220> FEATURE:
<223> OTHER INFORMATION: Synthetic-CDR3

<400> SEQUENCE: 16

Gly Val Ala
1

<210> SEQ ID NO 17
<211> LENGTH: 6
<212> TYPE: PRT
<213> ORGANISM: Artificial Sequence
<220> FEATURE:
<223> OTHER INFORMATION: Synthetic-CDR3

<400> SEQUENCE: 17
```

```
Gly Gly Ser Leu Ser Arg
1               5

<210> SEQ ID NO 18
<211> LENGTH: 25
<212> TYPE: PRT
<213> ORGANISM: Artificial Sequence
<220> FEATURE:
<223> OTHER INFORMATION: Synthetic-FR1

<400> SEQUENCE: 18

Asp Val Gln Leu Val Glu Ser Gly Gly Gly Val Val Gln Pro Gly Gly
1               5                   10                  15

Ser Leu Arg Leu Ser Cys Val Ala Ser
            20                  25

<210> SEQ ID NO 19
<211> LENGTH: 25
<212> TYPE: PRT
<213> ORGANISM: Artificial Sequence
<220> FEATURE:
<223> OTHER INFORMATION: Synthetic-FR1

<400> SEQUENCE: 19

Glu Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 20
<211> LENGTH: 14
<212> TYPE: PRT
<213> ORGANISM: Artificial Sequence
<220> FEATURE:
<223> OTHER INFORMATION: Synthetic-FR2

<400> SEQUENCE: 20

Trp Tyr Arg Gln Ala Pro Gly Lys Glu Arg Glu Lys Val Ala
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic-FR2

<400> SEQUENCE: 21

Trp Val Arg Arg Pro Pro Gly Lys Gly Leu Glu Trp Val Ala
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic-FR2

<400> SEQUENCE: 22

Trp Tyr Arg Gln Ala Pro Gly Lys Lys Arg Glu Leu Val Ala
1               5                   10

<210> SEQ ID NO 23
<211> LENGTH: 14
<212> TYPE: PRT
```

```
<213> ORGANISM: Artificial Sequence
<220> FEATURE:
<223> OTHER INFORMATION: Synthetic-FR2

<400> SEQUENCE: 23

Trp Val Arg Gln Ala Pro Gly Lys Gly Pro Glu Trp Val Ser
1               5                   10

<210> SEQ ID NO 24
<211> LENGTH: 39
<212> TYPE: PRT
<213> ORGANISM: Artificial Sequence
<220> FEATURE:
<223> OTHER INFORMATION: Synthetic-FR3

<400> SEQUENCE: 24

Tyr Ala Asp Ser Ala Lys Gly Arg Phe Thr Ile Ser Arg Asp Glu Ser
1               5                   10                  15

Lys Asn Thr Val Tyr Leu Gln Met Asn Ser Leu Arg Pro Glu Asp Thr
            20                  25                  30

Ala Ala Tyr Tyr Cys Arg Ala
        35

<210> SEQ ID NO 25
<211> LENGTH: 39
<212> TYPE: PRT
<213> ORGANISM: Artificial Sequence
<220> FEATURE:
<223> OTHER INFORMATION: Synthetic-FR3

<400> SEQUENCE: 25

Tyr Ala Asp Ser Val Lys Gly Arg Phe Thr Ile Ser Arg Asp Asn Ala
1               5                   10                  15

Lys Asn Thr Leu Tyr Leu Gln Met Asn Ser Leu Arg Pro Glu Asp Thr
            20                  25                  30

Ala Leu Tyr Ile Cys Ala Asn
        35

<210> SEQ ID NO 26
<211> LENGTH: 39
<212> TYPE: PRT
<213> ORGANISM: Artificial Sequence
<220> FEATURE:
<223> OTHER INFORMATION: Synthetic-FR3

<400> SEQUENCE: 26

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Arg Pro Glu Asp Thr
            20                  25                  30

Ala Leu Tyr Tyr Cys Ala Ser
        35

<210> SEQ ID NO 27
<211> LENGTH: 39
<212> TYPE: PRT
<213> ORGANISM: Artificial Sequence
<220> FEATURE:
<223> OTHER INFORMATION: Synthetic-FR3

<400> SEQUENCE: 27

Tyr Ala Asp Ser Val Lys Gly Arg Phe Thr Ile Ser Arg Asp Asn Ser
1               5                   10                  15
```

Lys Asn Thr Leu Tyr Leu Gln Met Asn Ser Leu Arg Pro Glu Asp Thr
            20                  25                  30

Ala Leu Tyr Tyr Cys Thr Ile
        35

<210> SEQ ID NO 28
<211> LENGTH: 11
<212> TYPE: PRT
<213> ORGANISM: Artificial Sequence
<220> FEATURE:
<223> OTHER INFORMATION: Synthetic-FR4

<400> SEQUENCE: 28

Trp Gly Gln Gly Thr Leu Val Thr Val Ser Ser
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic-FR4

<400> SEQUENCE: 29

Arg Gly Gln Gly Thr Leu Val Thr Val Ser Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic-FR4

<400> SEQUENCE: 30

Ser Ser Gln Gly Thr Leu Val Thr Val Ser Ser
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Synthetic-CDR1

<400> SEQUENCE: 31

Ile Asn Phe Tyr Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic-CDR1

<400> SEQUENCE: 32

Ser Phe Ala Met Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic-CDR1

```
<400> SEQUENCE: 33

Ser Val Phe Ser Ser Ser Thr Met Glu
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic-CDR1

<400> SEQUENCE: 34

Ser Phe Gly Met Ser
1               5

<210> SEQ ID NO 35
<211> LENGTH: 16
<212> TYPE: PRT
<213> ORGANISM: Artificial Sequence
<220> FEATURE:
<223> OTHER INFORMATION: Synthetic-CDR2

<400> SEQUENCE: 35

His Ile Ser Ile Gly Asp Gln Thr Asp Tyr Ala Asp Ser Ala Lys Gly
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic-CDR2

<400> SEQUENCE: 36

Thr Ile Thr Asn Lys Gly Val Thr Ser Tyr Ala Asp Ser Val Lys Gly
1               5                   10                  15

<210> SEQ ID NO 37
<211> LENGTH: 20
<212> TYPE: PRT
<213> ORGANISM: Artificial Sequence
<220> FEATURE:
<223> OTHER INFORMATION: Synthetic-CDR2

<400> SEQUENCE: 37

Arg Ile Ala Pro Gly Glu Gly Thr Tyr Tyr Gly Ala Leu Tyr Ala Asp
1               5                   10                  15

Ser Val Lys Gly
            20

<210> SEQ ID NO 38
<211> LENGTH: 17
<212> TYPE: PRT
<213> ORGANISM: Artificial Sequence
<220> FEATURE:
<223> OTHER INFORMATION: Synthetic-CDR2

<400> SEQUENCE: 38

Ser Ile Ser Gly Ser Gly Ser Asp Thr Leu Tyr Ala Asp Ser Val Lys
1               5                   10                  15

Gly

<210> SEQ ID NO 39
<211> LENGTH: 30
<212> TYPE: PRT
```

<213> ORGANISM: Artificial Sequence
<220> FEATURE:
<223> OTHER INFORMATION: Synthetic-FR1

<400> SEQUENCE: 39

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Synthetic-FR1

<400> SEQUENCE: 40

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Synthetic-FR1

<400> SEQUENCE: 41

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Ile Phe Arg
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Synthetic-FR1

<400> SEQUENCE: 42

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Synthetic-FR3

<400> SEQUENCE: 43

Arg Phe Thr Ile Ser Arg Asp Glu Ser Lys Asn Thr Val Tyr Leu Gln
1               5                   10                  15

Met Asn Ser Leu Arg Pro Glu Asp Thr Ala Ala Tyr Tyr Cys Arg Ala
            20                  25                  30

<210> SEQ ID NO 44
<211> LENGTH: 32

```
<212> TYPE: PRT
<213> ORGANISM: Artificial Sequence
<220> FEATURE:
<223> OTHER INFORMATION: Synthetic-FR3

<400> SEQUENCE: 44

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Leu Tyr Ile Cys Ala Asn
                20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Synthetic-FR3

<400> SEQUENCE: 45

Arg Phe Thr Ile Ser Arg Asp Asn Ala Lys Asn Thr Val Tyr Leu Gln
1               5                   10                  15

Met Asn Ser Leu Arg Pro Glu Asp Thr Ala Leu Tyr Tyr Cys Ala Ser
                20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Synthetic-FR3

<400> SEQUENCE: 46

Arg Phe Thr Ile Ser Arg Asp Asn Ser Lys Asn Thr Leu Tyr Leu Gln
1               5                   10                  15

Met Asn Ser Leu Arg Pro Glu Asp Thr Ala Leu Tyr Tyr Cys Thr Ile
                20                  25                  30

<210> SEQ ID NO 47
<211> LENGTH: 119
<212> TYPE: PRT
<213> ORGANISM: Artificial Sequence
<220> FEATURE:
<223> OTHER INFORMATION: Synthetic-A0226015A08

<400> SEQUENCE: 47

Glu Val Gln Leu Val Glu Ser Gly Gly Gly Leu Val Gln Ala Gly Gly
1               5                   10                  15

Ser Leu Arg Leu Ser Cys Val Ala Ser Gly Ser Ile Phe Arg Ser Val
                20                  25                  30

Phe Ser Ser Ser Thr Met Glu Trp Tyr Arg Gln Pro Pro Gly Lys Lys
            35                  40                  45

Arg Glu Leu Val Ala Arg Ile Ala Pro Gly Asp Gly Thr Asn Tyr Gly
        50                  55                  60

Ala Leu Tyr Ala Asp Ser Val Lys Gly Arg Phe Thr Ile Ser Arg Asp
65                  70                  75                  80

Asp Ala Lys Lys Thr Val Asp Leu Gln Met Asn Ser Leu Lys Pro Glu
                85                  90                  95

Asp Thr Gly Val Tyr Phe Cys Ala Ser Gly Val Ala Trp Gly Gln Gly
                100                 105                 110

Thr Leu Val Thr Val Ser Ser
            115
```

```
<210> SEQ ID NO 48
<211> LENGTH: 123
<212> TYPE: PRT
<213> ORGANISM: Artificial Sequence
<220> FEATURE:
<223> OTHER INFORMATION: Synthetic-A0226018C08

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Phe
            20                  25                  30

Ala Met Thr Trp Val Arg Arg Pro Gly Lys Gly Leu Glu Trp Val
        35                  40                  45

Ala Thr Ile Thr Asn Gly Gly Val Thr Ser Tyr Arg Asp Ser Val Lys
    50                  55                  60

Gly Arg Phe Thr Ile Ser Arg Asp Asn Ala Lys Asn Thr Leu Tyr Leu
65                  70                  75                  80

Glu Met Thr Ser Leu Asn Pro Glu Asp Thr Ala Val Tyr Ile Cys Ala
                85                  90                  95

Asn Ala Arg Arg Thr Gly Pro Arg Ala Pro Thr Asp Ile Gly Ser Tyr
            100                 105                 110

Arg Gly Gln Gly Thr Leu Val Thr Val Ser Ser
        115                 120

<210> SEQ ID NO 49
<211> LENGTH: 433
<212> TYPE: PRT
<213> ORGANISM: Artificial Sequence
<220> FEATURE:
<223> OTHER INFORMATION: Synthetic-A022600027

<400> SEQUENCE: 49

Asp Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Phe Ser Arg Ile Tyr Pro Tyr Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Val Ala
                165                 170                 175

Ser Gly Phe Thr Phe Ser Ser Phe Ala Met Thr Trp Val Arg Arg Pro
            180                 185                 190
```

```
Pro Gly Lys Gly Leu Glu Trp Val Ala Thr Ile Thr Asn Gly Gly Val
        195                 200                 205

Thr Ser Tyr Arg Asp Ser Val Lys Gly Arg Phe Thr Ile Ser Arg Asp
    210                 215                 220

Asn Ala Lys Asn Thr Leu Tyr Leu Glu Met Thr Ser Leu Asn Pro Glu
225                 230                 235                 240

Asp Thr Ala Val Tyr Ile Cys Ala Asn Ala Arg Arg Thr Gly Pro Arg
                245                 250                 255

Ala Pro Thr Asp Ile Gly Ser Tyr Arg Gly Gln Gly Thr Leu Val Thr
            260                 265                 270

Val Ser Ser Gly Gly Gly Ser Gly Gly Gly Ser Gly Gly Gly Gly Gly
        275                 280                 285

Gly Ser Gly Gly Gly Ser Gly Gly Gly Ser Gly Gly Gly Gly Gly Gly
        290                 295                 300

Ser Gly Gly Gly Ser Glu Val Gln Leu Val Glu Ser Gly Gly Gly
305                 310                 315                 320

Val Val Gln Pro Gly Gly Ser Leu Arg Leu Ser Cys Ala Ala Ser Gly
                325                 330                 335

Leu Thr Phe Ser Ser Tyr Ala Met Gly Trp Phe Arg Gln Ala Pro Gly
            340                 345                 350

Lys Glu Arg Glu Arg Val Val Ser Ile Ser Arg Gly Gly Gly Tyr Thr
        355                 360                 365

Tyr Tyr Ala Asp Ser Val Lys Gly Arg Phe Thr Ile Ser Arg Asp Asn
    370                 375                 380

Ser Glu Asn Thr Val Tyr Leu Gln Met Asn Ser Leu Arg Pro Glu Asp
385                 390                 395                 400

Thr Ala Leu Tyr Tyr Cys Ala Ala Arg Tyr Trp Ala Thr Gly Ser
                405                 410                 415

Glu Tyr Glu Phe Asp Tyr Trp Gly Gln Gly Thr Leu Val Thr Val Ser
            420                 425                 430

Ser

<210> SEQ ID NO 50
<211> LENGTH: 429
<212> TYPE: PRT
<213> ORGANISM: Artificial Sequence
<220> FEATURE:
<223> OTHER INFORMATION: Synthetic-A022600031

<400> SEQUENCE: 50

Asp Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Phe Ser Arg Ile Tyr Pro Tyr Asp Tyr Trp Gly Gln Gly Thr Leu
            100                 105                 110
```

Val Thr Val Ser Ser Gly Gly Gly Ser Gly Gly Gly Ser Gly
        115                 120                 125

Gly Gly Gly Ser Gly Gly Gly Ser Gly Gly Gly Ser Gly Gly
130                 135                 140

Gly Gly Ser Gly Gly Gly Ser Glu Val Gln Leu Val Glu Ser Gly
145                 150                 155                 160

Gly Gly Leu Val Gln Ala Gly Gly Ser Leu Arg Leu Ser Cys Val Ala
                165                 170                 175

Ser Gly Ser Ile Phe Arg Ser Val Phe Ser Ser Thr Met Glu Trp
            180                 185                 190

Tyr Arg Gln Pro Pro Gly Lys Lys Arg Glu Leu Val Ala Arg Ile Ala
        195                 200                 205

Pro Gly Asp Gly Thr Asn Tyr Gly Ala Leu Tyr Ala Asp Ser Val Lys
    210                 215                 220

Gly Arg Phe Thr Ile Ser Arg Asp Asp Ala Lys Lys Thr Val Asp Leu
225                 230                 235                 240

Gln Met Asn Ser Leu Lys Pro Glu Asp Thr Gly Val Tyr Phe Cys Ala
                245                 250                 255

Ser Gly Val Ala Trp Gly Gln Gly Thr Leu Val Thr Val Ser Ser Gly
            260                 265                 270

Gly Gly Gly Ser Gly Gly Gly Ser Gly Gly Gly Ser Gly Gly
        275                 280                 285

Gly Gly Ser Gly Gly Gly Ser Gly Gly Gly Ser Gly Gly Gly
    290                 295                 300

Gly Ser Glu Val Gln Leu Val Glu Ser Gly Gly Val Val Gln Pro
305                 310                 315                 320

Gly Gly Ser Leu Arg Leu Ser Cys Ala Ala Ser Gly Leu Thr Phe Ser
                325                 330                 335

Ser Tyr Ala Met Gly Trp Phe Arg Gln Ala Pro Gly Lys Glu Arg Glu
            340                 345                 350

Arg Val Val Ser Ile Ser Arg Gly Gly Gly Tyr Thr Tyr Tyr Ala Asp
        355                 360                 365

Ser Val Lys Gly Arg Phe Thr Ile Ser Arg Asp Asn Ser Glu Asn Thr
    370                 375                 380

Val Tyr Leu Gln Met Asn Ser Leu Arg Pro Glu Asp Thr Ala Leu Tyr
385                 390                 395                 400

Tyr Cys Ala Ala Ala Arg Tyr Trp Ala Thr Gly Ser Glu Tyr Glu Phe
                405                 410                 415

Asp Tyr Trp Gly Gln Gly Thr Leu Val Thr Val Ser Ser
            420                 425

<210> SEQ ID NO 51
<211> LENGTH: 426
<212> TYPE: PRT
<213> ORGANISM: Artificial Sequence
<220> FEATURE:
<223> OTHER INFORMATION: Synthetic-A022600096

<400> SEQUENCE: 51

Asp Val Gln Leu Val Glu Ser Gly Gly Gly Leu Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
 50                  55                  60

Gly Arg Phe Thr Ile Ser Arg Asp Glu Ser Lys Asn Thr Val Tyr Leu
 65                  70                  75                  80

Gln Met Asn Ser Leu Arg Pro Glu Asp Thr Ala Leu Tyr Tyr Cys Arg
                 85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Gly Gly Gly Ser Gly Gly Gly Ser Gly Gly
130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Val Ala
            165                 170                 175

Ser Gly Phe Thr Phe Ser Ser Phe Ala Met Thr Trp Val Arg Arg Pro
            180                 185                 190

Pro Gly Lys Gly Leu Glu Trp Val Ala Thr Ile Thr Asn Gly Gly Val
        195                 200                 205

Thr Ser Tyr Arg Asp Ser Val Lys Gly Arg Phe Thr Ile Ser Arg Asp
    210                 215                 220

Asn Ala Lys Asn Thr Leu Tyr Leu Glu Met Thr Ser Leu Asn Pro Glu
225                 230                 235                 240

Asp Thr Ala Val Tyr Ile Cys Ala Asn Ala Arg Arg Thr Gly Pro Arg
            245                 250                 255

Ala Pro Thr Asp Ile Gly Ser Tyr Arg Gly Gln Gly Thr Leu Val Thr
            260                 265                 270

Val Ser Ser Gly Gly Gly Gly Ser Gly Gly Gly Gly Ser Gly Gly Gly
        275                 280                 285

Gly Ser Gly Gly Gly Gly Ser Gly Gly Gly Gly Ser Gly Gly Gly Gly
        290                 295                 300

Ser Gly Gly Gly Gly Ser Glu Val Gln Leu Val Glu Ser Gly Gly Gly
305                 310                 315                 320

Val Val Gln Pro Gly Gly Ser Leu Arg Leu Ser Cys Ala Ala Ser Gly
            325                 330                 335

Phe Thr Phe Arg Ser Phe Gly Met Ser Trp Val Arg Gln Ala Pro Gly
            340                 345                 350

Lys Gly Pro Glu Trp Val Ser Ile Ser Gly Ser Gly Ser Asp Thr
        355                 360                 365

Leu Tyr Ala Asp Ser Val Lys Gly Arg Phe Thr Ile Ser Arg Asp Asn
370                 375                 380

Ser Lys Asn Thr Leu Tyr Leu Gln Met Asn Ser Leu Arg Pro Glu Asp
385                 390                 395                 400

Thr Ala Leu Tyr Tyr Cys Thr Ile Gly Gly Ser Leu Ser Arg Ser Ser
            405                 410                 415

Gln Gly Thr Leu Val Thr Val Ser Ser Ala
            420                 425

<210> SEQ ID NO 52
<211> LENGTH: 394
<212> TYPE: PRT
<213> ORGANISM: Artificial Sequence
<220> FEATURE:
<223> OTHER INFORMATION: Synthetic-A022600102

<400> SEQUENCE: 52

Asp Val Gln Leu Val Glu Ser Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Leu Tyr Tyr Cys Arg
                85                  90                  95

Ala Leu Ser Arg Ile Trp Pro Tyr Asp Tyr Trp Gln Gly Thr Leu
            100                 105                 110

Val Thr Val Ser Ser Ala Ala Ala Glu Val Gln Leu Val Glu Ser Gly
            115                 120                 125

Gly Gly Leu Val Gln Pro Gly Gly Ser Leu Arg Leu Ser Cys Val Ala
130                 135                 140

Ser Gly Phe Thr Phe Ser Ser Phe Ala Met Thr Trp Val Arg Arg Pro
145                 150                 155                 160

Pro Gly Lys Gly Leu Glu Trp Val Ala Thr Ile Thr Asn Gly Gly Val
            165                 170                 175

Thr Ser Tyr Arg Asp Ser Val Lys Gly Arg Phe Thr Ile Ser Arg Asp
            180                 185                 190

Asn Ala Lys Asn Thr Leu Tyr Leu Glu Met Thr Ser Leu Asn Pro Glu
            195                 200                 205

Asp Thr Ala Val Tyr Ile Cys Ala Asn Ala Arg Arg Thr Gly Pro Arg
210                 215                 220

Ala Pro Thr Asp Ile Gly Ser Tyr Arg Gly Gln Gly Thr Leu Val Thr
225                 230                 235                 240

Val Ser Ser Gly Gly Gly Gly Ser Gly Gly Gly Gly Ser Gly Gly Gly
            245                 250                 255

Gly Ser Gly Gly Gly Gly Ser Gly Gly Gly Ser Gly Gly Gly Gly
            260                 265                 270

Ser Gly Gly Gly Gly Ser Glu Val Gln Leu Val Glu Ser Gly Gly Gly
            275                 280                 285

Val Val Gln Pro Gly Gly Ser Leu Arg Leu Ser Cys Ala Ala Ser Gly
            290                 295                 300

Phe Thr Phe Arg Ser Phe Gly Met Ser Trp Val Arg Gln Ala Pro Gly
305                 310                 315                 320

Lys Gly Pro Glu Trp Val Ser Ile Ser Gly Ser Gly Ser Asp Thr
            325                 330                 335

Leu Tyr Ala Asp Ser Val Lys Gly Arg Phe Thr Ile Ser Arg Asp Asn
            340                 345                 350

Ser Lys Asn Thr Leu Tyr Leu Gln Met Asn Ser Leu Arg Pro Glu Asp
            355                 360                 365

Thr Ala Leu Tyr Tyr Cys Thr Ile Gly Gly Ser Leu Ser Arg Ser Ser
            370                 375                 380

Gln Gly Thr Leu Val Thr Val Ser Ser Ala
385                 390

<210> SEQ ID NO 53
<211> LENGTH: 396
<212> TYPE: PRT
<213> ORGANISM: Artificial Sequence
<220> FEATURE:
<223> OTHER INFORMATION: Synthetic-A022600103

<400> SEQUENCE: 53

```
Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Leu Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
                165                 170                 175

Gly Val Thr Ser Tyr Arg Asp Ser Val Lys Gly Arg Phe Thr Ile Ser
            180                 185                 190

Arg Asp Asn Ala Lys Asn Thr Leu Tyr Leu Glu Met Thr Ser Leu Asn
        195                 200                 205

Pro Glu Asp Thr Ala Val Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Gly Ser Gly
                245                 250                 255

Gly Gly Gly Ser Gly Gly Gly Gly Ser Gly Gly Gly Gly Ser Gly Gly
            260                 265                 270

Gly Gly Ser Gly Gly Gly Gly Ser Glu Val Gln Leu Val Glu Ser Gly
        275                 280                 285

Gly Gly Val Val Gln Pro Gly Gly Ser Leu Arg Leu Ser Cys Ala Ala
    290                 295                 300

Ser Gly Phe Thr Phe Arg Ser Phe Gly Met Ser Trp Val Arg Gln Ala
305                 310                 315                 320

Pro Gly Lys Gly Pro Glu Trp Val Ser Ile Ser Gly Ser Gly Ser
                325                 330                 335

Asp Thr Leu Tyr Ala Asp Ser Val Lys Gly Arg Phe Thr Ile Ser Arg
            340                 345                 350

Asp Asn Ser Lys Asn Thr Leu Tyr Leu Gln Met Asn Ser Leu Arg Pro
        355                 360                 365

Glu Asp Thr Ala Leu Tyr Tyr Cys Thr Ile Gly Gly Ser Leu Ser Arg
```

```
                    370                 375                 380
Ser Ser Gln Gly Thr Leu Val Thr Val Ser Ser Ala
385                 390                 395

<210> SEQ ID NO 54
<211> LENGTH: 400
<212> TYPE: PRT
<213> ORGANISM: Artificial Sequence
<220> FEATURE:
<223> OTHER INFORMATION: Synthetic-A022600104

<400> SEQUENCE: 54

Asp Val Gln Leu Val Glu Ser Gly Gly Val Val Gln Pro Gly Gly
1               5                   10                  15

Ser Leu Arg Leu Ser Cys Val Ala Ser Gly Tyr Val His Lys Ile Asn
                20                  25                  30

Phe Tyr Gly Trp Tyr Arg Gln Ala Pro Gly Lys Glu Arg Glu Lys Val
                35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Leu Tyr Tyr Cys Arg
                85                  90                  95

Ala Leu Ser Arg Ile Trp Pro Tyr Asp Tyr Trp Gly Gln Gly Thr Leu
                100                 105                 110

Val Thr Val Ser Ser Gly Gly Gly Gly Ser Gly Gly Gly Ser Glu Val
            115                 120                 125

Gln Leu Val Glu Ser Gly Gly Gly Leu Val Gln Pro Gly Gly Ser Leu
            130                 135                 140

Arg Leu Ser Cys Val Ala Ser Gly Phe Thr Phe Ser Ser Phe Ala Met
145                 150                 155                 160

Thr Trp Val Arg Arg Pro Pro Gly Lys Gly Leu Glu Trp Val Ala Thr
                165                 170                 175

Ile Thr Asn Gly Gly Val Thr Ser Tyr Arg Asp Ser Val Lys Gly Arg
            180                 185                 190

Phe Thr Ile Ser Arg Asp Asn Ala Lys Asn Thr Leu Tyr Leu Glu Met
        195                 200                 205

Thr Ser Leu Asn Pro Glu Asp Thr Ala Val Tyr Ile Cys Ala Asn Ala
    210                 215                 220

Arg Arg Thr Gly Pro Arg Ala Pro Thr Asp Ile Gly Ser Tyr Arg Gly
225                 230                 235                 240

Gln Gly Thr Leu Val Thr Val Ser Ser Gly Gly Gly Ser Gly Gly
                245                 250                 255

Gly Gly Ser Gly Gly Gly Gly Ser Gly Gly Gly Ser Gly Gly Gly
            260                 265                 270

Gly Ser Gly Gly Gly Gly Ser Gly Gly Gly Ser Glu Val Gln Leu
        275                 280                 285

Val Glu Ser Gly Gly Gly Val Val Gln Pro Gly Gly Ser Leu Arg Leu
    290                 295                 300

Ser Cys Ala Ala Ser Gly Phe Thr Phe Arg Ser Phe Gly Met Ser Trp
305                 310                 315                 320

Val Arg Gln Ala Pro Gly Lys Gly Pro Glu Trp Val Ser Ser Ile Ser
                325                 330                 335

Gly Ser Gly Ser Asp Thr Leu Tyr Ala Asp Ser Val Lys Gly Arg Phe
```

```
                    340                 345                 350
Thr Ile Ser Arg Asp Asn Ser Lys Asn Thr Leu Tyr Leu Gln Met Asn
                355                 360                 365
Ser Leu Arg Pro Glu Asp Thr Ala Leu Tyr Tyr Cys Thr Ile Gly Gly
            370                 375                 380
Ser Leu Ser Arg Ser Ser Gln Gly Thr Leu Val Thr Val Ser Ser Ala
385                 390                 395                 400

<210> SEQ ID NO 55
<211> LENGTH: 411
<212> TYPE: PRT
<213> ORGANISM: Artificial Sequence
<220> FEATURE:
<223> OTHER INFORMATION: Synthetic-A022600105

<400> SEQUENCE: 55

Asp Val Gln Leu Val Glu Ser Gly Gly Gly Val Val Gln Pro Gly Gly
1               5                   10                  15
Ser Leu Arg Leu Ser Cys Val Ala Ser Gly Tyr Val His Lys Ile Asn
            20                  25                  30
Phe Tyr Gly Trp Tyr Arg Gln Ala Pro Gly Lys Glu Arg Glu Lys Val
        35                  40                  45
Ala His Ile Ser Ile Gly Asp Gln Thr Asp Tyr Ala Asp Ser Ala Lys
    50                  55                  60
Gly Arg Phe Thr Ile Ser Arg Asp Glu Ser Lys Asn Thr Val Tyr Leu
65                  70                  75                  80
Gln Met Asn Ser Leu Arg Pro Glu Asp Thr Ala Leu Tyr Tyr Cys Arg
                85                  90                  95
Ala Leu Ser Arg Ile Trp Pro Tyr Asp Tyr Trp Gly Gln Gly Thr Leu
            100                 105                 110
Val Thr Val Ser Ser Gly Gly Gly Gly Ser Gly Gly Gly Gly Ser Gly
        115                 120                 125
Gly Gly Gly Ser Gly Gly Gly Gly Ser Glu Val Gln Leu Val Glu Ser
    130                 135                 140
Gly Gly Gly Leu Val Gln Pro Gly Gly Ser Leu Arg Leu Ser Cys Val
145                 150                 155                 160
Ala Ser Gly Phe Thr Phe Ser Ser Phe Ala Met Thr Trp Val Arg Arg
                165                 170                 175
Pro Pro Gly Lys Gly Leu Glu Trp Val Ala Thr Ile Thr Asn Gly Gly
            180                 185                 190
Val Thr Ser Tyr Arg Asp Ser Val Lys Gly Arg Phe Thr Ile Ser Arg
        195                 200                 205
Asp Asn Ala Lys Asn Thr Leu Tyr Leu Glu Met Thr Ser Leu Asn Pro
    210                 215                 220
Glu Asp Thr Ala Val Tyr Ile Cys Ala Asn Ala Arg Arg Thr Gly Pro
225                 230                 235                 240
Arg Ala Pro Thr Asp Ile Gly Ser Tyr Arg Gly Gln Gly Thr Leu Val
                245                 250                 255
Thr Val Ser Ser Gly Gly Gly Gly Ser Gly Gly Gly Gly Ser Gly Gly
            260                 265                 270
Gly Gly Ser Gly Gly Gly Gly Ser Gly Gly Gly Gly Ser Gly Gly Gly
        275                 280                 285
Gly Ser Gly Gly Gly Gly Ser Glu Val Gln Leu Val Glu Ser Gly Gly
    290                 295                 300
Gly Val Val Gln Pro Gly Gly Ser Leu Arg Leu Ser Cys Ala Ala Ser
```

```
305                 310                 315                 320
Gly Phe Thr Phe Arg Ser Phe Gly Met Ser Trp Val Arg Gln Ala Pro
                325                 330                 335
Gly Lys Gly Pro Glu Trp Val Ser Ile Ser Gly Ser Gly Ser Asp
                340                 345                 350
Thr Leu Tyr Ala Asp Ser Val Lys Gly Arg Phe Thr Ile Ser Arg Asp
                355                 360                 365
Asn Ser Lys Asn Thr Leu Tyr Leu Gln Met Asn Ser Leu Arg Pro Glu
                370                 375                 380
Asp Thr Ala Leu Tyr Tyr Cys Thr Ile Gly Gly Ser Leu Ser Arg Ser
385                 390                 395                 400
Ser Gln Gly Thr Leu Val Thr Val Ser Ser Ala
                405                 410

<210> SEQ ID NO 56
<211> LENGTH: 550
<212> TYPE: PRT
<213> ORGANISM: Artificial Sequence
<220> FEATURE:
<223> OTHER INFORMATION: Synthetic-A022600122

<400> SEQUENCE: 56

Asp Val Gln Leu Val Glu Ser Gly Gly Gly Val Val Gln Pro Gly Gly
1               5                   10                  15
Ser Leu Arg Leu Ser Cys Val Ala Ser Gly Tyr Val His Lys Ile Asn
                20                  25                  30
Phe Tyr Gly Trp Tyr Arg Gln Ala Pro Gly Lys Glu Arg Glu Lys Val
                35                  40                  45
Ala His Ile Ser Ile Gly Asp Gln Thr Asp Tyr Ala Asp Ser Ala Lys
            50                  55                  60
Gly Arg Phe Thr Ile Ser Arg Asp Glu Ser Lys Asn Thr Val Tyr Leu
65                  70                  75                  80
Gln Met Asn Ser Leu Arg Pro Glu Asp Thr Ala Leu Tyr Tyr Cys Arg
                85                  90                  95
Ala Leu Ser Arg Ile Trp Pro Tyr Asp Tyr Trp Gly Gln Gly Thr Leu
                100                 105                 110
Val Thr Val Ser Ser Gly Gly Gly Ser Glu Val Gln Leu Val Glu
                115                 120                 125
Ser Gly Gly Gly Leu Val Gln Pro Gly Gly Ser Leu Arg Leu Ser Cys
                130                 135                 140
Val Ala Ser Gly Phe Thr Phe Ser Ser Phe Ala Met Thr Trp Val Arg
145                 150                 155                 160
Arg Pro Pro Gly Lys Gly Leu Glu Trp Val Ala Thr Ile Thr Asn Gly
                165                 170                 175
Gly Val Thr Ser Tyr Arg Asp Ser Val Lys Gly Arg Phe Thr Ile Ser
                180                 185                 190
Arg Asp Asn Ala Lys Asn Thr Leu Tyr Leu Glu Met Thr Ser Leu Asn
                195                 200                 205
Pro Glu Asp Thr Ala Val Tyr Ile Cys Ala Asn Ala Arg Arg Thr Gly
                210                 215                 220
Pro Arg Ala Pro Thr Asp Ile Gly Ser Tyr Arg Gly Gln Gly Thr Leu
225                 230                 235                 240
Val Thr Val Ser Ser Gly Gly Gly Gly Ser Gly Gly Gly Ser Gly
                245                 250                 255
Gly Gly Gly Ser Gly Gly Gly Gly Ser Gly Gly Gly Gly Ser Gly Gly
```

260                 265                 270
Gly Gly Ser Gly Gly Gly Ser Glu Val Gln Leu Val Glu Ser Gly
            275                 280                 285

Gly Gly Leu Val Gln Pro Gly Gly Ser Leu Arg Leu Ser Cys Val Ala
        290                 295                 300

Ser Gly Ser Ile Phe Arg Ser Val Phe Ser Ser Thr Met Glu Trp
305                 310                 315                 320

Tyr Arg Gln Pro Pro Gly Lys Lys Arg Glu Leu Val Ala Arg Ile Ala
                325                 330                 335

Pro Gly Asp Gly Thr Asn Tyr Gly Ala Leu Tyr Ala Asp Ser Val Lys
            340                 345                 350

Gly Arg Phe Thr Ile Ser Arg Asp Asp Ala Lys Lys Thr Val Asp Leu
        355                 360                 365

Gln Met Asn Ser Leu Lys Pro Glu Asp Thr Gly Val Tyr Phe Cys Ala
    370                 375                 380

Ser Gly Val Ala Trp Gly Gln Gly Thr Leu Val Thr Val Ser Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Gly Gly Gly Gly Ser Gly Gly Gly
            420                 425                 430

Gly Ser Glu Val Gln Leu Val Glu Ser Gly Gly Gly Val Val Gln Pro
        435                 440                 445

Gly Gly Ser Leu Arg Leu Ser Cys Ala Ala Ser Gly Phe Thr Phe Arg
    450                 455                 460

Ser Phe Gly Met Ser Trp Val Arg Gln Ala Pro Gly Lys Gly Pro Glu
465                 470                 475                 480

Trp Val Ser Ser Ile Ser Gly Ser Gly Ser Asp Thr Leu Tyr Ala Asp
                485                 490                 495

Ser Val Lys Gly Arg Phe Thr Ile Ser Arg Asp Asn Ser Lys Asn Thr
            500                 505                 510

Leu Tyr Leu Gln Met Asn Ser Leu Arg Pro Glu Asp Thr Ala Leu Tyr
        515                 520                 525

Tyr Cys Thr Ile Gly Gly Ser Leu Ser Arg Ser Ser Gln Gly Thr Leu
    530                 535                 540

Val Thr Val Ser Ser Ala
545                 550

<210> SEQ ID NO 57
<211> LENGTH: 535
<212> TYPE: PRT
<213> ORGANISM: Artificial Sequence
<220> FEATURE:
<223> OTHER INFORMATION: Synthetic-A022600131

<400> SEQUENCE: 57

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu

-continued

```
                65                  70                  75                  80
        Gln Met Asn Ser Leu Arg Pro Glu Asp Thr Ala Leu Tyr Tyr Cys Arg
                        85                  90                  95

Ala Leu Ser Arg Ile Trp Pro Tyr Asp Tyr Trp Gly Gln Gly Thr Leu
                        100                 105                 110

Val Thr Val Ser Ser Gly Gly Gly Ser Glu Val Gln Leu Val Glu
                        115                 120                 125

Ser Gly Gly Gly Leu Val Gln Pro Gly Gly Ser Leu Arg Leu Ser Cys
                        130                 135                 140

Val Ala Ser Gly Phe Thr Phe Ser Ser Phe Ala Met Thr Trp Val Arg
        145                 150                 155                 160

Arg Pro Pro Gly Lys Gly Leu Glu Trp Val Ala Thr Ile Thr Asn Gly
                        165                 170                 175

Gly Val Thr Ser Tyr Arg Asp Ser Val Lys Gly Arg Phe Thr Ile Ser
                        180                 185                 190

Arg Asp Asn Ala Lys Asn Thr Leu Tyr Leu Glu Met Thr Ser Leu Asn
                        195                 200                 205

Pro Glu Asp Thr Ala Val Tyr Ile Cys Ala Asn Ala Arg Arg Thr Gly
                        210                 215                 220

Pro Arg Ala Pro Thr Asp Ile Gly Ser Tyr Arg Gly Gln Gly Thr Leu
        225                 230                 235                 240

Val Thr Val Ser Ser Gly Gly Gly Gly Ser Gly Gly Gly Ser Gly
                        245                 250                 255

Gly Gly Ser Gly Gly Gly Ser Glu Val Gln Leu Val Glu Ser
                        260                 265                 270

Gly Gly Gly Leu Val Gln Pro Gly Gly Ser Leu Arg Leu Ser Cys Val
                        275                 280                 285

Ala Ser Gly Ser Ile Phe Arg Ser Val Phe Ser Ser Thr Met Glu
                        290                 295                 300

Trp Tyr Arg Gln Pro Pro Gly Lys Lys Arg Glu Leu Val Ala Arg Ile
        305                 310                 315                 320

Ala Pro Gly Asp Gly Thr Asn Tyr Gly Ala Leu Tyr Ala Asp Ser Val
                        325                 330                 335

Lys Gly Arg Phe Thr Ile Ser Arg Asp Asp Ala Lys Lys Thr Val Asp
                        340                 345                 350

Leu Gln Met Asn Ser Leu Lys Pro Glu Asp Thr Gly Val Tyr Phe Cys
                        355                 360                 365

Ala Ser Gly Val Ala Trp Gly Gln Gly Thr Leu Val Thr Val Ser Ser
                        370                 375                 380

Gly Gly Gly Gly Ser Gly Gly Gly Ser Gly Gly Gly Ser Gly
        385                 390                 395                 400

Gly Gly Gly Ser Gly Gly Gly Ser Gly Gly Gly Ser Gly Gly
                        405                 410                 415

Gly Gly Ser Glu Val Gln Leu Val Glu Ser Gly Gly Val Val Gln
                        420                 425                 430

Pro Gly Gly Ser Leu Arg Leu Ser Cys Ala Ala Ser Gly Phe Thr Phe
                        435                 440                 445

Arg Ser Phe Gly Met Ser Trp Val Arg Gln Ala Pro Gly Lys Gly Pro
                        450                 455                 460

Glu Trp Val Ser Ser Ile Ser Gly Ser Gly Ser Asp Thr Leu Tyr Ala
        465                 470                 475                 480

Asp Ser Val Lys Gly Arg Phe Thr Ile Ser Arg Asp Asn Ser Lys Asn
                        485                 490                 495
```

```
Thr Leu Tyr Leu Gln Met Asn Ser Leu Arg Pro Glu Asp Thr Ala Leu
            500                 505                 510

Tyr Tyr Cys Thr Ile Gly Gly Ser Leu Ser Arg Ser Ser Gln Gly Thr
        515                 520                 525

Leu Val Thr Val Ser Ser Ala
    530                 535

<210> SEQ ID NO 58
<211> LENGTH: 524
<212> TYPE: PRT
<213> ORGANISM: Artificial Sequence
<220> FEATURE:
<223> OTHER INFORMATION: Synthetic-A022600132

<400> SEQUENCE: 58

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Leu Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
                165                 170                 175

Gly Val Thr Ser Tyr Arg Asp Ser Val Lys Gly Arg Phe Thr Ile Ser
            180                 185                 190

Arg Asp Asn Ala Lys Asn Thr Leu Tyr Leu Glu Met Thr Ser Leu Asn
        195                 200                 205

Pro Glu Asp Thr Ala Val Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Arg Leu Ser Cys Val Ala Ser Gly Ser Ile Phe Arg Ser Val Phe Ser
        275                 280                 285

Ser Ser Thr Met Glu Trp Tyr Arg Gln Pro Pro Gly Lys Lys Arg Glu
    290                 295                 300

Leu Val Ala Arg Ile Ala Pro Gly Asp Gly Thr Asn Tyr Gly Ala Leu
305                 310                 315                 320
```

```
Tyr Ala Asp Ser Val Lys Gly Arg Phe Thr Ile Ser Arg Asp Asp Ala
                325                 330                 335

Lys Lys Thr Val Asp Leu Gln Met Asn Ser Leu Lys Pro Glu Asp Thr
            340                 345                 350

Gly Val Tyr Phe Cys Ala Ser Gly Val Ala Trp Gly Gln Gly Thr Leu
        355                 360                 365

Val Thr Val Ser Ser Gly Gly Gly Gly Ser Gly Gly Gly Gly Ser Gly
370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Glu Val Gln Leu Val Glu Ser Gly
            405                 410                 415

Gly Gly Val Val Gln Pro Gly Gly Ser Leu Arg Leu Ser Cys Ala Ala
        420                 425                 430

Ser Gly Phe Thr Phe Arg Ser Phe Gly Met Ser Trp Val Arg Gln Ala
    435                 440                 445

Pro Gly Lys Gly Pro Glu Trp Val Ser Ser Ile Ser Gly Ser Gly Ser
450                 455                 460

Asp Thr Leu Tyr Ala Asp Ser Val Lys Gly Arg Phe Thr Ile Ser Arg
465                 470                 475                 480

Asp Asn Ser Lys Asn Thr Leu Tyr Leu Gln Met Asn Ser Leu Arg Pro
                485                 490                 495

Glu Asp Thr Ala Leu Tyr Tyr Cys Thr Ile Gly Gly Ser Leu Ser Arg
            500                 505                 510

Ser Ser Gln Gly Thr Leu Val Thr Val Ser Ser Ala
        515                 520

<210> SEQ ID NO 59
<211> LENGTH: 550
<212> TYPE: PRT
<213> ORGANISM: Artificial Sequence
<220> FEATURE:
<223> OTHER INFORMATION: Synthetic-A022600133

<400> SEQUENCE: 59

Asp Val Gln Leu Val Glu Ser Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Leu Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Val Ala Ser Gly Ser Ile Phe Arg Ser Val Phe Ser Ser Ser Thr Met
145                 150                 155                 160
```

```
Glu Trp Tyr Arg Gln Pro Pro Gly Lys Lys Arg Glu Leu Val Ala Arg
                165                 170                 175

Ile Ala Pro Gly Asp Gly Thr Asn Tyr Gly Ala Leu Tyr Ala Asp Ser
            180                 185                 190

Val Lys Gly Arg Phe Thr Ile Ser Arg Asp Asp Ala Lys Lys Thr Val
        195                 200                 205

Asp Leu Gln Met Asn Ser Leu Lys Pro Glu Asp Thr Gly Val Tyr Phe
    210                 215                 220

Cys Ala Ser Gly Val Ala Trp Gly Gln Gly Thr Leu Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Gly Gly Gly Ser Gly Gly Gly Ser Gly
            260                 265                 270

Gly Gly Gly Ser Glu Val Gln Leu Val Glu Ser Gly Gly Leu Val
        275                 280                 285

Gln Pro Gly Gly Ser Leu Arg Leu Ser Cys Val Ala Ser Gly Phe Thr
    290                 295                 300

Phe Ser Ser Phe Ala Met Thr Trp Val Arg Arg Pro Pro Gly Lys Gly
305                 310                 315                 320

Leu Glu Trp Val Ala Thr Ile Thr Asn Gly Gly Val Thr Ser Tyr Arg
                325                 330                 335

Asp Ser Val Lys Gly Arg Phe Thr Ile Ser Arg Asp Asn Ala Lys Asn
            340                 345                 350

Thr Leu Tyr Leu Glu Met Thr Ser Leu Asn Pro Glu Asp Thr Ala Val
        355                 360                 365

Tyr Ile Cys Ala Asn Ala Arg Arg Thr Gly Pro Arg Ala Pro Thr Asp
    370                 375                 380

Ile Gly Ser Tyr Arg Gly Gln Gly Thr Leu Val Thr Val Ser Ser Gly
385                 390                 395                 400

Gly Gly Gly Ser Gly Gly Gly Gly Ser Gly Gly Gly Ser Gly Gly
                405                 410                 415

Gly Gly Ser Gly Gly Gly Ser Gly Gly Gly Ser Gly Gly Gly
            420                 425                 430

Gly Ser Glu Val Gln Leu Val Glu Ser Gly Gly Val Val Gln Pro
        435                 440                 445

Gly Gly Ser Leu Arg Leu Ser Cys Ala Ala Ser Gly Phe Thr Phe Arg
    450                 455                 460

Ser Phe Gly Met Ser Trp Val Arg Gln Ala Pro Gly Lys Gly Pro Glu
465                 470                 475                 480

Trp Val Ser Ser Ile Ser Gly Ser Gly Ser Asp Thr Leu Tyr Ala Asp
                485                 490                 495

Ser Val Lys Gly Arg Phe Thr Ile Ser Arg Asp Asn Ser Lys Asn Thr
            500                 505                 510

Leu Tyr Leu Gln Met Asn Ser Leu Arg Pro Glu Asp Thr Ala Leu Tyr
        515                 520                 525

Tyr Cys Thr Ile Gly Gly Ser Leu Ser Arg Ser Ser Gln Gly Thr Leu
    530                 535                 540

Val Thr Val Ser Ser Ala
545                 550

<210> SEQ ID NO 60
<211> LENGTH: 535
```

<212> TYPE: PRT
<213> ORGANISM: Artificial Sequence
<220> FEATURE:
<223> OTHER INFORMATION: Synthetic-A022600134

<400> SEQUENCE: 60

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Leu Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Val Ala Ser Gly Ser Ile Phe Arg Ser Val Phe Ser Ser Thr Met
145                 150                 155                 160

Glu Trp Tyr Arg Gln Pro Pro Gly Lys Lys Arg Glu Leu Val Ala Arg
                165                 170                 175

Ile Ala Pro Gly Asp Gly Thr Asn Tyr Gly Ala Leu Tyr Ala Asp Ser
            180                 185                 190

Val Lys Gly Arg Phe Thr Ile Ser Arg Asp Asp Ala Lys Lys Thr Val
        195                 200                 205

Asp Leu Gln Met Asn Ser Leu Lys Pro Glu Asp Thr Gly Val Tyr Phe
    210                 215                 220

Cys Ala Ser Gly Val Ala Trp Gly Gln Gly Thr Leu Val Thr Val Ser
225                 230                 235                 240

Ser Gly Gly Gly Gly Ser Gly Gly Gly Ser Gly Gly Gly Ser
                245                 250                 255

Gly Gly Gly Gly Ser Glu Val Gln Leu Val Glu Ser Gly Gly Gly Leu
            260                 265                 270

Val Gln Pro Gly Gly Ser Leu Arg Leu Ser Cys Val Ala Ser Gly Phe
        275                 280                 285

Thr Phe Ser Ser Phe Ala Met Thr Trp Val Arg Arg Pro Pro Gly Lys
    290                 295                 300

Gly Leu Glu Trp Val Ala Thr Ile Thr Asn Gly Gly Val Thr Ser Tyr
305                 310                 315                 320

Arg Asp Ser Val Lys Gly Arg Phe Thr Ile Ser Arg Asp Asn Ala Lys
                325                 330                 335

Asn Thr Leu Tyr Leu Glu Met Thr Ser Leu Asn Pro Glu Asp Thr Ala
            340                 345                 350

Val Tyr Ile Cys Ala Asn Ala Arg Arg Thr Gly Pro Arg Ala Pro Thr
        355                 360                 365

Asp Ile Gly Ser Tyr Arg Gly Gln Gly Thr Leu Val Thr Val Ser Ser
    370                 375                 380

```
Gly Gly Gly Gly Ser Gly Gly Gly Ser Gly Gly Gly Ser Gly
385                 390                 395                 400

Gly Gly Gly Ser Gly Gly Gly Ser Gly Gly Gly Ser Gly Gly
                405                 410                 415

Gly Gly Ser Glu Val Gln Leu Val Glu Ser Gly Gly Val Val Gln
            420                 425                 430

Pro Gly Gly Ser Leu Arg Leu Ser Cys Ala Ala Ser Gly Phe Thr Phe
        435                 440                 445

Arg Ser Phe Gly Met Ser Trp Val Arg Gln Ala Pro Gly Lys Gly Pro
    450                 455                 460

Glu Trp Val Ser Ser Ile Ser Gly Ser Gly Ser Asp Thr Leu Tyr Ala
465                 470                 475                 480

Asp Ser Val Lys Gly Arg Phe Thr Ile Ser Arg Asp Asn Ser Lys Asn
                485                 490                 495

Thr Leu Tyr Leu Gln Met Asn Ser Leu Arg Pro Glu Asp Thr Ala Leu
            500                 505                 510

Tyr Tyr Cys Thr Ile Gly Gly Ser Leu Ser Arg Ser Ser Gln Gly Thr
        515                 520                 525

Leu Val Thr Val Ser Ser Ala
    530                 535

<210> SEQ ID NO 61
<211> LENGTH: 524
<212> TYPE: PRT
<213> ORGANISM: Artificial Sequence
<220> FEATURE:
<223> OTHER INFORMATION: Synthetic-A022600135

<400> SEQUENCE: 61

Asp Val Gln Leu Val Glu Ser Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Leu Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Val Ala Ser Gly Ser Ile Phe Arg Ser Val Phe Ser Ser Ser Thr Met
145                 150                 155                 160

Glu Trp Tyr Arg Gln Pro Pro Gly Lys Lys Arg Glu Leu Val Ala Arg
                165                 170                 175

Ile Ala Pro Gly Asp Gly Thr Asn Tyr Gly Ala Leu Tyr Ala Asp Ser
            180                 185                 190

Val Lys Gly Arg Phe Thr Ile Ser Arg Asp Asp Ala Lys Lys Thr Val
        195                 200                 205
```

Asp Leu Gln Met Asn Ser Leu Lys Pro Glu Asp Thr Gly Val Tyr Phe
    210                 215                 220

Cys Ala Ser Gly Val Ala Trp Gly Gln Gly Thr Leu Val Thr Val Ser
225                 230                 235                 240

Ser Gly Gly Gly Ser Gly Gly Gly Ser Glu Val Gln Leu Val Glu
            245                 250                 255

Ser Gly Gly Gly Leu Val Gln Pro Gly Gly Ser Leu Arg Leu Ser Cys
            260                 265                 270

Val Ala Ser Gly Phe Thr Phe Ser Phe Ala Met Thr Trp Val Arg
        275                 280                 285

Arg Pro Pro Gly Lys Gly Leu Glu Trp Val Ala Thr Ile Thr Asn Gly
    290                 295                 300

Gly Val Thr Ser Tyr Arg Asp Ser Val Lys Gly Arg Phe Thr Ile Ser
305                 310                 315                 320

Arg Asp Asn Ala Lys Asn Thr Leu Tyr Leu Glu Met Thr Ser Leu Asn
                325                 330                 335

Pro Glu Asp Thr Ala Val Tyr Ile Cys Ala Asn Ala Arg Arg Thr Gly
            340                 345                 350

Pro Arg Ala Pro Thr Asp Ile Gly Ser Tyr Arg Gly Gln Gly Thr Leu
        355                 360                 365

Val Thr Val Ser Ser Gly Gly Gly Ser Gly Gly Gly Gly Ser Gly
    370                 375                 380

Gly Gly Gly Ser Gly Gly Gly Gly Ser Gly Gly Gly Ser Gly Gly Gly
385                 390                 395                 400

Gly Gly Ser Gly Gly Gly Ser Glu Val Gln Leu Val Glu Ser Gly
            405                 410                 415

Gly Gly Val Val Gln Pro Gly Gly Ser Leu Arg Leu Ser Cys Ala Ala
            420                 425                 430

Ser Gly Phe Thr Phe Arg Ser Phe Gly Met Ser Trp Val Arg Gln Ala
        435                 440                 445

Pro Gly Lys Gly Pro Glu Trp Val Ser Ser Ile Ser Gly Ser Gly Ser
    450                 455                 460

Asp Thr Leu Tyr Ala Asp Ser Val Lys Gly Arg Phe Thr Ile Ser Arg
465                 470                 475                 480

Asp Asn Ser Lys Asn Thr Leu Tyr Leu Gln Met Asn Ser Leu Arg Pro
                485                 490                 495

Glu Asp Thr Ala Leu Tyr Tyr Cys Thr Ile Gly Gly Ser Leu Ser Arg
            500                 505                 510

Ser Ser Gln Gly Thr Leu Val Thr Val Ser Ser Ala
        515                 520

<210> SEQ ID NO 62
<211> LENGTH: 396
<212> TYPE: PRT
<213> ORGANISM: Artificial Sequence
<220> FEATURE:
<223> OTHER INFORMATION: Synthetic-A022600167

<400> SEQUENCE: 62

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
                165                 170                 175

Gly Val Thr Ser Tyr Arg Asp Ser Val Lys Gly Arg Phe Thr Ile Ser
            180                 185                 190

Arg Asp Asn Ala Lys Asn Thr Leu Tyr Leu Glu Met Thr Ser Leu Asn
        195                 200                 205

Pro Glu Asp Thr Ala Val Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Gly Ser Gly
                245                 250                 255

Gly Gly Gly Ser Gly Gly Gly Gly Ser Gly Gly Gly Gly Ser Gly Gly
            260                 265                 270

Gly Gly Ser Gly Gly Gly Gly Ser Glu Val Gln Leu Val Glu Ser Gly
        275                 280                 285

Gly Gly Val Val Gln Pro Gly Gly Ser Leu Arg Leu Ser Cys Ala Ala
    290                 295                 300

Ser Gly Phe Thr Phe Arg Ser Phe Gly Met Ser Trp Val Arg Gln Ala
305                 310                 315                 320

Pro Gly Lys Gly Pro Glu Trp Val Ser Ser Ile Ser Gly Ser Gly Ser
                325                 330                 335

Asp Thr Leu Tyr Ala Asp Ser Val Lys Gly Arg Phe Thr Ile Ser Arg
            340                 345                 350

Asp Asn Ser Lys Asn Thr Leu Tyr Leu Gln Met Asn Ser Leu Arg Pro
        355                 360                 365

Glu Asp Thr Ala Leu Tyr Tyr Cys Thr Ile Gly Gly Ser Leu Ser Arg
    370                 375                 380

Ser Ser Gln Gly Thr Leu Val Thr Val Ser Ser Ala
385                 390                 395

<210> SEQ ID NO 63
<211> LENGTH: 550
<212> TYPE: PRT
<213> ORGANISM: Artificial Sequence
<220> FEATURE:
<223> OTHER INFORMATION: Synthetic-A022600168

<400> SEQUENCE: 63

Asp Val Gln Leu Val Glu Ser Gly Gly Gly Val Val Gln Pro Gly Gly
1               5                   10                  15

-continued

```
Ser Leu Arg Leu Ser Cys Val Ala Ser Gly Tyr Val His Lys Ile Asn
             20                  25                  30

Phe Tyr Gly Trp Tyr Arg Gln Ala Pro Gly Lys Glu Arg Glu Lys Val
         35                  40                  45

Ala His Ile Ser Ile Gly Asp Gln Thr Asp Tyr Ala Asp Ser Ala Lys
     50                  55                  60

Gly Arg Phe Thr Ile Ser Arg Asp Glu Ser Lys Asn Thr Val Tyr Leu
 65                  70                  75                  80

Gln Met Asn Ser Leu Arg Pro Glu Asp Thr Ala Ala Tyr Tyr Cys Arg
             85                  90                  95

Ala Leu Ser Arg Ile Trp Pro Tyr Asp Tyr Trp Gly Gln Gly Thr Leu
        100                 105                 110

Val Thr Val Ser Ser Gly Gly Gly Ser Glu Val Gln Leu Val Glu
    115                 120                 125

Ser Gly Gly Gly Leu Val Gln Pro Gly Gly Ser Leu Arg Leu Ser Cys
    130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
                165                 170                 175

Gly Val Thr Ser Tyr Arg Asp Ser Val Lys Gly Arg Phe Thr Ile Ser
            180                 185                 190

Arg Asp Asn Ala Lys Asn Thr Leu Tyr Leu Glu Met Thr Ser Leu Asn
        195                 200                 205

Pro Glu Asp Thr Ala Val Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Ser Gly Gly Gly Ser Gly
                245                 250                 255

Gly Gly Gly Ser Gly Gly Gly Ser Gly Gly Gly Ser Gly Gly
            260                 265                 270

Gly Gly Ser Gly Gly Gly Ser Glu Val Gln Leu Val Glu Ser Gly
        275                 280                 285

Gly Gly Leu Val Gln Pro Gly Gly Ser Leu Arg Leu Ser Cys Val Ala
    290                 295                 300

Ser Gly Ser Ile Phe Arg Ser Val Phe Ser Ser Thr Met Glu Trp
305                 310                 315                 320

Tyr Arg Gln Pro Pro Gly Lys Lys Arg Glu Leu Val Ala Arg Ile Ala
                325                 330                 335

Pro Gly Asp Gly Thr Asn Tyr Gly Ala Leu Tyr Ala Asp Ser Val Lys
            340                 345                 350

Gly Arg Phe Thr Ile Ser Arg Asp Asp Ala Lys Lys Thr Val Asp Leu
        355                 360                 365

Gln Met Asn Ser Leu Lys Pro Glu Asp Thr Gly Val Tyr Phe Cys Ala
    370                 375                 380

Ser Gly Val Ala Trp Gly Gln Gly Thr Leu Val Thr Val Ser Ser Gly
385                 390                 395                 400

Gly Gly Gly Ser Gly Gly Gly Ser Gly Gly Gly Ser Gly Gly
                405                 410                 415

Gly Gly Ser Gly Gly Gly Ser Gly Gly Gly Ser Gly Gly Gly
            420                 425                 430

Gly Ser Glu Val Gln Leu Val Glu Ser Gly Gly Gly Val Val Gln Pro
```

```
                435                 440                 445
Gly Gly Ser Leu Arg Leu Ser Cys Ala Ala Ser Gly Phe Thr Phe Arg
    450                 455                 460

Ser Phe Gly Met Ser Trp Val Arg Gln Ala Pro Gly Lys Gly Pro Glu
465                 470                 475                 480

Trp Val Ser Ser Ile Ser Gly Ser Gly Ser Asp Thr Leu Tyr Ala Asp
                485                 490                 495

Ser Val Lys Gly Arg Phe Thr Ile Ser Arg Asp Asn Ser Lys Asn Thr
            500                 505                 510

Leu Tyr Leu Gln Met Asn Ser Leu Arg Pro Glu Asp Thr Ala Leu Tyr
        515                 520                 525

Tyr Cys Thr Ile Gly Gly Ser Leu Ser Arg Ser Ser Gln Gly Thr Leu
    530                 535                 540

Val Thr Val Ser Ser Ala
545                 550

<210> SEQ ID NO 64
<211> LENGTH: 520
<212> TYPE: PRT
<213> ORGANISM: Artificial Sequence
<220> FEATURE:
<223> OTHER INFORMATION: Synthetic-A022600169

<400> SEQUENCE: 64

Asp Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Phe
            20                  25                  30

Ala Met Thr Trp Val Arg Arg Pro Gly Lys Gly Leu Glu Trp Val
        35                  40                  45

Ala Thr Ile Thr Asn Gly Gly Val Thr Ser Tyr Arg Asp Ser Val Lys
    50                  55                  60

Gly Arg Phe Thr Ile Ser Arg Asp Asn Ala Lys Asn Thr Leu Tyr Leu
65                  70                  75                  80

Glu Met Thr Ser Leu Asn Pro Glu Asp Thr Ala Val Tyr Ile Cys Ala
            85                  90                  95

Asn Ala Arg Arg Thr Gly Pro Arg Ala Pro Thr Asp Ile Gly Ser Tyr
            100                 105                 110

Arg Gly Gln Gly Thr Leu Val Thr Val Ser Ser Gly Gly Gly Gly Ser
        115                 120                 125

Glu Val Gln Leu Val Glu Ser Gly Gly Gly Val Val Gln Pro Gly Gly
    130                 135                 140

Ser Leu Arg Leu Ser Cys Val Ala Ser Gly Tyr Val His Lys Ile Asn
145                 150                 155                 160

Phe Tyr Gly Trp Tyr Arg Gln Ala Pro Gly Lys Glu Arg Glu Lys Val
                165                 170                 175

Ala His Ile Ser Ile Gly Asp Gln Thr Asp Tyr Ala Asp Ser Ala Lys
            180                 185                 190

Gly Arg Phe Thr Ile Ser Arg Asp Glu Ser Lys Asn Thr Val Tyr Leu
        195                 200                 205

Gln Met Asn Ser Leu Arg Pro Glu Asp Thr Ala Ala Tyr Tyr Cys Arg
    210                 215                 220

Ala Leu Ser Arg Ile Trp Pro Tyr Asp Tyr Trp Gly Gln Gly Thr Leu
225                 230                 235                 240

Val Thr Val Ser Ser Gly Gly Gly Gly Ser Glu Val Gln Leu Val Glu
```

245                 250                 255
Ser Gly Gly Gly Leu Val Gln Pro Gly Gly Ser Leu Arg Leu Ser Cys
            260                 265                 270

Val Ala Ser Gly Ser Ile Phe Arg Ser Val Phe Ser Ser Thr Met
        275                 280                 285

Glu Trp Tyr Arg Gln Pro Pro Gly Lys Lys Arg Glu Leu Val Ala Arg
        290                 295                 300

Ile Ala Pro Gly Asp Gly Thr Asn Tyr Gly Ala Leu Tyr Ala Asp Ser
305                 310                 315                 320

Val Lys Gly Arg Phe Thr Ile Ser Arg Asp Asp Ala Lys Lys Thr Val
                325                 330                 335

Asp Leu Gln Met Asn Ser Leu Lys Pro Glu Asp Thr Gly Val Tyr Phe
            340                 345                 350

Cys Ala Ser Gly Val Ala Trp Gly Gln Gly Thr Leu Val Thr Val Ser
            355                 360                 365

Ser Gly Gly Gly Gly Ser Gly Gly Gly Gly Ser Gly Gly Gly Gly Ser
        370                 375                 380

Gly Gly Gly Gly Ser Gly Gly Gly Ser Gly Gly Gly Ser Gly
385                 390                 395                 400

Gly Gly Gly Ser Glu Val Gln Leu Val Glu Ser Gly Gly Val Val
                405                 410                 415

Gln Pro Gly Gly Ser Leu Arg Leu Ser Cys Ala Ala Ser Gly Phe Thr
            420                 425                 430

Phe Arg Ser Phe Gly Met Ser Trp Val Arg Gln Ala Pro Gly Lys Gly
            435                 440                 445

Pro Glu Trp Val Ser Ser Ile Ser Gly Ser Gly Ser Asp Thr Leu Tyr
        450                 455                 460

Ala Asp Ser Val Lys Gly Arg Phe Thr Ile Ser Arg Asp Asn Ser Lys
465                 470                 475                 480

Asn Thr Leu Tyr Leu Gln Met Asn Ser Leu Arg Pro Glu Asp Thr Ala
                485                 490                 495

Leu Tyr Tyr Cys Thr Ile Gly Gly Ser Leu Ser Arg Ser Ser Gln Gly
            500                 505                 510

Thr Leu Val Thr Val Ser Ser Ala
            515                 520

<210> SEQ ID NO 65
<211> LENGTH: 524
<212> TYPE: PRT
<213> ORGANISM: Artificial Sequence
<220> FEATURE:
<223> OTHER INFORMATION: Synthetic-A022600170

<400> SEQUENCE: 65

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg

```
                    85                  90                  95
Ala Leu Ser Arg Ile Trp Pro Tyr Asp Tyr Trp Gly Gln Gly Thr Leu
                100                 105                 110

Val Thr Val Ser Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
                165                 170                 175

Gly Val Thr Ser Tyr Arg Asp Ser Val Lys Gly Arg Phe Thr Ile Ser
                180                 185                 190

Arg Asp Asn Ala Lys Asn Thr Leu Tyr Leu Glu Met Thr Ser Leu Asn
            195                 200                 205

Pro Glu Asp Thr Ala Val Tyr Ile Cys Ala Asn Ala Arg Arg Thr Gly
        210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Gly Ser Gly
                245                 250                 255

Gly Gly Ser Gly Gly Gly Gly Ser Gly Gly Gly Gly Ser Gly Gly Gly
            260                 265                 270

Gly Gly Ser Gly Gly Gly Gly Ser Glu Val Gln Leu Val Glu Ser Gly
        275                 280                 285

Gly Gly Leu Val Gln Pro Gly Gly Ser Leu Arg Leu Ser Cys Val Ala
    290                 295                 300

Ser Gly Ser Ile Phe Arg Ser Val Phe Ser Ser Thr Met Glu Trp
305                 310                 315                 320

Tyr Arg Gln Pro Pro Gly Lys Lys Arg Glu Leu Val Ala Arg Ile Ala
                325                 330                 335

Pro Gly Asp Gly Thr Asn Tyr Gly Ala Leu Tyr Ala Asp Ser Val Lys
            340                 345                 350

Gly Arg Phe Thr Ile Ser Arg Asp Asp Ala Lys Lys Thr Val Asp Leu
        355                 360                 365

Gln Met Asn Ser Leu Lys Pro Glu Asp Thr Gly Val Tyr Phe Cys Ala
    370                 375                 380

Ser Gly Val Ala Trp Gly Gln Gly Thr Leu Val Thr Val Ser Ser Gly
385                 390                 395                 400

Gly Gly Gly Ser Gly Gly Gly Ser Glu Val Gln Leu Val Glu Ser Gly
                405                 410                 415

Gly Gly Val Val Gln Pro Gly Gly Ser Leu Arg Leu Ser Cys Ala Ala
            420                 425                 430

Ser Gly Phe Thr Phe Arg Ser Phe Gly Met Ser Trp Val Arg Gln Ala
        435                 440                 445

Pro Gly Lys Gly Pro Glu Trp Val Ser Ser Ile Ser Gly Ser Gly Ser
450                 455                 460

Asp Thr Leu Tyr Ala Asp Ser Val Lys Gly Arg Phe Thr Ile Ser Arg
465                 470                 475                 480

Asp Asn Ser Lys Asn Thr Leu Tyr Leu Gln Met Asn Ser Leu Arg Pro
                485                 490                 495

Glu Asp Thr Ala Leu Tyr Tyr Cys Thr Ile Gly Gly Ser Leu Ser Arg
            500                 505                 510
```

```
Ser Ser Gln Gly Thr Leu Val Thr Val Ser Ser Ala
        515                 520

<210> SEQ ID NO 66
<211> LENGTH: 498
<212> TYPE: PRT
<213> ORGANISM: Artificial Sequence
<220> FEATURE:
<223> OTHER INFORMATION: Synthetic-A022600172

<400> SEQUENCE: 66

Asp Val Gln Leu Val Glu Ser Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
                35                  40                  45

Ala His Ile Ser Ile Gly Asp Gln Thr Asp Tyr Ala Asp Ser Ala Lys
        50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
                165                 170                 175

Gly Val Thr Ser Tyr Arg Asp Ser Val Lys Gly Arg Phe Thr Ile Ser
            180                 185                 190

Arg Asp Asn Ala Lys Asn Thr Leu Tyr Leu Glu Met Thr Ser Leu Asn
        195                 200                 205

Pro Glu Asp Thr Ala Val Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Val Val Gln Pro Gly Gly Ser Leu
            260                 265                 270

Arg Leu Ser Cys Ala Ala Ser Gly Phe Thr Phe Arg Ser Phe Gly Met
        275                 280                 285

Ser Trp Val Arg Gln Ala Pro Gly Lys Gly Pro Glu Trp Val Ser Ser
    290                 295                 300

Ile Ser Gly Ser Gly Ser Asp Thr Leu Tyr Ala Asp Ser Val Lys Gly
305                 310                 315                 320

Arg Phe Thr Ile Ser Arg Asp Asn Ser Lys Asn Thr Leu Tyr Leu Gln
                325                 330                 335

Met Asn Ser Leu Arg Pro Glu Asp Thr Ala Leu Tyr Tyr Cys Thr Ile
            340                 345                 350
```

```
Gly Gly Ser Leu Ser Arg Ser Ser Gln Gly Thr Leu Thr Val Ser
        355                 360                 365

Ser Gly Gly Gly Gly Ser Gly Gly Gly Ser Glu Val Gln Leu Val Glu
    370                 375                 380

Ser Gly Gly Gly Leu Val Gln Pro Gly Gly Ser Leu Arg Leu Ser Cys
385                 390                 395                 400

Val Ala Ser Gly Ser Ile Phe Arg Ser Val Phe Ser Ser Ser Thr Met
                405                 410                 415

Glu Trp Tyr Arg Gln Pro Pro Gly Lys Lys Arg Glu Leu Val Ala Arg
                420                 425                 430

Ile Ala Pro Gly Asp Gly Thr Asn Tyr Gly Ala Leu Tyr Ala Asp Ser
                435                 440                 445

Val Lys Gly Arg Phe Thr Ile Ser Arg Asp Asp Ala Lys Lys Thr Val
            450                 455                 460

Asp Leu Gln Met Asn Ser Leu Lys Pro Glu Asp Thr Gly Val Tyr Phe
465                 470                 475                 480

Cys Ala Ser Gly Val Ala Trp Gly Gln Gly Thr Leu Val Thr Val Ser
                485                 490                 495

Ser Ala

<210> SEQ ID NO 67
<211> LENGTH: 498
<212> TYPE: PRT
<213> ORGANISM: Artificial Sequence
<220> FEATURE:
<223> OTHER INFORMATION: Synthetic-A022600174

<400> SEQUENCE: 67

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
                20                  25                  30

Phe Tyr Gly Trp Tyr Arg Gln Ala Pro Gly Lys Glu Arg Glu Lys Val
            35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
                100                 105                 110

Val Thr Val Ser Ser Gly Gly Gly Gly Ser Glu Val Gln Leu Val Glu
            115                 120                 125

Ser Gly Gly Gly Leu Val Gln Pro Gly Gly Ser Leu Arg Leu Ser Cys
    130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
                165                 170                 175

Gly Val Thr Ser Tyr Arg Asp Ser Val Lys Gly Arg Phe Thr Ile Ser
                180                 185                 190

Arg Asp Asn Ala Lys Asn Thr Leu Tyr Leu Glu Met Thr Ser Leu Asn
            195                 200                 205
```

```
Pro Glu Asp Thr Ala Val Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Arg Leu Ser Cys Val Ala Ser Gly Ser Ile Phe Arg Ser Val Phe Ser
        275                 280                 285

Ser Ser Thr Met Glu Trp Tyr Arg Gln Pro Pro Gly Lys Lys Arg Glu
    290                 295                 300

Leu Val Ala Arg Ile Ala Pro Gly Asp Gly Thr Asn Tyr Gly Ala Leu
305                 310                 315                 320

Tyr Ala Asp Ser Val Lys Gly Arg Phe Thr Ile Ser Arg Asp Asp Ala
                325                 330                 335

Lys Lys Thr Val Asp Leu Gln Met Asn Ser Leu Lys Pro Glu Asp Thr
            340                 345                 350

Gly Val Tyr Phe Cys Ala Ser Gly Val Ala Trp Gly Gln Gly Thr Leu
        355                 360                 365

Val Thr Val Ser Ser Gly Gly Gly Gly Ser Gly Gly Gly Ser Glu Val
    370                 375                 380

Gln Leu Val Glu Ser Gly Gly Gly Val Val Gln Pro Gly Gly Ser Leu
385                 390                 395                 400

Arg Leu Ser Cys Ala Ala Ser Gly Phe Thr Phe Arg Ser Phe Gly Met
                405                 410                 415

Ser Trp Val Arg Gln Ala Pro Gly Lys Gly Pro Glu Trp Val Ser Ser
            420                 425                 430

Ile Ser Gly Ser Gly Ser Asp Thr Leu Tyr Ala Asp Ser Val Lys Gly
        435                 440                 445

Arg Phe Thr Ile Ser Arg Asp Asn Ser Lys Asn Thr Leu Tyr Leu Gln
    450                 455                 460

Met Asn Ser Leu Arg Pro Glu Asp Thr Ala Leu Tyr Tyr Cys Thr Ile
465                 470                 475                 480

Gly Gly Ser Leu Ser Arg Ser Ser Gln Gly Thr Leu Val Thr Val Ser
                485                 490                 495

Ser Ala
```

<210> SEQ ID NO 68
<211> LENGTH: 524
<212> TYPE: PRT
<213> ORGANISM: Artificial Sequence
<220> FEATURE:
<223> OTHER INFORMATION: Synthetic-A022600175

<400> SEQUENCE: 68

```
Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
```

```
                65                  70                  75                  80
        Gln Met Asn Ser Leu Arg Pro Glu Asp Thr Ala Ala Tyr Tyr Cys Arg
                            85                  90                  95

Ala Leu Ser Arg Ile Trp Pro Tyr Asp Tyr Trp Gly Gln Gly Thr Leu
                        100                 105                 110

Val Thr Val Ser Ser Gly Gly Gly Ser Glu Val Gln Leu Val Glu
                        115                 120                 125

Ser Gly Gly Gly Leu Val Gln Pro Gly Gly Ser Leu Arg Leu Ser Cys
                    130                 135                 140

Val Ala Ser Gly Phe Thr Phe Ser Ser Phe Ala Met Thr Trp Val Arg
        145                 150                 155                 160

Arg Pro Pro Gly Lys Gly Leu Glu Trp Val Ala Thr Ile Thr Asn Gly
                        165                 170                 175

Gly Val Thr Ser Tyr Arg Asp Ser Val Lys Gly Arg Phe Thr Ile Ser
                        180                 185                 190

Arg Asp Asn Ala Lys Asn Thr Leu Tyr Leu Glu Met Thr Ser Leu Asn
                        195                 200                 205

Pro Glu Asp Thr Ala Val Tyr Ile Cys Ala Asn Ala Arg Arg Thr Gly
                    210                 215                 220

Pro Arg Ala Pro Thr Asp Ile Gly Ser Tyr Arg Gly Gln Gly Thr Leu
        225                 230                 235                 240

Val Thr Val Ser Ser Gly Gly Gly Gly Ser Gly Gly Gly Ser Glu Val
                        245                 250                 255

Gln Leu Val Glu Ser Gly Gly Gly Leu Val Gln Pro Gly Gly Ser Leu
                    260                 265                 270

Arg Leu Ser Cys Val Ala Ser Gly Ser Ile Phe Arg Ser Val Phe Ser
                    275                 280                 285

Ser Ser Thr Met Glu Trp Tyr Arg Gln Pro Pro Gly Lys Lys Arg Glu
                    290                 295                 300

Leu Val Ala Arg Ile Ala Pro Gly Asp Gly Thr Asn Tyr Gly Ala Leu
        305                 310                 315                 320

Tyr Ala Asp Ser Val Lys Gly Arg Phe Thr Ile Ser Arg Asp Asp Ala
                        325                 330                 335

Lys Lys Thr Val Asp Leu Gln Met Asn Ser Leu Lys Pro Glu Asp Thr
                        340                 345                 350

Gly Val Tyr Phe Cys Ala Ser Gly Val Ala Trp Gly Gln Gly Thr Leu
                    355                 360                 365

Val Thr Val Ser Ser Gly Gly Gly Gly Ser Gly Gly Gly Gly Ser Gly
                        370                 375                 380

Gly Gly Gly Ser Gly Gly Gly Gly Ser Gly Gly Gly Gly Ser Gly Gly
        385                 390                 395                 400

Gly Gly Ser Gly Gly Gly Gly Ser Glu Val Gln Leu Val Glu Ser Gly
                        405                 410                 415

Gly Gly Val Val Gln Pro Gly Gly Ser Leu Arg Leu Ser Cys Ala Ala
                    420                 425                 430

Ser Gly Phe Thr Phe Arg Ser Phe Gly Met Ser Trp Val Arg Gln Ala
                    435                 440                 445

Pro Gly Lys Gly Pro Glu Trp Val Ser Ser Ile Ser Gly Ser Gly Ser
                    450                 455                 460

Asp Thr Leu Tyr Ala Asp Ser Val Lys Gly Arg Phe Thr Ile Ser Arg
        465                 470                 475                 480

Asp Asn Ser Lys Asn Thr Leu Tyr Leu Gln Met Asn Ser Leu Arg Pro
                        485                 490                 495
```

```
Glu Asp Thr Ala Leu Tyr Tyr Cys Thr Ile Gly Gly Ser Leu Ser Arg
                500                 505                 510

Ser Ser Gln Gly Thr Leu Val Thr Val Ser Ser Ala
            515                 520

<210> SEQ ID NO 69
<211> LENGTH: 396
<212> TYPE: PRT
<213> ORGANISM: Artificial Sequence
<220> FEATURE:
<223> OTHER INFORMATION: Synthetic-A022600178

<400> SEQUENCE: 69

Asp Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Phe
            20                  25                  30

Ala Met Thr Trp Val Arg Arg Pro Gly Lys Gly Leu Glu Trp Val
        35                  40                  45

Ala Thr Ile Thr Asn Gly Gly Val Thr Ser Tyr Arg Asp Ser Val Lys
50                  55                  60

Gly Arg Phe Thr Ile Ser Arg Asp Asn Ala Lys Asn Thr Leu Tyr Leu
65                  70                  75                  80

Glu Met Thr Ser Leu Asn Pro Glu Asp Thr Ala Val Tyr Ile Cys Ala
                85                  90                  95

Asn Ala Arg Arg Thr Gly Pro Arg Ala Pro Thr Asp Ile Gly Ser Tyr
            100                 105                 110

Arg Gly Gln Gly Thr Leu Val Thr Val Ser Ser Gly Gly Gly Gly Ser
        115                 120                 125

Glu Val Gln Leu Val Glu Ser Gly Gly Gly Val Gln Pro Gly Gly
    130                 135                 140

Ser Leu Arg Leu Ser Cys Val Ala Ser Gly Tyr Val His Lys Ile Asn
145                 150                 155                 160

Phe Tyr Gly Trp Tyr Arg Gln Ala Pro Gly Lys Glu Arg Glu Lys Val
                165                 170                 175

Ala His Ile Ser Ile Gly Asp Gln Thr Asp Tyr Ala Asp Ser Ala Lys
            180                 185                 190

Gly Arg Phe Thr Ile Ser Arg Asp Glu Ser Lys Asn Thr Val Tyr Leu
        195                 200                 205

Gln Met Asn Ser Leu Arg Pro Glu Asp Thr Ala Ala Tyr Tyr Cys Arg
    210                 215                 220

Ala Leu Ser Arg Ile Trp Pro Tyr Asp Tyr Trp Gly Gln Gly Thr Leu
225                 230                 235                 240

Val Thr Val Ser Ser Gly Gly Gly Gly Ser Gly Gly Gly Gly Ser Gly
                245                 250                 255

Gly Gly Gly Ser Gly Gly Gly Gly Ser Gly Gly Gly Gly Ser Gly Gly
            260                 265                 270

Gly Gly Ser Gly Gly Gly Gly Ser Glu Val Gln Leu Val Glu Ser Gly
        275                 280                 285

Gly Gly Val Val Gln Pro Gly Gly Ser Leu Arg Leu Ser Cys Ala Ala
    290                 295                 300

Ser Gly Phe Thr Phe Arg Ser Phe Gly Met Ser Trp Val Arg Gln Ala
305                 310                 315                 320

Pro Gly Lys Gly Pro Glu Trp Val Ser Ser Ile Ser Gly Ser Gly Ser
                325                 330                 335
```

```
Asp Thr Leu Tyr Ala Asp Ser Val Lys Gly Arg Phe Thr Ile Ser Arg
            340                 345                 350

Asp Asn Ser Lys Asn Thr Leu Tyr Leu Gln Met Asn Ser Leu Arg Pro
            355                 360                 365

Glu Asp Thr Ala Leu Tyr Tyr Cys Thr Ile Gly Gly Ser Leu Ser Arg
370                 375                 380

Ser Ser Gln Gly Thr Leu Val Thr Val Ser Ser Ala
385                 390                 395

<210> SEQ ID NO 70
<211> LENGTH: 370
<212> TYPE: PRT
<213> ORGANISM: Artificial Sequence
<220> FEATURE:
<223> OTHER INFORMATION: Synthetic-A022600179

<400> SEQUENCE: 70

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
                165                 170                 175

Gly Val Thr Ser Tyr Arg Asp Ser Val Lys Gly Arg Phe Thr Ile Ser
            180                 185                 190

Arg Asp Asn Ala Lys Asn Thr Leu Tyr Leu Glu Met Thr Ser Leu Asn
        195                 200                 205

Pro Glu Asp Thr Ala Val Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Val Val Gln Pro Gly Gly Ser Leu
            260                 265                 270

Arg Leu Ser Cys Ala Ala Ser Gly Phe Thr Phe Arg Ser Phe Gly Met
        275                 280                 285

Ser Trp Val Arg Gln Ala Pro Gly Lys Gly Pro Glu Trp Val Ser Ser
    290                 295                 300
```

```
Ile Ser Gly Ser Gly Ser Asp Thr Leu Tyr Ala Asp Ser Val Lys Gly
305                 310                 315                 320

Arg Phe Thr Ile Ser Arg Asp Asn Ser Lys Asn Thr Leu Tyr Leu Gln
            325                 330                 335

Met Asn Ser Leu Arg Pro Glu Asp Thr Ala Leu Tyr Tyr Cys Thr Ile
        340                 345                 350

Gly Gly Ser Leu Ser Arg Ser Ser Gln Gly Thr Leu Val Thr Val Ser
            355                 360                 365

Ser Ala
    370

<210> SEQ ID NO 71
<211> LENGTH: 383
<212> TYPE: PRT
<213> ORGANISM: Artificial Sequence
<220> FEATURE:
<223> OTHER INFORMATION: Synthetic-A022600370

<400> SEQUENCE: 71

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Tyr Tyr Cys Arg
            85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Gly Ser Glu Val Gln Leu Val Glu
        115                 120                 125

Ser Gly Gly Gly Val Val Gln Pro Gly Gly Ser Leu Arg Leu Ser Cys
    130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
            165                 170                 175

Gly Val Thr Ser Tyr Arg Asp Ser Val Lys Gly Arg Phe Thr Ile Ser
        180                 185                 190

Arg Asp Asn Ala Lys Asn Thr Leu Tyr Leu Glu Met Thr Ser Leu Arg
    195                 200                 205

Pro Glu Asp Thr Ala Leu Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Gly Ser Gly
            245                 250                 255

Gly Gly Ser Gly Gly Gly Gly Ser Glu Val Gln Leu Val Glu Ser
        260                 265                 270

Gly Gly Gly Val Val Gln Pro Gly Gly Ser Leu Arg Leu Ser Cys Ala
    275                 280                 285
```

-continued

Ala Ser Gly Phe Thr Phe Arg Ser Phe Gly Met Ser Trp Val Arg Gln
            290                 295                 300

Ala Pro Gly Lys Gly Pro Glu Trp Val Ser Ser Ile Ser Gly Ser Gly
305                 310                 315                 320

Ser Asp Thr Leu Tyr Ala Asp Ser Val Lys Gly Arg Phe Thr Ile Ser
                325                 330                 335

Arg Asp Asn Ser Lys Asn Thr Leu Tyr Leu Gln Met Asn Ser Leu Arg
            340                 345                 350

Pro Glu Asp Thr Ala Leu Tyr Tyr Cys Thr Ile Gly Gly Ser Leu Ser
            355                 360                 365

Arg Ser Ser Gln Gly Thr Leu Val Thr Val Ser Ser Gly Gly Cys
370                 375                 380

<210> SEQ ID NO 72
<211> LENGTH: 500
<212> TYPE: PRT
<213> ORGANISM: Artificial Sequence
<220> FEATURE:
<223> OTHER INFORMATION: Synthetic-A022600372

<400> SEQUENCE: 72

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Gly Ser Glu Val Gln Leu Val Glu
        115                 120                 125

Ser Gly Gly Gly Val Val Gln Pro Gly Gly Ser Leu Arg Leu Ser Cys
    130                 135                 140

Val Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Gly
                165                 170                 175

Gly Val Thr Ser Tyr Arg Asp Ser Val Lys Gly Arg Phe Thr Ile Ser
            180                 185                 190

Arg Asp Asn Ala Lys Asn Thr Leu Tyr Leu Glu Met Thr Ser Leu Arg
        195                 200                 205

Pro Glu Asp Thr Ala Leu Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Val Val Gln Pro Gly Gly Ser Leu
            260                 265                 270

```
Arg Leu Ser Cys Val Ala Ser Gly Ser Ile Phe Arg Ser Val Phe Ser
            275                 280                 285

Ser Ser Thr Met Glu Trp Tyr Arg Gln Pro Pro Gly Lys Lys Arg Glu
    290                 295                 300

Leu Val Arg Ile Ala Pro Gly Asp Gly Thr Asn Tyr Gly Ala Leu
305                 310                 315                 320

Tyr Ala Asp Ser Val Lys Gly Arg Phe Thr Ile Ser Arg Asp Asp Ala
                325                 330                 335

Lys Lys Thr Val Asp Leu Gln Met Asn Ser Leu Arg Pro Glu Asp Thr
                340                 345                 350

Gly Leu Tyr Phe Cys Ala Ser Gly Val Ala Trp Gly Gln Gly Thr Leu
            355                 360                 365

Val Thr Val Ser Ser Gly Gly Gly Gly Ser Gly Gly Gly Ser Glu Val
        370                 375                 380

Gln Leu Val Glu Ser Gly Gly Gly Val Val Gln Pro Gly Gly Ser Leu
385                 390                 395                 400

Arg Leu Ser Cys Ala Ala Ser Gly Phe Thr Phe Arg Ser Phe Gly Met
                405                 410                 415

Ser Trp Val Arg Gln Ala Pro Gly Lys Gly Pro Glu Trp Val Ser Ser
            420                 425                 430

Ile Ser Gly Ser Gly Ser Asp Thr Leu Tyr Ala Asp Ser Val Lys Gly
        435                 440                 445

Arg Phe Thr Ile Ser Arg Asp Asn Ser Lys Asn Thr Leu Tyr Leu Gln
            450                 455                 460

Met Asn Ser Leu Arg Pro Glu Asp Thr Ala Leu Tyr Tyr Cys Thr Ile
465                 470                 475                 480

Gly Gly Ser Leu Ser Arg Ser Ser Gln Gly Thr Leu Val Thr Val Ser
                485                 490                 495

Ser Gly Gly Cys
            500

<210> SEQ ID NO 73
<211> LENGTH: 255
<212> TYPE: PRT
<213> ORGANISM: Artificial Sequence
<220> FEATURE:
<223> OTHER INFORMATION: Synthetic-A022600373

<400> SEQUENCE: 73

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125
```

Gly Gly Gly Ser Gly Gly Gly Ser Glu Val Gln Leu Val Glu Ser
            130             135             140

Gly Gly Gly Val Val Gln Pro Gly Gly Ser Leu Arg Leu Ser Cys Ala
145             150             155             160

Ala Ser Gly Phe Thr Phe Arg Ser Phe Gly Met Ser Trp Val Arg Gln
            165             170             175

Ala Pro Gly Lys Gly Pro Glu Trp Val Ser Ile Ser Gly Ser Gly
            180             185             190

Ser Asp Thr Leu Tyr Ala Asp Ser Val Lys Gly Arg Phe Thr Ile Ser
            195             200             205

Arg Asp Asn Ser Lys Asn Thr Leu Tyr Leu Gln Met Asn Ser Leu Arg
            210             215             220

Pro Glu Asp Thr Ala Leu Tyr Tyr Cys Thr Ile Gly Gly Ser Leu Ser
225             230             235             240

Arg Ser Ser Gln Gly Thr Leu Val Thr Val Ser Ser Gly Gly Cys
            245             250             255

<210> SEQ ID NO 74
<211> LENGTH: 242
<212> TYPE: PRT
<213> ORGANISM: Artificial Sequence
<220> FEATURE:
<223> OTHER INFORMATION: Synthetic-T017000698

<400> SEQUENCE: 74

Asp Val Gln Leu Val Glu Ser Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
            35                  40                  45

Ala His Ile Ser Ile Gly Asp Gln Thr Asp Tyr Ala Asp Ser Ala Lys
        50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
            100             105             110

Val Thr Val Ser Ser Gly Gly Gly Gly Ser Gly Gly Gly Ser Glu Val
            115             120             125

Gln Leu Val Glu Ser Gly Gly Val Val Gln Pro Gly Gly Ser Leu
            130             135             140

Arg Leu Ser Cys Ala Ala Ser Gly Phe Thr Phe Arg Ser Phe Gly Met
145             150             155             160

Ser Trp Val Arg Gln Ala Pro Gly Lys Gly Pro Glu Trp Val Ser Ser
            165             170             175

Ile Ser Gly Ser Gly Ser Asp Thr Leu Tyr Ala Asp Ser Val Lys Gly
            180             185             190

Arg Phe Thr Ile Ser Arg Asp Asn Ser Lys Asn Thr Leu Tyr Leu Gln
            195             200             205

Met Asn Ser Leu Arg Pro Glu Asp Thr Ala Leu Tyr Tyr Cys Thr Ile
            210             215             220

Gly Gly Ser Leu Ser Arg Ser Ser Gln Gly Thr Leu Val Thr Val Ser
225             230             235             240

Ser Ala

```
<210> SEQ ID NO 75
<211> LENGTH: 119
<212> TYPE: PRT
<213> ORGANISM: Artificial Sequence
<220> FEATURE:
<223> OTHER INFORMATION: Synthetic-A022600314

<400> SEQUENCE: 75
```

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Ile Phe Arg Ser Val
            20                  25                  30

Phe Ser Ser Ser Thr Met Glu Trp Tyr Arg Gln Ala Pro Gly Lys Lys
        35                  40                  45

Arg Glu Leu Val Ala Arg Ile Ala Pro Gly Glu Gly Thr Tyr Tyr Gly
    50                  55                  60

Ala Leu Tyr Ala Asp Ser Val Lys Gly Arg Phe Thr Ile Ser Arg Asp
65                  70                  75                  80

Asn Ala Lys Asn Thr Val Tyr Leu Gln Met Asn Ser Leu Arg Pro Glu
                85                  90                  95

Asp Thr Ala Leu Tyr Tyr Cys Ala Ser Gly Val Ala Trp Gly Gln Gly
            100                 105                 110

Thr Leu Val Thr Val Ser Ser
        115

```
<210> SEQ ID NO 76
<211> LENGTH: 123
<212> TYPE: PRT
<213> ORGANISM: Artificial Sequence
<220> FEATURE:
<223> OTHER INFORMATION: Synthetic-A022600345

<400> SEQUENCE: 76
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Phe
            20                  25                  30

Ala Met Thr Trp Val Arg Arg Pro Gly Lys Gly Leu Glu Trp Val
        35                  40                  45

Ala Thr Ile Thr Asn Ala Gly Val Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Leu Tyr Ile Cys Ala
                85                  90                  95

Asn Ala Arg Arg Thr Gly Pro Arg Ala Pro Thr Asp Ile Gly Ser Tyr
            100                 105                 110

Arg Gly Gln Gly Thr Leu Val Thr Val Ser Ser
        115                 120

```
<210> SEQ ID NO 77
<211> LENGTH: 123
<212> TYPE: PRT
<213> ORGANISM: Artificial Sequence
<220> FEATURE:
<223> OTHER INFORMATION: Synthetic-A022600351
```

<400> SEQUENCE: 77

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Phe
            20                  25                  30

Ala Met Thr Trp Val Arg Arg Pro Gly Lys Gly Leu Glu Trp Val
        35                  40                  45

Ala Thr Ile Thr Asn Lys Gly Val Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Leu Tyr Ile Cys Ala
            85                  90                  95

Asn Ala Arg Arg Thr Gly Pro Arg Ala Pro Thr Asp Ile Gly Ser Tyr
            100                 105                 110

Arg Gly Gln Gly Thr Leu Val Thr Val Ser Ser
            115                 120

<210> SEQ ID NO 78
<211> LENGTH: 381
<212> TYPE: PRT
<213> ORGANISM: Artificial Sequence
<220> FEATURE:
<223> OTHER INFORMATION: Synthetic-A022600412

<400> SEQUENCE: 78

Asp Val Gln Leu Val Glu Ser Gly Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
            85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Ser Glu Val Gln Leu Val Glu
        115                 120                 125

Ser Gly Gly Gly Val Val Gln Pro Gly Gly Ser Leu Arg Leu Ser Cys
        130                 135                 140

Ala Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Ala
            165                 170                 175

Gly Val Thr Ser Tyr Ala Asp Ser Val Lys Gly Arg Phe Thr Ile Ser
            180                 185                 190

Arg Asp Asn Ala Lys Asn Thr Leu Tyr Leu Gln Met Asn Ser Leu Arg
            195                 200                 205

Pro Glu Asp Thr Ala Leu Tyr Ile Cys Ala Asn Ala Arg Arg Thr Gly
        210                 215                 220

Pro Arg Ala Pro Thr Asp Ile Gly Ser Tyr Arg Gly Gln Gly Thr Leu

```
                    225                 230                 235                 240
Val Thr Val Ser Ser Gly Gly Gly Ser Gly Gly Gly Ser Gly
                245                 250                 255

Gly Gly Gly Ser Gly Gly Gly Ser Glu Val Gln Leu Val Glu Ser
                260                 265                 270

Gly Gly Gly Val Val Gln Pro Gly Gly Ser Leu Arg Leu Ser Cys Ala
            275                 280                 285

Ala Ser Gly Phe Thr Phe Arg Ser Phe Gly Met Ser Trp Val Arg Gln
290                 295                 300

Ala Pro Gly Lys Gly Pro Glu Trp Val Ser Ile Ser Gly Ser Gly
305                 310                 315                 320

Ser Asp Thr Leu Tyr Ala Asp Ser Val Lys Gly Arg Phe Thr Ile Ser
                325                 330                 335

Arg Asp Asn Ser Lys Asn Thr Leu Tyr Leu Gln Met Asn Ser Leu Arg
            340                 345                 350

Pro Glu Asp Thr Ala Leu Tyr Tyr Cys Thr Ile Gly Gly Ser Leu Ser
            355                 360                 365

Arg Ser Ser Gln Gly Thr Leu Val Thr Val Ser Ser Ala
            370                 375                 380

<210> SEQ ID NO 79
<211> LENGTH: 509
<212> TYPE: PRT
<213> ORGANISM: Artificial Sequence
<220> FEATURE:
<223> OTHER INFORMATION: Synthetic-A022600425

<400> SEQUENCE: 79

Asp Val Gln Leu Val Glu Ser Gly Gly Val Val Gln Pro Gly Gly
1                 5                  10                  15

Ser Leu Arg Leu Ser Cys Val Ala Ser Gly Tyr Val His Lys Ile Asn
                20                  25                  30

Phe Tyr Gly Trp Tyr Arg Gln Ala Pro Gly Lys Glu Arg Glu Lys Val
            35                  40                  45

Ala His Ile Ser Ile Gly Asp Gln Thr Asp Tyr Ala Asp Ser Ala Lys
50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Ser Glu Val Gln Leu Val Glu
            115                 120                 125

Ser Gly Gly Gly Val Val Gln Pro Gly Gly Ser Leu Arg Leu Ser Cys
130                 135                 140

Ala Ala Ser Gly Ser Ile Phe Arg Ser Val Phe Ser Ser Ser Thr Met
145                 150                 155                 160

Glu Trp Tyr Arg Gln Ala Pro Gly Lys Lys Arg Glu Leu Val Ala Arg
                165                 170                 175

Ile Ala Pro Gly Glu Gly Thr Tyr Tyr Gly Ala Leu Tyr Ala Asp Ser
            180                 185                 190

Val Lys Gly Arg Phe Thr Ile Ser Arg Asp Asn Ala Lys Asn Thr Val
            195                 200                 205

Tyr Leu Gln Met Asn Ser Leu Arg Pro Glu Asp Thr Ala Leu Tyr Tyr
```

```
Cys Ala Ser Gly Val Ala Trp Gly Gln Gly Thr Leu Val Thr Val Ser
225                 230                 235                 240

Ser Gly Gly Gly Gly Ser Gly Gly Gly Ser Gly Gly Gly Gly Ser
            245                 250                 255

Gly Gly Gly Gly Ser Glu Val Gln Leu Val Glu Ser Gly Gly Val
            260                 265                 270

Val Gln Pro Gly Gly Ser Leu Arg Leu Ser Cys Ala Ala Ser Gly Phe
            275                 280                 285

Thr Phe Ser Ser Phe Ala Met Thr Trp Val Arg Arg Pro Pro Gly Lys
            290                 295                 300

Gly Leu Glu Trp Val Ala Thr Ile Thr Asn Ala Gly Val Thr Ser Tyr
305                 310                 315                 320

Ala Asp Ser Val Lys Gly Arg Phe Thr Ile Ser Arg Asp Asn Ala Lys
                325                 330                 335

Asn Thr Leu Tyr Leu Gln Met Asn Ser Leu Arg Pro Glu Asp Thr Ala
            340                 345                 350

Leu Tyr Ile Cys Ala Asn Ala Arg Arg Thr Gly Pro Arg Ala Pro Thr
            355                 360                 365

Asp Ile Gly Ser Tyr Arg Gly Gln Gly Thr Leu Val Thr Val Ser Ser
            370                 375                 380

Gly Gly Gly Gly Ser Gly Gly Gly Ser Glu Val Gln Leu Val Glu Ser
385                 390                 395                 400

Gly Gly Gly Val Val Gln Pro Gly Gly Ser Leu Arg Leu Ser Cys Ala
                405                 410                 415

Ala Ser Gly Phe Thr Phe Arg Ser Phe Gly Met Ser Trp Val Arg Gln
            420                 425                 430

Ala Pro Gly Lys Gly Pro Glu Trp Val Ser Ser Ile Ser Gly Ser Gly
            435                 440                 445

Ser Asp Thr Leu Tyr Ala Asp Ser Val Lys Gly Arg Phe Thr Ile Ser
450                 455                 460

Arg Asp Asn Ser Lys Asn Thr Leu Tyr Leu Gln Met Asn Ser Leu Arg
465                 470                 475                 480

Pro Glu Asp Thr Ala Leu Tyr Tyr Cys Thr Ile Gly Gly Ser Leu Ser
                485                 490                 495

Arg Ser Gln Gly Thr Leu Val Thr Val Ser Ser Ala
            500                 505

<210> SEQ ID NO 80
<211> LENGTH: 509
<212> TYPE: PRT
<213> ORGANISM: Artificial Sequence
<220> FEATURE:
<223> OTHER INFORMATION: Synthetic-A022600426

<400> SEQUENCE: 80

Asp Val Gln Leu Val Glu Ser Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
            35                  40                  45

Ala His Ile Ser Ile Gly Asp Gln Thr Asp Tyr Ala Asp Ser Ala Lys
            50                  55                  60

Gly Arg Phe Thr Ile Ser Arg Asp Glu Ser Lys Asn Thr Val Tyr Leu
```

```
                65                  70                  75                  80
        Gln Met Asn Ser Leu Arg Pro Glu Asp Thr Ala Tyr Tyr Cys Arg
                        85                  90                  95
        Ala Leu Ser Arg Ile Trp Pro Tyr Asp Tyr Trp Gly Gln Gly Thr Leu
                        100                 105                 110
        Val Thr Val Ser Ser Gly Gly Gly Ser Glu Val Gln Leu Val Glu
                        115                 120                 125
        Ser Gly Gly Gly Val Val Gln Pro Gly Gly Ser Leu Arg Leu Ser Cys
                130                 135                 140
        Ala Ala Ser Gly Ser Ile Phe Arg Ser Val Phe Ser Ser Thr Met
        145                 150                 155                 160
        Glu Trp Tyr Arg Gln Ala Pro Gly Lys Lys Arg Glu Leu Val Ala Arg
                        165                 170                 175
        Ile Ala Pro Gly Glu Gly Thr Tyr Tyr Gly Ala Leu Tyr Ala Asp Ser
                        180                 185                 190
        Val Lys Gly Arg Phe Thr Ile Ser Arg Asp Asn Ala Lys Asn Thr Val
                195                 200                 205
        Tyr Leu Gln Met Asn Ser Leu Arg Pro Glu Asp Thr Ala Leu Tyr Tyr
                210                 215                 220
        Cys Ala Ser Gly Val Ala Trp Gly Gln Gly Thr Leu Val Thr Val Ser
        225                 230                 235                 240
        Ser Gly Gly Gly Gly Ser Gly Gly Gly Ser Gly Gly Gly Gly Ser
                        245                 250                 255
        Gly Gly Gly Gly Ser Glu Val Gln Leu Val Glu Ser Gly Gly Val
                        260                 265                 270
        Val Gln Pro Gly Gly Ser Leu Arg Leu Ser Cys Ala Ala Ser Gly Phe
                275                 280                 285
        Thr Phe Ser Ser Phe Ala Met Thr Trp Val Arg Pro Pro Gly Lys
                        290                 295                 300
        Gly Leu Glu Trp Val Ala Thr Ile Thr Asn Lys Gly Val Thr Ser Tyr
        305                 310                 315                 320
        Ala Asp Ser Val Lys Gly Arg Phe Thr Ile Ser Arg Asp Asn Ala Lys
                        325                 330                 335
        Asn Thr Leu Tyr Leu Gln Met Asn Ser Leu Arg Pro Glu Asp Thr Ala
                        340                 345                 350
        Leu Tyr Ile Cys Ala Asn Ala Arg Arg Thr Gly Pro Arg Ala Pro Thr
                        355                 360                 365
        Asp Ile Gly Ser Tyr Arg Gly Gln Gly Thr Leu Val Thr Val Ser Ser
                370                 375                 380
        Gly Gly Gly Gly Ser Gly Gly Ser Glu Val Gln Leu Val Glu Ser
        385                 390                 395                 400
        Gly Gly Gly Val Val Gln Pro Gly Gly Ser Leu Arg Leu Ser Cys Ala
                        405                 410                 415
        Ala Ser Gly Phe Thr Phe Arg Ser Phe Gly Met Ser Trp Val Arg Gln
                        420                 425                 430
        Ala Pro Gly Lys Gly Pro Glu Trp Val Ser Ser Ile Ser Gly Ser Gly
                        435                 440                 445
        Ser Asp Thr Leu Tyr Ala Asp Ser Val Lys Gly Arg Phe Thr Ile Ser
                450                 455                 460
        Arg Asp Asn Ser Lys Asn Thr Leu Tyr Leu Gln Met Asn Ser Leu Arg
        465                 470                 475                 480
        Pro Glu Asp Thr Ala Leu Tyr Tyr Cys Thr Ile Gly Gly Ser Leu Ser
                        485                 490                 495
```

Arg Ser Ser Gln Gly Thr Leu Val Thr Val Ser Ser Ala
        500                 505

<210> SEQ ID NO 81
<211> LENGTH: 498
<212> TYPE: PRT
<213> ORGANISM: Artificial Sequence
<220> FEATURE:
<223> OTHER INFORMATION: Synthetic-A022600427

<400> SEQUENCE: 81

Asp Val Gln Leu Val Glu Ser Gly Gly Val Val Gln Pro Gly Gly
1               5                   10                  15

Ser Leu Arg Leu Ser Cys Val Ala Ser Gly Tyr Val His Lys Ile Asn
            20                  25                  30

Phe Tyr Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Thr Val Tyr Leu
65                  70                  75                  80

Gln Met Asn Ser Leu Arg Pro Glu Asp Thr Ala Ala Tyr Tyr Cys Arg
                85                  90                  95

Ala Leu Ser Arg Ile Trp Pro Tyr Asp Tyr Trp Gly Gln Gly Thr Leu
            100                 105                 110

Val Thr Val Ser Ser Gly Gly Gly Gly Ser Glu Val Gln Leu Val Glu
        115                 120                 125

Ser Gly Gly Gly Val Val Gln Pro Gly Gly Ser Leu Arg Leu Ser Cys
    130                 135                 140

Ala Ala Ser Gly Phe Thr Phe Ser Ser Phe Ala Met Thr Trp Val Arg
145                 150                 155                 160

Arg Pro Pro Gly Lys Gly Leu Glu Trp Val Ala Thr Ile Thr Asn Ala
                165                 170                 175

Gly Val Thr Ser Tyr Ala Asp Ser Val Lys Gly Arg Phe Thr Ile Ser
            180                 185                 190

Arg Asp Asn Ala Lys Asn Thr Leu Tyr Leu Gln Met Asn Ser Leu Arg
        195                 200                 205

Pro Glu Asp Thr Ala Leu Tyr Ile Cys Ala Asn Ala Arg Arg Thr Gly
    210                 215                 220

Pro Arg Ala Pro Thr Asp Ile Gly Ser Tyr Arg Gly Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Val Val Gln Pro Gly Gly Ser Leu
            260                 265                 270

Arg Leu Ser Cys Ala Ala Ser Gly Ser Ile Phe Arg Ser Val Phe Ser
        275                 280                 285

Ser Ser Thr Met Glu Trp Tyr Arg Gln Ala Pro Gly Lys Lys Arg Glu
    290                 295                 300

Leu Val Ala Arg Ile Ala Pro Gly Glu Gly Thr Tyr Tyr Gly Ala Leu
305                 310                 315                 320

Tyr Ala Asp Ser Val Lys Gly Arg Phe Thr Ile Ser Arg Asp Asn Ala
                325                 330                 335

Lys Asn Thr Val Tyr Leu Gln Met Asn Ser Leu Arg Pro Glu Asp Thr
            340                 345                 350

-continued

```
Ala Leu Tyr Tyr Cys Ala Ser Gly Val Ala Trp Gly Gln Gly Thr Leu
        355                 360                 365

Val Thr Val Ser Ser Gly Gly Gly Ser Gly Gly Gly Ser Glu Val
    370                 375                 380

Gln Leu Val Glu Ser Gly Gly Val Val Gln Pro Gly Gly Ser Leu
385                 390                 395                 400

Arg Leu Ser Cys Ala Ala Ser Gly Phe Thr Phe Arg Ser Phe Gly Met
                405                 410                 415

Ser Trp Val Arg Gln Ala Pro Gly Lys Gly Pro Glu Trp Val Ser Ser
            420                 425                 430

Ile Ser Gly Ser Gly Ser Asp Thr Leu Tyr Ala Asp Ser Val Lys Gly
        435                 440                 445

Arg Phe Thr Ile Ser Arg Asp Asn Ser Lys Asn Thr Leu Tyr Leu Gln
    450                 455                 460

Met Asn Ser Leu Arg Pro Glu Asp Thr Ala Leu Tyr Tyr Cys Thr Ile
465                 470                 475                 480

Gly Gly Ser Leu Ser Arg Ser Ser Gln Gly Thr Leu Val Thr Val Ser
                485                 490                 495

Ser Ala

<210> SEQ ID NO 82
<211> LENGTH: 115
<212> TYPE: PRT
<213> ORGANISM: Artificial Sequence
<220> FEATURE:
<223> OTHER INFORMATION: Synthetic-Alb8

<400> SEQUENCE: 82

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 83
<211> LENGTH: 116
<212> TYPE: PRT
<213> ORGANISM: Artificial Sequence
<220> FEATURE:
<223> OTHER INFORMATION: Synthetic-Alb8-A

<400> SEQUENCE: 83

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30
```

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
            85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 84
<211> LENGTH: 115
<212> TYPE: PRT
<213> ORGANISM: Artificial Sequence
<220> FEATURE:
<223> OTHER INFORMATION: Synthetic-Alb23

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
            85                  90                  95

Thr Ile Gly Gly Ser Leu Ser Arg Ser Ser Gln Gly Thr Leu Val Thr
            100                 105                 110

Val Ser Ser
        115

<210> SEQ ID NO 85
<211> LENGTH: 116
<212> TYPE: PRT
<213> ORGANISM: Artificial Sequence
<220> FEATURE:
<223> OTHER INFORMATION: Synthetic-Alb23-A

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys

```
                    85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 86
<211> LENGTH: 115
<212> TYPE: PRT
<213> ORGANISM: Artificial Sequence
<220> FEATURE:
<223> OTHER INFORMATION: Synthetic-Alb83

<400> SEQUENCE: 86

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 87
<211> LENGTH: 116
<212> TYPE: PRT
<213> ORGANISM: Artificial Sequence
<220> FEATURE:
<223> OTHER INFORMATION: Synthetic-Alb83-A

<400> SEQUENCE: 87

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 88
<211> LENGTH: 115
```

```
<212> TYPE: PRT
<213> ORGANISM: Artificial Sequence
<220> FEATURE:
<223> OTHER INFORMATION: Synthetic-Alb132

<400> SEQUENCE: 88

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 89
<211> LENGTH: 116
<212> TYPE: PRT
<213> ORGANISM: Artificial Sequence
<220> FEATURE:
<223> OTHER INFORMATION: Synthetic-Alb132-A

<400> SEQUENCE: 89

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 90
<211> LENGTH: 115
<212> TYPE: PRT
<213> ORGANISM: Artificial Sequence
<220> FEATURE:
<223> OTHER INFORMATION: Synthetic-Alb73

<400> SEQUENCE: 90

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
```

```
                    20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser
        115

<210> SEQ ID NO 91
<211> LENGTH: 116
<212> TYPE: PRT
<213> ORGANISM: Artificial Sequence
<220> FEATURE:
<223> OTHER INFORMATION: Synthetic-Alb73-A

<400> SEQUENCE: 91

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 92
<211> LENGTH: 115
<212> TYPE: PRT
<213> ORGANISM: Artificial Sequence
<220> FEATURE:
<223> OTHER INFORMATION: Synthetic-Alb82

<400> SEQUENCE: 92

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80
```

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 93
<211> LENGTH: 116
<212> TYPE: PRT
<213> ORGANISM: Artificial Sequence
<220> FEATURE:
<223> OTHER INFORMATION: Synthetic-Alb82-A

<400> SEQUENCE: 93

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 94
<211> LENGTH: 115
<212> TYPE: PRT
<213> ORGANISM: Artificial Sequence
<220> FEATURE:
<223> OTHER INFORMATION: Synthetic-Alb199

<400> SEQUENCE: 94

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Lys
            100                 105                 110

Val Ser Ser
        115

<210> SEQ ID NO 95

<211> LENGTH: 116
<212> TYPE: PRT
<213> ORGANISM: Artificial Sequence
<220> FEATURE:
<223> OTHER INFORMATION: Synthetic-Alb199-A

<400> SEQUENCE: 95

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 96
<211> LENGTH: 116
<212> TYPE: PRT
<213> ORGANISM: Artificial Sequence
<220> FEATURE:
<223> OTHER INFORMATION: Synthetic-Alb223

<400> SEQUENCE: 96

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 97
<211> LENGTH: 115
<212> TYPE: PRT
<213> ORGANISM: Artificial Sequence
<220> FEATURE:
<223> OTHER INFORMATION: Synthetic-Alb216

<400> SEQUENCE: 97

Glu Val Gln Leu Val Glu Ser Gly Gly Gly Val Val Gln Pro Gly Gly
1               5                   10                  15

```
Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Lys
            100                 105                 110

Val Ser Ser
        115

<210> SEQ ID NO 98
<211> LENGTH: 116
<212> TYPE: PRT
<213> ORGANISM: Artificial Sequence
<220> FEATURE:
<223> OTHER INFORMATION: Synthetic-Alb216-A

<400> SEQUENCE: 98

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 99
<211> LENGTH: 3
<212> TYPE: PRT
<213> ORGANISM: Artificial Sequence
<220> FEATURE:
<223> OTHER INFORMATION: Synthetic-linker

<400> SEQUENCE: 99

Ala Ala Ala
1

<210> SEQ ID NO 100
<211> LENGTH: 5
<212> TYPE: PRT
<213> ORGANISM: Artificial Sequence
<220> FEATURE:
<223> OTHER INFORMATION: Synthetic-linker

<400> SEQUENCE: 100

Gly Gly Gly Gly Ser
```

1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic-linker

<400> SEQUENCE: 101

Ser Gly Gly Ser Gly Gly Ser
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic-linker

<400> SEQUENCE: 102

Gly Gly Gly Gly Ser Gly Gly Ser
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic-linker

<400> SEQUENCE: 103

Gly Gly Gly Gly Ser Gly Gly Gly Ser
1               5

<210> SEQ ID NO 104
<211> LENGTH: 10
<212> TYPE: PRT
<213> ORGANISM: Artificial Sequence
<220> FEATURE:
<223> OTHER INFORMATION: Synthetic-linker

<400> SEQUENCE: 104

Gly Gly Gly Gly Ser Gly Gly Gly Gly Ser
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic-linker

<400> SEQUENCE: 105

Gly Gly Gly Gly Ser Gly Gly Gly Gly Ser Gly Gly Gly Gly Ser
1               5                   10                  15

<210> SEQ ID NO 106
<211> LENGTH: 18
<212> TYPE: PRT
<213> ORGANISM: Artificial Sequence
<220> FEATURE:
<223> OTHER INFORMATION: Synthetic-linker

<400> SEQUENCE: 106

Gly Gly Gly Gly Ser Gly Gly Gly Gly Ser Gly Gly Gly Gly Ser Gly
1               5                   10                  15

Gly Ser

<210> SEQ ID NO 107
<211> LENGTH: 20
<212> TYPE: PRT
<213> ORGANISM: Artificial Sequence
<220> FEATURE:
<223> OTHER INFORMATION: Synthetic-linker

<400> SEQUENCE: 107

Gly Gly Gly Gly Ser Gly Gly Gly Gly Ser Gly Gly Gly Gly Ser Gly
1               5                   10                  15

Gly Gly Gly Ser
            20

<210> SEQ ID NO 108
<211> LENGTH: 25
<212> TYPE: PRT
<213> ORGANISM: Artificial Sequence
<220> FEATURE:
<223> OTHER INFORMATION: Synthetic-linker

<400> SEQUENCE: 108

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 109
<211> LENGTH: 30
<212> TYPE: PRT
<213> ORGANISM: Artificial Sequence
<220> FEATURE:
<223> OTHER INFORMATION: Synthetic-linker

<400> SEQUENCE: 109

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 110
<211> LENGTH: 35
<212> TYPE: PRT
<213> ORGANISM: Artificial Sequence
<220> FEATURE:
<223> OTHER INFORMATION: Synthetic-linker

<400> SEQUENCE: 110

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 111
<211> LENGTH: 40
<212> TYPE: PRT
<213> ORGANISM: Artificial Sequence
<220> FEATURE:
<223> OTHER INFORMATION: Synthetic-linker

<400> SEQUENCE: 111

```
Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Gly Ser
        35                  40

<210> SEQ ID NO 112
<211> LENGTH: 15
<212> TYPE: PRT
<213> ORGANISM: Artificial Sequence
<220> FEATURE:
<223> OTHER INFORMATION: Synthetic-linker

<400> SEQUENCE: 112

Glu Pro Lys Ser Cys Asp Lys Thr His Thr Cys Pro Pro Cys Pro
1               5                   10                  15

<210> SEQ ID NO 113
<211> LENGTH: 24
<212> TYPE: PRT
<213> ORGANISM: Artificial Sequence
<220> FEATURE:
<223> OTHER INFORMATION: Synthetic-linker

<400> SEQUENCE: 113

Gly Gly Gly Gly Ser Gly Gly Gly Ser Glu Pro Lys Ser Cys Asp Lys
1               5                   10                  15

Thr His Thr Cys Pro Pro Cys Pro
                20

<210> SEQ ID NO 114
<211> LENGTH: 12
<212> TYPE: PRT
<213> ORGANISM: Artificial Sequence
<220> FEATURE:
<223> OTHER INFORMATION: Synthetic-linker

<400> SEQUENCE: 114

Glu Pro Lys Thr Pro Lys Pro Gln Pro Ala Ala Ala
1               5                   10

<210> SEQ ID NO 115
<211> LENGTH: 62
<212> TYPE: PRT
<213> ORGANISM: Artificial Sequence
<220> FEATURE:
<223> OTHER INFORMATION: Synthetic-linker

<400> SEQUENCE: 115

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
        50                  55                  60

<210> SEQ ID NO 116
<211> LENGTH: 5
<212> TYPE: PRT
<213> ORGANISM: Artificial Sequence
```

```
<220> FEATURE:
<223> OTHER INFORMATION: Synthetic-C-terminus

<400> SEQUENCE: 116

Val Thr Val Ser Ser
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic-C-terminus

<400> SEQUENCE: 117

Val Lys Val Ser Ser
1               5

<210> SEQ ID NO 118
<211> LENGTH: 5
<212> TYPE: PRT
<213> ORGANISM: Artificial Sequence
<220> FEATURE:
<223> OTHER INFORMATION: Synthetic-C-terminus

<400> SEQUENCE: 118

Val Gln Val Ser Ser
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic-C-terminus

<400> SEQUENCE: 119

Val Thr Val Lys Ser
1               5

<210> SEQ ID NO 120
<211> LENGTH: 5
<212> TYPE: PRT
<213> ORGANISM: Artificial Sequence
<220> FEATURE:
<223> OTHER INFORMATION: Synthetic-C-terminus

<400> SEQUENCE: 120

Val Thr Val Gln Ser
1               5

<210> SEQ ID NO 121
<211> LENGTH: 5
<212> TYPE: PRT
<213> ORGANISM: Artificial Sequence
<220> FEATURE:
<223> OTHER INFORMATION: Synthetic-C-terminus

<400> SEQUENCE: 121

Val Lys Val Lys Ser
1               5

<210> SEQ ID NO 122
<211> LENGTH: 5
<212> TYPE: PRT
<213> ORGANISM: Artificial Sequence
<220> FEATURE:
```

<223> OTHER INFORMATION: Synthetic-C-terminus

<400> SEQUENCE: 122

Val Lys Val Gln Ser
1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic-C-terminus

<400> SEQUENCE: 123

Val Gln Val Lys Ser
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic-C-terminus

<400> SEQUENCE: 124

Val Gln Val Gln Ser
1               5

<210> SEQ ID NO 125
<211> LENGTH: 6
<212> TYPE: PRT
<213> ORGANISM: Artificial Sequence
<220> FEATURE:
<223> OTHER INFORMATION: Synthetic-C-terminus

<400> SEQUENCE: 125

Val Thr Val Ser Ser Ala
1               5

<210> SEQ ID NO 126
<211> LENGTH: 6
<212> TYPE: PRT
<213> ORGANISM: Artificial Sequence
<220> FEATURE:
<223> OTHER INFORMATION: Synthetic-C-terminus

<400> SEQUENCE: 126

Val Lys Val Ser Ser Ala
1               5

<210> SEQ ID NO 127
<211> LENGTH: 6
<212> TYPE: PRT
<213> ORGANISM: Artificial Sequence
<220> FEATURE:
<223> OTHER INFORMATION: Synthetic-C-terminus

<400> SEQUENCE: 127

Val Gln Val Ser Ser Ala
1               5

<210> SEQ ID NO 128
<211> LENGTH: 6
<212> TYPE: PRT
<213> ORGANISM: Artificial Sequence
<220> FEATURE:
<223> OTHER INFORMATION: Synthetic-C-terminus -continued

<400> SEQUENCE: 128

Val Thr Val Lys Ser Ala
1               5

<210> SEQ ID NO 129
<211> LENGTH: 6
<212> TYPE: PRT
<213> ORGANISM: Artificial Sequence
<220> FEATURE:
<223> OTHER INFORMATION: Synthetic-C-terminus

<400> SEQUENCE: 129

Val Thr Val Gln Ser Ala
1               5

<210> SEQ ID NO 130
<211> LENGTH: 6
<212> TYPE: PRT
<213> ORGANISM: Artificial Sequence
<220> FEATURE:
<223> OTHER INFORMATION: Synthetic-C-terminus

<400> SEQUENCE: 130

Val Lys Val Lys Ser Ala
1               5

<210> SEQ ID NO 131
<211> LENGTH: 6
<212> TYPE: PRT
<213> ORGANISM: Artificial Sequence
<220> FEATURE:
<223> OTHER INFORMATION: Synthetic-C-terminus

<400> SEQUENCE: 131

Val Lys Val Gln Ser Ala
1               5

<210> SEQ ID NO 132
<211> LENGTH: 6
<212> TYPE: PRT
<213> ORGANISM: Artificial Sequence
<220> FEATURE:
<223> OTHER INFORMATION: Synthetic-C-terminus

<400> SEQUENCE: 132

Val Gln Val Lys Ser Ala
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic-C-terminus

<400> SEQUENCE: 133

Val Gln Val Gln Ser Ala
1               5

<210> SEQ ID NO 134
<211> LENGTH: 580
<212> TYPE: PRT
<213> ORGANISM: Artificial Sequence
<220> FEATURE:
<223> OTHER INFORMATION: Synthetic-Human GPC3 (P51654)

<400> SEQUENCE: 134

```
Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
        355                 360                 365

Asp Lys Lys Val Leu Lys Val Ala His Val Glu His Glu Glu Thr Leu
370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415
```

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
        435                 440                 445

Glu Leu Lys Met Lys Gly Pro Glu Pro Val Val Ser Gln Ile Ile Asp
450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
                500                 505                 510

Met Ile Lys Val Lys Asn Gln Leu Arg Phe Leu Ala Glu Leu Ala Tyr
            515                 520                 525

Asp Leu Asp Val Asp Asp Ala Pro Gly Asn Ser Gln Gln Ala Thr Pro
        530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 135
<211> LENGTH: 96
<212> TYPE: PRT
<213> ORGANISM: Artificial Sequence
<220> FEATURE:
<223> OTHER INFORMATION: Synthetic-Human TCR alpha constant domain
      (derived from P01848)

<400> SEQUENCE: 135

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

<210> SEQ ID NO 136
<211> LENGTH: 131
<212> TYPE: PRT
<213> ORGANISM: Artificial Sequence
<220> FEATURE:
<223> OTHER INFORMATION: Synthetic-Human TCR beta constant domain
      (derived from P01850)

<400> SEQUENCE: 136

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

```
Ala Thr Gly Phe Phe Pro Asp His Val Glu Leu Ser Trp Trp Val Asn
         35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Ala Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys
    130

<210> SEQ ID NO 137
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 137

Lys Glu Arg Glu
1

<210> SEQ ID NO 138
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 138

Lys Gln Arg Glu
1

<210> SEQ ID NO 139
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 139

Gly Leu Glu Trp
1

<210> SEQ ID NO 140
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 140

Lys Glu Arg Glu Leu
1               5

<210> SEQ ID NO 141
<211> LENGTH: 5
<212> TYPE: PRT
<213> ORGANISM: Artificial Sequence
```

```
<220> FEATURE:
<223> OTHER INFORMATION: Synthetic-Motif from Table A-0

<400> SEQUENCE: 141

Lys Glu Arg Glu Phe
1               5

<210> SEQ ID NO 142
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 142

Lys Gln Arg Glu Leu
1               5

<210> SEQ ID NO 143
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 143

Lys Gln Arg Glu Phe
1               5

<210> SEQ ID NO 144
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 144

Lys Glu Arg Glu Gly
1               5

<210> SEQ ID NO 145
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 145

Lys Gln Arg Glu Trp
1               5

<210> SEQ ID NO 146
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 146

Lys Gln Arg Glu Gly
1               5

<210> SEQ ID NO 147
<211> LENGTH: 4
<212> TYPE: PRT
<213> ORGANISM: Artificial Sequence
<220> FEATURE:
```

```
<223> OTHER INFORMATION: Synthetic-Motif from Table A-0

<400> SEQUENCE: 147

Thr Glu Arg Glu
1

<210> SEQ ID NO 148
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 148

Thr Glu Arg Glu Leu
1               5

<210> SEQ ID NO 149
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 149

Thr Gln Arg Glu
1

<210> SEQ ID NO 150
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 150

Thr Gln Arg Glu Leu
1               5

<210> SEQ ID NO 151
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 151

Lys Glu Cys Glu
1

<210> SEQ ID NO 152
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 152

Lys Glu Cys Glu Leu
1               5

<210> SEQ ID NO 153
<211> LENGTH: 5
<212> TYPE: PRT
<213> ORGANISM: Artificial Sequence
<220> FEATURE:
<223> OTHER INFORMATION: Synthetic-Motif from Table A-0
```

```
<400> SEQUENCE: 153

Lys Glu Cys Glu Arg
1               5

<210> SEQ ID NO 154
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 154

Lys Gln Cys Glu
1

<210> SEQ ID NO 155
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 155

Lys Gln Cys Glu Leu
1               5

<210> SEQ ID NO 156
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 156

Arg Glu Arg Glu
1

<210> SEQ ID NO 157
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 157

Arg Glu Arg Glu Gly
1               5

<210> SEQ ID NO 158
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 158

Arg Gln Arg Glu
1

<210> SEQ ID NO 159
<211> LENGTH: 5
<212> TYPE: PRT
<213> ORGANISM: Artificial Sequence
<220> FEATURE:
<223> OTHER INFORMATION: Synthetic-Motif from Table A-0
```

```
<400> SEQUENCE: 159

Arg Gln Arg Glu Leu
1               5

<210> SEQ ID NO 160
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 160

Arg Gln Arg Glu Phe
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 161

Arg Gln Arg Glu Trp
1               5

<210> SEQ ID NO 162
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 162

Gln Glu Arg Glu
1

<210> SEQ ID NO 163
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 163

Gln Glu Arg Glu Gly
1               5

<210> SEQ ID NO 164
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 164

Gln Gln Arg Glu
1

<210> SEQ ID NO 165
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 165
```

```
Gln Gln Arg Glu Trp
1               5

<210> SEQ ID NO 166
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 166

Gln Gln Arg Glu Leu
1               5

<210> SEQ ID NO 167
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 167

Gln Gln Arg Glu Phe
1               5

<210> SEQ ID NO 168
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 168

Lys Gly Arg Glu
1

<210> SEQ ID NO 169
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 169

Lys Gly Arg Glu Gly
1               5

<210> SEQ ID NO 170
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 170

Lys Asp Arg Glu
1

<210> SEQ ID NO 171
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 171
```

```
Lys Asp Arg Glu Val
1               5

<210> SEQ ID NO 172
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 172

Asp Glu Cys Lys Leu
1               5

<210> SEQ ID NO 173
<211> LENGTH: 5
<212> TYPE: PRT
<213> ORGANISM: Artificial Sequence
<220> FEATURE:
<223> OTHER INFORMATION: Synthetic-Motif from Table A-0

<400> SEQUENCE: 173

Asn Val Cys Glu Leu
1               5

<210> SEQ ID NO 174
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 174

Gly Val Glu Trp
1

<210> SEQ ID NO 175
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 175

Glu Pro Glu Trp
1

<210> SEQ ID NO 176
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 176

Gly Leu Glu Arg
1

<210> SEQ ID NO 177
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 177

Asp Gln Glu Trp
```

```
<210> SEQ ID NO 178
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 178

Asp Leu Glu Trp
1

<210> SEQ ID NO 179
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 179

Gly Ile Glu Trp
1

<210> SEQ ID NO 180
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 180

Glu Leu Glu Trp
1

<210> SEQ ID NO 181
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 181

Gly Pro Glu Trp
1

<210> SEQ ID NO 182
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 182

Glu Trp Leu Pro
1

<210> SEQ ID NO 183
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 183

Gly Pro Glu Arg
1
```

```
<210> SEQ ID NO 184
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 184

Gly Leu Glu Arg
1

<210> SEQ ID NO 185
<211> LENGTH: 4
<212> TYPE: PRT
<213> ORGANISM: Artificial Sequence
<220> FEATURE:
<223> OTHER INFORMATION: Synthetic-Motif from Table A-0

<400> SEQUENCE: 185

Glu Leu Glu Trp
1
```

POLYPEPTIDES COMPRISING IMMUNOGLOBULIN SINGLE VARIABLE DOMAINS TARGETING GLYPICAN-3 AND T CELL RECEPTOR

RELATED APPLICATION

This application claims the benefit under 35 U.S.C. § 119(e) of U.S. Provisional Application Ser. No. 63/127,224, filed Dec. 18, 2020, the entire contents of which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Mar. 28, 2022, is named A084870220US01-SUBSEQ-CRP.txt, and is 187,892 bytes in size.

1 FIELD OF THE INVENTION

The present technology relates to polypeptides targeting Glypican-3 (GPC3) and T cell receptor (TCR). It also relates to nucleic acid molecules encoding the polypeptide and vectors comprising the nucleic acids, and to compositions comprising the polypeptide, nucleic acid or vector. The technology further relates to these products for use in a method of treating a subject suffering from a disease involving abnormal cells, such as cancerous or infected cells. Moreover, the technology relates to methods of producing these products.

2 TECHNOLOGICAL BACKGROUND

Cytotoxic T cells (CTL) are T lymphocytes that kill cancer cells, cells that are infected (particularly with viruses), or cells that are damaged in other ways. T lymphocytes (also called T cells) express the T cell receptor (TCR) and the CD3 receptor on the cell surface. The αβ TCR-CD3 complex (or "TCR complex") is composed of six different type I single-spanning transmembrane proteins: the TCRα and TCRβ chains that form the TCR heterodimer responsible for ligand recognition, and the non-covalently associated CD3γ, CD3δ, CD3ε and ζ chains, which bear cytoplasmic sequence motifs that are tyrosine phosphorylated upon receptor activation and recruit a large number of signalling components (Call et al. 2004, Molecular Immunology 40: 1295-1305).

Both α and β chains of the heterodimeric T cell receptor (TCR) consist of a constant domain and a variable domain. T cells are activated upon TCR recognition of cognate peptide presented by self-MHC molecules, with signal transduction initiated by tyrosine phosphorylated CD3 complexes, leading to T cell proliferation and differentiation.

Bispecific antibodies have been engineered that have a tumour recognition part on the one arm (target-binding arm) whereas the other arm of the molecule has specificity for a T cell antigen (effector-binding arm), often CD3. These bispecific antibodies, so called T-cell engagers (TCE), are multitargeting molecules that enhance the patient's immune response to malignant cells. Co-engagement of T-cell and tumour cell by the multispecific antibody leads to the formation of a cytolytic synapse between the T cell and the tumour cell, that induces T-cell activation and results in tumour cell killing.

While the majority of T cell activating bispecific antibodies target the CD3 complex on the T cell, some bispecific binders that target the constant domain of the αβ T cell receptor have been described in WO 2016/180969 A1.

Glypican-3 (GPC3) is a GPI anchored cell surface glycoprotein consisting of heparan sulfate GAG chains and a core protein. It has been implicated in embryogenesis and early development, controlling cell growth and differentiation. Whereas the expression of GPC3 is high during development, its expression is nearly absent in normal adult tissue, with moderate/low expression in renal proximal tubules and bronchial cells. Consistent with its role in early development, high level of GPC3 is also expressed in placenta.

GPC3 likely regulates early development via multiple signalling cascades, including the Wnt, Hh and YAP pathways. In addition, GPC3 is able to interact with basic growth factors, such as FGF2 to regulate cell growth. In an experimental setting, overexpression of GPC3 can inhibit FGF2-induced cell proliferation. By contrast, GPC3 also negatively regulates BMP7, an inhibitory growth factor. Altogether, the activity of GPC3 can be highly contextual, as it is able to not only inhibit cell proliferation, but also can promote carcinogenesis in liver and other forms of cancer.

GPC3 expression is especially prevalent in tumour tissue from hepatocellular carcinoma (HCC), a disease with significant unmet needs. Soluble GPC3 can also be detected in serum of HCC patients and has been used to differentiate from liver diseases with different aetiologies.

Bispecific antibody constructs have been proposed in multiple formats. For example, bispecific antibody formats may involve the chemical conjugation of two antibodies or fragments thereof (Brennan, M, et al., Science, 1985. 229 (4708): p. 81-83; Glennie, M. J., et al., J Immunol, 1987. 139(7): p. 2367-2375).

Disadvantages of such bispecific antibody formats include, however, high molecular weight and high viscosity at high concentration, making e.g. subcutaneous administration challenging, and in that each binding unit requires the interaction of two variable domains for specific and high affinity binding, having implications on polypeptide stability and efficiency of production. Such bispecific antibody formats may also potentially lead to CMC issues related to poor production efficiency and low titers and/or mispairing of the light chains or mispairing of the heavy chains.

Therefore, there is a need for antibody constructs that bind both to a target cell and a T cell with sufficient affinity to induce a cytotoxic response. At the same time, such constructs should not induce a cytotoxic response to non-target cells, i.e. cells that do not express the target antigen or only express it at low levels. Thereby, a balance can be struck between efficacy and safety. It is further desirable that such constructs can be efficiently produced, e.g. in microbial hosts. Such constructs should ideally also exhibit a half-life in the subject to be treated that is long enough such that consecutive treatments can be conveniently spaced apart. Furthermore, it is desirable to limit the reactivity of such constructs to pre-existing antibodies in the subject to be treated (i.e. antibodies present in the subject before the first treatment with the antibody construct). Moreover, the polypeptides should exert no or only minimal undesired side effects, e.g. provoked by cytotoxic activity on non-target cells.

3 SUMMARY OF THE INVENTION

The present inventors found that a polypeptide targeting specifically GPC3 and TCR at the same time leads to efficient T cell-mediated killing of GPC3 expressing cells in vitro. Said polypeptides could be efficiently produced (e.g. in microbial hosts). Furthermore, such polypeptides could be shown to exhibit limited reactivity to pre-existing antibodies in the subject to be treated (i.e., antibodies present in the subject before the first treatment with the antibody construct). In preferred embodiments such polypeptides exhibit a half-life in the subject to be treated that is long enough such that consecutive treatments can be conveniently spaced apart. Moreover, such polypeptides showed only limited activity against cells expressing no or low levels of GPC3. This suggests the possibility of inducing a highly specific T cell-mediated cytotoxic response against GPC3 positive cancer target cells, while exhibiting a favourable safety profile.

In one aspect, the polypeptide comprises or consists of at least three immunoglobulin single variable domains (ISVDs), wherein at least two ISVDs specifically bind to GPC3 and one ISVD specifically binds to the constant domain of a TCR on a T cell. Preferably, the at least two ISVDs specifically binding to GPC3 specifically bind to human GPC3 and the ISVD specifically binding to TCR specifically binds to human TCR. More preferably, the at least two ISVDs specifically binding to GPC3 are distinct ISVDs. In another aspect, the polypeptide comprising or consisting of at least three ISVDs preferably further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a serum protein, preferably to a human serum protein such as human serum albumin.

In one aspect the present technology provides a polypeptide comprising or consisting of at least one immunoglobulin single variable domain (ISVD) that specifically binds to GPC3. In a further embodiment, the polypeptide of the present technology comprises or consists of at least two ISVDs that specifically bind to GPC3, wherein the two ISVDs are optionally linked via a peptidic linker. Preferably, the two ISVDs specifically binding to GPC3 are distinct ISVDs. Moreover, the polypeptide preferably further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a serum protein, preferably to a human serum protein such as human serum albumin.

In another aspect, the polypeptide of the present technology comprises or consists of an ISVD that specifically binds to constant domain of a TCR on a T cell and at least one ISVD that specifically binds to GPC3, wherein the two ISVDs are optionally linked via a peptidic linker. Such a polypeptide can be used to redirect T cells for killing of cells expressing GPC3. Ideally, the ISVD binding to TCR is the only binding moiety comprised in said polypeptide that specifically binds to a, e.g. human, T cell. Moreover, the examples show that when the ISVD that specifically binds to TCR is located at the N-terminus of such a polypeptide, better T-cell mediated cytotoxicity is achieved compared to when the same anti-TCR ISVD not located at the N-terminus. The ISVD that specifically binds to TCR is thus preferably located N-terminally from the at least one ISVD that specifically binds to GPC3. Most preferably, the ISVD that specifically binds to TCR is located at the N-terminus of a polypeptide comprising the same. Moreover, the polypeptide preferably further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a serum protein, preferably to a human serum protein such as human serum albumin.

Also provided is a nucleic acid molecule capable of expressing the polypeptide, a nucleic acid or vector comprising the nucleic acid, and a composition comprising the polypeptide, the nucleic acid or the vector. The composition is preferably a pharmaceutical composition.

Also provided is a host cell or (non-human) host comprising the nucleic acid or vector that encodes the polypeptide as disclosed herein.

Further provided is a method for producing the polypeptide as disclosed herein, said method at least comprising the steps of:

a. expressing, in a suitable host cell or host organism or in another suitable expression system, a nucleic acid sequence encoding the polypeptide; optionally followed by:

b. isolating and/or purifying the polypeptide.

Moreover, the present technology provides the polypeptide, the composition comprising the polypeptide, or the composition comprising the nucleic acid or vector comprising the nucleotide sequence that encodes the polypeptide, for use as a medicament. Preferably, the polypeptide or composition is for use in the treatment of cancer, such as liver cancer or lung cancer.

In addition, provided is a method of treating cancer, wherein said method comprises administering, to a subject in need thereof, a pharmaceutically active amount of the polypeptide or a composition according to the present disclosure. The cancer is preferably selected from liver cancer or lung cancer. In some embodiments, the method further comprises administering one or more additional therapeutic agents.

Further provided is the use of the polypeptide or composition in the preparation of a pharmaceutical composition for treating cancer, preferably liver cancer or lung cancer.

In particular, the present technology provides the following embodiments:

Embodiment 1. A polypeptide that comprises or consists of at least three immunoglobulin single variable domains (ISVDs), wherein each of said ISVDs comprises three complementarity determining regions (CDR1 to CDR3, respectively), wherein the at least three ISVDs are optionally linked via one or more peptidic linkers, and wherein:

a) a first ISVD comprises
  i. a CDR1 that is the amino acid sequence of SEQ ID NO: 6 or an amino acid sequence with 2 or 1 amino acid difference(s) with SEQ ID NO: 6;
  ii. a CDR2 that is the amino acid sequence of SEQ ID NO: 10 or an amino acid sequence with 2 or 1 amino acid difference(s) with SEQ ID NO: 10; and iii. a CDR3 that is the amino acid sequence of SEQ ID NO: 14 or an amino acid sequence with 2 or 1 amino acid difference(s) with SEQ ID NO: 14;
b) a second ISVD comprises
iv. a CDR1 that is the amino acid sequence of SEQ ID NO: 7 or an amino acid sequence with 2 or 1 amino acid difference(s) with SEQ ID NO: 7;
v. a CDR2 that is the amino acid sequence of SEQ ID NO: 11 or an amino acid sequence with 2 or 1 amino acid difference(s) with SEQ ID NO: 11; and
vi. a CDR3 that is the amino acid sequence of SEQ ID NO: 15 or an amino acid sequence with 2 or 1 amino acid difference(s) with SEQ ID NO: 15; and
c) a third ISVD comprises
vii. a CDR1 that is the amino acid sequence of SEQ ID NO: 8 or an amino acid sequence with 2 or 1 amino acid difference(s) with SEQ ID NO: 8;
viii. a CDR2 that is the amino acid sequence of SEQ ID NO: 12 or an amino acid sequence with 2 or 1 amino acid difference(s) with SEQ ID NO: 12; and
ix. a CDR3 that is the amino acid sequence of SEQ ID NO: 16 or an amino acid sequence with 2 or 1 amino acid difference(s) with SEQ ID NO: 16,
wherein the order of the ISVDs indicates their relative position to each other considered from the N-terminus to the C-terminus of said polypeptide, wherein the first ISVDs is optionally located at the N-terminus of said polypeptide.

Embodiment 2. The polypeptide according to embodiment 1, wherein:
a) said first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14;
b) said second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15; and
c) said third ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16.

Embodiment 3. The polypeptide according to any of embodiments 1 or 2, wherein:
a) the amino acid sequence of said first ISVD exhibits a sequence identity of more than 90% with SEQ ID NO: 2;
b) the amino acid sequence of said second ISVD exhibits a sequence identity of more than 90% with SEQ ID NO: 3; and
c) the amino acid sequence of said third ISVD exhibits a sequence identity of more than 90% identity with SEQ ID NO: 4.

Embodiment 4. The polypeptide according to any of embodiments 1 to 3, wherein:
a) said first ISVD consists of the amino acid sequence of SEQ ID NO: 2;
b) said second ISVD consists of the amino acid sequence of SEQ ID NO: 3; and
c) said third ISVD consists of the amino acid sequence of SEQ ID NO: 4.

Embodiment 5. The polypeptide according to any of embodiments 1 to 4, wherein the first ISVD and the second ISVD are linked to each other via a linker consisting of less than 10 amino acids, preferably less than 6 amino acids, wherein the linker most preferably is a 5GS linker.

Embodiment 6. The polypeptide according to any of embodiments 1 to 5, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 7. The polypeptide according to embodiment 6, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 8. The polypeptide according to any one of embodiments 6 or 7, in which said one or more other binding units that provide the polypeptide with increased half-life is chosen from the group consisting of binding units that can bind to serum albumin (such as human serum albumin) or a serum immunoglobulin (such as IgG).

Embodiment 9. The polypeptide according to embodiment 8, in which said binding unit that provides the polypeptide with increased half-life is an ISVD that binds to human serum albumin.

Embodiment 10. The polypeptide according to embodiment 9, wherein the ISVD binding to human serum albumin comprises
i. a CDR1 that is the amino acid sequence of SEQ ID NO: 9 or an amino acid sequence with 2 or 1 amino acid difference(s) with SEQ ID NO: 9;
ii. a CDR2 that is the amino acid sequence of SEQ ID NO: 13 or an amino acid sequence with 2 or 1 amino acid difference(s) with SEQ ID NO: 13; and
iii. a CDR3 that is the amino acid sequence of SEQ ID NO: 17 or an amino acid sequence with 2 or 1 amino acid difference(s) with SEQ ID NO: 17.

Embodiment 11. The polypeptide according to any of embodiments 9 or 10, wherein the ISVD binding to human serum albumin comprises a CDR1 being the amino acid sequence of SEQ ID NO: 9, a CDR2 being the amino acid sequence of SEQ ID NO: 13 and a CDR3 being the amino acid sequence of SEQ ID NO: 17.

Embodiment 12. The polypeptide according to any of embodiments 9 to 11, wherein the amino acid sequence of said ISVD binding to human serum albumin exhibits a sequence identity of more than 90% with SEQ ID NO: 5.

Embodiment 13. The polypeptide according to any of embodiments 9 to 12, wherein said ISVD binding to human serum albumin consists of the amino acid sequence of SEQ ID NO: 5.

Embodiment 14. The polypeptide according to any of embodiments 1 to 13, wherein the polypeptide comprises or consists of an amino acid sequence exhibiting a sequence identity of more than 90% with SEQ ID NO: 1.

Embodiment 15. The polypeptide according to any of embodiments 1 to 14, wherein the polypeptide comprises or consists of the amino acid sequence of SEQ ID NO: 1.

Embodiment 16. A polypeptide that comprises or consists of at least one immunoglobulin single variable domain (ISVD), wherein said ISVD comprises three complementarity determining regions (CDR1 to CDR3, respectively), and wherein the at least one ISVD comprises:

a) a CDR1 that is the amino acid sequence of SEQ ID NO: 7 or an amino acid sequence with 2 or 1 amino acid difference(s) with SEQ ID NO: 7;
  a CDR2 that is the amino acid sequence of SEQ ID NO: 11 or an amino acid sequence with 2 or 1 amino acid difference(s) with SEQ ID NO: 11; and
  a CDR3 that is the amino acid sequence of SEQ ID NO: 15 or an amino acid sequence with 2 or 1 amino acid difference(s) with SEQ ID NO: 15, or
b) a CDR1 that is the amino acid sequence of SEQ ID NO: 8 or an amino acid sequence with 2 or 1 amino acid difference(s) with SEQ ID NO: 8;
  a CDR2 that is the amino acid sequence of SEQ ID NO: 12 or an amino acid sequence with 2 or 1 amino acid difference(s) with SEQ ID NO: 12; and
  a CDR3 that is the amino acid sequence of SEQ ID NO: 16 or an amino acid sequence with 2 or 1 amino acid difference(s) with SEQ ID NO: 16.

Embodiment 17. The polypeptide according to embodiment 16, wherein the at least one ISVD comprises:
a) a CDR1 being the amino acid sequence of SEQ ID NO: 7, a CDR2 being the amino acid sequence of SEQ ID NO: 11 and a CDR3 being the amino acid sequence of SEQ ID NO: 15, or
b) a CDR1 being the amino acid sequence of SEQ ID NO: 8, a CDR2 being the amino acid sequence of SEQ ID NO: 12 and a CDR3 being the amino acid sequence of SEQ ID NO: 16.

Embodiment 18. The polypeptide according to any of embodiments 16 or 17, wherein the amino acid sequence of the at least one ISVD comprises:
a) a sequence identity of more than 90% with SEQ ID NO: 3, or
b) a sequence identity of more than 90% identity with SEQ ID NO: 4.

Embodiment 19. The polypeptide according to any of embodiments 16 to 18, wherein said at least one ISVD comprises or consists of:
a) the amino acid sequence of SEQ ID NO: 3, or
b) the amino acid sequence of SEQ ID NO: 4.

Embodiment 20. A polypeptide that comprises or consists of at least two ISVDs, wherein each of said ISVDs comprises three complementarity determining regions (CDR1 to CDR3, respectively), wherein the at least two ISVDs are optionally linked via one or more peptidic linkers, and wherein:
a) a first and a second ISVD comprise
  i. a CDR1 that is the amino acid sequence of SEQ ID NO: 7 or an amino acid sequence with 2 or 1 amino acid difference(s) with SEQ ID NO: 7;
  ii. a CDR2 that is the amino acid sequence of SEQ ID NO: 11 or an amino acid sequence with 2 or 1 amino acid difference(s) with SEQ ID NO: 11; and
  iii. a CDR3 that is the amino acid sequence of SEQ ID NO: 15 or an amino acid sequence with 2 or 1 amino acid difference(s) with SEQ ID NO: 15,
b) a first and a second ISVD comprise
  i. a CDR1 that is the amino acid sequence of SEQ ID NO: 8 or an amino acid sequence with 2 or 1 amino acid difference(s) with SEQ ID NO: 8;
  ii. a CDR2 that is the amino acid sequence of SEQ ID NO: 12 or an amino acid sequence with 2 or 1 amino acid difference(s) with SEQ ID NO: 12; and
  iii. a CDR3 that is the amino acid sequence of SEQ ID NO: 16 or an amino acid sequence with 2 or 1 amino acid difference(s) with SEQ ID NO: 16,
c) a first ISVD comprises
  i. a CDR1 that is the amino acid sequence of SEQ ID NO: 7 or an amino acid sequence with 2 or 1 amino acid difference(s) with SEQ ID NO: 7;
  ii. a CDR2 that is the amino acid sequence of SEQ ID NO: 11 or an amino acid sequence with 2 or 1 amino acid difference(s) with SEQ ID NO: 11; and
  iii. a CDR3 that is the amino acid sequence of SEQ ID NO: 15 or an amino acid sequence with 2 or 1 amino acid difference(s) with SEQ ID NO: 15, and
  a second ISVD comprises
  iv. a CDR1 that is the amino acid sequence of SEQ ID NO: 8 or an amino acid sequence with 2 or 1 amino acid difference(s) with SEQ ID NO: 8;
  v. a CDR2 that is the amino acid sequence of SEQ ID NO: 12 or an amino acid sequence with 2 or 1 amino acid difference(s) with SEQ ID NO: 12; and
  vi. a CDR3 that is the amino acid sequence of SEQ ID NO: 16 or an amino acid sequence with 2 or 1 amino acid difference(s) with SEQ ID NO: 16,
d) a first ISVD comprises
  i. a CDR1 that is the amino acid sequence of SEQ ID NO: 8 or an amino acid sequence with 2 or 1 amino acid difference(s) with SEQ ID NO: 8;
  ii. a CDR2 that is the amino acid sequence of SEQ ID NO: 12 or an amino acid sequence with 2 or 1 amino acid difference(s) with SEQ ID NO: 12; and
  iii. a CDR3 that is the amino acid sequence of SEQ ID NO: 16 or an amino acid sequence with 2 or 1 amino acid difference(s) with SEQ ID NO: 16, and
  a second ISVD comprises
  iv. a CDR1 that is the amino acid sequence of SEQ ID NO: 7 or an amino acid sequence with 2 or 1 amino acid difference(s) with SEQ ID NO: 7;
  v. a CDR2 that is the amino acid sequence of SEQ ID NO: 11 or an amino acid sequence with 2 or 1 amino acid difference(s) with SEQ ID NO: 11; and
  vi. a CDR3 that is the amino acid sequence of SEQ ID NO: 15 or an amino acid sequence with 2 or 1 amino acid difference(s) with SEQ ID NO: 15,
e) a first ISVD comprises
  i. a CDR1 that is the amino acid sequence of SEQ ID NO: 6 or an amino acid sequence with 2 or 1 amino acid difference(s) with SEQ ID NO: 6;
  ii. a CDR2 that is the amino acid sequence of SEQ ID NO: 10 or an amino acid sequence with 2 or 1 amino acid difference(s) with SEQ ID NO: 10; and
  iii. a CDR3 that is the amino acid sequence of SEQ ID NO: 14 or an amino acid sequence with 2 or 1 amino acid difference(s) with SEQ ID NO: 14, and
  a second ISVD comprises
  iv. a CDR1 that is the amino acid sequence of SEQ ID NO: 7 or an amino acid sequence with 2 or 1 amino acid difference(s) with SEQ ID NO: 7;
  v. a CDR2 that is the amino acid sequence of SEQ ID NO: 11 or an amino acid sequence with 2 or 1 amino acid difference(s) with SEQ ID NO: 11; and
  vi. a CDR3 that is the amino acid sequence of SEQ ID NO: 15 or an amino acid sequence with 2 or 1 amino acid difference(s) with SEQ ID NO: 15,
f) a first ISVD comprises
  i. a CDR1 that is the amino acid sequence of SEQ ID NO: 7 or an amino acid sequence with 2 or 1 amino acid difference(s) with SEQ ID NO: 7;
  ii. a CDR2 that is the amino acid sequence of SEQ ID NO: 11 or an amino acid sequence with 2 or 1 amino acid difference(s) with SEQ ID NO: 11; and iii. a CDR3 that is the amino acid sequence of SEQ ID NO: 15 or an amino acid sequence with 2 or 1 amino acid difference(s) with SEQ ID NO: 15, and
a second ISVD comprises
iv. a CDR1 that is the amino acid sequence of SEQ ID NO: 6 or an amino acid sequence with 2 or 1 amino acid difference(s) with SEQ ID NO: 6;
v. a CDR2 that is the amino acid sequence of SEQ ID NO: 10 or an amino acid sequence with 2 or 1 amino acid difference(s) with SEQ ID NO: 10; and
vi. a CDR3 that is the amino acid sequence of SEQ ID NO: 14 or an amino acid sequence with 2 or 1 amino acid difference(s) with SEQ ID NO: 14,
g) a first ISVD comprises
i. a CDR1 that is the amino acid sequence of SEQ ID NO: 6 or an amino acid sequence with 2 or 1 amino acid difference(s) with SEQ ID NO: 6;
ii. a CDR2 that is the amino acid sequence of SEQ ID NO: 10 or an amino acid sequence with 2 or 1 amino acid difference(s) with SEQ ID NO: 10; and
iii. a CDR3 that is the amino acid sequence of SEQ ID NO: 14 or an amino acid sequence with 2 or 1 amino acid difference(s) with SEQ ID NO: 14, and
a second ISVD comprises
iv. a CDR1 that is the amino acid sequence of SEQ ID NO: 8 or an amino acid sequence with 2 or 1 amino acid difference(s) with SEQ ID NO: 8;
v. a CDR2 that is the amino acid sequence of SEQ ID NO: 12 or an amino acid sequence with 2 or 1 amino acid difference(s) with SEQ ID NO: 12; and
vi. a CDR3 that is the amino acid sequence of SEQ ID NO: 16 or an amino acid sequence with 2 or 1 amino acid difference(s) with SEQ ID NO: 16, or
h) a first ISVD comprises
i. a CDR1 that is the amino acid sequence of SEQ ID NO: 8 or an amino acid sequence with 2 or 1 amino acid difference(s) with SEQ ID NO: 8;
ii. a CDR2 that is the amino acid sequence of SEQ ID NO: 12 or an amino acid sequence with 2 or 1 amino acid difference(s) with SEQ ID NO: 12; and
iii. a CDR3 that is the amino acid sequence of SEQ ID NO: 16 or an amino acid sequence with 2 or 1 amino acid difference(s) with SEQ ID NO: 16, and
a second ISVD comprises
iv. a CDR1 that is the amino acid sequence of SEQ ID NO: 6 or an amino acid sequence with 2 or 1 amino acid difference(s) with SEQ ID NO: 6;
v. a CDR2 that is the amino acid sequence of SEQ ID NO: 10 or an amino acid sequence with 2 or 1 amino acid difference(s) with SEQ ID NO: 10; and
vi. a CDR3 that is the amino acid sequence of SEQ ID NO: 14 or an amino acid sequence with 2 or 1 amino acid difference(s) with SEQ ID NO: 14,
wherein the order of the ISVDs indicates their relative position to each other considered from the N-terminus to the C-terminus of said polypeptide.

Embodiment 21. The polypeptide according to embodiment 20, wherein:
a) the first and the second ISVD comprise a CDR1 being the amino acid sequence of SEQ ID NO: 7, a CDR2 being the amino acid sequence of SEQ ID NO: 11 and a CDR3 being the amino acid sequence of SEQ ID NO: 15,
b) the first and the second ISVD comprise a CDR1 being the amino acid sequence of SEQ ID NO: 8, a CDR2 being the amino acid sequence of SEQ ID NO: 12 and a CDR3 being the amino acid sequence of SEQ ID NO: 16,
c) the first ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, and the second ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16,
d) the first ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16, and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15,
e) the first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15,
f) the first ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, and the second ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14,
g) the first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, and the second ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16, or
h) the first ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16, and the second ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14.

Embodiment 22. The polypeptide according to any of embodiments 20 or 21, wherein:
a) the amino acid sequence of the first and the second ISVD exhibits a sequence identity of more than 90% with SEQ ID NO: 3,
b) the amino acid sequence of the first and the second ISVD exhibits a sequence identity of more than 90% with SEQ ID NO: 4,
c) the amino acid sequence of the first ISVD exhibits a sequence identity of more than 90% with SEQ ID NO: 3, and the second ISVD exhibits a sequence identity of more than 90% identity with SEQ ID NO: 4,
d) the amino acid sequence of the first ISVD exhibits a sequence identity of more than 90% with SEQ ID NO: 4, and the second ISVD exhibits a sequence identity of more than 90% identity with SEQ ID NO: 3, e) the amino acid sequence of the first ISVD exhibits a sequence identity of more than 90% with SEQ ID NO: 2, and the second ISVD exhibits a sequence identity of more than 90% identity with SEQ ID NO: 3, f) the amino acid sequence of the first ISVD exhibits a sequence identity of more than 90% with SEQ ID NO: 3, and the second ISVD exhibits a sequence identity of more than 90% identity with SEQ ID NO: 2 g) the amino acid sequence of the first ISVD exhibits a sequence identity of more than 90% with SEQ ID NO: 2, and the second ISVD exhibits a sequence identity of more than 90% identity with SEQ ID NO: 4, or h) the amino acid sequence of the first ISVD exhibits a sequence identity of more than 90% with SEQ ID NO: 4, and the second ISVD exhibits a sequence identity of more than 90% identity with SEQ ID NO: 2.

Embodiment 23. The polypeptide according to any of embodiments 20 to 22, wherein:
a) the first and the second ISVD consist of the amino acid sequence of SEQ ID NO: 3,
b) the first and the second ISVD consist of the amino acid sequence of SEQ ID NO: 4,
c) the first ISVD consists of the amino acid sequence of SEQ ID NO: 3, and the second ISVD consists of the amino acid sequence of SEQ ID NO: 4,
d) the first ISVD consists of the amino acid sequence of SEQ ID NO: 4, and the second ISVD consists of the amino acid sequence of SEQ ID NO: 3,
e) the first ISVD consists of the amino acid sequence of SEQ ID NO: 2, and the second ISVD consists of the amino acid sequence of SEQ ID NO: 3,
f) the first ISVD consists of the amino acid sequence of SEQ ID NO: 3, and the second ISVD consists of the amino acid sequence of SEQ ID NO: 2,
g) the first ISVD consists of the amino acid sequence of SEQ ID NO: 2, and the second ISVD consists of the amino acid sequence of SEQ ID NO: 4, or
h) the first ISVD consists of the amino acid sequence of SEQ ID NO: 4, and the second ISVD consists of the amino acid sequence of SEQ ID NO: 2.

Embodiment 24. The polypeptide according to any of embodiments 20 to 23, wherein the polypeptide comprises or consists of an amino acid sequence selected from SEQ ID NOs: 1, 49-72 and 78-81.

Embodiment 25. The polypeptide according to any of embodiments 16 to 24, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 26. The polypeptide according to embodiment 25, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 27. The polypeptide according to any one of embodiments 25 to 26, in which said one or more other binding units that provide the polypeptide with increased half-life is chosen from the group consisting of binding units that can bind to serum albumin (such as human serum albumin) or a serum immunoglobulin (such as IgG).

Embodiment 28. The polypeptide according to embodiment 27, in which said binding unit that provides the polypeptide with increased half-life is an ISVD that binds to human serum albumin.

Embodiment 29. The polypeptide according to embodiment 28, wherein the ISVD binding to human serum albumin comprises
  i. a CDR1 that is the amino acid sequence of SEQ ID NO: 9 or an amino acid sequence with 2 or 1 amino acid difference(s) with SEQ ID NO: 9;
  ii. a CDR2 that is the amino acid sequence of SEQ ID NO: 13 or an amino acid sequence with 2 or 1 amino acid difference(s) with SEQ ID NO: 13; and
  iii. a CDR3 that is the amino acid sequence of SEQ ID NO: 17 or an amino acid sequence with 2 or 1 amino acid difference(s) with SEQ ID NO: 17.

Embodiment 30. The polypeptide according to any of embodiments 28 to 29, wherein the ISVD binding to human serum albumin comprises a CDR1 being is the amino acid sequence of SEQ ID NO: 9, a CDR2 being the amino acid sequence of SEQ ID NO: 13 and a CDR3 being the amino acid sequence of SEQ ID NO: 17.

Embodiment 31. The polypeptide according to any of embodiments 28 to 30, wherein the amino acid sequence of said ISVD binding to human serum albumin exhibits a sequence identity of more than 90% with SEQ ID NO: 5.

Embodiment 32. The polypeptide according to any of embodiments 28 to 31, wherein said ISVD binding to human serum albumin consists of the amino acid sequence of SEQ ID NO: 5.

Embodiment 33. A nucleic acid comprising a nucleotide sequence that encodes a polypeptide according to any of embodiments 1 to 32, preferably according to any of embodiments 1 to 15.

Embodiment 34. A host or host cell comprising a nucleic acid according to embodiment 33.

Embodiment 35. A method for producing a polypeptide according to any of embodiments 1 to 32, preferably according to any of embodiments 1 to 15, said method at least comprising the steps of:
  a) expressing, in a suitable host cell or host organism or in another suitable expression system, a nucleic acid according to embodiment 33; optionally followed by:
  b) isolating and/or purifying the polypeptide according to any of embodiments 1 to 32, preferably according to any of embodiments 1 to 15.

Embodiment 36. A composition comprising at least one polypeptide according to any of embodiments 1 to 32, preferably according to any of embodiments 1 to 15, or a nucleic acid according to embodiment 33.

Embodiment 37. The composition according to embodiment 36, which is a pharmaceutical composition which further comprises at least one pharmaceutically acceptable carrier, diluent or excipient and/or adjuvant, and optionally comprises one or more further pharmaceutically active polypeptides and/or compounds.

Embodiment 38. A polypeptide according to any of embodiments 1 to 32, preferably according to any of embodiments 1 to 15, or a composition according to embodiment 36 or 37, for use as a medicament.

Embodiment 39. A polypeptide according to any of embodiments 1 to 32, preferably according to any of embodiments 1 to 15, or a composition according to embodiment 36 or 37, for use in the treatment of cancer, preferably liver cancer or lung cancer.

Embodiment 40. The polypeptide or composition for use according to embodiment 39, wherein the liver cancer is hepatocellular carcinoma (HCC).

Embodiment 41. The polypeptide or composition for use according to embodiment 39, wherein the lung cancer is non-small cell lung cancer (NSCLC), preferably squamous cell carcinoma (SCC).

Embodiment 42. A method of treating cancer, preferably liver cancer or lung cancer, wherein said method comprises administering, to a subject in need thereof, a pharmaceutically active amount of a polypeptide according to any of embodiments 1 to 32, preferably according to any of embodiments 1 to 15, or a composition according to embodiment 36 or 37.

Embodiment 43. The method according to embodiment 42, wherein the liver cancer is hepatocellular carcinoma.

Embodiment 44. The method according to embodiment 42, wherein the lung cancer is non-small cell lung cancer (NSCLC), preferably squamous cell carcinoma (SCC).

Embodiment 45. Use of a polypeptide according to any of embodiments 1 to 32, preferably according to any of embodiments 1 to 15, or a composition according to embodiment 36 or 37, in the preparation of a medicament.

Embodiment 46. Use of a polypeptide according to any of embodiments 1 to 32, preferably according to embodiments 1 to 15, or a composition according to embodiment 36 or 37, in the preparation of a pharmaceutical composition for treating cancer, preferably liver cancer or lung cancer.

Embodiment 47. Use of the polypeptide or a composition according to embodiment 46, wherein the liver cancer is hepatocellular carcinoma.

Embodiment 48. Use of the polypeptide or the composition according to embodiment 46, wherein the lung cancer is non-small cell lung cancer (NSCLC), preferably squamous cell carcinoma (SCC).

4 BRIEF DESCRIPTION OF THE DRAWINGS

Figure 1B:
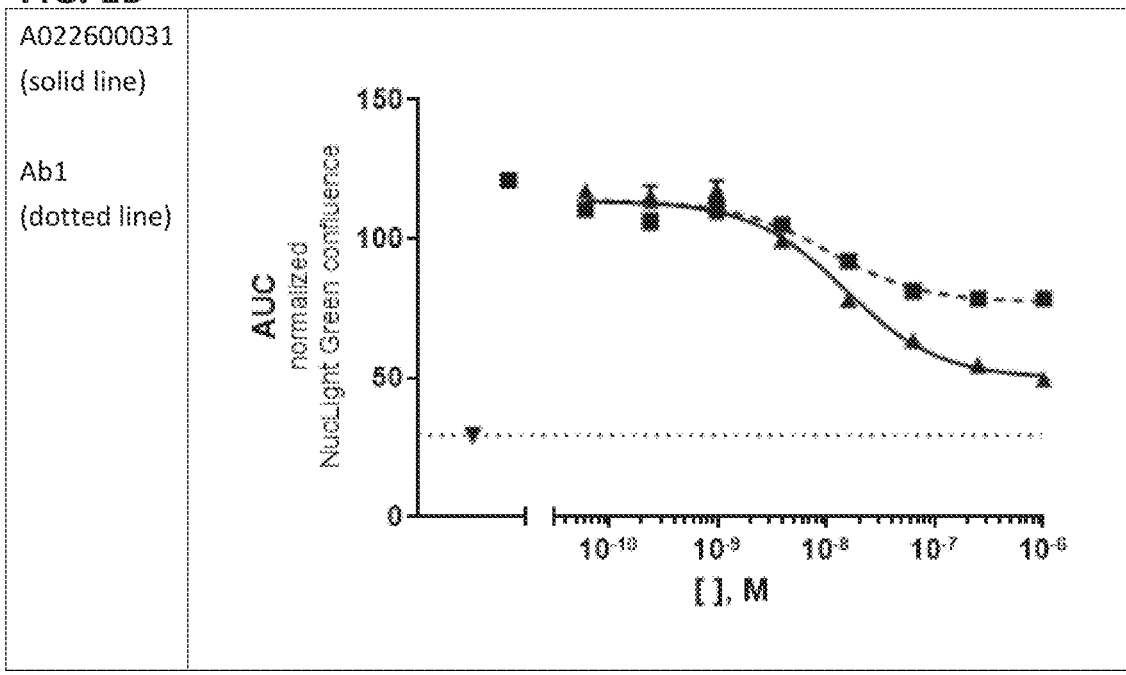

FIGS. 1A-1B: Dose-dependent killing of the trispecific GPC3 T-cell engagers A022600027 (FIG. 1A), A022600031 (FIG. 1B solid line) and a construct with the reference Ab1 (FIG. 1B dotted line) in the Incucyte based human TDC (T-cell dependent cytotoxicity) HepG2-Nuclight green assay using an effector to target ratio of 15:1, analyzed at 60 h after seeding. Controls (left) are: (solid square) No compound and (solid triangle) Brefeldin A 1 µM for 100% killing.

Figure 2:
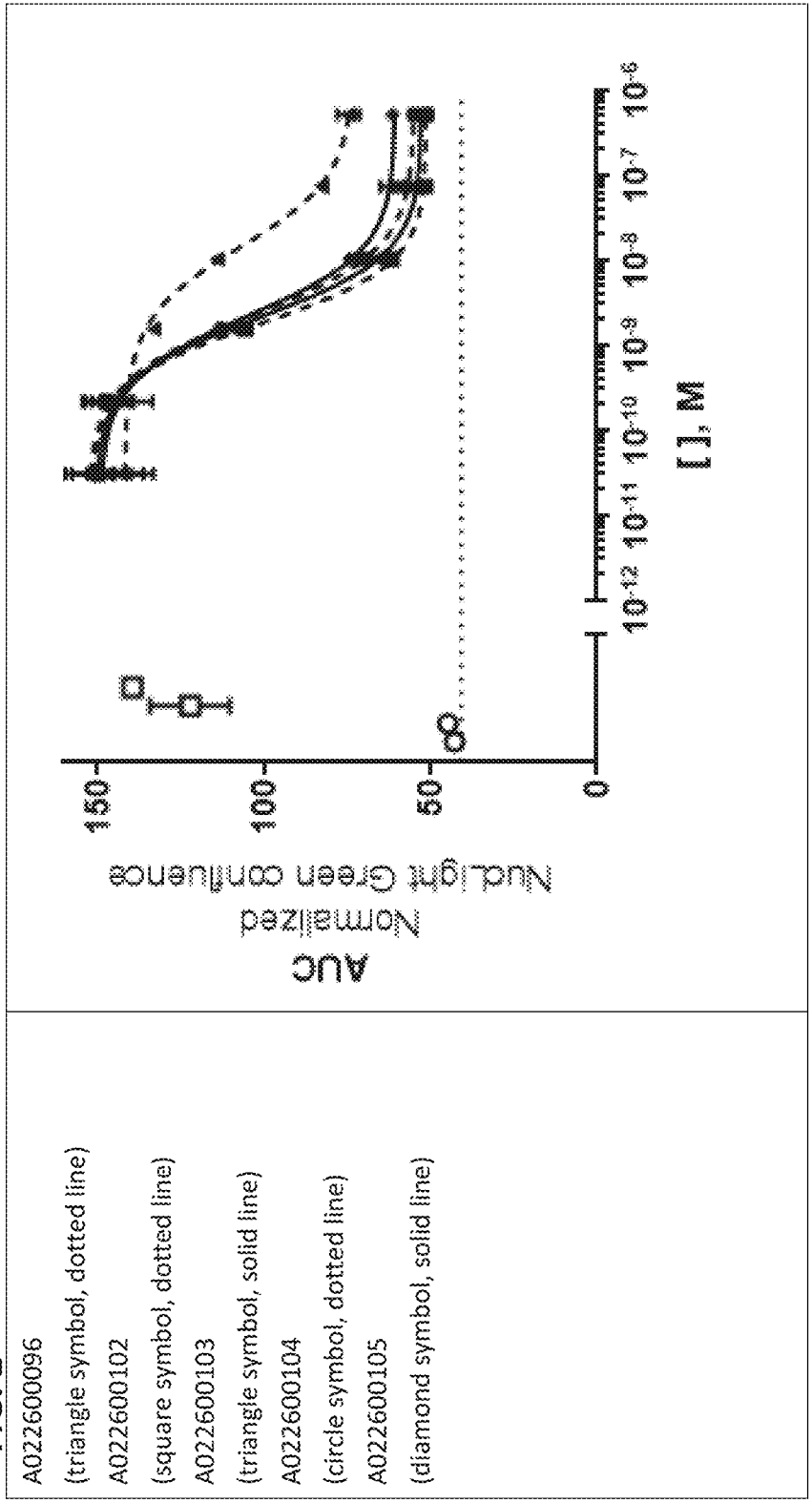

FIG. 2: Dose-dependent killing of the trispecific GPC3 ISVD T-cell engagers in the Incucyte based human TDC HepG2-Nuclight green assay using an effector to target ratio of 15:1, analyzed at 72 h after seeding. The figure represents Step 1 of format optimization where trispecific trivalent T-cell engager formats differ in linker length between anti-TCR ISVD and anti-GPC3 ISVD. Controls (left) are: No compound (open square) and reference for 100% killing (open circle).

Figure 3:
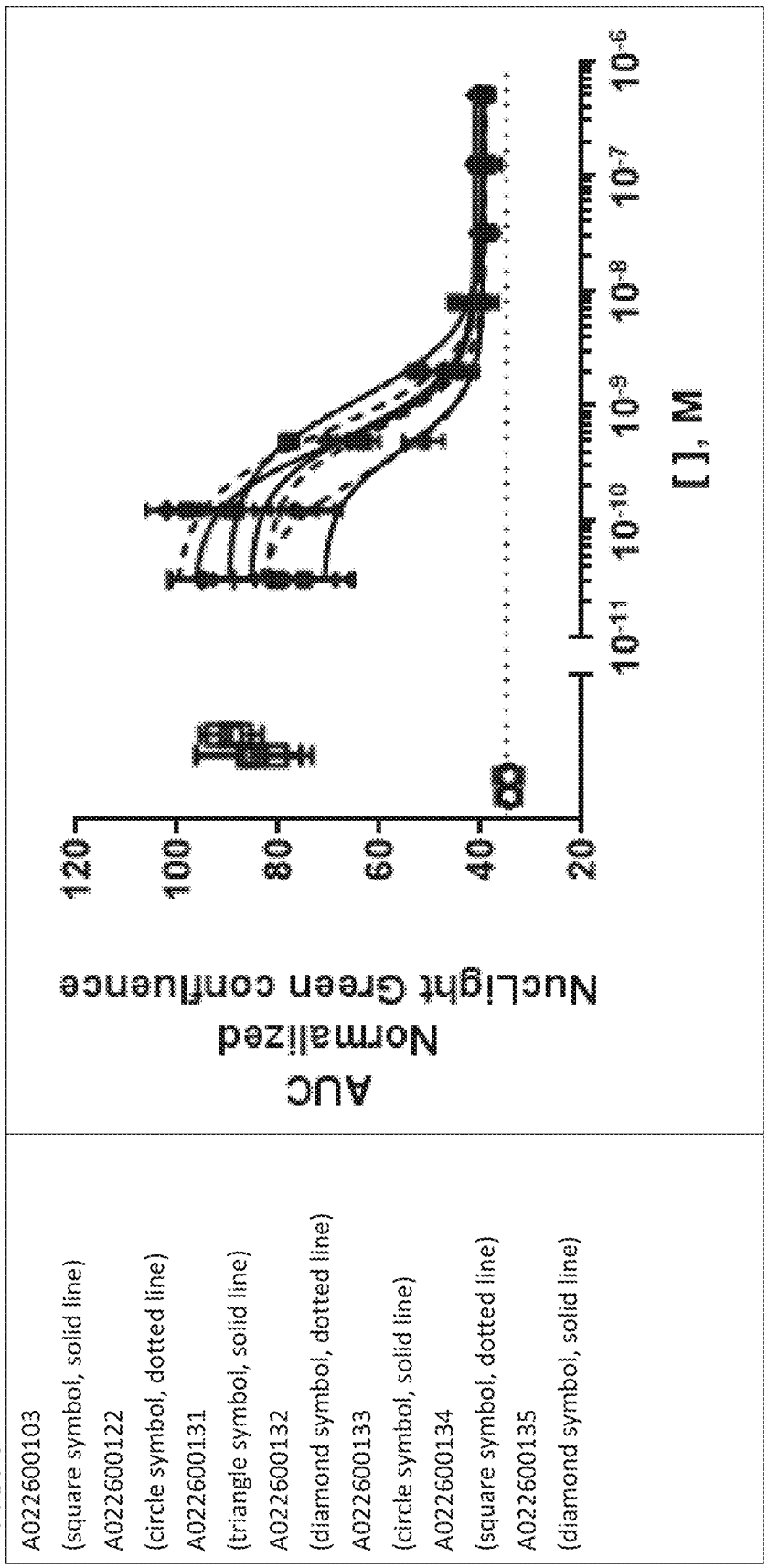

FIG. 3: Dose-dependent killing of the trispecific GPC3 ISVD T-cell engagers in the Incucyte based human TDC HepG2-Nuclight green assay using an effector to target ratio of 15:1, analyzed at 60 h after seeding. The Figure represents Step 2 of format optimization where trispecific tetravalent T-cell engager formats differ in the orientation of and the linker length between the biparatopic GPC3 binding ISVDs. Controls (left) are: No compound (open square) and reference for 100% killing (open circle).

FIGS. 4A-4B: Step 3 of GPC3 T-cell engager format optimization: the anti-TCR ISVD T017000624 was substituted by the sequenced optimized variant TCE01 in the trivalent and tetravalent formats. Dose-dependent killing of the trispecific GPC3 ISVD T-cell engagers in the Incucyte based human TDC HepG2-Nuclight green assay (FIG. 4A) and in the xCELLigence based human TDC Huh7 assay (FIG. 4B), using an effector to target ratio of 15:1, analyzed at 60 h after seeding. Controls (left) are: No compound (open square) and reference for 100% killing (open circle).

FIGS. 5A-5B: Dose-dependent killing of the trispecific GPC3 ISVD T-cell engagers in the Incucyte based human TDC HepG2-Nuclight green assay (FIG. 5A) and in the xCELLigence based human TDC Huh7 assay (FIG. 5B), using an effector to target ratio of 15:1, analyzed at 60 h after seeding. Step 4 of GPC3 T-cell engager format optimization is represented where the orientation of the anti-TCR ISVD was changed with the anti-GPC3 ISVD or the orientation of anti-GPC3 ISVD was changed with anti-Albumin ISVD. Controls (left) are: (open square) No compound and (open circle) reference for 100% killing.

FIGS. 6A-6B: Dose-dependent killing of the trispecific GPC3 ISVD T-cell engagers in the Incucyte based human TDC HepG2-Nuclight green assay (FIG. 6A) and in the xCELLigence based human TDC Huh7 assay (FIG. 6B), using an effector to target ratio of 15:1, analyzed at 60 h after seeding. Step 5 of GPC3 T-cell engager format optimization is represented where the linker lengths are varied. Controls (left) are: (open square) No compound and (open circle) reference for 100% killing.

FIGS. 7A-7C: Assessment of impact of soluble GPC3 (sGPC3) on cytotoxicity of the trispecific GPC3 ISVD T-cell engagers in the xCELLigence based human TDC Huh7 assay using an effector to target ratio of 15:1, analyzed at 60 h after seeding (FIG. 7A), and on T-cell activation by the trispecific GPC3 ISVD T-cell engagers in the presence (FIG. 7B) and absence (FIG. 7C) of target cells (Huh7). Controls (left) are: No compound (open circle, FIG. 7A) and isotype control (open circle, FIGS. 7B and 7C).

FIGS. 8A-8B: Time-course of T-cell engager internalization (FIG. 8A) and GPC3 expression (FIG. 8B) measured at 37° C. at time points 0.5 h, 3 h, 24 h and 48 h. Controls (left) are measurements at 0.5 h for each compound at 4° C.

FIGS. 9A-9F: Dose-dependent killing of the trispecific GPC3 T-cell engagers in the xCELLigence based human TDC assay on different tumor cell lines expressing decreasing expression levels of GPC3 using an effector to target ratio of 15:1: HepG2 analysed at 60 h (FIG. 9A), NCI-H661 analysed at 75 h (FIG. 9B), Huh-7 analysed at 60 h (FIG. 9C), MKN-45 analysed at 65 h (FIG. 9D), BxPC-3 analysed at 65 h (FIG. 9E), NCI-H292 analysed at 60 h (FIG. 9F). Controls (left) are: (open square) No compound (effector and T cells only).

FIGS. 10A-10B: Dose-dependent killing of the five selected trispecific GPC3 ISVD based T-cell engagers in the xCELLigence based human TDC assay on two tumor cell lines using an effector to target ratio of 15:1 and analyzed at 60 h, NCI-H661 (FIG. 10A) and BxPC-3 (FIG. 10B). Controls (left) are: No compound (open square, effector and T cells only) and T017000698 at 30 nM (open diamond).

Figure 11B:
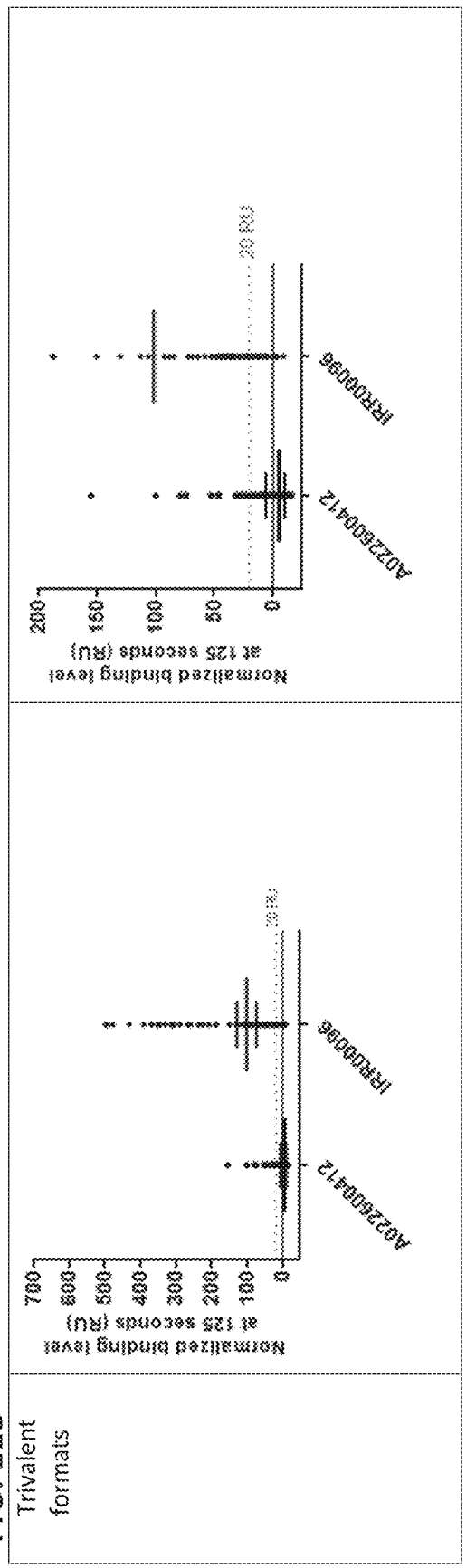

FIGS. 11A-11B: Median and interquartile range of the pre-existing antibody reactivity from 96 normal human serum samples on tetravalent (FIG. 11A) and trivalent (FIG. 11B) selected ISVD based GPC3 T-cell engager formats.

Figure 12:
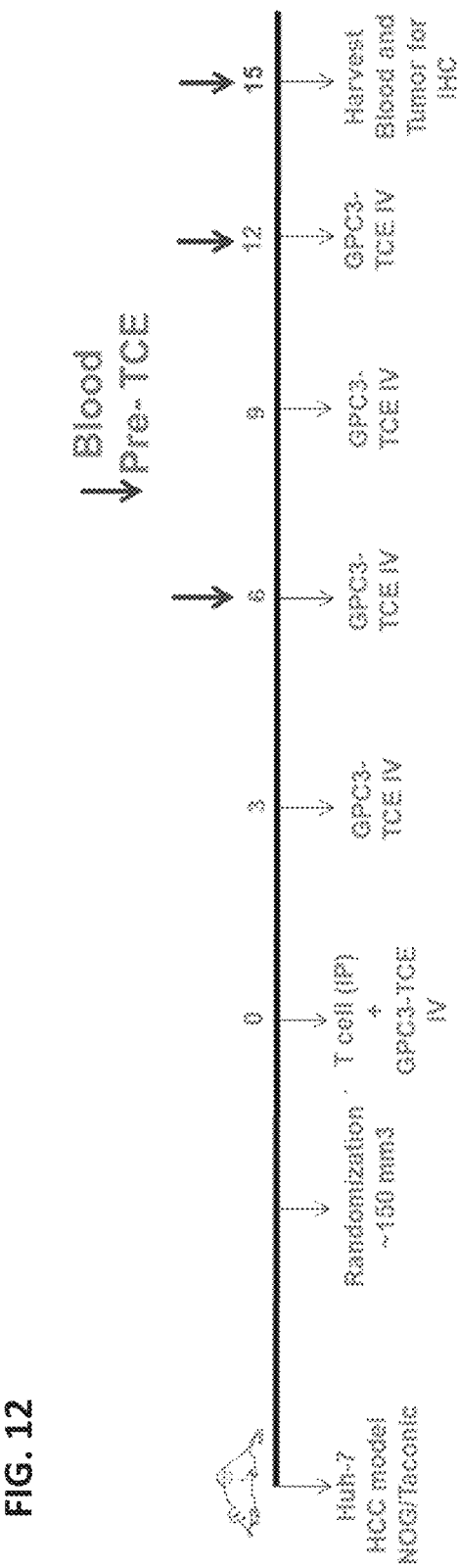

FIG. 12: Study design for efficacy model. Huh-7 tumor cells were subcutaneously injected in NOG mice. The tumors grew until the mean tumor volume of approximately 150 mm³ was reached. At this point, in vitro expanded T cells were injected into each mouse intraperitoneally (D0). The treatment with A022600424 injected intravenously started on D0, 3 h after T cell injection and continued on D3, D6, D9 and D12 (q3d). Four dose levels of A022600424 were tested (0.1 mg/kg, 0.2 mg/kg, 0.7 mg/kg and 2 mg/kg). The control T017000698 was injected in a control group at 2 mg/kg on D0, D3, D6, D9 and D12 (q3d). Survival blood sampling was done on D6 and D12 prior to administration of test compounds. All mice were sacrificed on D15, blood and tumor samples were collected.

Figure 13:
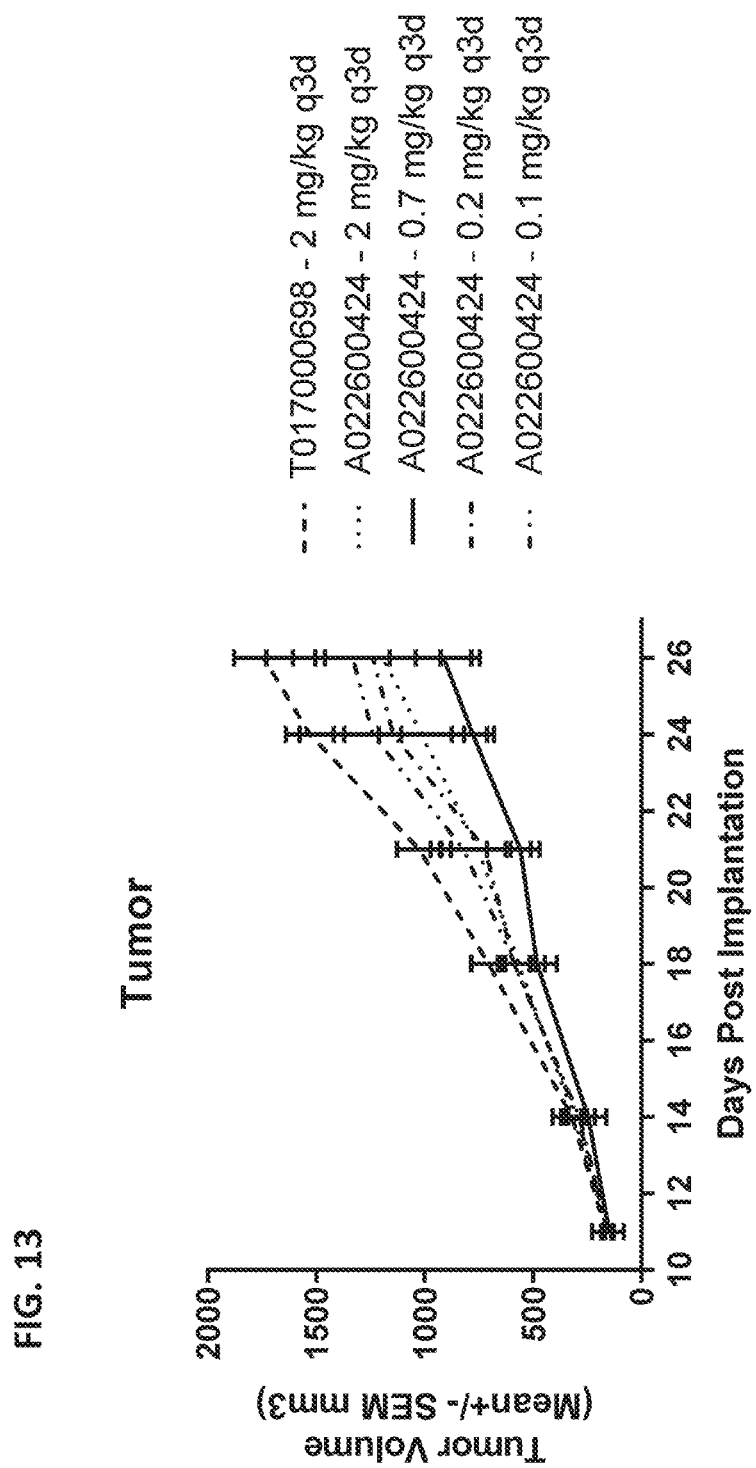

FIG. 13: Results of the efficacy model. Four dose levels of A022600424 were tested (0.1 mg/kg, 0.2 mg/kg, 0.7 mg/kg and 2 mg/kg). The control T017000698 was injected in a control group at 2 mg/kg.

5 DETAILED DESCRIPTION OF THE INVENTION

The present technology aims at providing a novel type of drug for treating cancer, such as liver cancer or lung cancer.

The present inventors found that a polypeptide targeting specifically GPC3 and TCR at the same time leads to efficient T cell-mediated killing of GPC3 expressing cells in vitro. Said polypeptides could be efficiently produced (e.g. in microbial hosts). Furthermore, such polypeptides could be shown to exhibit limited reactivity to pre-existing antibodies in the subject to be treated (i.e., antibodies present in the subject before the first treatment with the antibody construct). In preferred embodiments such polypeptides exhibit a half-life in the subject to be treated that is long enough such that consecutive treatments can be conveniently spaced apart. Moreover, such polypeptides showed only limited activity against cells expressing no or low levels of GPC3. This suggests the possibility of inducing a highly specific T cell-mediated cytotoxic response against GPC3 positive target cells.

Apart from the above, the GPC3-binding ISVDs disclosed herein provide high affinity-binding to human and cyno GPC3 and can thus be readily used in monovalent or multivalent form for other applications in which binding to GPC3 is required.

5.1 Polypeptides

Monospecific-Monovalent Polypeptides

In one aspect, the polypeptide is monospecific and monovalent.

The term "monospecific" refers to the binding to one (specific) type of target molecule(s). A monospecific polypeptide thus specifically binds to GPC3.

The term "monovalent" indicates the presence of only one binding units/building block that (specifically) targets a molecule, such as an ISVDs.

Accordingly, in one aspect the present technology provides a monospecific-monovalent polypeptide comprising or consisting of one ISVD that specifically binds to GPC3, preferably human GPC3, which comprises three complementarity determining regions (CDR1 to CDR3, respectively). The ISVD can be selected from an ISVD comprising:

a) a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15; or b) a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 16 or an amino acid sequence with 2 or 1 amino acid difference(s) with SEQ ID NO: 16.

Preferably, the ISVD specifically binding to GPC3 is selected from an ISVD comprising:

a) a CDR1 that is the amino acid sequence of SEQ ID NO: 7, a CDR2 that is the amino acid sequence of SEQ ID NO: 11 and a CDR3 that is the amino acid sequence of SEQ ID NO: 15; or b) a CDR1 that is the amino acid sequence of SEQ ID NO: 8, a CDR2 that is the amino acid sequence of SEQ ID NO: 12 and a CDR3 that is the amino acid sequence of SEQ ID NO: 16.

In a further embodiment of this aspect of the technology, the ISVD specifically binding to GPC3 is selected from an ISVD comprising:

a) an amino acid sequence with a sequence identity of more than 90% with SEQ ID NO: 3, preferably wherein the ISVD comprises or consists of the amino acid sequence of SEQ ID NO: 3; or b) an amino acid sequence with a sequence identity of more than 90% with SEQ ID NO: 4, preferably wherein the ISVD comprises or consists of the amino acid sequence of SEQ ID NO: 4.

In another aspect the present technology provides a monospecific-monovalent polypeptide comprising or consisting of one ISVD that specifically binds to the constant domain of a TCR on a T cell, preferably human TCR, which comprises three complementarity determining regions (CDR1 to CDR3, respectively). The ISVD can be an ISVD comprising a CDR1 that is the amino acid sequence of SEQ ID NO: 6 or an amino acid sequence with 2 or 1 amino acid difference(s) with SEQ ID NO: 6, a CDR2 that is the amino acid sequence of SEQ ID NO: 10 or an amino acid sequence with 2 or 1 amino acid difference(s) with SEQ ID NO: 10, and a CDR3 that is the amino acid sequence of SEQ ID NO: 14 or an amino acid sequence with 2 or 1 amino acid difference(s) with SEQ ID NO: 14.

Preferably, the ISVD specifically binding to TCR is an ISVD comprising a CDR1 that is the amino acid sequence of SEQ ID NO: 6, a CDR2 that is the amino acid sequence of SEQ ID NO: 10 and a CDR3 that is the amino acid sequence of SEQ ID NO: 14.

In a further embodiment of this aspect of the technology, the ISVD specifically binding to TCR is an ISVD comprising an amino acid sequence with a sequence identity of more than 90% with SEQ ID NO: 2, preferably wherein the ISVD comprises or consists of the amino acid sequence of SEQ ID NO: 2.

These monovalent compounds can also serve as building blocks for multivalent and/or multispecific polypeptides.

An ISVD located at the N-terminus of a (monovalent or multivalent) polypeptide comprising the same preferably does not exhibit glutamic acid (E) at its N-terminal end. Therefore, glutamic acid (E) at position 1 is typically substituted by aspartic acid (D) in an ISVD located at the N-terminus of the polypeptide. Thus, for example, if SEQ ID NOs: 3, 4 or 5 are located at the N-terminus of the polypeptide, these sequences will typically exhibit a E1D substitution. Conversely, if SEQ ID NO: 2 is not located at the N-terminus, this sequence will typically exhibit a D1E mutation. Thus, generally, the first position of SEQ ID NOs: 2-5 can be E or D, depending on whether these sequences are located at the N-terminus or not. In a preferred embodiment, the first amino acid of the first ISVD comprised in the polypeptide of the present technology is an aspartic acid (D).

Monospecific-Multivalent Polypeptides

In another aspect, the polypeptide is monospecific and at least bivalent, but can also be e.g., trivalent, tetravalent, pentavalent, hexavalent, etc.

The terms "bivalent", "trivalent", "tetravalent", "pentavalent", or "hexavalent" all fall under the term "multivalent" and indicate the presence of two, three, four, five or six binding units/building blocks, respectively, such as ISVDs.

Accordingly, in one aspect the present technology provides a monospecific-bivalent polypeptide comprising or consisting of two ISVDs that specifically bind to GPC3, preferably human GPC3, wherein each of the two ISVDs comprises three complementarity determining regions (CDR1 to CDR3, respectively), wherein the two ISVDs are preferably linked via one or more peptidic linkers, and wherein:

a) a first and a second ISVD comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15;

b) a first and a second ISVD comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 16 or an amino acid sequence with 2 or 1 amino acid difference(s) with SEQ ID NO: 16;

c) a first ISVD comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15, and
a second ISVD comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 16 or an amino acid sequence with 2 or 1 amino acid difference(s) with SEQ ID NO: 16; or d) a first ISVD comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 16 or an amino acid sequence with 2 or 1 amino acid difference(s) with SEQ ID NO: 16, and
a second ISVD comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15.

Preferably, the monospecific-bivalent polypeptide comprises or consists of two ISVDs that specifically bind to GPC3, wherein:

a) the first and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15;

b) the first and the second ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16;

c) the first ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, and the second ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16; or d) the first ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16, and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15.

In a further embodiment of this aspect of the technology, the monospecific-bivalent polypeptide comprises or consists of two ISVDs that specifically bind to GPC3, wherein:

a) the amino acid sequence of the first and the second ISVD exhibits a sequence identity of more than 90% with SEQ ID NO: 3, wherein the first and the second ISVD preferably consists of the amino acid sequence of SEQ ID NO: 3;

b) the amino acid sequence of the first and the second ISVD exhibits a sequence identity of more than 90% with SEQ ID NO: 4, wherein the first and the second ISVD preferably consists of the amino acid sequence of SEQ ID NO: 4:

c) the amino acid sequence of the first ISVD exhibits a sequence identity of more than 90% with SEQ ID NO: 3 and the second ISVD exhibits a sequence identity of more than 90% identity with SEQ ID NO: 4, preferably wherein the first ISVD consists of the amino acid sequence of SEQ ID NO: 3 and the second ISVD consists of the amino acid sequence of SEQ ID NO: 4; or d) the amino acid sequence of the first ISVD exhibits a sequence identity of more than 90% with SEQ ID NO: 4 and the second ISVD exhibits a sequence identity of more than 90% identity with SEQ ID NO: 3, preferably wherein the first ISVD consists of the amino acid sequence of SEQ ID NO: 4 and the second ISVD consists of the amino acid sequence of SEQ ID NO: 3.

The terms "first ISVD" and "second ISVD" in this regard only indicate the relative position of the specifically recited ISVDs binding to GPC3 to each other, wherein the numbering is started from the N-terminus of the polypeptide. The "first ISVD" is thus closer to the N-terminus than the "second ISVD". Accordingly, the "second ISVD" is thus closer to the C-terminus than the "first ISVD". Since the numbering is not absolute and only indicates the relative position of the two ISVDs it does not exclude the possibility that additional binding units/building blocks such as ISVDs binding to GPC3, TCR or serum albumin, respectively, can be present in the polypeptide. Moreover, it does not exclude the possibility that other binding units/building blocks such as ISVDs can be placed in between. For instance, as described further below (see in particular, section "multispecific-multivalent polypeptides" and 5.4 "(In vivo) half-life extension"), the polypeptide can further comprise another ISVD binding to human serum albumin that can even be located between the "first ISVD" and "second ISVD" (such a construct is then referred to as multispecific as described in the subsequent section).

In a preferred embodiment, the (at least two) ISVDs of the monospecific-multivalent polypeptides, in particular of the above described monospecific-bivalent polypeptides, are linked via peptidic linkers. The use of peptidic linkers to connect two or more (poly)peptides is well known in the art. Exemplary peptidic linkers that can be used with the monospecific-multivalent polypeptides, in particular with the above described monospecific-bivalent polypeptides, are shown in Table A-5. One often used class of peptidic linkers is known as the "Gly-Ser" or "GS" linkers. These are linkers that essentially consist of glycine (G) and serine (S) residues, and usually comprise one or more repeats of a peptide motif such as the GGGGS (SEQ ID NO: 100) motif (for example, exhibiting the formula (Gly-Gly-Gly-Gly-Ser)$_n$ in which n may be 1, 2, 3, 4, 5, 6, 7 or more). Some often used examples of such GS linkers are 9GS linkers (GGGGSGGGS, SEQ ID NO: 103) 15GS linkers (n=3) and 35GS linkers (n=7). Reference is for example made to Chen et al., Adv. Drug Deliv. Rev. 2013 Oct. 15; 65(10): 1357-1369; and Klein et al., Protein Eng. Des. Sel. (2014) 27 (10): 325-330. In one embodiment, the ISVDs of the monospecific-multivalent polypeptides, in particular the monospecific-bivalent polypeptides are linked via a linker set forth in Table A-5. In one embodiment, the (at least) two ISVDs are linked via a 35GS or a 9GS linker. In a preferred embodiment, the (at least) two ISVDs are linked via a 9GS linker(s).

Multispecific-Multivalent Polypeptides

In a further aspect, the polypeptide is at least bispecific, but can also be e.g., trispecific, tetraspecific, pentaspecific, etc. Moreover, the polypeptide is at least bivalent, but can also be e.g., trivalent, tetravalent, pentavalent, hexavalent, etc.

The terms "bispecific", "trispecific", "tetraspecific", "pentaspecific", etc., all fall under the term "multispecific" and refer to binding to two, three, four, five, etc., different target molecules, respectively.

The terms "bivalent", "trivalent", "tetravalent", "pentavalent", "hexavalent", etc. all fall under the term "multivalent" and indicate the presence of two, three, four, five, six, etc., binding units/building blocks, respectively, such as ISVDs.

For example, the polypeptide may be bispecific-bivalent, such as a polypeptide comprising or consisting of two ISVDs, wherein one ISVD specifically binds to GPC3 and one ISVD specifically binds to the constant domain of a TCR on a T cell, wherein the GPC3 and TCR are preferably human GPC3 and human TCR. The polypeptide may also be bispecific-trivalent, such as a polypeptide comprising or consisting of three ISVDs, wherein two ISVD specifically bind to GPC3 and one ISVD specifically binds to the constant domain of a TCR on a T cell, wherein the GPC3 and TCR are preferably human GPC3 and human TCR. In another example, the polypeptide may be trispecific-tetravalent, such as a polypeptide comprising or consisting of four ISVDs, wherein two ISVDs specifically bind to human GPC3, one ISVD specifically binds to the constant domain of a human TCR on a T cell and one ISVD binds to human serum albumin. Such a polypeptide may at the same time be biparatopic, for example if two ISVDs bind two different epitopes on human GPC3. The term "biparatopic" refers to binding to two different parts (e.g., epitopes) of the same target molecule. A preferred trispecific-tetravalent polypeptide is e.g., ISVD construct A022600424, comprising two ISVDs specifically binding to human GPC3, one ISVD specifically binding to the constant domain of a human TCR on a T cell, one ISVD binding to human serum albumin, and which is biparatopic for binding to GPC3.

In one embodiment, the present technology provides a bispecific-bivalent polypeptide comprising or consisting of at least two ISVDs, wherein each of said ISVDs comprises three complementarity determining regions (CDR1 to CDR3, respectively), wherein the at least two ISVDs are optionally linked via one or more peptidic linkers, and wherein:

a) a first ISVD comprises
 i. a CDR1 that is the amino acid sequence of SEQ ID NO: 6 or an amino acid sequence with 2 or 1 amino acid difference(s) with SEQ ID NO: 6;
 ii. a CDR2 that is the amino acid sequence of SEQ ID NO: 10 or an amino acid sequence with 2 or 1 amino acid difference(s) with SEQ ID NO: 10; and
 iii. a CDR3 that is the amino acid sequence of SEQ ID NO: 14 or an amino acid sequence with 2 or 1 amino acid difference(s) with SEQ ID NO: 14, and
 a second ISVD comprises
 iv. a CDR1 that is the amino acid sequence of SEQ ID NO: 7 or an amino acid sequence with 2 or 1 amino acid difference(s) with SEQ ID NO: 7;
 v. a CDR2 that is the amino acid sequence of SEQ ID NO: 11 or an amino acid sequence with 2 or 1 amino acid difference(s) with SEQ ID NO: 11; and
 vi. a CDR3 that is the amino acid sequence of SEQ ID NO: 15 or an amino acid sequence with 2 or 1 amino acid difference(s) with SEQ ID NO: 15, b) a first ISVD comprises
 i. a CDR1 that is the amino acid sequence of SEQ ID NO: 7 or an amino acid sequence with 2 or 1 amino acid difference(s) with SEQ ID NO: 7;
 ii. a CDR2 that is the amino acid sequence of SEQ ID NO: 11 or an amino acid sequence with 2 or 1 amino acid difference(s) with SEQ ID NO: 11; and
 iii. a CDR3 that is the amino acid sequence of SEQ ID NO: 15 or an amino acid sequence with 2 or 1 amino acid difference(s) with SEQ ID NO: 15, and
 a second ISVD comprises
 iv. a CDR1 that is the amino acid sequence of SEQ ID NO: 6 or an amino acid sequence with 2 or 1 amino acid difference(s) with SEQ ID NO: 6;
 v. a CDR2 that is the amino acid sequence of SEQ ID NO: 10 or an amino acid sequence with 2 or 1 amino acid difference(s) with SEQ ID NO: 10; and vi. a CDR3 that is the amino acid sequence of SEQ ID NO: 14 or an amino acid sequence with 2 or 1 amino acid difference(s) with SEQ ID NO: 14,
c) a first ISVD comprises
  i. a CDR1 that is the amino acid sequence of SEQ ID NO: 6 or an amino acid sequence with 2 or 1 amino acid difference(s) with SEQ ID NO: 6;
  ii. a CDR2 that is the amino acid sequence of SEQ ID NO: 10 or an amino acid sequence with 2 or 1 amino acid difference(s) with SEQ ID NO: 10; and
  iii. a CDR3 that is the amino acid sequence of SEQ ID NO: 14 or an amino acid sequence with 2 or 1 amino acid difference(s) with SEQ ID NO: 14, and
  a second ISVD comprises
  iv. a CDR1 that is the amino acid sequence of SEQ ID NO: 8 or an amino acid sequence with 2 or 1 amino acid difference(s) with SEQ ID NO: 8;
  v. a CDR2 that is the amino acid sequence of SEQ ID NO: 12 or an amino acid sequence with 2 or 1 amino acid difference(s) with SEQ ID NO: 12; and
  vi. a CDR3 that is the amino acid sequence of SEQ ID NO: 16 or an amino acid sequence with 2 or 1 amino acid difference(s) with SEQ ID NO: 16, or
d) a first ISVD comprises
  i. a CDR1 that is the amino acid sequence of SEQ ID NO: 8 or an amino acid sequence with 2 or 1 amino acid difference(s) with SEQ ID NO: 8;
  ii. a CDR2 that is the amino acid sequence of SEQ ID NO: 12 or an amino acid sequence with 2 or 1 amino acid difference(s) with SEQ ID NO: 12; and
  iii. a CDR3 that is the amino acid sequence of SEQ ID NO: 16 or an amino acid sequence with 2 or 1 amino acid difference(s) with SEQ ID NO: 16, and
  a second ISVD comprises
  iv. a CDR1 that is the amino acid sequence of SEQ ID NO: 6 or an amino acid sequence with 2 or 1 amino acid difference(s) with SEQ ID NO: 6;
  v. a CDR2 that is the amino acid sequence of SEQ ID NO: 10 or an amino acid sequence with 2 or 1 amino acid difference(s) with SEQ ID NO: 10; and
  vi. a CDR3 that is the amino acid sequence of SEQ ID NO: 14 or an amino acid sequence with 2 or 1 amino acid difference(s) with SEQ ID NO: 14.

In a preferred embodiment, such a polypeptide comprises or consists of at least two ISVDs, wherein each of said ISVDs comprises three complementarity determining regions (CDR1 to CDR3, respectively), wherein the at least two ISVDs are optionally linked via one or more peptidic linkers, and wherein
  a) the first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15,
  b) the first ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, and the second ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14,
  c) the first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, and the second ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16, or
  d) the first ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16, and the second ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14.

Thus, such a polypeptide can be a polypeptide, wherein:
  a) the amino acid sequence of the first ISVD exhibits a sequence identity of more than 90% with SEQ ID NO: 2, and the second ISVD exhibits a sequence identity of more than 90% identity with SEQ ID NO: 3,
  b) the amino acid sequence of the first ISVD exhibits a sequence identity of more than 90% with SEQ ID NO: 3, and the second ISVD exhibits a sequence identity of more than 90% identity with SEQ ID NO: 2
  c) the amino acid sequence of the first ISVD exhibits a sequence identity of more than 90% with SEQ ID NO: 2, and the second ISVD exhibits a sequence identity of more than 90% identity with SEQ ID NO: 4, or
  d) the amino acid sequence of the first ISVD exhibits a sequence identity of more than 90% with SEQ ID NO: 4, and the second ISVD exhibits a sequence identity of more than 90% identity with SEQ ID NO: 2.

Preferably, in such a polypeptide:
  a) the first ISVD consists of the amino acid sequence of SEQ ID NO: 2, and the second ISVD consists of the amino acid sequence of SEQ ID NO: 3,
  b) the first ISVD consists of the amino acid sequence of SEQ ID NO: 3, and the second ISVD consists of the amino acid sequence of SEQ ID NO: 2,
  c) the first ISVD consists of the amino acid sequence of SEQ ID NO: 2, and the second ISVD consists of the amino acid sequence of SEQ ID NO: 4, or
  d) the first ISVD consists of the amino acid sequence of SEQ ID NO: 4, and the second ISVD consists of the amino acid sequence of SEQ ID NO: 2.

In another aspect, the present technology provides a trispecific-trivalent polypeptide comprising the bispecific-bivalent polypeptides described above and a third ISVD binding to human serum albumin as described in detail below (section 5.4; "(In vivo) half-life extension").

In one embodiment, the present technology provides a bispecific-trivalent polypeptide comprising or consisting of at least three ISVDs, wherein each of said ISVDs comprises three complementarity determining regions (CDR1 to CDR3, respectively), wherein the at least three ISVDs are optionally linked via one or more peptidic linkers, and wherein:
  a) a first ISVD specifically binds the constant domain of a TCR on a T cell and comprises a CDR1 that is the amino acid sequence of SEQ ID NO: 6 or an amino acid sequence with 2 or 1 amino acid difference(s) with SEQ ID NO: 6, a CDR2 that is the amino acid sequence of SEQ ID NO: 10 or an amino acid sequence with 2 or 1 amino acid difference(s) with SEQ ID NO: 10, and a CDR3 that is the amino acid sequence of SEQ ID NO: 14 or an amino acid sequence with 2 or 1 amino acid difference(s) with SEQ ID NO: 14;

b) a second ISVD specifically binds GPC3 and comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15; and c) a third ISVD specifically binds GPC3 and comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 16 or an amino acid sequence with 2 or 1 amino acid difference(s) with SEQ ID NO: 16, wherein the TCR and GPC3 bound by said polypeptide is preferably human TCR and human GPC3, respectively.

In a preferred embodiment of the multispecific-multivalent polypeptide:

a) said first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14;

b) said second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15; and c) said third ISVD comprises a CDR1 being the amino acid sequence of SEQ ID NO: 8, a CDR2 being the amino acid sequence of SEQ ID NO: 12 and a CDR3 being the amino acid sequence of SEQ ID NO: 16.

In a further aspect of the multispecific-multivalent polypeptide:

a) the amino acid sequence of said first ISVD exhibits a sequence identity of more than 90% with SEQ ID NO: 2, wherein preferably said first ISVD consists of the amino acid sequence of SEQ ID NO: 2;

b) the amino acid sequence of said second ISVD exhibits a sequence identity of more than 90% with SEQ ID NO: 3, wherein preferably said second ISVD consists of the amino acid sequence of SEQ ID NO: 3; and c) the amino acid sequence of said third ISVD exhibits a sequence identity of more than 90% identity with SEQ ID NO: 4, wherein preferably said third ISVD consists of the amino acid sequence of SEQ ID NO: 4.

The terms "first ISVD", "second ISVD", "third ISVD", etc., in this regard only indicate the relative position of the ISVDs to each other, wherein the numbering is started from the N-terminus of the polypeptide. The "first ISVD" is thus closer to the N-terminus than the "second ISVD", whereas the "second ISVD" is closer to the N-terminus than the "third ISVD". Accordingly, the ISVD arrangement is inverse when considered from the C-terminus. Since the numbering is not absolute and only indicates the relative position of the at least four ISVDs it is not excluded that other binding units/building blocks such as additional ISVDs binding to GPC3, or ISVDs binding to another target may be present in the polypeptide. Moreover, it does not exclude the possibility that other binding units/building blocks such as ISVDs can be placed in between. For instance, as described further below (see in particular, section 5.4 "(In vivo) half-life extension" below), the polypeptide can further comprise another ISVD binding to human serum albumin that can even be located between e.g. the "third ISVD" and "fourth ISVD".

In a further aspect the present technology thus provides a trispecific-tetravalent polypeptide comprising the bispecific-trivalent polypeptides described above and a fourth ISVD binding to human serum albumin as described in detail below (section 5.4; "(In vivo) half-life extension").

In a preferred embodiment, the first ISVD binding to TCR is positioned at the N-terminus of the polypeptide.

In another aspect the present technology provides a bispecific-bivalent polypeptide comprising an ISVD that specifically binds to GPC3 as described in detail for the monospecific-monovalent polypeptides above (section 5.1; "Monospecific-monovalent polypeptides") and an ISVD binding to human serum albumin as described in detail below (section 5.4; "(In vivo) half-life extension").

In another aspect the present technology provides a bispecific-trivalent polypeptide comprising the monospecific-bivalent polypeptides above (section 5.1; "monospecific-bivalent polypeptides") and an ISVD binding to human serum albumin as described in detail below (section 5.4; "(In vivo) half-life extension").

The components, preferably ISVDs, of said multispecific-multivalent polypeptides described herein may be linked to each other by one or more suitable linkers, such as peptidic linkers.

The use of linkers to connect two or more (poly)peptides is well known in the art. Exemplary peptidic linkers are shown in Table A-5. One often used class of peptidic linker are known as the "Gly-Ser" or "GS" linkers. These are linkers that essentially consist of glycine (G) and serine (S) residues, and usually comprise one or more repeats of a peptide motif such as the GGGGS (SEQ ID NO: 100) motif (for example, exhibiting the formula (Gly-Gly-Gly-Gly-Ser)$_n$ in which n may be 1, 2, 3, 4, 5, 6, 7 or more). Some often used examples of such GS linkers are 9GS linkers (GGGGSGGGS, SEQ ID NO: 103) 15GS linkers (n=3) and 35GS linkers (n=7). Reference is for example made to Chen et al., Adv. Drug Deliv. Rev. 2013 Oct. 15; 65(10): 1357-1369; and Klein et al., Protein Eng. Des. Sel. (2014) 27 (10): 325-330. In the polypeptide(s) disclosed herein, the use of 5GS and 9GS linkers to link the components of the polypeptide to each other is preferred. Preferably, a linker of less than 10 amino acids, such as less than 6 amino acids, in particular a 5GS linker, is used to link a first ISVD specifically binding to TCR to a second ISVD specifically binding to GPC3.

In one aspect of the multispecific-multivalent polypeptide, the polypeptide comprising or consisting of at least three ISVDs, comprises the at least two ISVDs specifically binding to GPC3 and one ISVD specifically binding to TCR. In this aspect of the technology, the ISVD binding to TCR is linked to one of the at least two ISVDs binding to GPC3 via a 5GS linker, whereas the at least two ISVDs specifically binding to GPC3 are linked to each other via a 9GS linker. In further aspect, the multispecific-multivalent polypeptide further comprises an ISVD binding to albumin, which is further linked via a 9 GS linker to the ISVD binding to GPC3 that is not linked to the ISVD binding to TCR (as described in section 5.4 "(In vivo) half-life extension" below). The inventors surprisingly found that such a configuration can increase the efficiency of the polypeptide in eliciting a T cell-mediated cytotoxic response.

Accordingly, it is preferred that the polypeptide comprises or consists of the following, in the order starting from the N-terminus of the polypeptide: a first ISVD specifically binding to TCR, a second ISVD specifically binding to GPC3, a third ISVD specifically binding to GPC3, and an optional binding unit providing the polypeptide with increased half-life as defined herein. The binding unit providing the polypeptide with increased half-life is preferably an ISVD, that preferably binds to serum albumin.

It is even more preferred that the polypeptide comprises or consists of the following, in the order starting from the N-terminus of the polypeptide: an ISVD specifically binding to TCR, a linker, a second ISVD specifically binding to GPC3, a linker, a third ISVD specifically binding to GPC3, a linker, and an ISVD binding to human serum albumin, wherein the linker between the first and second ISVDs is preferably a 5GS linker, whereas the other linkers are preferably 9GS linkers.

Such configurations of the polypeptide can provide for strong potencies with regard to treating cancer as well as low binding to pre-existing antibodies.

Preferably, the multispecific-multivalent polypeptide exhibits reduced binding by pre-existing antibodies in human serum. To this end, in one embodiment, the polypeptide exhibits a valine (V) at amino acid position 11 and a leucine (L) at amino acid position 89 (according to Kabat numbering) in at least one ISVD (and preferably the ISVD at the C-terminal end of the polypeptide), but preferably in each ISVD. In another embodiment, the polypeptide exhibits an extension of 1 to 5 (preferably naturally occurring) amino acids, such as a single alanine (A) extension, at the C-terminus of the C-terminal ISVD. The C-terminus of an ISVD is normally VTVSS (SEQ ID NO: 116). In another embodiment, the polypeptide exhibits a lysine (K) or glutamine (Q) at position 110 (according to Kabat numbering) in at least one ISVD. In another embodiment, the ISVD exhibits a lysine (K) or glutamine (Q) at position 112 (according to Kabat numbering) in at least on ISVD. In these embodiments, the C-terminus of the ISVD is VKVSS (SEQ ID NO: 117), VQVSS (SEQ ID NO: 118), VTVKS (SEQ ID NO: 119), VTVQS (SEQ ID NO: 120), VKVKS (SEQ ID NO: 121), VKVQS (SEQ ID NO: 122), VQVKS (SEQ ID NO: 123), or VQVQS (SEQ ID NO: 124) such that after addition of a single alanine the C-terminus of the polypeptide for example exhibits the sequence VTVSSA (SEQ ID NO: 125), VKVSSA (SEQ ID NO: 126), VQVSSA (SEQ ID NO: 127), VTVKSA (SEQ ID NO: 128), VTVQSA (SEQ ID NO: 129), VKVKSA (SEQ ID NO: 130), VKVQSA (SEQ ID NO: 131), VQVKSA (SEQ ID NO: 132), or VQVQSA (SEQ ID NO: 133), preferably VTVSSA (see Table A-7). In another embodiment, the polypeptide exhibits a valine (V) at amino acid position 11 and a leucine (L) at amino acid position 89 (according to Kabat numbering) in at least the C-terminal ISVD, optionally a lysine (K) or glutamine (Q) at position 110 (according to Kabat numbering) in at least one ISVD, and exhibits an extension of 1 to 5 (preferably naturally occurring) amino acids, such as a single alanine (A) extension, at the C-terminus of the C-terminal ISVD (such that the C-terminus of the polypeptide for example consists of the sequence VTVSSA, VKVSSA or VQVSSA, preferably VTVSSA). See e.g. WO2012/175741 and WO2015/173325 for further information in this regard.

In a preferred embodiment, the multispecific-multivalent polypeptide comprises or consists of an amino acid sequence exhibiting a sequence identity of more than 90%, such as more than 95% or more than 99%, with SEQ ID NO: 1, wherein more preferably the CDRs of the four ISVDs are as defined in items A to D using the Abm definition (or A' to D' if using the Kabat definition) set forth in sections "5.2 Immunoglobulin single variable domains" and "5.4 (In vivo) half-life extension" below, respectively, wherein in particular:

- the first ISVD specifically binding to the constant domain of a TCR on a T cell comprises a CDR1 being the amino acid sequence of SEQ ID NO: 6, a CDR2 being the amino acid sequence of SEQ ID NO: 10 and a CDR3 being the amino acid sequence of SEQ ID NO: 14;
- the second ISVD specifically binding to GPC3 comprises a CDR1 being the amino acid sequence of SEQ ID NO: 7, a CDR2 being the amino acid sequence of SEQ ID NO: 11 and a CDR3 being the amino acid sequence of SEQ ID NO: 15;
- the third ISVD specifically binding to GPC3 comprises a CDR1 being the amino acid sequence of SEQ ID NO: 8, a CDR2 being the amino acid sequence of SEQ ID NO: 12 and a CDR3 being the amino acid sequence of SEQ ID NO: 16; and
- the fourth ISVD binding to human serum albumin comprises a CDR1 being the amino acid sequence of SEQ ID NO: 9, a CDR2 being the amino acid sequence of SEQ ID NO: 13 and a CDR3 being the amino acid sequence of SEQ ID NO: 17, or alternatively if using the Kabat definition:

- the first ISVD specifically binding to TCR comprises a CDR1 being the amino acid sequence of SEQ ID NO: 31, a CDR2 being the amino acid sequence of SEQ ID NO: 35 and a CDR3 being the amino acid sequence of SEQ ID NO: 14;
- the second ISVD specifically binding to GPC3 comprises a CDR1 being the amino acid sequence of SEQ ID NO: 32, a CDR2 being the amino acid sequence of SEQ ID NO: 36 and a CDR3 being the amino acid sequence of SEQ ID NO: 15;
- the third ISVD specifically binding to GPC3 comprises a CDR1 being the amino acid sequence of SEQ ID NO: 33, a CDR2 being the amino acid sequence of SEQ ID NO: 37 and a CDR3 being the amino acid sequence of SEQ ID NO: 16; and
- the fourth ISVD binding to human serum albumin comprises a CDR1 being the amino acid sequence of SEQ ID NO: 34, a CDR2 being the amino acid sequence of SEQ ID NO: 38 and a CDR3 being the amino acid sequence of SEQ ID NO: 17.

In some aspects, the polypeptide comprises or consists of an amino acid sequence selected from SEQ ID NOs: 1, 49-72 and 78-81.

Preferably, the polypeptide comprises or consists of the amino acid sequence of SEQ ID NO: 1 (see Table A-3). In a most preferred embodiment, the polypeptide consists of the amino acid sequence of SEQ ID NO: 1.

The polypeptide preferably exhibits at least half the binding affinity, more preferably at least the same binding affinity, to human TCR and to human GPC3 as compared to a polypeptide consisting of the amino acid of SEQ ID NO: 1 wherein the binding affinity is measured using the same method, such as Surface Plasmon Resonance (SPR).

5.2 Immunoglobulin Single Variable Domains

The term "immunoglobulin single variable domain" (ISVD), interchangeably used with "single variable domain", defines immunoglobulin molecules wherein the antigen binding site is present on, and formed by, a single immunoglobulin domain. This sets immunoglobulin single variable domains apart from "conventional" immunoglobulins (e.g. monoclonal antibodies) or their fragments (such as Fab, Fab', $F(ab')_2$, scFv, di-scFv), wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')$_2$ fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a $V_H$-$V_L$ pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single $V_H$, a single $V_{HH}$ or single $V_L$ domain.

As such, the single variable domain may be a light chain variable domain sequence (e.g., a $V_L$-sequence) or a suitable fragment thereof; or a heavy chain variable domain sequence (e.g., a $V_H$-sequence or $V_{HH}$ sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

An immunoglobulin single variable domain (ISVD) can for example be a heavy chain ISVD, such as a $V_H$, $V_{HH}$, including a camelized $V_H$ or humanized $V_{HH}$. Preferably, it is a $V_{HH}$, including a camelized $V_H$ or humanized $V_{HH}$. Heavy chain ISVDs can be derived from a conventional four-chain antibody or from a heavy chain antibody.

For example, the immunoglobulin single variable domain may be a single domain antibody (or an amino acid sequence that is suitable for use as a single domain antibody), a "dAb" or dAb (or an amino acid sequence that is suitable for use as a dAb); other single variable domains, or any suitable fragment of any one thereof.

In particular, the immunoglobulin single variable domain may be an immunoglobulin single variable domain (such as a $V_{HH}$, including a humanized $V_{HH}$ or camelized $V_H$) or a suitable fragment thereof. Nanobody®, Nanobodies® and Nanoclone® are registered trademarks of Ablynx N.V.

"$V_{HH}$ domains", also known as $V_{HH}$S, $V_{HH}$ antibody fragments, and $V_{HH}$ antibodies, have originally been described as the antigen binding immunoglobulin variable domain of "heavy chain antibodies" (i.e., of "antibodies devoid of light chains"; Hamers-Casterman et al. Nature 363: 446-448, 1993). The term "$V_{HH}$ domain" has been chosen in order to distinguish these variable domains from the heavy chain variable domains that are present in conventional 4-chain antibodies (which are referred to herein as "$V_H$ domains") and from the light chain variable domains that are present in conventional 4-chain antibodies (which are referred to herein as "$V_L$ domains"). For a further description of $V_{HH}$'s, reference is made to the review article by Muyldermans (Reviews in Molecular Biotechnology 74: 277-302, 2001).

Typically, the generation of immunoglobulins involves the immunization of experimental animals, fusion of immunoglobulin producing cells to create hybridomas and screening for the desired specificities. Alternatively, immunoglobulins can be generated by screening of naïve or synthetic libraries e.g. by phage display.

The generation of immunoglobulin sequences has been described extensively in various publications, among which WO 94/04678, Hamers-Casterman et a. 1993 and Muyldermans et al. 2001 can be exemplified. In these methods, camelids are immunized with the target antigen in order to induce an immune response against said target antigen. The repertoire of VHHs obtained from said immunization is further screened for VHHs that bind the target antigen.

In these instances, the generation of antibodies requires purified antigen for immunization and/or screening. Antigens can be purified from natural sources, or in the course of recombinant production.

Immunization and/or screening for immunoglobulin sequences can be performed using peptide fragments of such antigens.

The present technology may use immunoglobulin sequences of different origin, comprising mouse, rat, rabbit, donkey, human and camelid immunoglobulin sequences. The technology also includes fully human, humanized or chimeric sequences. For example, the technology comprises camelid immunoglobulin sequences and humanized camelid immunoglobulin sequences, or camelized domain antibodies, e.g. camelized dAb as described by Ward et al (see for example WO 94/04678 and Davies and Riechmann (1994 and 1996)). Moreover, the technology also uses fused immunoglobulin sequences, e.g. forming a multivalent and/or multispecific construct (for multivalent and multispecific polypeptides containing one or more $V_{HH}$ domains and their preparation, reference is also made to Conrath et al., J. Biol. Chem., Vol. 276, 10. 7346-7350, 2001, as well as to for example WO 96/34103 and WO 99/23221), and immunoglobulin sequences comprising tags or other functional moieties, e.g. toxins, labels, radiochemicals, etc., which are derivable from the immunoglobulin sequences of the present technology.

A "humanized $V_{HH}$" comprises an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art (e.g. WO 2008/020079). Again, it should be noted that such humanized $V_{HH}$S can be obtained in any suitable manner known per se and thus are not strictly limited to polypeptides that have been obtained using a polypeptide that comprises a naturally occurring VHH domain as a starting material.

A "camelized $V_H$" comprises an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description herein and the prior art (e.g. WO 2008/020079). Such "camelizing" substitutions are preferably inserted at amino acid positions that form and/or are present at the $V_H$-$V_L$ interface, and/or at the so-called Camelidae hallmark residues, as defined herein (see for example WO 94/04678 and Davies and Riechmann (1994 and 1996), supra). Preferably, the $V_H$ sequence that is used as a starting material or starting point for generating or designing the camelized $V_H$ is preferably a $V_H$ sequence from a mammal, more preferably the $V_H$ sequence of a human being, such as a $V_H3$ sequence. However, it should be noted that such camelized $V_H$ can be obtained in any suitable manner known per se and thus are not strictly limited to polypeptides that have been obtained using a polypeptide that comprises a naturally occurring $V_H$ domain as a starting material.

A preferred structure of an immunoglobulin single variable domain sequence can be considered to be comprised of four framework regions ("FRs"), which are referred to in the art and herein as "Framework region 1" ("FR1"); as "Framework region 2" ("FR2"); as "Framework region 3" ("FR3"); and as "Framework region 4" ("FR4"), respectively; which framework regions are interrupted by three complementary determining regions ("CDRs"), which are referred to in the art and herein as "Complementarity Determining Region 1" ("CDR1"); as "Complementarity Determining Region 2" ("CDR2"); and as "Complementarity Determining Region 3" ("CDR3"), respectively.

As further described in paragraph q) on pages 58 and 59 of WO 08/020079, the amino acid residues of an immunoglobulin single variable domain can be numbered according to the general numbering for $V_H$ domains given by Kabat et al. ("Sequence of proteins of immunological interest", US Public Health Services, NIH Bethesda, MD, Publication No. 91), as applied to $V_{HH}$ domains from Camelids in the article of Riechmann and Muyldermans, 2000 (J. Immunol. Methods 240 (1-2): 185-195; see for example FIG. 2 of this publication). It should be noted that—as is well known in the art for $V_H$ domains and for $V_{HH}$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a $V_H$ domain and a $V_{HH}$ domain will usually be in the range of from 110 to 120, often between 112 and 115. It should however be noted that smaller and longer sequences may also be suitable for the purposes described herein.

In the present application, unless indicated otherwise, CDR sequences were determined according to the AbM definition as described in Kontermann and Dübel (Eds. 2010, Antibody Engineering, vol 2, Springer Verlag Heidelberg Berlin, Martin, Chapter 3, pp. 33-51). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

Determination of CDR regions may also be done according to different methods. In the CDR determination according to Kabat, FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

In such an immunoglobulin sequence, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence or $V_{HH}$ sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

In particular, the framework sequences present in the ISVD sequence used in the technology may contain one or more of hallmark residues (as defined herein), such that the ISVD sequence is a $V_{HH}$, including a humanized $V_{HH}$ or camelized $V_H$. Some preferred, but non-limiting examples of (suitable combinations of) such framework sequences will become clear from the further disclosure herein.

Again, as generally described herein for the immunoglobulin sequences, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived).

However, it should be noted that the technology is not limited as to the origin of the ISVD sequence (or of the nucleotide sequence used to express it), nor as to the way that the ISVD sequence or nucleotide sequence is (or has been) generated or obtained. Thus, the ISVD sequences may be naturally occurring sequences (from any suitable species) or synthetic or semi-synthetic sequences. In a specific but non-limiting aspect, the ISVD sequence is a naturally occurring sequence (from any suitable species) or a synthetic or semi-synthetic sequence, including but not limited to "humanized" (as defined herein) immunoglobulin sequences (such as partially or fully humanized mouse or rabbit immunoglobulin sequences, and in particular partially or fully humanized $V_{HH}$ sequences), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

Similarly, nucleotide sequences may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

As described above, an ISVD may be a Nanobody® or a suitable fragment thereof. For a general description of Nanobodies, reference is made to the further description below, as well as to the prior art cited herein. In this respect, it should however be noted that this description and the prior art mainly described Nanobodies of the so-called "$V_H3$ class" (i.e. Nanobodies with a high degree of sequence homology to human germline sequences of the $V_H3$ class such as DP-47, DP-51 or DP-29). It should however be noted that the technology in its broadest sense can generally use any type of Nanobody, and for example also uses the Nanobodies belonging to the so-called "$V_H4$ class" (i.e. Nanobodies with a high degree of sequence homology to human germline sequences of the $V_H4$ class such as DP-78), as for example described in WO 2007/118670.

Generally, Nanobodies (in particular $V_{HH}$ sequences, including (partially) humanized $V_{HH}$ sequences and camelized $V_H$ sequences) can be characterized by the presence of one or more "Hallmark residues" (as described herein) in one or more of the framework sequences (again as further described herein). Thus, generally, a Nanobody can be defined as an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
one or more of the amino acid residues at positions 11, 37, 44, 45, 47, 83, 84, 103, 104 and 108 according to the Kabat numbering are chosen from the Hallmark residues mentioned in Table A-0 below.

TABLE A-0

Hallmark Residues in Nanobodies

| Position | Human Vh3 | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | $F^{(1)}$, Y, V, L, A, H, S, I, W, C, N, G, D, T, P, preferably $F^{(1)}$ or Y |
| 44$^{(8)}$ | G | $E^{(3)}$, $Q^{(3)}$, $G^{(2)}$, D, A, K, R, L, P, S, V, H, T, N, W, M, I; preferably $G^{(2)}$, $E^{(3)}$ or $Q^{(3)}$; most preferably $G^{(2)}$ or $Q^{(3)}$. |
| 45$^{(8)}$ | L | $L^{(2)}$, $R^{(3)}$, P, H, F, G, Q, S, E, T, Y, C, I, D, V; preferably $L^{(2)}$ or $R^{(3)}$ |
| 47$^{(8)}$ | W, Y | $F^{(1)}$, $L^{(1)}$ or $W^{(2)}$ G, I, S, A, V, M, R, Y, E, P, T, C, H, K, Q, N, D; preferably $W^{(2)}$, $L^{(1)}$ or $F^{(1)}$ |
| 83 | R or K; usually R | R, $K^{(5)}$, T, $E^{(5)}$, Q, N, S, I, V, G, M, L, A, D, Y, H; preferably K or R; most preferably K |
| 84 | A, T, D; predominantly A | $P^{(5)}$, S, H, L, A, V, I, T, F, D, R, Y, N, Q, G, E; preferably P |
| 103 | W | $W^{(4)}$, $R^{(6)}$, G, S, K, A, M, Y, L, F, T, N, V, Q, $P^{(6)}$, E, C; preferably W |
| 104 | G | G, A, S, T, D, P, N, E, C, L; preferably G |
| 108 | L, M or T; predominantly L | Q, $L^{(7)}$, R, P, E, K, S, T, M, A, H; preferably Q or $L^{(7)}$ |

Notes:
$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.
$^{(4)}$With both GLEW at positions 44-47 and KERE or KQRE at positions 43-46.
$^{(5)}$Often as KP or EP at positions 83-84 of naturally occurring $V_{HH}$ domains.
$^{(6)}$In particular, but not exclusively, in combination with GLEW at positions 44-47.
$^{(7)}$With the proviso that when positions 44-47 are GLEW, position 108 is always Q in (non-humanized) $V_{HH}$ sequences that also contain a W at 103.
$^{(8)}$The GLEW group also contains GLEW-like sequences at positions 44-47, such as for example GVEW, EPEW, GLER, DQEW, DLEW, GIEW, ELEW, GPEW, EWLP, GPER, GLER and ELEW.

The technology inter alia uses ISVDs that can bind to the constant domain of a TCR or GPC3. In the context of the present technology, "binding to" a certain target molecule has the usual meaning in the art as understood in the context of antibodies and their respective antigens.

The multispecific-multivalent polypeptide may comprise one or more ISVDs specifically binding to GPC3. For example, the polypeptide may comprise two ISVDs that specifically bind to GPC3 and an ISVD that specifically binds to TCR.

The ISVDs used in the technology can form part of a polypeptide, which comprises or consists of at least two ISVDs, such that the polypeptide can specifically bind to GPC3 and TCR.

Accordingly, the target molecules of the ISVDs used in the technology are GPC3 and the constant domain of the TCR, respectively. Binding to TCR can be achieved, for example, by binding to the TCRalpha subunit and/or the TCR beta subunit. Examples are mammalian GPC3 and TCR. While human GPC3 (Uniprot accession P51654, see Table A-8) and human TCR (see Table A-8) are preferred, the versions from other species are also amenable to the present technology, for example GPC3 and TCR from mice, rats, rabbits, cats, dogs, goats, sheep, horses, pigs, non-human primates, such as cynomolgus monkeys (also referred to herein as "cyno"), or camelids, such as llama or alpaca.

Specific examples of ISVDs specifically binding to the constant domain of a TCR on a T cell that can be used in the technology are as described in the following item A:

A. An ISVD that specifically binds to human TCR and comprises
   i. a CDR1 that is the amino acid sequence of SEQ ID NO: 6 or an amino acid sequence with 2 or 1 amino acid difference(s) with SEQ ID NO: 6;
   ii. a CDR2 that is the amino acid sequence of SEQ ID NO: 10 or an amino acid sequence with 2 or 1 amino acid difference(s) with SEQ ID NO: 10; and
   iii. a CDR3 that is the amino acid sequence of SEQ ID NO: 14 or an amino acid sequence with 2 or 1 amino acid difference(s) with SEQ ID NO: 14,
   preferably a CDR1 being the amino acid sequence of SEQ ID NO: 6, a CDR2 being the amino acid sequence of SEQ ID NO: 10 and a CDR3 being the amino acid sequence of SEQ ID NO: 14.

In a preferred embodiment, the ISVD binds to the constant domain of a human TCR-α of SEQ ID NO: 135 and/or of a TCR-β of SEQ ID NO: 136, or polymorphic variants or isoforms thereof.

Preferred examples of such an ISVD that specifically binds to human TCR comprise one or more (and preferably all) framework regions as indicated for ISVD TCE01 in Table A-2 (in addition to the CDRs as defined in the preceding item A), and most preferred is an ISVD that consists of the full amino acid sequence of ISVD TCE01 (SEQ ID NO: 2; see Table A-1 and A-2).

Also, in a preferred embodiment, the amino acid sequence of the ISVD specifically binding to human TCR may exhibit a sequence identity of more than 90%, such as more than 95% or more than 99%, with SEQ ID NO: 2, wherein the CDRs are as defined in the preceding item A. In particular, the ISVD specifically binding to TCR most preferably is the amino acid sequence of SEQ ID NO: 2.

When such an ISVD binding to TCR exhibits 2 or 1 amino acid difference in at least one CDR relative to a corresponding reference CDR sequence (item A above), the ISVD preferably exhibits at least half the binding affinity, more preferably at least the same binding affinity to human TCR as the construct TCE01 set forth in SEQ ID NO: 2, wherein the binding affinity is measured using the same method, such as SPR.

Specific examples of ISVDs specifically binding to GPC3 that can be used in the technology are as described in the following items B and C:

B. An ISVD that specifically binds to human GPC3 and comprises
   i. a CDR1 that is the amino acid sequence of SEQ ID NO: 7 or an amino acid sequence with 2 or 1 amino acid difference(s) with SEQ ID NO: 7;
   ii. a CDR2 that is the amino acid sequence of SEQ ID NO: 11 or an amino acid sequence with 2 or 1 amino acid difference(s) with SEQ ID NO: 11; and
   iii. a CDR3 that is the amino acid sequence of SEQ ID NO: 15 or an amino acid sequence with 2 or 1 amino acid difference(s) with SEQ ID NO: 15,
   preferably a CDR1 being the amino acid sequence of SEQ ID NO: 7, a CDR2 being the amino acid sequence of SEQ ID NO: 11 and a CDR3 being the amino acid sequence of SEQ ID NO: 15.

C. An ISVD that specifically binds to human GPC3 and comprises
   i. a CDR1 that is the amino acid sequence of SEQ ID NO: 8 or an amino acid sequence with 2 or 1 amino acid difference(s) with SEQ ID NO: 8;
   ii. a CDR2 that is the amino acid sequence of SEQ ID NO: 12 or an amino acid sequence with 2 or 1 amino acid difference(s) with SEQ ID NO: 12; and
   iii. a CDR3 that is the amino acid sequence of SEQ ID NO: 16 or an amino acid sequence with 2 or 1 amino acid difference(s) with SEQ ID NO: 16,
   preferably a CDR1 being the amino acid sequence of SEQ ID NO: 8, a CDR2 being the amino acid sequence of SEQ ID NO: 12 and a CDR3 being the amino acid sequence of SEQ ID NO: 16.

In a preferred embodiment, the ISVD binds to human GPC3 of SEQ ID NO: 134.

Preferred examples of such an ISVD that specifically binds to human GPC3 comprise one or more (and preferably all) framework regions as indicated for ISVD A022600351 and A022600314, respectively, in Table A-2 (in addition to the CDRs as defined in the preceding items B and C, respectively), and most preferred is an ISVD that consists of the full amino acid sequence of ISVD A022600351 or A022600314 (SEQ ID NOs: 3 or 4, see Table A-1 and A-2).

Also, in a preferred embodiment, the amino acid sequence of an ISVD(s) specifically binding to human GPC3 may exhibit a sequence identity of more than 90%, such as more than 95% or more than 99%, with SEQ ID NO: 3 or 4, respectively, wherein the CDRs are as defined in the preceding item B or C, respectively. In particular, the ISVD binding to human GPC3 most preferably is the amino acid sequence of SEQ ID NOs: 3 or 4.

When such an ISVD binding to human GPC3 exhibits 2 or 1 amino acid difference in at least one CDR relative to a corresponding reference CDR sequence (item B or C above), the ISVD preferably exhibits at least half the binding affinity, more preferably at least the same binding affinity to human GPC3 as construct A022600351 or A022600314 set forth in SEQ ID NO: 3 and 4, respectively, wherein the binding affinity is measured using the same method, such as SPR.

Preferably, each of the ISVDs as defined under items A to C above is comprised in the polypeptide.

Such a polypeptide comprising each of the ISVDs as defined under items A to C above preferably exhibits at least half the binding affinity, more preferably at least the same binding affinity, to human TCR and to human GPC3 as a polypeptide consisting of the amino acid of SEQ ID NO: 1, wherein the binding affinity is measured using the same method, such as SPR.

The SEQ ID NOs referred to in the above items A to C and item D below (see section 5.4 "(In vivo) half-life extension") are based on the CDR definition according to the AbM definition (see Table A-2). It is noted that the SEQ ID NOs defining the same CDRs according to the Kabat definition (see Table A-2-1) can likewise be used in the above items A to C and item D below (see section 5.4 "(In vivo) half-life extension").

Accordingly, the specific examples of ISVDs specifically binding to the constant domain of a TCR on a T cell or GPC3 that can be used in the technology are as described above using the AbM definition can be also described using the Kabat definition as set forth in items A' to C' below:

A'. An ISVD that specifically binds to human TCR and comprises
  i. a CDR1 that is the amino acid sequence of SEQ ID NO: 31 or an amino acid sequence with 2 or 1 amino acid difference(s) with SEQ ID NO: 31;
  ii. a CDR2 that is the amino acid sequence of SEQ ID NO: 35 or an amino acid sequence with 2 or 1 amino acid difference(s) with SEQ ID NO: 35; and
  iii. a CDR3 that is the amino acid sequence of SEQ ID NO: 14 or an amino acid sequence with 2 or 1 amino acid difference(s) with SEQ ID NO: 14,
  preferably a CDR1 being the amino acid sequence of SEQ ID NO: 31, a CDR2 being the amino acid sequence of SEQ ID NO: 35 and a CDR3 being the amino acid sequence of SEQ ID NO: 14.

Preferred examples of such an ISVD that specifically binds to human TCR comprise one or more (and preferably all) framework regions as indicated for ISVD TCE01, respectively, in Table A-2-1 (in addition to the CDRs as defined in the preceding item A'), and most preferred is an ISVD that consists of the full amino acid sequence of ISVD TCE01 (SEQ ID NO: 2; see Table A-1 and A-2-1).

B'. An ISVD that specifically binds to human GPC3 and comprises
  i. a CDR1 that is the amino acid sequence of SEQ ID NO: 32 or an amino acid sequence with 2 or 1 amino acid difference(s) with SEQ ID NO: 32;
  ii. a CDR2 that is the amino acid sequence of SEQ ID NO: 36 or an amino acid sequence with 2 or 1 amino acid difference(s) with SEQ ID NO: 36; and
  iii. a CDR3 that is the amino acid sequence of SEQ ID NO: 15 or an amino acid sequence with 2 or 1 amino acid difference(s) with SEQ ID NO: 15,
  preferably a CDR1 being the amino acid sequence of SEQ ID NO: 32, a CDR2 being the amino acid sequence of SEQ ID NO: 36 and a CDR3 being the amino acid sequence of SEQ ID NO: 15.

C'. An ISVD that specifically binds to human GPC3 and comprises
  i. a CDR1 that is the amino acid sequence of SEQ ID NO: 33 or an amino acid sequence with 2 or 1 amino acid difference(s) with SEQ ID NO: 33;
  ii. a CDR2 that is the amino acid sequence of SEQ ID NO: 37 or an amino acid sequence with 2 or 1 amino acid difference(s) with SEQ ID NO: 37; and
  iii. a CDR3 that is the amino acid sequence of SEQ ID NO: 16 or an amino acid sequence with 2 or 1 amino acid difference(s) with SEQ ID NO: 16,
  preferably a CDR1 being the amino acid sequence of SEQ ID NO: 33, a CDR2 being the amino acid sequence of SEQ ID NO: 37 and a CDR3 being the amino acid sequence of SEQ ID NO: 16.

Preferred examples of such an ISVD(s) that specifically binds to human GPC3 comprise one or more (and preferably all) framework regions as indicated for ISVD A022600351 and A022600314, respectively, in Table A-2-1 (in addition to the CDRs as defined in the preceding items B' and C', respectively), and most preferred is an ISVD that consists of the full amino acid sequence of ISVD A022600351 or A022600314 (SEQ ID NOs: 3 or 4, see Table A-1 and A-2-1).

The percentage of "sequence identity" between a first amino acid sequence and a second amino acid sequence may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (i.e. at a single position).

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

An "amino acid difference" as used herein refers to a deletion, insertion or substitution of a single amino acid residue vis-à-vis a reference sequence, and preferably is a substitution.

Amino acid substitutions are preferably conservative substitutions. Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, lie, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into lie or into Val; Lys into Arg, into Gln or into Glu; Met into Leu, into Tyr or into lie; Phe into Met, into Leu or into Tyr; Ser into Thr; Thr into Ser; Trp into Tyr; Tyr into Trp; and/or Phe into Val, into lie or into Leu.

5.3 Specificity

The terms "specificity", "binding specifically" or "specific binding" refer to the number of different target molecules, such as antigens, from the same organism to which a particular binding unit, such as an ISVD, can bind with sufficiently high affinity (see below). "Specificity", "binding specifically" or "specific binding" are used interchangeably herein with "selectivity", "binding selectively" or "selective binding". Binding units, such as ISVDs, preferably specifically bind to their designated targets.

The specificity/selectivity of a binding unit can be determined based on affinity. The affinity denotes the strength or stability of a molecular interaction. The affinity is commonly given as by the KD, or dissociation constant, which is expressed in units of mol/liter (or M). The affinity can also be expressed as an association constant, KA, which equals 1/KD and is expressed in units of (mol/liter)$^{-1}$ (or M$^{-1}$).

The affinity is a measure for the binding strength between a moiety and a binding site on the target molecule: the lower the value of the KD, the stronger the binding strength between a target molecule and a targeting moiety.

Typically, binding units used in the present technology (such as ISVDs) will bind to their targets with a dissociation constant (KD) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant (KA) of $10^5$ to $10^{12}$ liter/moles or more, and preferably $10^7$ to $10^{12}$ liter/moles or more and more preferably $10^8$ to $10^{12}$ liter/moles).

Any KD value greater than $10^{-4}$ mol/liter (or any KA value lower than $10^4$ liters/mol) is generally considered to indicate non-specific binding.

The KD for biological interactions, such as the binding of immunoglobulin sequences to an antigen, which are considered specific are typically in the range of $10^{-5}$ moles/liter (10000 nM or 10 µM) to $10^{-12}$ moles/liter (0.001 nM or 1 µM) or less.

Accordingly, specific/selective binding may mean that— using the same measurement method, e.g. SPR—a binding unit (or polypeptide comprising the same) binds to TCR and/or GPC3 with a KD value of $10^{-5}$ to $10^{-12}$ moles/liter or less and binds to related targets with a KD value greater than $10^{-4}$ moles/liter. Examples of related targets for GPC3 are GPC1, GPC2, GPC4, GPC5 or GPC6. Thus, in an embodiment of the technology, the ISVDs comprised in the polypeptide that bind to GPC3, bind to GPC3 with a KD value of $10^{-5}$ to $10^{-12}$ moles/liter or less and bind to GPC1, GPC2, GPC4, GPC5 and GPC6 of the same species with a KD value greater than $10^{-4}$ moles/liter.

Thus, the polypeptide preferably exhibits at least half the binding affinity, more preferably at least the same binding affinity, to human TCR and to human GPC3 as compared to a polypeptide consisting of the amino acid of SEQ ID NO: 1, wherein the binding affinity is measured using the same method, such as SPR.

Specific binding to a certain target from a certain species does not exclude that the binding unit can also specifically bind to the analogous target from a different species. For example, specific binding to human TCR does not exclude that the binding unit (or a polypeptide comprising the same) can also specifically bind to TCR from cynomolgus monkeys. Likewise, for example, specific binding to human GPC3 does not exclude that the binding unit (or a polypeptide comprising the same) can also specifically bind to GPC3 from cynomolgus monkeys ("cyno").

The ISVD with SEQ ID NO: 2 that binds to human TCR and that is comprised in the polypeptides of the current technology, exhibits improved binding characteristics compared to ISVD T0170056G05, which is described in WO 2016/180969 A1. More specifically, the ISVD with SEQ ID NO:2 is derived from T017056G05 and comprises specific mutations in CDR1 and CDR3 which result in improved cross-reactivity for binding to human and non-human primate (such as cynomolgus monkey) TCR compared to ISVD T0170056G05.

When an ISVD is said to exhibit "improved cross-reactivity for binding to human and non-human primate TCR" compared to another ISVD, it means that for said ISVD the ratio of the binding activity (such as expressed in terms of KD or $k_{off}$) for human TCR and for non-human primate TCR is lower than that same ratio calculated for the other ISVD in the same assay.

Good cross-reactivity for binding to human and non-human primate TCR allows for the assessment of toxicity of a multispecific T cell engaging polypeptide in preclinical studies conducted on non-human primates.

Specific binding of a binding unit to its designated target can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned below. In this respect, it will also be clear that it may not be possible to measure dissociation constants of more than $10^{-4}$ moles/liter or $10^{-3}$ moles/liter (e.g. of $10^{-2}$ moles/liter). Optionally, as will also be clear to the skilled person, the (actual or apparent) dissociation constant may be calculated on the basis of the (actual or apparent) association constant (KA), by means of the relationship [KD=1/KA].

The affinity of a molecular interaction between two molecules can be measured via different techniques known per se, such as the well-known surface plasmon resonance (SPR) biosensor technique (see for example Ober et al. 2001, Intern. Immunology 13: 1551-1559).

The term "surface plasmon resonance", as used herein, refers to an optical phenomenon that allows for the analysis of real-time biospecific interactions by detection of alterations in protein concentrations within a biosensor matrix, where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIAcore® system (BIAcore International AB, a GE Healthcare company, Uppsala, Sweden and Piscataway, NJ). For further descriptions, see Jonsson et al. (1993, Ann. Biol. Clin. 51: 19-26), Jonsson et al. (1991 Biotechniques 11: 620-627), Johnsson et al. (1995, J. Mol. Recognit. 8: 125-131), and Johnnson et al. (1991, Anal. Biochem. 198: 268-277).

Another well-known biosensor technique to determine affinities of biomolecular interactions is bio-layer interferometry (BLI) (see for example Abdiche et al. 2008, Anal. Biochem. 377: 209-217). The term "bio-layer Interferometry" or "BLI", as used herein, refers to a label-free optical technique that analyzes the interference pattern of light reflected from two surfaces: an internal reference layer (reference beam) and a layer of immobilized protein on the biosensor tip (signal beam). A change in the number of molecules bound to the tip of the biosensor causes a shift in the interference pattern, reported as a wavelength shift (nm), the magnitude of which is a direct measure of the number of molecules bound to the biosensor tip surface. Since the interactions can be measured in real-time, association and dissociation rates and affinities can be determined. BLI can for example be performed using the well-known Octet® Systems (ForteBio, a division of Pall Life Sciences, Menlo Park, USA).

Alternatively, affinities can be measured in Kinetic Exclusion Assay (KinExA) (see for example Drake et al. 2004, Anal. Biochem., 328: 35-43), using the KinExA® platform (Sapidyne Instruments Inc, Boise, USA). The term "KinExA", as used herein, refers to a solution-based method to measure true equilibrium binding affinity and kinetics of unmodified molecules. Equilibrated solutions of an antibody/antigen complex are passed over a column with beads precoated with antigen (or antibody), allowing the free antibody (or antigen) to bind to the coated molecule. Detection of the antibody (or antigen) thus captured is accomplished with a fluorescently labeled protein binding the antibody (or antigen).

The GYROLAB® immunoassay system provides a platform for automated bioanalysis and rapid sample turnaround (Fraley et al. 2013, Bioanalysis 5: 1765-74).

5.4 (In Vivo) Half-Life Extension

The polypeptide may further comprise one or more other groups, residues, moieties or binding units, optionally linked via one or more peptidic linkers, in which said one or more other groups, residues, moieties or binding units provide the polypeptide with increased (in vivo) half-life, compared to the corresponding polypeptide without said one or more other groups, residues, moieties or binding units. In vivo half-life extension means, for example, that the polypeptide exhibits an increased half-life in a mammal, such as a human subject, after administration. Half-life can be expressed for example as t½beta.

The type of groups, residues, moieties or binding units is not generally restricted and may for example be chosen from the group consisting of a polyethylene glycol molecule, serum proteins or fragments thereof, binding units that can bind to serum proteins, an Fc portion, and small proteins or peptides that can bind to serum proteins.

More specifically, said one or more other groups, residues, moieties or binding units that provide the polypeptide with increased half-life can be chosen from the group consisting of binding units that can bind to serum albumin, such as human serum albumin, or a serum immunoglobulin, such as IgG, and preferably is a binding unit that can bind to human serum albumin. The binding unit is preferably an ISVD.

For example, WO 04/041865 describes Nanobodies® binding to serum albumin (and in particular against human serum albumin) that can be linked to other proteins (such as one or more other Nanobodies binding to a desired target) in order to increase the half-life of said protein.

The international application WO 06/122787 describes a number of Nanobodies® against (human) serum albumin. These Nanobodies® include the Nanobody® called Alb-1 (SEQ ID NO: 52 in WO 06/122787) and humanized variants thereof, such as Alb-8 (SEQ ID NO: 62 in WO 06/122787). Again, these can be used to extend the half-life of therapeutic proteins and polypeptide and other therapeutic entities or moieties.

Moreover, WO2012/175400 describes a further improved version of Alb-1, called Alb-23.

In a preferred embodiment, the polypeptide comprises a serum albumin binding moiety selected from Alb-1, Alb-3, Alb-4, Alb-5, Alb-6, Alb-7, Alb-8, Alb-9, Alb-10 and Alb-23, preferably Alb-8 or Alb-23 or its variants, as shown in pages 7-9 of WO2012/175400 and the albumin binders described in WO 2012/175741, WO2015/173325, WO2017/080850, WO2017/085172, WO2018/104444, WO2018/134235, WO2018/134234. Some preferred serum albumin binders are also shown in Table A-4. A particularly preferred further component of the polypeptide is as described in item D:

D. An ISVD that binds to human serum albumin and comprises
  i. a CDR1 that is the amino acid sequence of SEQ ID NO: 9 or an amino acid sequence with 2 or 1 amino acid difference(s) with SEQ ID NO: 9;
  ii. a CDR2 that is the amino acid sequence of SEQ ID NO: 13 or an amino acid sequence with 2 or 1 amino acid difference(s) with SEQ ID NO: 13; and
  iii. a CDR3 that is the amino acid sequence of SEQ ID NO: 17 or an amino acid sequence with 2 or 1 amino acid difference(s) with SEQ ID NO: 17;
  preferably a CDR1 being the amino acid sequence of SEQ ID NO: 9, a CDR2 being the amino acid sequence of SEQ ID NO: 13 and a CDR3 being the amino acid sequence of SEQ ID NO: 17.

Preferred examples of such an ISVD that binds to human serum albumin comprise one or more (and preferably all) framework regions as indicated for ISVD ALB23002 in Table A-2 (in addition to the CDRs as defined in the preceding item D), and most preferred is an ISVD that consists of the full amino acid sequence of ISVD ALB23002 (SEQ ID NO: 5, see Table A-1 and A-2).

Item D can be also described using the Kabat definition as:

D'. An ISVD that binds to human serum albumin and comprises
  i. a CDR1 that is the amino acid sequence of SEQ ID NO: 34 or an amino acid sequence with 2 or 1 amino acid difference(s) with SEQ ID NO: 34;
  ii. a CDR2 that is the amino acid sequence of SEQ ID NO: 38 or an amino acid sequence with 2 or 1 amino acid difference(s) with SEQ ID NO: 38; and
  iii. a CDR3 that is the amino acid sequence of SEQ ID NO: 17 or an amino acid sequence with 2 or 1 amino acid difference(s) with SEQ ID NO: 17;
  preferably a CDR1 being the amino acid sequence of SEQ ID NO: 34, a CDR2 being the amino acid sequence of SEQ ID NO: 38 and a CDR3 being the amino acid sequence of SEQ ID NO: 17.

Preferred examples of such an ISVD that binds to human serum albumin comprise one or more (and preferably all) framework regions as indicated for ISVD ALB23002 in Table A-2-1 (in addition to the CDRs as defined in the preceding item D'), and most preferred is an ISVD consists of the full amino acid sequence of ISVD ALB23002 (SEQ ID NO: 5, see Table A-1 and A-2-1).

Also, in a preferred embodiment, the amino acid sequence of an ISVD binding to human serum albumin may exhibit a sequence identity of more than 90%, such as more than 95% or more than 99%, with SEQ ID NO: 5, wherein the CDRs are as defined in the preceding item D or D'. In particular, the ISVD binding to human serum albumin preferably is the amino acid sequence of SEQ ID NO: 5.

When such an ISVD binding to human serum albumin exhibits 2 or 1 amino acid difference in at least one CDR relative to a corresponding reference CDR sequence (item D or D' above), the ISVD exhibits at least half the binding affinity, preferably at least the same binding affinity to human serum albumin as construct ALB23002 set forth in SEQ ID NO: 5, wherein the binding affinity is measured using the same method, such as SPR.

When such an ISVD binding to human serum albumin is at a C-terminal position it can exhibit a C-terminal alanine (A) or glycine (G) extension (preferably A) and is preferably selected from SEQ ID NOs: 83, 85, 87, 89, 91, 93, 95, 96 and 98, most preferably SEQ ID NO: 96, which represents SEQ ID NO: 5 with a single alanine extension (see table A-4 below). In some embodiments, the ISVD binding to human serum albumin is at another position than the C-terminal position (i.e. is not the C-terminal ISVD of the polypeptide) and is selected from SEQ ID NOs: 5, 82, 84, 86, 88, 90, 92, 94 and 97 (see table A-4 below).

5.5 Nucleic Acid Molecules

Also provided is a nucleic acid molecule encoding the polypeptide as disclosed herein.

A "nucleic acid molecule" (used interchangeably with "nucleic acid") is a chain of nucleotide monomers linked to each other via a phosphate backbone to form a nucleotide sequence. A nucleic acid may be used to transform/transfect a host cell or host organism, e.g. for expression and/or production of a polypeptide. Suitable hosts or host cells for production purposes will be clear to the skilled person, and may for example be any suitable fungal, prokaryotic or eukaryotic cell or cell line or any suitable fungal, prokaryotic or eukaryotic organism. A host or host cell comprising a nucleic acid encoding the polypeptide is also encompassed by the technology.

A nucleic acid may be for example DNA, RNA, or a hybrid thereof, and may also comprise (e.g. chemically) modified nucleotides, like PNA. It can be single- or double-stranded, and is preferably in the form of double-stranded DNA. For example, the nucleotide sequences may be genomic DNA or cDNA.

The nucleic acids can be prepared or obtained in a manner known per se, and/or can be isolated from a suitable natural source. Nucleotide sequences encoding naturally occurring (poly)peptides can for example be subjected to site-directed mutagenesis, so as to provide a nucleic acid molecule encoding polypeptide with sequence variation. Also, as will be clear to the skilled person, to prepare a nucleic acid, also several nucleotide sequences, such as at least one nucleotide sequence encoding a targeting moiety and for example nucleic acids encoding one or more linkers can be linked together in a suitable manner.

Techniques for generating nucleic acids will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers.

5.6 Vectors

Also provided is a vector comprising the nucleic acid molecule encoding the polypeptide as disclosed herein. A vector as used herein is a vehicle suitable for carrying genetic material into a cell. A vector includes naked nucleic acids, such as plasmids or mRNAs, or nucleic acids embedded into a bigger structure, such as liposomes or viral vectors.

Vectors generally comprise at least one nucleic acid that is optionally linked to one or more regulatory elements, such as for example one or more suitable promoter(s), enhancer(s), terminator(s), etc.). The vector preferably is an expression vector, i.e. a vector suitable for expressing an encoded polypeptide or construct under suitable conditions, e.g. when the vector is introduced into a (e.g. human) cell. For DNA-based vectors, this usually includes the presence of elements for transcription (e.g. a promoter and a polyA signal) and translation (e.g. Kozak sequence).

Preferably, in the vector, said at least one nucleic acid and said regulatory elements are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promotor). Generally, when two nucleotide sequences are operably linked, they will be in the same orientation and usually also in the same reading frame. They will usually also be essentially contiguous, although this may also not be required.

Preferably, any regulatory elements of the vector are such that they are capable of providing their intended biological function in the intended host cell or host organism.

For instance, a promoter, enhancer or terminator should be "operable" in the intended host cell or host organism, by which is meant that for example said promoter should be capable of initiating or otherwise controlling/regulating the transcription and/or the expression of a nucleotide sequence—e.g. a coding sequence—to which it is operably linked.

5.7 Compositions

The technology also provides a composition comprising at least one polypeptide as disclosed herein, at least one nucleic acid molecule encoding a polypeptide as disclosed herein or at least one vector comprising such a nucleic acid molecule. The composition may be a pharmaceutical composition. The composition may further comprise at least one pharmaceutically acceptable carrier, diluent or excipient and/or adjuvant, and optionally comprise one or more further pharmaceutically active polypeptides and/or compounds.

5.8 Host Organisms

The technology also pertains to host cells or host organisms comprising the polypeptide as disclosed herein, the nucleic acid encoding the polypeptide as disclosed herein, and/or the vector comprising the nucleic acid molecule encoding the polypeptide as disclosed herein.

Suitable host cells or host organisms are clear to the skilled person, and are for example any suitable fungal, prokaryotic or eukaryotic cell or cell line or any suitable fungal, prokaryotic or eukaryotic organism. Specific examples include HEK293 cells, CHO cells, *Escherichia coli* or *Pichia pastoris*. The most preferred host is *Pichia pastoris*.

5.9 Methods and Uses of the Polypeptide

The technology also provides a method for producing the polypeptide as disclosed herein. The method may comprise transforming/transfecting a host cell or host organism with a nucleic acid encoding the polypeptide, expressing the polypeptide in the host, optionally followed by one or more isolation and/or purification steps. Specifically, the method may comprise:

a) expressing, in a suitable host cell or host organism or in another suitable expression system, a nucleic acid sequence encoding the polypeptide; optionally followed by:

b) isolating and/or purifying the polypeptide.

Suitable host cells or host organisms for production purposes will be clear to the skilled person, and may for example be any suitable fungal, prokaryotic or eukaryotic cell or cell line or any suitable fungal, prokaryotic or eukaryotic organism. Specific examples include HEK293 cells, CHO cells, *Escherichia coli* or *Pichia pastoris*. The most preferred host is *Pichia pastoris*.

The polypeptide, a nucleic acid molecule or vector as described, or a composition comprising the polypeptide, nucleic acid molecule or vector—preferably the polypeptide or a composition comprising the same—are useful as a medicament.

Accordingly, the technology provides the polypeptide, nucleic acid molecule or vector as described, or a composition comprising the polypeptide, nucleic acid molecule or vector for use as a medicament.

Also provided is the polypeptide, nucleic acid molecule or vector as described, or a composition comprising the polypeptide, nucleic acid molecule or vector for use in the treatment of cancer.

Further provided is a method of treating cancer, wherein said method comprises administering, to a subject in need thereof, a pharmaceutically active amount of the polypeptide, nucleic acid molecule or vector as described, or a composition comprising the polypeptide, nucleic acid molecule or vector.

Further provided is the use of the polypeptide, nucleic acid molecule or vector as described, or a composition comprising the polypeptide, nucleic acid molecule or vector in the preparation of a medicament.

Further provided is the use of the polypeptide, nucleic acid molecule or vector as described, or a composition comprising the polypeptide, nucleic acid molecule or vector in the preparation of a pharmaceutical composition, preferably for treating cancer.

The cancer can be any type of GPC3 expressing cancer. The cancer preferably is liver cancer or lung cancer, preferably liver cancer. Liver cancer is preferably hepatocellular carcinoma. Lung cancer is preferably non-small cell lung cancer (NSCLC), most preferably squamous cell carcinoma (SCC).

Preferably, the GPC3 expressing cancer cells express (on average) at least half the amount of GPC3 protein, preferably at least the same amount of GPC3 protein as Huh7 cells (on average). Huh7 cells are publicly available from e.g. the National Institutes of Biomedical Innovation, Health and Nutrition, JCRB Cell Bank, under accession number JCRB0403.

The expressed GPC3 preferably refers to cell surface-exposed GPC3. The expression of (cell surface-exposed) GPC3 on a cell (and the amount thereof) can be readily determined by routine methods commonly known in the art, such as flow cytometry, immunohistochemistry or as described in the examples.

A "subject" as referred to in the context of the technology can be any animal, preferably a mammal. Among mammals, a distinction can be made between humans and non-human mammals. Non-human animals may be for example companion animals (e.g. dogs, cats), livestock (e.g. bovine, equine, ovine, caprine, or porcine animals), or animals used generally for research purposes and/or for producing antibodies (e.g. mice, rats, rabbits, cats, dogs, goats, sheep, horses, pigs, non-human primates, such as cynomolgus monkeys, or camelids, such as llama or alpaca).

In the context of prophylactic and/or therapeutic purposes, the subject can be any animal, and more specifically any mammal, but preferably is a human subject.

Substances (including polypeptides, nucleic acid molecules and vectors) or compositions may be administered to a subject by any suitable route of administration, for example by enteral (such as oral or rectal) or parenteral (such as epicutaneous, sublingual, buccal, nasal, intra-articular, intradermal, intramuscular, intraperitoneal, intravenous, subcutaneous, transdermal, or transmucosal) administration. Parenteral administration, such as intramuscular, subcutaneous or intradermal, administration is preferred. Most preferred is subcutaneous administration.

An effective amount of a polypeptide, a nucleic acid molecule or vector as described, or a composition comprising the polypeptide, nucleic acid molecule or vector can be administered to a subject in order to provide the intended treatment results.

One or more doses can be administered. If more than one dose is administered, the doses can be administered in suitable intervals in order to maximize the effect of the polypeptide, composition, nucleic acid molecule or vector.

TABLE A-1

Amino acid sequences of the different monovalent ISVD building blocks identified within the pentavalent polypeptide A022600424 ("ID" refers to the SEQ ID NO as used herein)

| Name | ID | Amino acid sequence |
|---|---|---|
| TCE01 | 2 | DVQLVESGGGVVQPGGSLRLSCVASGYVHKINFYGWYRQAPGKEREKVA HISIGDQTDYADSAKGRFTISRDESKNTVYLQMNSLRPEDTAAYYCRALSRI WPYDYWGQGTLVTVSS |
| A022600351* | 3 | EVQLVESGGGVVQPGGSLRLSCAASGFTFSSFAMTWVRRPPGKGLEWVA TITNKGVTSYADSVKGRFTISRDNAKNTLYLQMNSLRPEDTALYICANARRT GPRAPTDIGSYRGQGTLVTVSS |
| A022600314° | 4 | EVQLVESGGGVVQPGGSLRLSCAASGSIFRSVFSSSTMEWYRQAPGKKREL VARIAPGEGTYYGALYADSVKGRFTISRDNAKNTVYLQMNSLRPEDTALYY CASGVAWGQGTLVTVSS |
| ALB23002 | 5 | EVQLVESGGGVVQPGGSLRLSCAASGFTFRSFGMSWVRQAPGKGPEWVS SISGSGSDTLYADSVKGRFTISRDNSKNTLYLQMNSLRPEDTALYYCTIGGSL SRSSQGTLVTVSS |

*Sequence optimized variant of A02260018C08 (SEQ ID NO: 48)
°Sequence optimized variant of A02260015A08 (SEQ ID NO: 47)

TABLE A-2

Sequences for CDRs and frameworks ("ID" refers to the given SEQ ID NO)

| ID | ISVD | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 2 | TCE01 | 18 | DVQLVESGG GVVQPGGSL RLSCVAS | 6 | GYVHKI NFYG | 20 | WYRQAPG KEREKVA | 10 | HISIGD QTD | 24 | YADSAKGRFTISRDE SKNTVYLQMNSLRPE DTAAYYCRA | 14 | LSRIWPYDY | 28 | WGQGT LVTVSS |
| 3 | A022600351* | 19 | EVQLVESGG GVVQPGGSL RLSCAAS | 7 | GFTFSSF AMT | 21 | WVRRPPGK GLEWVA | 11 | TITNKG VTS | 25 | YADSVKGRFTISRDN AKNTLYLQMNSLRPE DTALYICAN | 15 | ARRTGPRAP TDIGSY | 29 | RGQGTL VTVSS |
| 4 | A022600314° | 19 | EVQLVESGG GVVQPGGSL RLSCAAS | 8 | GSIFRSV FSSSTM E | 22 | WYRQAPG KKRELVA | 12 | RIAPGE GTYYG AL | 26 | YADSVKGRFTISRDN AKNTVYLQMNSLRPE DTALYYCAS | 16 | GVA | 28 | WGQGT LVTVSS |
| 5 | ALB23002 | 19 | EVQLVESGG GVVQPGGSL RLSCAAS | 9 | GFTFRSF GMS | 23 | WVRQAPG KGPEWVS | 13 | SISGSG SDTL | 27 | YADSVKGRFTISRDN SKNTLYLQMNSLRPE DTALYYCTI | 17 | GGSLSR | 30 | SSQGTL VTVSS |

*Sequence optimized variant of A02260018C08 (SEQ ID NO: 48)
°Sequence optimized variant of A02260015A08 (SEQ ID NO: 47)

TABLE A-2-1

Sequences for CDRs and frameworks ("ID" refers to the given SEQ ID NO)

| ID | ISVD | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 2 | TCE01 | 39 | DVQLVESGG GVVQPGGSL RLSCVASGY VHK | 31 | INFYG | 20 | WYRQAPG KEREKVA | 35 | HISIGD QTDYA DSAKG | 43 | RFTISRDESKNTVY LQMNSLRPEDTAAY YCRA | 14 | LSRIWPYDY | 28 | WGQGT LVTVSS |
| 3 | A022600351* | 40 | EVQLVESGG GVVQPGGSL RLSCAASGF TFS | 32 | SFAMT | 21 | WVRRPPG KGLEWVA | 36 | TITNKG VTSYA DSVKG | 44 | RFTISRDNAKNTLY LQMNSLRPEDTALY ICAN | 15 | ARRTGPRAP TDIGSY | 29 | RGQGTL VTVSS |
| 4 | A022600314° | 41 | EVQLVESGG GVVQPGGSL RLSCAASGS IFR | 33 | SVFSSST ME | 22 | WYRQAPG KKRELVA | 37 | RIAPGE GTYYG ALYADS VKG | 45 | RFTISRDNAKNTVY LQMNSLRPEDTALY YCAS | 16 | GVA | 28 | WGQGT LVTVSS |
| 5 | ALB23002 | 42 | EVQLVESGG GVVQPGGSL RLSCAASGF TFR | 34 | SFGMS | 23 | WVRQAPG KGPEWVS | 38 | SISGSG SDTLYA DSVKG | 46 | RFTISRDNSKNTLY LQMNSLRPEDTALY YCTI | 17 | GGSLSR | 30 | SSQGTL VTVSS |

*Sequence optimized variant of A02260018C08 (SEQ ID NO: 48)
°Sequence optimized variant of A02260015A08 (SEQ ID NO: 47)

TABLE A-3

Amino acid sequences of selected multivalent ISVD

| Name | ID | Amino acid sequence |
|---|---|---|
| A022600424 | 1 | DVQLVESGGGVVQPGGSLRLSCVASGYVHKINFYGWYRQAPGKEREKVAHISIGDQTDYADSAKGRF TISRDESKNTVYLQMNSLRPEDTAAYYCRALSRIWPYDYWGQGTLVTVSSGGGGSEVQLVESGGGVV QPGGSLRLSCAASGFTFSSFAMTWVRRPPGKGLEWVATITNKGVTSYADSVKGRFTISRDNAKNTLY LQMNSLRPEDTALYICANARRTGPRAPTDIGSYRGQGTLVTVSSGGGGSGGGSEVQLVESGGGVVQP GGSLRLSCAASGSIFRSVFSSSTMEWYRQAPGKKRELVARIAPGEGTYYGALYADSVKGRFTISRDN AKNTVYLQMNSLRPEDTALYYCASGVAWGQGTLVTVSSGGGGSGGGSEVQLVESGGGVVQPGGSLRL SCAASGFTFRSFGMSWVRQAPGKGPEWVSSISGSGSDTLYADSVKGRFTISRDNSKNTLYLQMNSLR PEDTALYYCTIGGSLSRSSQGTLVTVSSA |

TABLE A-4

Serum albumin binding ISVD sequences ("ID" refers to the SEQ ID NO as used herein)

| Name | ID | Amino acid sequence |
|---|---|---|
| Alb8 | 82 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Alb8-A | 83 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| Alb23 | 84 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| Alb23-A | 85 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSA |
| Alb83 | 86 | EVQLVESGGGVVQPGNSLRLSCAASGFTFSSFGMSWVRQAPGKGLEWVSSISGSGSDTLYADSVKGRFTISRDNAKTTLYLQMNSLRPEDTATYYCTIGGSLSRSSQGTLVTVSS |
| Alb83-A | 87 | EVQLVESGGGVVQPGNSLRLSCAASGFTFSSFGMSWVRQAPGKGLEWVSSISGSGSDTLYADSVKGRFTISRDNAKTTLYLQMNSLRPEDTATYYCTIGGSLSRSSQGTLVTVSSA |
| Alb132 | 88 | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVTVSS |
| Alb132-A | 89 | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVTVSSA |
| Alb73 | 90 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSS |
| Alb73-A | 91 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSSA |
| Alb82 | 92 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSS |
| Alb82-A | 93 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| Alb199 | 94 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSS |
| Alb199-A | 95 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |
| Alb23002 | 5 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSS |
| Alb223 | 96 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |
| Alb216 | 97 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVKVSS |
| Alb216-A | 98 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVKVSSA |

TABLE A-5

| Name | ID | Amino acid sequence |
|---|---|---|
| 3A linker | 99 | AAA |
| 5GS linker | 100 | GGGGS |
| 7GS linker | 101 | SGGSGGS |
| 8GS linker | 102 | GGGGSGGS |
| 9GS linker | 103 | GGGGSGGGS |
| 10GS linker | 104 | GGGGSGGGGS |
| 15GS linker | 105 | GGGGSGGGGSGGGGS |
| 18GS linker | 106 | GGGGSGGGGSGGGGSGGS |
| 20GS linker | 107 | GGGGSGGGGSGGGGSGGGGS |
| 25GS linker | 108 | GGGGSGGGGSGGGGSGGGGSGGGGS |
| 30GS linker | 109 | GGGGSGGGGSGGGGSGGGGSGGGGSGGGGS |
| 35GS linker | 110 | GGGGSGGGGSGGGGSGGGGSGGGGSGGGGSGGGGS |
| 40GS linker | 111 | GGGGSGGGGSGGGGSGGGGSGGGGSGGGGSGGGGSGGGGS |
| G1 hinge | 112 | EPKSCDKTHTCPPCP |
| 9GS-G1 hinge | 113 | GGGGSGGGSEPKSCDKTHTCPPCP |
| Llama upper long hinge region | 114 | EPKTPKPQPAAA |
| G3 hinge | 115 | ELKTPLGDTTHTCPRCPEPKSCDTPPPCPRCPEPKSCDTPPPCPRCPEPKSCDTPPPCPRCP |

TABLE A-6

Amino acid sequences of selected multivalent polypeptides ("ID" refers to the given SEQ ID NO)

| SEQ ID | | Sequence |
|---|---|---|
| 49 | A022600027 | DVQLVESGGGLVQPGGSLRLSCVASGDVHKINFLGWYRQAPGKEREKVA HISIGDQTDYADSAKGRFTISRDESKNMVYLQMNSLKPEDTAVYFCRAFSR IYPYDYWGQGTLVTVSSGGGGSGGGGSGGGGSGGGGSGGGGSGGGGS GGGGSEVQLVESGGGLVQPGGSLRLSCVASGFTFSSFAMTWVRRPPGKG LEWVATITNGGVTSYRDSVKGRFTISRDNAKNTLYLEMTSLNPEDTAVYIC ANARRTGPRAPTDIGSYRGQGTLVTVSSGGGGSGGGGSGGGGSGGGGS GGGGSGGGGSGGGGSEVQLVESGGGVVQPGGSLRLSCAASGLTFSSYA MGWFRQAPGKERERVVSISRGGGYTYYADSVKGRFTISRDNSENTVYLQ MNSLRPEDTALYYCAAARYWATGSEYEFDYWGQGTLVTVSS |
| 50 | A022600031 | DVQLVESGGGLVQPGGSLRLSCVASGDVHKINFLGWYRQAPGKEREKVA HISIGDQTDYADSAKGRFTISRDESKNMVYLQMNSLKPEDTAVYFCRAFSR IYPYDYWGQGTLVTVSSGGGGSGGGGSGGGGSGGGGSGGGGSGGGGS GGGGSEVQLVESGGGLVQAGGSLRLSCVASGSIFRSVFSSSTMEWYRQPP GKKRELVARIAPGDGTNYGALYADSVKGRFTISRDDAKKTVDLQMNSLKP EDTGVYFCASGVAWGQGTLVTVSSGGGGSGGGGSGGGGSGGGGSGGG GSGGGGSGGGGSEVQLVESGGGVVQPGGSLRLSCAASGLTFSSYAMGW FRQAPGKERERVVSISRGGGYTYYADSVKGRFTISRDNSENTVYLQMNSLR PEDTALYYCAAARYWATGSEYEFDYWGQGTLVTVSS |
| 51 | A022600096 | DVQLVESGGGLVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSGGGGSGGGGSGGGGSGGGGSGGGGS GGGGSEVQLVESGGGLVQPGGSLRLSCVASGFTFSSFAMTWVRRPPGKG LEWVATITNGGVTSYRDSVKGRFTISRDNAKNTLYLEMTSLNPEDTAVYIC ANARRTGPRAPTDIGSYRGQGTLVTVSSGGGGSGGGGSGGGGSGGGGS GGGGSGGGGSGGGGSEVQLVESGGGVVQPGGSLRLSCAASGFTFRSFG MSWVRQAPGKGPEWVSSISGSGSDTLYADSVKGRFTISRDNSKNTLYLQ MNSLRPEDTALYYCTIGGSLSRSSQGTLVTVSSA |

TABLE A-6-continued

Amino acid sequences of selected multivalent polypeptides ("ID" refers to the given SEQ ID NO)

| SEQ ID | | Sequence |
|---|---|---|
| 52 | A022600102 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSAAAEVQLVESGGGLVQPGGSLRLSCVASGFTFS SFAMTWVRRPPGKGLEWVATITNGGVTSYRDSVKGRFTISRDNAKNTLYL EMTSLNPEDTAVYICANARRTGPRAPTDIGSYRGQGTLVTVSSGGGGSGG GGSGGGGSGGGGSGGGGSGGGGSGGGGSEVQLVESGGGVVQPGGSLR LSCAASGFTFRSFGMSWVRQAPGKGPEWVSSISGSGSDTLYADSVKGRFT ISRDNSKNTLYLQMNSLRPEDTALYYCTIGGSLSRSSQGTLVTVSSA |
| 53 | A022600103 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVQLVESGGGLVQPGGSLRLSCVASGFT FSSFAMTWVRRPPGKGLEWVATITNGGVTSYRDSVKGRFTISRDNAKNTL YLEMTSLNPEDTAVYICANARRTGPRAPTDIGSYRGQGTLVTVSSGGGGS GGGGSGGGGSGGGGSGGGGSGGGGSGGGGSEVQLVESGGGVVQPGG SLRLSCAASGFTFRSFGMSWVRQAPGKGPEWVSSISGSGSDTLYADSVKG RFTISRDNSKNTLYLQMNSLRPEDTALYYCTIGGSLSRSSQGTLVTVSSA |
| 54 | A022600104 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSGGGSEVQLVESGGGLVQPGGSLRLSCV ASGFTFSSFAMTWVRRPPGKGLEWVATITNGGVTSYRDSVKGRFTISRDN AKNTLYLEMTSLNPEDTAVYICANARRTGPRAPTDIGSYRGQGTLVTVSSG GGGSGGGGSGGGGSGGGGSGGGGSGGGGSGGGGSEVQLVESGGGVV QPGGSLRLSCAASGFTFRSFGMSWVRQAPGKGPEWVSSISGSGSDTLYA DSVKGRFTISRDNSKNTLYLQMNSLRPEDTALYYCTIGGSLSRSSQGTLVTV SSA |
| 55 | A022600105 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSGGGGSGGGGSGGGGSEVQLVESGGGL VQPGGSLRLSCVASGFTFSSFAMTWVRRPPGKGLEWVATITNGGVTSYR DSVKGRFTISRDNAKNTLYLEMTSLNPEDTAVYICANARRTGPRAPTDIGS YRGQGTLVTVSSGGGGSGGGGSGGGGSGGGGSGGGGSGGGGSGGGGS EVQLVESGGGVVQPGGSLRLSCAASGFTFRSFGMSWVRQAPGKGPEWV SSISGSGSDTLYADSVKGRFTISRDNSKNTLYLQMNSLRPEDTALYYCTIGG SLSRSSQGTLVTVSSA |
| 56 | A022600122 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVQLVESGGGLVQPGGSLRLSCVASGFT FSSFAMTWVRRPPGKGLEWVATITNGGVTSYRDSVKGRFTISRDNAKNTL YLEMTSLNPEDTAVYICANARRTGPRAPTDIGSYRGQGTLVTVSSGGGGS GGGGSGGGGSGGGGSGGGGSGGGGSEVQLVESGGGLVQPGG SLRLSCVASGSIFRSVFSSSTMEWYRQPPGKKRELVARIAPGDGTNYGALY ADSVKGRFTISRDDAKKTVDLQMNSLKPEDTGVYFCASGVAWGQGTLVT VSSGGGGSGGGGSGGGGSGGGGSGGGGSGGGGSGGGGSEVQLVESGG GVVQPGGSLRLSCAASGFTFRSFGMSWVRQAPGKGPEWVSSISGSGSDT LYADSVKGRFTISRDNSKNTLYLQMNSLRPEDTALYYCTIGGSLSRSSQGTL VTVSSA |
| 57 | A022600131 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVQLVESGGGLVQPGGSLRLSCVASGFT FSSFAMTWVRRPPGKGLEWVATITNGGVTSYRDSVKGRFTISRDNAKNTL YLEMTSLNPEDTAVYICANARRTGPRAPTDIGSYRGQGTLVTVSSGGGGS GGGGSGGGGSGGGGSEVQLVESGGGLVQPGGSLRLSCVASGSIFRSVFSS STMEWYRQPPGKKRELVARIAPGDGTNYGALYADSVKGRFTISRDDAKKT VDLQMNSLKPEDTGVYFCASGVAWGQGTLVTVSSGGGGSGGGGSGGG GSGGGGSGGGGSGGGGSGGGGSEVQLVESGGGVVQPGGSLRLSCAASG FTFRSFGMSWVRQAPGKGPEWVSSISGSGSDTLYADSVKGRFTISRDNSK NTLYLQMNSLRPEDTALYYCTIGGSLSRSSQGTLVTVSSA |
| 58 | A022600132 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVQLVESGGGLVQPGGSLRLSCVASGFT FSSFAMTWVRRPPGKGLEWVATITNGGVTSYRDSVKGRFTISRDNAKNTL YLEMTSLNPEDTAVYICANARRTGPRAPTDIGSYRGQGTLVTVSSGGGGS GGGSEVQLVESGGGLVQPGGSLRLSCVASGSIFRSVFSSSTMEWYRQPPG KKRELVARIAPGDGTNYGALYADSVKGRFTISRDDAKKTVDLQMNSLKPE DTGVYFCASGVAWGQGTLVTVSSGGGGSGGGGSGGGGSGGGGSGGG GSGGGGSGGGGSEVQLVESGGGVVQPGGSLRLSCAASGFTFRSFGMSW VRQAPGKGPEWVSSISGSGSDTLYADSVKGRFTISRDNSKNTLYLQMNSL RPEDTALYYCTIGGSLSRSSQGTLVTVSSA |

TABLE A-6-continued

Amino acid sequences of selected multivalent polypeptides ("ID" refers to the given SEQ ID NO)

| SEQ ID | | Sequence |
|---|---|---|
| 59 | A022600133 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVOLVESGGGLVQPGGSLRLSCVASGS1 FRSVFSSSTMEWYRQPPGKKRELVARIAPGDGTNYGALYADSVKGRFTISR DDAKKTVDLQMNSLKPEDTGVYFCASGVAWGQGTLVTVSSGGGGSGGGG GSGGGGSGGGGSGGGGSGGGGSGGGGSEVQLVESGGGLVQPGGSLRL SCVASGFTFSSFAMTWVRRPPGKGLEWVATITNGGVTSYRDSVKGRFTIS RDNAKNTLYLEMTSLNPEDTAVYICANARRTGPRAPTDIGSYRGQGTLVT VSSGGGGSGGGGSGGGGSGGGGSGGGGSGGGGSGGGGSEVQLVESGG GVVQPGGSLRLSCAASGFTFRSFGMSWVRQAPGKGPEWVSSISGSGSDT LYADSVKGRFTISRDNSKNTLYLQMNSLRPEDTALYYCTIGGSLSRSSQGTL VTVSSA |
| 60 | A022600134 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVOLVESGGGLVQPGGSLRLSCVASGS1 FRSVFSSSTMEWYRQPPGKKRELVARIAPGDGTNYGALYADSVKGRFTISR DDAKKTVDLQMNSLKPEDTGVYFCASGVAWGQGTLVTVSSGGGGSGGGG GSGGGGSGGGGSEVQLVESGGGLVQPGGSLRLSCVASGFTFSSFAMTWV RRPPGKGLEWVATITNGGVTSYRDSVKGRFTISRDNAKNTLYLEMTSLNPE DTAVYICANARRTGPRAPTDIGSYRGQGTLVTVSSGGGGSGGGGSGGGG SGGGGSGGGGSGGGGSGGGGSEVQLVESGGGVVQPGGSLRLSCAASGF TFRSFGMSWVRQAPGKGPEWVSSISGSGSDTLYADSVKGRFTISRDNSKN TLYLQMNSLRPEDTALYYCTIGGSLSRSSQGTLVTVSSA |
| 61 | A022600135 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVOLVESGGGLVQPGGSLRLSCVASGS1 FRSVFSSSTMEWYRQPPGKKRELVARIAPGDGTNYGALYADSVKGRFTISR DDAKKTVDLQMNSLKPEDTGVYFCASGVAWGQGTLVTVSSGGGGSGGGG SEVQLVESGGGLVQPGGSLRLSCVASGFTFSSFAMTWVRRPPGKGLEWV ATITNGGVTSYRDSVKGRFTISRDNAKNTLYLEMTSLNPEDTAVYICANAR RTGPRAPTDIGSYRGQGTLVTVSSGGGGSGGGGSGGGGSGGGGSGGGG SGGGGSGGGGSEVQLVESGGGVVQPGGSLRLSCAASGFTFRSFGMSWV RQAPGKGPEWVSSISGSGSDTLYADSVKGRFTISRDNSKNTLYLQMNSLR PEDTALYYCTIGGSLSRSSQGTLVTVSSA |
| 62 | A022600167 | DVQLVESGGGVVQPGGSLRLSCVASGYVHKINFYGWYRQAPGKEREKVA HISIGDQTDYADSAKGRFTISRDESKNTVYLQMNSLRPEDTAAYYCRALSRI WPYDYWGQGTLVTVSSGGGGSEVQLVESGGGLVQPGGSLRLSCVASGFT FSSFAMTWVRRPPGKGLEWVATITNGGVTSYRDSVKGRFTISRDNAKNTL YLEMTSLNPEDTAVYICANARRTGPRAPTDIGSYRGQGTLVTVSSGGGGS GGGGSGGGGSGGGGSGGGGSGGGGSGGGGSEVQLVESGGGVVQPGG SLRLSCAASGFTFRSFGMSWVRQAPGKGPEWVSSISGSGSDTLYADSVKG RFTISRDNSKNTLYLQMNSLRPEDTALYYCTIGGSLSRSSQGTLVTVSSA |
| 63 | A022600168 | DVQLVESGGGVVQPGGSLRLSCVASGYVHKINFYGWYRQAPGKEREKVA HISIGDQTDYADSAKGRFTISRDESKNTVYLQMNSLRPEDTAAYYCRALSRI WPYDYWGQGTLVTVSSGGGGSEVQLVESGGGLVQPGGSLRLSCVASGFT FSSFAMTWVRRPPGKGLEWVATITNGGVTSYRDSVKGRFTISRDNAKNTL YLEMTSLNPEDTAVYICANARRTGPRAPTDIGSYRGQGTLVTVSSGGGGS GGGGSGGGGSGGGGSGGGGSGGGGSGGGGSEVQLVESGGGLVQPGG SLRLSCVASGSIFRSVFSSSTMEWYRQPPGKKRELVARIAPGDGTNYGALY ADSVKGRFTISRDDAKKTVDLQMNSLKPEDTGVYFCASGVAWGQGTLVT VSSGGGGSGGGGSGGGGSGGGGSGGGGSGGGGSGGGGSEVQLVESGG GVVQPGGSLRLSCAASGFTFRSFGMSWVRQAPGKGPEWVSSISGSGSDT LYADSVKGRFTISRDNSKNTLYLQMNSLRPEDTALYYCTIGGSLSRSSQGTL VTVSSA |
| 64 | A022600169 | DVQLVESGGGLVQPGGSLRLSCVASGFTFSSFAMTWVRRPPGKGLEWVA TITNGGVTSYRDSVKGRFTISRDNAKNTLYLEMTSLNPEDTAVYICANARRT GPRAPTDIGSYRGQGTLVTVSSGGGGSEVQLVESGGGVVQPGGSLRLSCV ASGYVHKINFYGWYRQAPGKEREKVAHISIGDQTDYADSAKGRFTISRDES KNTVYLQMNSLRPEDTAAYYCRALSRIWPYDYWGQGTLVTVSSGGGGSE VOLVESGGGLVQPGGSLRLSCVASGSIFRSVFSSSTMEWYRQPPGKKREL VARIAPGDGTNYGALYADSVKGRFTISRDDAKKTVDLQMNSLKPEDTGVY FCASGVAWGQGTLVTVSSGGGGSGGGGSGGGGSGGGGSGGGGSGGGG GSGGGGSEVQLVESGGGVVQPGGSLRLSCAASGFTFRSFGMSWVRQAP GKGPEWVSSISGSGSDTLYADSVKGRFTISRDNSKNTLYLQMNSLRPEDTA LYYCTIGGSLSRSSQGTLVTVSSA |
| 65 | A022600170 | DVQLVESGGGVVQPGGSLRLSCVASGYVHKINFYGWYRQAPGKEREKVA HISIGDQTDYADSAKGRFTISRDESKNTVYLQMNSLRPEDTAAYYCRALSRI WPYDYWGQGTLVTVSSGGGGSEVQLVESGGGLVQPGGSLRLSCVASGFT FSSFAMTWVRRPGKGLEWVATITNGGVTSYRDSVKGRFTISRDNAKNTL |

TABLE A-6-continued

Amino acid sequences of selected multivalent polypeptides ("ID" refers to the given SEQ ID NO)

| SEQ ID | | Sequence |
|---|---|---|
| | | YLEMTSLNPEDTAVYICANARRTGPRAPTDIGSYRGQGTLVTVSSGGGGS
GGGGSGGGGSGGGGSGGGGSGGGGSGGGGSEVQLVESGGGLVQPGG
SLRLSCVASGSIFRSVFSSSTMEWYRQPPGKKRELVARIAPGDGTNYGALY
ADSVKGRFTISRDDAKKTVDLQMNSLKPEDTGVYFCASGVAWGQGTLVT
VSSGGGGSGGGSEVQLVESGGGVVQPGGSLRLSCAASGFTFRSFGMSW
VRQAPGKGPEWVSSISGSGSDTLYADSVKGRFTISRDNSKNTLYLQMNSL
RPEDTALYYCTIGGSLSRSSQGTLVTVSSA |
| 66 | A022600172 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGLVQPGGSLRLSCVASGFT
FSSFAMTWVRRPPGKGLEWVATITNGGVTSYRDSVKGRFTISRDNAKNTL
YLEMTSLNPEDTAVYICANARRTGPRAPTDIGSYRGQGTLVTVSSGGGGS
GGGGSEVQLVESGGGVVQPGGSLRLSCAASGFTFRSFGMSWVRQAPGKG
PEWVSSISGSGSDTLYADSVKGRFTISRDNSKNTLYLQMNSLRPEDTALYY
CTIGGSLSRSSQGTLVTVSSGGGGSGGGSEVQLVESGGGLVQPGGSLRLSC
VASGSIFRSVFSSSTMEWYRQPPGKKRELVARIAPGDGTNYGALYADSVK
GRFTISRDDAKKTVDLQMNSLKPEDTGVYFCASGVAWGQGTLVTVSSA |
| 67 | A022600174 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGLVQPGGSLRLSCVASGFT
FSSFAMTWVRRPPGKGLEWVATITNGGVTSYRDSVKGRFTISRDNAKNTL
YLEMTSLNPEDTAVYICANARRTGPRAPTDIGSYRGQGTLVTVSSGGGGS
GGGSEVQLVESGGGLVQPGGSLRLSCVASGSIFRSVFSSSTMEWYRQPPG
KKRELVARIAPGDGTNYGALYADSVKGRFTISRDDAKKTVDLQMNSLKPE
DTGVYFCASGVAWGQGTLVTVSSGGGGSGGGSEVQLVESGGGVVQPG
GSLRLSCAASGFTFRSFGMSWVRQAPGKGPEWVSSISGSGSDTLYADSVK
GRFTISRDNSKNTLYLQMNSLRPEDTALYYCTIGGSLSRSSQGTLVTVSSA |
| 68 | A022600175 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGLVQPGGSLRLSCVASGFT
FSSFAMTWVRRPPGKGLEWVATITNGGVTSYRDSVKGRFTISRDNAKNTL
YLEMTSLNPEDTAVYICANARRTGPRAPTDIGSYRGQGTLVTVSSGGGGS
GGGSEVQLVESGGGLVQPGGSLRLSCVASGSIFRSVFSSSTMEWYRQPPG
KKRELVARIAPGDGTNYGALYADSVKGRFTISRDDAKKTVDLQMNSLKPE
DTGVYFCASGVAWGQGTLVTVSSGGGGSGGGSGGGGSGGGGSGGG
GSGGGGSGGGGSEVQLVESGGGVVQPGGSLRLSCAASGFTFRSFGMSW
VRQAPGKGPEWVSSISGSGSDTLYADSVKGRFTISRDNSKNTLYLQMNSL
RPEDTALYYCTIGGSLSRSSQGTLVTVSSA |
| 69 | A022600178 | DVQLVESGGGLVQPGGSLRLSCVASGFTFSSFAMTWVRRPPGKGLEWVA
TITNGGVTSYRDSVKGRFTISRDNAKNTLYLEMTSLNPEDTAVYICANARRT
GPRAPTDIGSYRGQGTLVTVSSGGGGSEVQLVESGGGVVQPGGSLRLSCV
ASGYVHKINFYGWYRQAPGKEREKVAHISIGDQTDYADSAKGRFTISRDES
KNTVYLQMNSLRPEDTAAYYCRALSRIWPYDYWGQGTLVTVSSGGGGSG
GGGSGGGSGGGGSGGGGSGGGGSGGGGSEVQLVESGGGVVQPGGSL
RLSCAASGFTFRSFGMSWVRQAPGKGPEWVSSISGSGSDTLYADSVKGRF
TISRDNSKNTLYLQMNSLRPEDTALYYCTIGGSLSRSSQGTLVTVSSA |
| 70 | A022600179 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGLVQPGGSLRLSCVASGFT
FSSFAMTWVRRPPGKGLEWVATITNGGVTSYRDSVKGRFTISRDNAKNTL
YLEMTSLNPEDTAVYICANARRTGPRAPTDIGSYRGQGTLVTVSSGGGGS
GGGSEVQLVESGGGVVQPGGSLRLSCAASGFTFRSFGMSWVRQAPGKG
PEWVSSISGSGSDTLYADSVKGRFTISRDNSKNTLYLQMNSLRPEDTALYY
CTIGGSLSRSSQGTLVTVSSA |
| 71 | A022600370 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGVVQPGGSLRLSCVASGF
TFSSFAMTWVRRPPGKGLEWVATITNGGVTSYRDSVKGRFTISRDNAKNT
LYLEMTSLRPEDTALYICANARRTGPRAPTDIGSYRGQGTLVTVSSGGGGS
GGGGSGGGSGGGGSEVQLVESGGGVVQPGGSLRLSCAASGFTFRSFG
MSWVRQAPGKGPEWVSSISGSGSDTLYADSVKGRFTISRDNSKNTLYLQ
MNSLRPEDTALYYCTIGGSLSRSSQGTLVTVSSGGC |
| 72 | A022600372 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGVVQPGGSLRLSCVASGF
TFSSFAMTWVRRPPGKGLEWVATITNGGVTSYRDSVKGRFTISRDNAKNT
LYLEMTSLRPEDTALYICANARRTGPRAPTDIGSYRGQGTLVTVSSGGGGS
GGGSEVQLVESGGGVVQPGGSLRLSCVASGSIFRSVFSSSTMEWYRQPPG |

TABLE A-6-continued

Amino acid sequences of selected multivalent polypeptides ("ID" refers to the given SEQ ID NO)

| SEQ ID | | Sequence |
|---|---|---|
| | | KKRELVARIAPGDGTNYGALYADSVKGRFTISRDDAKKTVDLQMNSLRPE
DTGLYFCASGVAWGQGTLVTVSSGGGGSGGGSEVQLVESGGGVVQPGG
SLRLSCAASGFTFRSFGMSWVRQAPGKGPEWVSSISGSGSDTLYADSVKG
RFTISRDNSKNTLYLQMNSLRPEDTALYYCTIGGSLSRSSQGTLVTVSSGGC |
| 73 | A022600373 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSGGGGSGGGGSGGGGSEVQLVESGGG
VVQPGGSLRLSCAASGFTFRSFGMSWVRQAPGKGPEWVSSISGSGSDTL
YADSVKGRFTISRDNSKNTLYLQMNSLRPEDTALYYCTIGGSLSRSSQGTLV
TVSSGGC |
| 74 | T017000698 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSGGGSEVQLVESGGGVVQPGGSLRLSCA
ASGFTFRSFGMSWVRQAPGKGPEWVSSISGSGSDTLYADSVKGRFTISRD
NSKNTLYLQMNSLRPEDTALYYCTIGGSLSRSSQGTLVTVSSA |
| 78 | A022600412 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGVVQPGGSLRLSCAASGF
TFSSFAMTWVRRPPGKGLEWVATITNAGVTSYADSVKGRFTISRDNAKNT
LYLQMNSLRPEDTALYICANARRTGPRAPTDIGSYRGQGTLVTVSSGGGG
SGGGGSGGGGSGGGGSEVQLVESGGGVVQPGGSLRLSCAASGFTFRSFG
MSWVRQAPGKGPEWVSSISGSGSDTLYADSVKGRFTISRDNSKNTLYLQ
MNSLRPEDTALYYCTIGGSLSRSSQGTLVTVSSA |
| 1 | A022600424 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGVVQPGGSLRLSCAASGF
TFSSFAMTWVRRPPGKGLEWVATITNKGVTSYADSVKGRFTISRDNAKNT
LYLQMNSLRPEDTALYICANARRTGPRAPTDIGSYRGQGTLVTVSSGGGG
SGGGGSEVQLVESGGGVVQPGGSLRLSCAASGSIFRSVFSSSTMEWYRQAP
GKKRELVARIAPGEGTYYGALYADSVKGRFTISRDNAKNTVYLQMNSLRPE
DTALYYCASGVAWGQGTLVTVSSGGGGSGGGSEVQLVESGGGVVQPGG
SLRLSCAASGFTFRSFGMSWVRQAPGKGPEWVSSISGSGSDTLYADSVKG
RFTISRDNSKNTLYLQMNSLRPEDTALYYCTIGGSLSRSSQGTLVTVSSA |
| 79 | A022600425 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGVVQPGGSLRLSCAASGSI
FRSVFSSSTMEWYRQAPGKKRELVARIAPGEGTYYGALYADSVKGRFTISR
DNAKNTVYLQMNSLRPEDTALYYCASGVAWGQGTLVTVSSGGGGSGGG
GSGGGGSGGGGSEVQLVESGGGVVQPGGSLRLSCAASGFTFSSFAMTW
VRRPPGKGLEWVATITNAGVTSYADSVKGRFTISRDNAKNTLYLQMNSLR
PEDTALYICANARRTGPRAPTDIGSYRGQGTLVTVSSGGGGSGGGSEVQL
VESGGGVVQPGGSLRLSCAASGFTFRSFGMSWVRQAPGKGPEWVSSISG
SGSDTLYADSVKGRFTISRDNSKNTLYLQMNSLRPEDTALYYCTIGGSLSRS
SQGTLVTVSSA |
| 80 | A022600426 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGVVQPGGSLRLSCAASGSI
FRSVFSSSTMEWYRQAPGKKRELVARIAPGEGTYYGALYADSVKGRFTISR
DNAKNTVYLQMNSLRPEDTALYYCASGVAWGQGTLVTVSSGGGGSGGG
GSGGGGSEVQLVESGGGVVQPGGSLRLSCAASGFTFSSFAMTW
VRRPPGKGLEWVATITNKGVTSYADSVKGRFTISRDNAKNTLYLQMNSLR
PEDTALYICANARRTGPRAPTDIGSYRGQGTLVTVSSGGGGSGGGSEVQL
VESGGGVVQPGGSLRLSCAASGFTFRSFGMSWVRQAPGKGPEWVSSISG
SGSDTLYADSVKGRFTISRDNSKNTLYLQMNSLRPEDTALYYCTIGGSLSRS
SQGTLVTVSSA |
| 81 | A022600427 | DVQLVESGGGVVQPGGSLRLSCVASGYVHKINFYGWYRQAPGKEREKVA
HISIGDQTDYADSAKGRFTISRDESKNTVYLQMNSLRPEDTAAYYCRALSRI
WPYDYWGQGTLVTVSSGGGGSEVQLVESGGGVVQPGGSLRLSCAASGF
TFSSFAMTWVRRPPGKGLEWVATITNAGVTSYADSVKGRFTISRDNAKNT
LYLQMNSLRPEDTALYICANARRTGPRAPTDIGSYRGQGTLVTVSSGGGG
SGGGSEVQLVESGGGVVQPGGSLRLSCAASGSIFRSVFSSSTMEWYRQAP
GKKRELVARIAPGEGTYYGALYADSVKGRFTISRDNAKNTVYLQMNSLRPE
DTALYYCASGVAWGQGTLVTVSSGGGGSGGGSEVQLVESGGGVVQPGG
SLRLSCAASGFTFRSFGMSWVRQAPGKGPEWVSSISGSGSDTLYADSVKG
RFTISRDNSKNTLYLQMNSLRPEDTALYYCTIGGSLSRSSQGTLVTVSSA |

TABLE A-7

C-termini with or without C-terminal extensions ("ID" refers to the given SEQ ID NO as used herein)

| ID | Amino acid sequence |
|---|---|
| 116 | VTVSS |
| 117 | VKVSS |
| 118 | VQVSS |
| 119 | VTVKS |
| 120 | VTVQS |
| 121 | VKVKS |
| 122 | VKVQS |
| 123 | VQVKS |
| 124 | VQVQS |
| 125 | VTVSSA |
| 126 | VKVSSA |
| 127 | VQVSSA |
| 128 | VTVKSA |
| 129 | VTVQSA |
| 130 | VKVKSA |
| 131 | VKVQSA |
| 132 | VQVKSA |
| 133 | VQVQSA |

TABLE A-8

Amino acid sequences related to GPC3 and TCR

| ID | description | Amino acid sequence |
|---|---|---|
| 134 | Human GPC3 (P51654) | MAGTVRTACLVVAMLLSLDFPGQAQPPPPPPDATCHQVRSFFQRLQPGL KWVPETPVPGSDLQVCLPKGPTCCSRKMEEKYQLTARLNMEQLLQSASM ELKFLIIQNAAVFQEAFEIVVRHAKNYTNAMFKNNYPSLTPQAFEFVGEFFT DVSLYILGSDINVDDMVNELFDSLFPVIYTQLMNPGLPDSALDINECLRGA RRDLKVFGNFPKLIMTQVSKSLQVTRIFLQALNLGIEVINTTDHLKFSKDCG RMLTRMWYCSYCQGLMMVKPCGGYCNVVMQGCMAGVVEIDKYWRE YILSLEELVNGMYRIYDMENVLLGLFSTIHDSIQYVQKNAGKLTTTIGKLCA HSQQRQYRSAYYPEDLFIDKKVLKVAHVEHEETLSSRRRELIQKLKSFISFYS ALPGYICSHSPVAENDTLCWNGQELVERYSQKAARNGMKNQFNLHELK MKGPEPVVSQIIDKLKHINQLLRTMSMPKGRVLDKNLDEEGFESGDCGDD EDECIGGSGDGMIKVKNQLRFLAELAYDLDVDDAPGNSQQATPKDNEIST FHNLGNVHSPLKLLTSMAISVVCFFFLVH |
| 135 | Human TCR alpha constant domain (derived from P01848) | PNIQNPDPAVYQLRDSKSSDKSVCLFTDFDSQTNVSQSKDSDVYITDKTVL DMRSMDFKSNSAVAWSNKSDFACANAFNNSIIPEDTFFPSPESSC |
| 136 | Human TCR beta constant domain (derived from P01850) | EDLNKVFPPEVAVFEPSEAEISHTQKATLVCLATGFFPDHVELSWWVNGK EVHSGVSTDPQPLKEQPALNDSRYALSSRLRVSATFWQNPRNHFRCQVQ FYGLSENDEWTQDRAKPVTQIVSAEAWGRADC |

6 EXAMPLES

6.1 Example 1: Discovery of ISVDs Specifically Binding to GPC3

2 Llamas and 1 alpaca were immunized with DNA double gene vector containing the sequence encoding the human glypican-3 isoform 2 precursor [NP_004475; 580 AA; *Homo sapiens*]. Later, the animals were boosted with recombinant human Glypican-3 (R&D Systems, cat nr. 2119-GP).

Following the final immunogen injection, blood samples were collected and peripheral blood mononuclear cells (PBMCs) were prepared using Ficoll-Hypaque according to the manufacturer's instructions (Amersham Biosciences, Piscataway, NJ, US) and total RNA was extracted and stored.

Total RNA was used as starting material for RT-PCR to amplify ISVD encoding gene fragments. These fragments were cloned into phagemid vector pAX212. Phage were prepared according to standard protocols (Antibody Phage Display: Methods and Protocols (First Edition, 2002, O'Brian and Aitken eds., Humana Press, Totowa, NJ) and stored after filter sterilization at 4° C. until further use. From each immunized animal a phage library was constructed, yielding library sizes of $3 \times 10^8$, $6 \times 10^8$ and $8 \times 10^8$ cfu.

The phage display libraries were probed using recombinant protein. Briefly, the phage particles were added to the biotinylated antigen (human GPC3 R&D Systems, cat nr. 2119-GP; cyno GPC3 DGPI DHS-HIS, in-house produced (accession number P51654; Q3-R358; 5359-H559, S495A, S509A); all biotinylated using standard protocols) at 50 nM (in PBS supplemented with 2% Marvel and 0.05% Tween 20). The biotinylated antigen was captured on streptavidin or anti-biotin coated magnetic beads (Invitrogen). Unbound phage were washed away (with PBS supplemented with 0.05% Tween 20); bound phage were eluted by addition of trypsin (1 mg/mL in PBS). Eluted phage were allowed to infect exponentially growing *E. coli* TG-1 cells to use for either a subsequent selection round (after rescue with helper phage), and/or for screening of individual clones after plating out on agar plates. For this, individual colonies were picked into 96-deep-well plates containing 0.5 mL medium and grown overnight. 80 μL of the overnight culture of each clone were mixed with 40 μL of 60% glycerol in 2×TY and stored at −80° C.

For small-scale production of ISVDs, 96 deep well plates (1 mL volume) were inoculated with the overnight cultures. ISVD expression was induced by adding IPTG to a final concentration of 1 mM. Periplasmic extracts were prepared by freezing the cell pellets and dissolving them in 100 μL PBS. Cell debris was removed by centrifugation.

Periplasmic extracts were screened in an ELISA for binding to human and cyno GPC3. 384-well high binding SpectraPlates (PerkinElmer, 6007509) were coated overnight at 4° C. with 1 μg/mL of protein (in PBS). The plates were then blocked for at least one hour (PBS, 1% casein) at RT. 1:10 dilutions (in PBS, 0.1% casein, 0.05% Tween 20) of periplasmic extracts were added for one hour at RT. Unbound periplasmic extracts were washed away (PBS supplemented with 0.05% Tween 20) and bound ISVDs were detected using mouse anti-FLAG-HRP (Sigma-Aldrich, cat nr A8592) and a subsequent enzymatic reaction in the presence of the substrate esTMB (3,3',5,5'-tetramentylbenzidine; SDT).

Positive hits in ELISA were DNA-sequenced and non-redundant clones were further analyzed for off-rates on human and cyno GPC3 as well as binding to cells expressing human and cyno GPC3.

Off-rates of ISVDs were determined on a ProteOn XPR36 instrument (Bio-Rad Laboratories, Inc.). ProteOn GLC Sensor Chips were coated with cyno Glypican-3 AGPI-HIS (in-house produced; accession number P51654; Q3-R358; 5359-H559) and human GPC3 (R&D Systems, cat nr. 2119-GP). Periplasmic extracts were diluted 1:10 in ProteOn PBS Tween buffer (PBS, pH 7.4, 0.005% Tween 20 (167-2720, BioRad)). Experiments were carried out at 25° C. Data obtained was double referenced by reference lane subtraction as well as subtraction of a blank buffer injection. Processed curves were used for off-rate analysis based on the Langmuir dissociation (off-rate analysis) model.

Periplasmic extracts were screened for human and cyno GPC3 binding in flow cytometry using CHO Flp-In cells (Invitrogen cat nr. K6010) expressing either human GPC3 (accession number P51654; Q25-R358, S359-H580) or cyno GPC3 (accession number P51654; Q3-R358; S359-H559), respectively. In brief, 1×10¹ cells were incubated in 1:5 diluted periplasmic extracts for 30 min at 4° C., and then washed 3 times. As a control, the parental CHO Flp-In cell line (Invitrogen cat nr. K6010) was included. Next, cells were incubated with 1 μg/mL monoclonal anti-FLAG® M2 antibody (Sigma-Aldrich, cat nr F1804) for 30 min at 4° C., washed again, and incubated for 30 min at 4° C. with goat anti-mouse PE labelled antibody (1:100; Jackson Immunoresearch, cat nr. 115-115-164). Samples were washed and resuspended in FACS Buffer (D-PBS (Gibco) with 10% FBS (Sigma) and 0.05% sodium azide (Merck)) supplemented with 5 nM TOPRO3 (Molecular Probes, cat nr T3605). Cell suspensions were then analyzed on a FACS Array. Gating was set on live, intact cells using forward/side scatter and TOPRO3 channel fluorescence parameters. Mean PE channel fluorescence values higher than those obtained for control conditions including a non-binding ISVD indicated a hit.

Based on off-rate analysis and binding to human and cyno GPC3-expressing CHO cells (Table 2), two ISVDs were selected (Table 1).

TABLE 1

Amino acid sequences of anti-GPC3 ISVDs

| ISVD ID | SEQUENCE |
| --- | --- |
| A0226015A08 (SEQ ID NO: 47) | EVQLVESGGGLVQAGGSLRLSCVASGSIFRSVFSSSTMEWYRQPPGKKRELV ARIAPGDGTNYGALYADSVKGRFTISRDDAKKTVDLQMNSLKPEDTGVYFC ASGVAWGQGTLVTVSS |
| A0226018C08 (SEQ ID NO: 48) | EVQLVESGGGLVQPGGSLRLSCVASGFTFSSFAMTWVRRPPGKGLEWVATI TNGGVTSYRDSVKGRFTISRDNAKNTLYLEMTSLNPEDTAVYICANARRTGP RAPTDIGSYRGQGTLVTVSS |

TABLE 2

Summary of the screening results of anti-GPC3 ISVDs A0226015A08 and A0226018C08

| ISVD ID | $k_{off}$ hGPC3 (1/s) | $k_{off}$ cyGPC3 (1/s) | Ratio MFI hGPC3 CHO/CHO | Ratio MFI cyGPC3 CHO/CHO |
| --- | --- | --- | --- | --- |
| A0226015A08 | 3.3E−04 | 4.0E−04 | 58.2 | 13.7 |
| A0226018C08 | 9.7E−04 | 1.1E−03 | 158.9 | 19.9 |

6.2 Example 2: Generation of Trispecific GPC3 ISVD Based T-Cell Engager

The selected anti-GPC3 ISVDs (sequences in Table 1) were formatted in a trispecific construct with a fixed T-cell engager ISVD which binds to the constant domain of the TCR (T0170056G05, anti-TCR) at the N-terminus and a fixed albumin binding ISVD (ALBX00001) at the C-terminus. The building blocks in the construct are genetically linked by a flexible 35GS (GlySer linker), resulting in the format anti-TCR-35GS-anti-GPC3-35GS-ALBX00001 (Table 3). Amino acid sequences are shown in Table A-6.

Multivalent ISVDs were expressed in *Pichia pastoris*. *P. pastoris* NRRL Y-11430 cells containing ISVD constructs of interest were grown in BGCM medium. Subsequently, medium was switched to BMCM and the constructs were further grown and induced by stepwise addition of methanol. The cells were spun down and the supernatant (containing the secreted ISVD) was collected.

Multivalent ISVDs were purified on protein A resin followed by a desalting step and if necessary, preparative SEC in D-PBS.

TABLE 3

Sample ID and description of trispecific ISVDs constructs

| Sample ID | SEQ ID NO | Description |
|---|---|---|
| A022600027 | 49 | T0170056G05-35GS-A0226018C08-35GS-ALBX00001 |
| A022600031 | 50 | T0170056G05-35GS-A0226015A08-35GS-ALBX00001 |

6.3 Example 3: T-Cell Dependent Cytotoxicity of Trispecific GPC3 ISVD T-Cell Engagers The trispecific T-cell engagers containing the anti-GPC3 ISVDs (Table 3) were characterized in a T-cell dependent cytotoxicity assay (TDC). HepG2 (ATCC, clone HB8065), a liver cancer cell line with high expression of GPC3, was labelled with Nuclight Green (Essen Bioscience, cat no. 4624) and used as target for T-cell killing in the presence of the trispecific T-cell engager constructs comprising A0226015A08 or A0226018C08 (i.e. constructs A022600031 or A022600027, respectively) or in the presence of a construct with a reference GPC3 binding single domain antibody (Ab1) in the format anti-TCR-35GS-anti-GPC3-35GS-HLE (HLE=half-life extender). To this end, plates (96-well F-bottom, Greiner, cat no 655180) were pre-blocked with 200 µL/well assay medium (2 h, 37° C.). Simultaneous addition of each assay component was performed in a total volume of 200 µL/well: (1) 50 µL of diluted/titrated compounds (Nbs; Brefeldin A (Sigma-Aldrich, cat no B7651); (2) 25 µL of diluted HSA (Sigma-Aldrich, cat no A8763-10G) (final concentration: 30 µM); (3) 25 µL of diluted Cytotox Red (Essen Bioscience, cat no 4632) (final concentration: 250 nM) (4) 50 µL of human T-cells (T cells were isolated from buffy coats (Red Cross) using the RosetteSep T cell enrichment cocktail (StemCell, cat no. 15061) and 50 µL of HepG2 Nuclight green (fresh in DNEM, High Glucose, GlutaMAX, Pyruvate, Life Technologies-Gibco, cat no 31966) in a 15:1 ratio. Plates were placed in an IncuCyte ZOOM for readout in all three channels (phase-contrast, green and red) with intervals of 4 or 6 hours, for a total of 72 h.

The tested trispecific GPC3 T-cell engagers induced human T-cell mediated killing of HepG2 Nuclight green in a dose-dependent manner as shown in FIG. 1. The IC50 values and maximum percentage of killing are shown in Table 4.

TABLE 4

IC50 (M) and maximum percentage of killing (%) of the trispecific GPC3 ISVD T-cell engagers in the Incucyte based human TDC HepG2-Nuclight green assay using an effector to target ratio of 15:1, analyzed at 60 h after seeding

| Sample ID | IC50 (M) | Max % of killing |
|---|---|---|
| A022600027 | 8.6E−09 | 80 |
| A022600031 | 1.5E−08 | 75 |
| Ab1 | 1.3E−08 | 40 |

6.4 Example 4: Epitope Binning of GPC3 Binders

Epitope binning of the anti-GPC3 ISVDs was done via flow cytometry allowing periplasmic extracts of the monovalent ISVDs A0226015A08 or A0226018C08 to compete with the ISVDs in the purified trispecific format. To this end, $4 \times 10^4$ human GPC3 CHO Flp-In cells (reference, see example 1) were incubated with 1/15 and 1/150 dilutions of periplasmic extracts, 150 nM competitor (trispecific ISVD format; oversaturating concentration) and 0.2 µg/mL of monoclonal anti-FLAG® M2 antibody (Sigma-Aldrich, cat nr F1804) and rat anti-mouse APC (BD-Pharmingen, cat no 550874), for 5 h at RT and 300 rpm. The samples were read in the iQue Screener. No competition was observed between A0226015A08 and A0226018C08 revealing that they bind to different, non-overlapping epitopes.

6.5 Example 5: Optimization of Format for GPC3 ISVD T-Cell Engagers

The GPC3 ISVD T-cell engagers in the format described in Table 3, do not reach full efficacy in the T-cell dependent cytotoxicity (TDC) HepG2 Nuclight green assay as indicated by the maximum percentage of killing (Example 3). To increase potency and efficacy, trispecific constructs were generated in which the anti-GPC3 ISVDs were combined with a sequence optimized variant of the anti-TCR ISVD T0170056G05, i.e. T017000624, at the N-terminus, an albumin binding ISVD, ALB23002-A (SEQ ID NO: 5 with C-terminal single alanine extension), at the C-terminus and the GPC3 binding ISVD(s) in the central position of the construct (Tables 5 and 6). The optimization encompassed two steps: Step 1—optimization of the linker length between the anti-TCR ISVD and an anti-GPC3 ISVD (trispecific trivalent format); Step 2—generation of biparatopic GPC3 ISVD T-cell engagers (trispecific tetravalent format) and optimization of the linker length between the two GPC3 binding ISVDs. Amino acid sequences are shown in Table A-6.

The generated formats were tested int TDC HepG2 Nuclight green assay, as described in Example 3. Analysis for the Step 1 and Step 2 formats was performed 72 h or 60 h after seeding, respectively.

Tables 5 and 6 show the IC50 values and the maximum % killing for the different formats in Step 1 and Step 2, respectively, of format optimization in the TDC HepG2 Nuclight green assay.

In Step 1, the trispecific GPC3 ISVD T-cell engagers showed cell tumor killing with increased efficacy (increased maximum killing) with decreasing length of the linker between the anti-TCR ISVD and anti-GPC3 ISVD, from 72% (35GS linker) to 94% (AAA linker) (FIG. 2). In Step 2, GPC3 biparatopic T-cell engagers were tested for which A0226018C08 and A0226015A08 were combined in the same construct and placed in different orientations and with different linker lengths between the two building blocks. Here, no impact of the tested variables on efficacy was observed (FIG. 3).

TABLE 5

IC50 (M) and maximum percentage of killing (%) of the trispecific GPC3 ISVD
T-cell engagers in the Incucyte based human TDC HepG2-Nuclight green assay
using an effector to target ratio of 15:1, analyzed at 72 h after seeding

| Step | Sample ID | SEQ ID NO | Description | IC50 (M) | Max % Killing |
|---|---|---|---|---|---|
| 1 | A022600096 | 51 | T017000624-35GS-A0226018C08-35GS-ALB23002-A | 1.4E−09 | 72 |
|  | A022600105 | 55 | T017000624-20GS-A0226018C08-35GS-ALB23002-A | 2.14E−09 | 85 |
|  | A022600104 | 54 | T017000624-9GS-A0226018C08-35GS-ALB23002-A | 2.13E−09 | 90 |
|  | A022600103 | 53 | T017000624-5GS-A0226018C08-35GS-ALB23002-A | 2.04E−09 | 92 |
|  | A022600102 | 52 | T017000624-AAA-A0226018C08-35GS-ALB23002-A | 1.72E−09 | 94 |

TABLE 6

IC50 (M) and maximum percentage of killing (%) of the trispecific GPC3 ISVD
T-cell engagers in the Incucyte based human TDC HepG2-Nuclight green assay
using an effector to target ratio of 15:1, analyzed at 72 h after seeding

| Step | Sample ID | SEQ ID NO | Description | IC50 (M) | Max % Killing |
|---|---|---|---|---|---|
| 2 | A022600103 | 53 | T017000624-5GS-A0226018C08-35GS-ALB23002-A | 5.43E−10 | 90 |
|  | A022600122 | 56 | T017000624-5GS-A0226018C08-35GS-A0226015A08-35GS-ALB23002-A | 4.45E−10 | 92 |
|  | A022600131 | 57 | T017000624-5GS-A0226018C08-20GS-A0226015A08-35GS-ALB23002-A | 4.44E−10 | 94 |
|  | A022600132 | 58 | T017000624-5GS-A0226018C08-9GS-A0226015A08-35GS-ALB23002-A | 7.02E−10 | 91 |
|  | A022600133 | 59 | T017000624-5GS-A0226015A08-35GS-A0226018C08-35GS-ALB23002-A | 4.08E−10 | 92 |
|  | A022600134 | 60 | T017000624-5GS-A0226015A08-20GS-A0226018C08-35GS-ALB23002-A | 5.28E−10 | 92 |
|  | A022600135 | 61 | T017000624-5GS-A0226015A08-9GS-A0226018C08-35GS-ALB23002-A | 6.11E−10 | 91 |

To evaluate the ability to kill a liver cancer cell line expressing medium levels of GPC3 compared to the high levels of HepG2, a TDC Huh7 assay was performed. To this end, the xCELLigence© (Acea) system was used. Firstly, 96-well E-plates (Acea, Cat no 5232368001) containing 50 μL of assay medium with a 4× concentration (120 μM) of Alburex 20 Human serum albumin (CSL Behring, Cat no 2160-979) (final assay concentration 30 μM) were placed inside the xCELLigence® for background measurement. After background measurement, simultaneous addition of each assay component was performed to a total volume of 200 μL/well: (1) 50 μL of diluted/titrated compounds; (2) 50 μL of single cell suspensions of Huh7 (HSRRB, clone JCRB0403); (3) 50 μL of single suspensions of effector cells (human T-cells, obtained as described in Example 3) to match an effector:target ratio of 15:1. Plates were placed in the xCELLigence® with 400 sweeps at 15-minute intervals. At the appropriate timepoint (ca. 60 h), cell indexes (CI) were analyzed, where a CI of 0 represented 100% killing.

In a 3$^{rd}$ Step of GPC3 T-cell engager format optimization the anti-TCR ISVD T017000624 was substituted by the sequenced optimized variant T017000680 (TCE01, SEQ ID NO: 2) in the trivalent and tetravalent formats. Potency and efficacy was assessed in the HepG2 and Huh7 TDC assay, as described above. The formats, their description and functionality is summarized in Table 7. Data is depicted in FIG. 4. The third step of format optimization resulted in a further small increase in efficacy across constructs. From this exercise GPC3 T-cell engager formats A022600167 and A022600168 were taken forward.

Step 4 of GPC3 T-cell engager format optimization consisted in changing the orientation of the anti-TCR ISVD with the anti-GPC3 ISVD, but this had an influence on potency on efficacy (Table 8, FIG. 5). For the trivalent format the killing efficacy was lost. For the tetravalent formats functionality could still be observed, be it with a decrease in potency and efficacy; the killing efficacy decreased by 20% on HepG2 Nuclight green and by 40% on Huh7.

Moreover, changing orientation of anti-GPC3 ISVD with anti-Albumin ISVD also had an influence on efficacy of killing. From this exercise no changes were made to GPC3 T-cell engager formats A022600167 and A022600168.

Step 5 of GPC3 T-cell engager format optimization consisted in varying the linker lengths (Table 9, FIG. 6). Decreasing the linker length before the anti-Albumin ISVD in the trivalent format resulted in decreased efficacy. This is not seen in the tetravalent format, so in this case a choice can be made between 9GS and 35GS linker lengths.

From the set of GPC3 T-cell engager formats A022600167 and A022600168 represent the trispecific trivalent and tetravalent formats with the highest potency and efficacy in the TDC assays. While efficacies are comparable, the trivalent format A022600167 and the tetravalent format A022600168 differ in potency. In the HepG2 TDC assay, A022600167 is 5-fold less potent than A022600168 while in the Huh7 TDC assay the difference increases to 50-fold.

TABLE 7

Step 3 of GPC3 ISVD T-cell engager format optimization. IC50 (M) and maximum percentage of killing (%) of trispecific GPC3 ISVD T-cell engagers in the Incucyte based human TDC HepG2-Nuclight green assay and in the xCELLigence based human TDC Huh7 assay, using an effector to target ratio of 15:1, analyzed at 60 h after seeding

| Sample ID | SEQ ID NO | Description | HepG2 on Incucyte IC50 (M) | HepG2 on Incucyte Max % killing | Huh7 on xCELLigence IC50 (M) | Huh7 on xCELLigence Max % killing |
|---|---|---|---|---|---|---|
| A022600103 | 53 | T017000624-5GS-A0226018C08-35GS-ALB23002-A | 1.23E−09 | 96 | 7.11E−09 | 71 |
| A022600167 | 62 | TCE01-5GS-A0226018C08-35GS-ALB23002-A | 1.92E−09 | 98 | 8.61E−09 | 91 |
| A022600122 | 56 | T017000624-5GS-A0226018C08-35GS-A0226015A08-35GS-ALB23002-A | 5.3E−10 | 93 | 2.61E−10 | 101 |
| A022600168 | 63 | TCE01-5GS-A0226018C08-35GS-A0226015A08-35GS-ALB23002-A | 3.67E−10 | 103 | 1.98E−10 | 107 |
| A022600132 | 58 | T017000624-5GS-A0226018C08-9GS-A0226015A08-35GS-ALB23002-A | 6.83E−10 | 83 | 2.9E−10 | 95 |
| A022600175 | 68 | TCE01-5GS-A0226018C08-9GS-A0226015A08-35GS-ALB23002-A | 5.27E−10 | 96 | 5.86E−11 | 99 |

TABLE 8

Step 4 of GPC3 ISVD T-cell engager format optimization. IC50 (M) and maximum percentage of killing (%) of trispecific GPC3 ISVD T-cell engagers in the Incucyte based human TDC HepG2-Nuclight green assay and in the xCELLigence based human TDC Huh7 assay, using an effector to target ratio of 15:1, analyzed at 60 h after seeding

| Sample ID | SEQ ID NO | Description | HepG2 on Incucyte IC50 (M) | HepG2 on Incucyte Max % killing | Huh7 on xCELLigence IC50 (M) | Huh7 on xCELLigence Max % killing |
|---|---|---|---|---|---|---|
| A022600167 | 62 | TCE01-5GS-A0226018C08-35GS-ALB23002-A | 1.92E−09 | 98 | 8.61E−09 | 91 |
| A022600178 | 69 | A0226018C08-5GS-TCE01-35GS-ALB23002-A | no effect | | no effect | |
| A022600168 | 63 | TCE01-5GS-A0226018C08-35GS-A0226015A08-35GS-ALB23002-A | 3.67E−10 | 103 | 1.98E−10 | 107 |
| A022600169 | 64 | A0226018C08-5GS-TCE01-5GS-A0226015A08-35GS-ALB23002-A | 6.41E−10 | 81 | 1.02E−09 | 61 |
| A022600174 | 67 | TCE01-5GS-A0226018C08-9GS-A0226015A08-9GS-ALB23002-A | 6.73E−10 | 96 | 6.26E−11 | 99 |
| A022600172 | 66 | TCE01-5GS-A0226018C08-9GS-ALB23002-9GS-A0226015A08-A | 6.01E−10 | 81 | 6.70E−11 | 90 |

TABLE 9

Step 5 of GPC3 T-cell engager format optimization. IC50 (M) and maximum percentage of killing (%) of trispecific GPC3 ISVD T-cell engagers in the Incucyte based human TDC HepG2-Nuclight green assay and in the xCELLigence based human TDC Huh7 assay, using an effector to target ratio of 15:1, analyzed at 60 h after seeding

| Sample ID | SEQ ID NO | Description | HepG2 on Incucyte IC50 (M) | HepG2 on Incucyte Max % killing | Huh7 on xCELLigence IC50 (M) | Huh7 on xCELLigence Max % killing |
|---|---|---|---|---|---|---|
| A022600167 | 62 | TCE01-5GS-A0226018C08-35GS-ALB23002-A | 1.92E−09 | 98 | 8.61E−09 | 91 |
| A022600179 | 70 | TCE01-5GS-A0226018C08-9GS-ALB23002-A | 2.92E−09 | 76 | 6.13E−09 | 66 |
| A022600168 | 63 | TCE01-5GS-A0226018C08-35GS-A0226015A08-35GS-ALB23002-A | 3.67E−10 | 103 | 1.98E−10 | 107 |
| A022600170 | 65 | TCE01-5GS-A0226018C08-35GS-A0226015A08-9GS-ALB23002-A | 3.19E−10 | 97 | 1.86E−10 | 103 |
| A022600175 | 68 | TCE01-5GS-A0226018C08-9GS-A0226015A08-35GS-ALB23002-A | 5.27E−10 | 96 | 5.86E−11 | 99 |
| A022600174 | 67 | TCE01-5GS-A0226018C08-9GS-A0226015A08-9GS-ALB23002-A | 6.73E−10 | 96 | 6.26E−11 | 99 |

6.6 Example 6: Assessment of T-Cell Activation Induction in the Presence of Soluble GPC3

GPC3 can be released into circulation in a soluble form, with levels increased in up to 50% of HCC patients. Soluble GPC3 antibody aggregates in circulation could lead to immune complex deposition and related toxicities. Thus, it is important to assess the effect on T cell activation of soluble GPC3 in presence of the GPC3 T-cell engager.

Reported serum levels of GPC3 can vary between 10 to 300 ng/mL, which corresponds to 0.1 to 10 nM. The assessment was done using 1, 10 and 100 nM of soluble GPC3, in the presence of the trispecific GPC3 ISVD T-cell engagers A022600167 and 168, in three ways: (1) Cytotoxicity in the presence of target cells (Huh-7) and soluble GPC3 (FIG. 7A): no additional killing was observed compared to in the absence of soluble GPC3; (2) CD69 upregulation in presence of target cells and soluble GPC3 (FIG. 7B): no additional T-cell activation was observed compared to in the absence of soluble GPC3; (3) CD69 upregulation in absence of target cells and presence of soluble GPC3 (FIG. 7C): no T-cell activation was seen. The risk of toxicity effects due to increased serum levels of soluble GPC3 is therefore considered low.

The cytotoxicity assay on Huh-7 was performed as described in Example 5. CD69 expression on T-cells was determined by flow cytometry using an anti-CD69 antibody (BD Pharmigen, cat no. 557050) and anti-mouse IgG1 antibody (BD Pharmigen, cat no. 556650).

6.7 Example 7: GPC3 Mediated T-Cell Engager Internalization

GPC3 is known to internalize and its internalization rate may have an impact on the efficacy of the compound. The internalization rate and the GPC3 receptor density in the presence of the trispecific GPC3 ISVD T-cell engagers equivalent to A022600167 and A022600168 and of a reference CD3-GPC3 bispecific T-cell engager antibody (Ab2) (Table 10) were assessed in Huh-7 cells over a time course of 48 h.

Internalization was determined by labeling A022600167 and A022600168 and Ab2 with pHAb (Promega, cat no. G9841), a pH sensor dye with low fluorescence at pH>7 and a strong increase in fluorescence as the pH of the solution becomes acidic. For this labeling, formats with an extra -GGC at the C-terminus were generated in order to have a single site incorporation of the label (Table 10): A022600167-GGC corresponds to A022600370, A022600168-GGC corresponds to A022600372 and as a control a format without a GPC3 ISVD, A022600373 was generated. The assay was read on a BD FACSArray with a yellow laser (pHAb: excitation maximum at 532 nm, emission maximum at 560 nm). The internalization rate was determined by quantifying the internalization at 37° C. at different timepoints (0.5 h, 3 h, 24 h and 48 h) compared to 4° C. at 0.5 h (Table 10, FIG. 8A).

The receptor expression was determined using a fixed concentration of a 3×FLAG-His6-tagged ISVD (20 nM) that binds to a different GPC3 epitope than A02260018C08 and A02260015A08 in combination with APC labelled anti-FLAG for detection on a BD FACSArray with a red laser (Table 10, FIG. 8B).

The internalization rate was calculated as the slope of the kinetic curve with arbitrary units. The trispecific GPC3 ISVD T-cell engagers show a slower internalization rate than the reference bispecific T-cell engager Ab2. Internalization of the GPC3 ISVD T-cell engagers is GPC3 mediated as the control format without a GPC3 binding ISVD (A022600373) does not show internalization. No decrease of GPC3 cell surface expression within 48 h was observed (Table 10, FIG. 8).

TABLE 10

Internalization rate of pHAb labelled trispecific GPC3 T-cell engagers

| Sample ID | SEQ ID NO | Description | pHAb degree of labeling | Internalization rate (normalized slope n = 2) |
|---|---|---|---|---|
| A022600370 | 71 | TCE01-5GS-A0226018C08-35GS-ALB23002-GGC | 1 | 194 |
| A022600372 | 72 | TCE01-5GS-A0226018C08-35GS-A0226015A08-35GS-ALB23002-GGC | 1 | 297 |
| A022600373 | 73 | TCE01-20GS-ALB23002-GGC | 1 | 2 |
| Ab2 | — | — | 1.4 | 597 |

6.8 Example 8: GPC3 Expression Profiling of Cancer Cell Lines and Correlation with Functionality of GPC3 T-Cell Engagers GPC3 protein expression levels for a panel of cancer cell lines was determined both by immunocytochemistry (ICC) and using the QIFIKIT® (Dako, Cat no K0078) according to the manufacturer's instructions (Table 11). Additionally, immunohistochemistry (IHC) was performed on hepatocellular carcinoma and normal kidney samples.

ICC and IHC was performed using the Ventana discovery XT robot (Ventana medical system, Roche). The cell lines and the tissue samples were first fixed on 4% formalin and subsequently paraffin embedded. After deparaffinization, cells were conditioned with buffer CC1 standard (Ventana, Cat no 950-124) at a temperature of 95° C. for 48 minutes, followed by a blocking step of 4 minutes with each of Blocker A and B (Ventana, Cat no 760-104). Mouse monoclonal IgG2a anti-GPC3 antibody (Ventana, Cat no 790-4564) was applied for 60 minutes at room temperature, followed by 4 minutes of fixation with 0.05% Glutaraldehyde in 5M NaCl (Prolabo, Cat no 20879-238). Biotinylated goat anti-mouse IgG2a antibody (Southern Biotech, Cat no 1080-080) at 1/200 dilution in antibody diluent (Ventana; Cat no 760-108) was applied for 32 minutes at room temperature. Detection was performed with the DABMap Kit (Ventana; Cat no 760-124). Sections were counterstained for 4 minutes with Hematoxylin II (Ventana, Cat no 790-2208) and post-counterstained for 4 minutes with bluing agent (Ventana, Cat no 760-2037), followed by deshydratation and mounting with Cytoseal XYL (Richard-Allan Scientific, Cat no 8312-4). Immunohistochemical staining was evaluated by a semi-quantitative assessment of both the intensity of staining of the cells (graded as 0: no staining, 1 (or +): weak, 2 (or ++): moderate; 3 (or +++): strong) and percentage of positive cells in every intensity categories. Histoscore (H-score) was calculated according to following formula:

H-score=3×(cell % with grade 3)+2×(cell % with grade 2)+1×(cell % with grade 1).

The range of the possible score was from 0 to 300, as described in literature (Detre et al., J Clin Pathol 1995; 48:876-878 and Lui et al., Journal of Latex Class filed, august 2015, vol 14, No. 8). Determination of H-score in HCC was based on evaluation of membranous expression of GPC3.

Within the panel of cell lines tested, as determined with the QIFIKIT®, Hep-G2 (ATCC, clone HB-8065; 5.2E5 receptors/cell) showed the highest level of expression of GPC3 followed by NCI-H661 (ATCC, clone HTB-183; 3.4E5 receptors/cell) and Huh-7 (HSRRB, clone JCRB0403; 6.8E4 receptors/cell), the latter considered as medium expressing cell line. These cell lines originated from liver and lung cancers which are relevant GPC3 expressing solid tumors. The low or very low GPC3 expressing cell lines, which did not show any staining in ICC, were MKN-45 (DSMZ, clone ACC409; 1.5E4 receptors/cell), NCI-H23 (ATCC, clone CRL-5800; 2.6E3 receptors/cell), BxPC-3 (ATCC, clone CRL-1687; 1.5E3 receptors/cell) and NCI-H292 (ATCC, clone CRL-1848; 6E2 receptors/cell).

For comparison between the cancer cell lines and patient tumour samples, the H-scores were determined for both. GPC3 positive cancer cell lines in ICC, i.e. Huh-7, NCI-H661 and HepG2, showed H-scores of superior to 80 (Table 11), which corresponds to the average H-score determined for the GPC3 positive hepatocellular carcinoma (HCC) samples in IHC of 80.75 (Table 12). Normal kidney GPC3 positive samples show an average H-score of 0.75 (Table 12) while the cancer cell lines MKN-45, NCI-H23, BxPC-3 and NCI-H292 were negative for GPC3 staining (Table 11). These cell lines were taken as representatives of GPC3 normal-like expression level cells.

To assess the functionality of the trispecific GPC3 T-cell engagers with the same panel of cancer cell lines, TDC assays were performed using the xCELLigence system, as described in Example 5; results are shown in Table 13 and FIG. 9. For the GPC3 high expressing cell lines, Hep-G2 and NCI-H661, the trispecific GPC3 ISVD T-cell engagers A022600167 and A022600168 show similar potency (NCI-H661) and 10-fold lower potency (Hep-G2), compared to the bispecific T-cell engager Ab2. For the medium expressing cell line, Huh-7, A022600168, the tetravalent format with biparatopic binding to GPC3, shows the same potency as Ab2, while the potency of the trivalent format A022600167 is 10-fold lower. For the GPC3 low expressing cell lines, MKN-45 and BxPC-3, Ab2 shows a potency in the nM range, while the trispecific GPC3 ISVD T-cell engagers show no killing effect. For the very low GPC3 expressing cell line, NCI-H292, none of the compounds show an effect. The T-cell engager lacking a GPC3 binding ISVD, T017000698, does not show any killing effect on any cell line, confirming the GPC3 specific effect of the trispecific GPC3 T-cell engagers.

In conclusion, Ab2 is a potent T-cell engager able to kill cancer cell lines with GPC3 expression levels as low as a thousand receptors per cell and H-score 0. In comparison, the trispecific T-cell engager formats potently kill high and medium GPC3 expressing cancer cell lines with H-scores similar to HCC and large cell lung cancer samples while sparing cell lines expressing GPC3 levels below ten thousand receptors per cell and with H-scores below the average of normal kidney samples.

TABLE 11

GPC3 expression levels of different cancer cell lines.

| Cell line | Cancer tissue | Expression RNA FPKM | Expression protein #GPC3/cell | Expression protein ICC (H-score) |
|---|---|---|---|---|
| Hep-G2 | Liver | 2253 | 619006 | 70%+++, 25%++ (260) |
| NCI-H661 | Lung | 237 | 346756 | 40%++ (80) |
| Huh-7 | Liver | 549 | 78027 | 20%++, 40%+ (80) |
| MKN-45 | Stomach | 20.9 | 7453 | 0 |
| NCI-H23 | Lung | 3.17 | 2255 | 0 |
| BxPC3 | Pancreas | 5.3 | 1332 | 0 |
| NCI-H292 | Lung | 0.04 | 452 | 0 |

TABLE 12

GPC3 H-score determined by immunohistochemistry on Hepatocellular carcinoma and normal kidney samples (based on evaluation of membranous expression of GPC3).

| | Total cases | H-score | Total GPC3+ cases | H-score |
|---|---|---|---|---|
| HCC | 288 | 52.22 | 187 | 80.75 |
| Normal kidney | 35 | 0.17 | 8 | 0.75 |

TABLE 13

IC50 (M) of the GPC3 T-cell engagers in the xCELLigence based human TDC assay on different tumor cell lines expressing decreasing expression levels of GPC3 using an effector to target ratio of 15:1: HepG2 analysed at 60 h, NCI-H661 analysed at 75 h, Huh-7 analysed at 60 h, MKN-45 analysed at 65 h, BxPC-3 analysed at 65 h, NCI-H292 analysed at 60 h.

| Sample ID | SEQ ID NO | Description | Hep-G2 | NCI-H661 | Huh-7 | MKN-45 | BxPC-3 | NCI-H292 |
|---|---|---|---|---|---|---|---|---|
| A022600167 | 62 | TCE01-5GS-A0226018C08-35GS-ALB23002-A | 9.2E−11 | 1.8E−10 | 4.7E−10 | n.a. | n.a. | n.a. |
| A022600168 | 63 | TCE01-5GS-A0226018C08-35GS-A0226015A08-35GS-ALB23002-A | 7.3E−11 | 1.4E−10 | 2.4E−11 | n.a. | n.a. | n.a. |
| T017000698 | 74 | TCE01-9GS-ALB23002-A | n.a. | n.a. | n.a. | n.a. | n.a. | n.a. |
| Ab2 | — | Bispecific CD3-GPC3 | 1.1E−11 | 2.8E−11 | 3.0E−11 | 2.0E−09 | 3.6E−09 | n.a. | n.a. = not available

6.9 Example 9: Sequence Optimization of A0226015A08 and A0226018C08

The ISVDs A0226015A08 and A0226018C08 were further sequence optimized.

Sequence optimization involves replacing one or more specific amino acid residues in the sequence in order to improve one or more (desired) properties of the ISVDs.

Some examples of such sequence optimization are mentioned in the further description herein and for example include, without limitation:

1) Substitutions in parental wild type ISVD sequences to yield ISVD sequences that are more identical to the human VH3-JH germline consensus sequences, a process called humanization. To this end, specific amino acids, with the exception of the so-called hallmark residues, in the FRs that differ between the ISVD and the human VH3-JH germline consensus are altered to the human counterpart in such a way that the protein structure, activity and stability are kept intact.
2) Substitutions towards the llama germline to increase the stability of the ISVD, which is defined as camelisation. To this end, the parental wild type ISVD amino acid sequence is aligned to the llama IGHV germline amino acid sequence of the ISVD (identified as the top hit from a BlastP analysis of the ISVD against the llama IGHV germlines).
3) Substitutions that improve long-term stability or properties under storage, substitutions that increase expression levels in a desired host cell or host organism, and/or substitutions that remove or reduce (undesired) post-translational modification(s) (such as glycosylation or phosphorylation), again depending on the desired host cell or host organism.
4) Mutations on position 11 towards Val and on position 89 towards Leu (according to Kabat) to minimize the binding of any naturally occurring pre-existing antibodies.

Sequence optimization of A0226015A08 yielded the final sequence optimized variant A022600314, which comprises 13 amino acid substitutions (i.e. L11V, A14P, V23A, P40A, D52cE, N54Y, D73N, K76N, D79Y, K83R, G88A, V89L, F91Y) (Table 14) compared to the parental ISVD clone A0226015A08.

Sequence optimization of A0226018C08 yielded two sequence optimized variants, A022600345, which comprises 8 amino acid substitutions (i.e. L11V, V23A, G54A, R60A, E81Q, T82aN, N83R, V89L) and A022600351, which comprises 8 amino acid substitutions (i.e. L11V, V23A, G54K, R60A, E81Q, T82aN, N83R, V89L) (Table 14), compared to the parental ISVD clone A0226018C08.

TABLE 14

Amino acid sequences of the sequence optimized versions of A0226015A08 and A0226018C08.

| Sample ID | SEQ ID NO | Description | Sequence |
|---|---|---|---|
| A022600314 | 75 (same as 4) | A0226015A08(L11V, A14P, V23A, P40A, D52cE, N54Y, D73N, K76N, D79Y, K83R, G88A, V89L, F91Y) | EVQLVESGGGVVQPGGSLRLSCAASGSIFR SVFSSSTMEWYRQAPGKKRELVARIAPGE GTYYGALYADSVKGRFTISRDNAKNTVYLQ MNSLRPEDTALYYCASGVAWGQGTLVTVSS |
| A022600345 | 76 | A0226018C08(L11V, V23A, G54A, R6DA, E81Q, T82aN, N83R, V89L) | EVQLVESGGGVVQPGGSLRLSCAASGFTFS SFAMTWVRRPPGKGLEWVATITNAGVTS YADSVKGRFTISRDNAKNTLYLQMNSLRPE DTALYICANARRTGPRAPTDIGSYRGQGTL VTVSS |
| A022600351 | 77 (same as 3) | A0226018C08(L11V, V23A, G54K, R60A, E81Q, T82aN, N83R, V89L) | EVQLVESGGGVVQPGGSLRLSCAASGFTFS SFAMTWVRRPPGKGLEWVATITNKGVTSY ADSVKGRFTISRDNAKNTLYLQMNSLRPED TALYICANARRTGPRAPTDIGSYRGQGTLV TVSS |

Properties of the sequence optimized variants in comparison to the parental ISVD were assessed as follows:

Variants were evaluated for binding to HepG2, Huh-7 and CHO Flip-In cyno-GPC3 cells by flow cytometry, as described in Example 1.

Thermal stability of the variants was tested in a thermal shift assay (TSA) using a Lightcycler (Roche). In this assay, the parental ISVDs and their variants are incubated at different pH in the presence of SYPRO™ orange and a temperature gradient is applied. When an ISVD starts denaturing, SYPRO™ orange binds leading to an increase in fluorescence, allowing determination of the melting temperature (Tm) for a certain pH.

Results are summarized in Table 15 and Table 16.

Compared with the parental ISVD A0226015A08, A022600314 exhibited a decrease in binding potency for the different cell lines expressing human GPC3 or cyno GPC3 of less than 2-fold. Tm decreased slightly by 5° C. and within acceptable values. The % framework identity in the framework regions compared to the reference hIGHV3-23SO/IGHJ4 for A022600314 is 88.8% based on the AbM definition (see Antibody Engineering, Vol 2 by Kontermann & Dübel (Eds), Springer Verlag Heidelberg Berlin, 2010) and 85.1% based on the Kabat definition.

Compared with the parental ISVD A0226018C08, the binding potency of variants A022600345 and A022600351 for the different cell lines expressing human GPC3 or cyno GPC3 is increased 2-fold. The Tm for variants A022600345 and A022600351 increased to 75 and 74° C., respectively.

TABLE 15

Results of the analysis of the sequence optimization variant A0226000314 of the parental ISVD A0226015A08.

| Sample ID | Mutations | EC50 (M) HepG2 | EC50 (M) Huh-7 | EC50 (M) CHO-cGPC3 | Tm (° C.) at pH 7 TSA |
|---|---|---|---|---|---|
| A0226015A08 | WT | 7.5E−09 | 6.6E−09 | 7.8E−09 | 70 |
| A022600314 | L11V, A14P, V23A, P40A, D52cE, N54Y, D73N, K76N, D79Y, K83R, G88A, V89L, F91Y | 1.6E−08 | 9.3E−09 | 1.2E−08 | 65 |

TABLE 16

Results of the analysis of the sequence optimization variants A022600345 and A022600351 of the parental ISVD A0226018C08.

| Sample ID | Mutations | EC50 (M) HepG2 | EC50 (M) Huh-7 | EC50 (M) CHO-cGPC3 | Tm (° C.) at pH 7 TSA |
|---|---|---|---|---|---|
| A0226018C08 | WT | 9.15E−10 | 6.96E−10 | 4.9E−10 | 67 |
| A022600345 | L11V, V23A, G54A, R60A, E81Q, T82aN, N83R, V89L | 3.91E−10 | 2.76E−10 | 1.5E−10 | 75 |
| A022600351 | L11V, V23A, G54K, R60A, E81Q, T82aN, N83R, V89L | 4.31E−10 | 4.77E−10 | 2.1E−10 | 74 |

The % framework identity in the framework regions compared to the reference hIGHV3-23SO/IGHJ4 for both, A022600345 and A022600351, is 89.9% based on the AbM definition and 89.7% based on the Kabat definition.

6.10 Example 10: Generation of Trispecific Sequence Optimized GPC3 ISVD T-Cell Engager The sequence optimized GPC3 ISVDs A022600314 (optimized variant of A0226015A08), A022600345 and A022600351 (optimized variants of A0226018C08) were used for the generation of five trispecific GPC3 T-cell engager formats for assessment of optimal combination of building blocks and linker length as described in Table 17.

TABLE 17

Selection of different trispecific GPC3 ISVD T-cell engager formats evaluated

| Sample ID | SEQ ID NO | Description |
|---|---|---|
| A022600427 | 81 | TCE01-5GS-A022600345-9GS-A022600314-9GS-ALB23002-A |
| A022600424 | 1 | TCE01-5GS-A022600351-9GS-A022600314-9GS-ALB23002-A |
| A022600425 | 79 | TCE01-5GS-A022600314-20GS-A022600345-9GS-ALB23002-A |
| A022600426 | 80 | TCE01-5GS-A022600314-20GS-A022600351-9GS-ALB23002-A |
| A022600412 | 78 | TCE01-5GS-A022600345-20GS-ALB23002-A |

The five selected formats were tested in the xCELLingence based TDC assay with different cancer cell lines for functionality, as described in Example 8. Results are depicted in Table 18. For high and medium GPC3 expressing cell lines HepG2, NCI-H661 and Huh-7, higher potencies were obtained for the tetravalent formats compared to the trivalent format. For high GPC3 expressing cell line NCI-H661, tetravalent formats A022600424 and A022600427 are more potent than A022600425 and A022600426. For the GPC3 low expressing cell lines, NCI-H23 and BxPC-3, the lack of a killing effect was confirmed for all trispecific GPC3 ISVD T-cell engager formats.

FIG. 10 shows the dose-dependent killing curves for the xCELLingence based TDC assay, exemplified by cell lines NCI-H661 and BxPC-3, using three different T-cell donors for the five selected ISVD formats.

TABLE 18

IC50 (M) of GPC3 T-cell engagers in the xCELLigence based human TDC assay on different tumor cell lines using an effector to target ratio of 15:1 and analyzed at 60 h.

| Sample ID | IC50 (M) HepG2 | IC50 (M) NCI-H661 | IC50 (M) Huh-7 | IC50 (M) NCI-H23 | IC50 (M) BxPC-3 |
|---|---|---|---|---|---|
| A022600427 | 1.03E−10 | 1.00E−10 | 1.37E−10 | no fit | no fit |
| A022600424 | 1.15E−10 | 1.14E−10 | 1.16E−10 | no fit | no fit |
| A022600425 | 1.11E−10 | 2.59E−10 | 1.58E−10 | no fit | no fit |
| A022600426 | 1.25E−10 | 2.64E−10 | 1.09E−10 | no fit | no fit |
| A022600412 | 3.82E−10 | 6.18E−10 | 1.53E−09 | na | no fit |
| Ab2 | 1.49E−11 | 4.60E−11 | 8.41E−11 | 1.28E−09 | 1.09E−09 | na = not available;
no fit = no curve fit obtained,
IC50 estimated as >1E−7M

Binding of pre-existing antibodies to the 5 selected formats was assessed using a SPR-based setup (Example 14). FIG. 11 shows that for all formats only low levels of pre-existing antibody binding were observed, compatible with developability requirements.

Performance in *Pichia pastoris* was assessed for the 5 formats, focusing on product titer and purity during upstream processing (USP) at 5 L fermentor scale, as well as on yield, after downstream processing (DSP) (Table 19). A022600424 and A022600426 were identified as preferred ISVD development candidates combining low percentage of high molecular weight (HMW) species, low percentage of variants on RPC with a high titer and best overall DSP yield.

TABLE 19

Performance of the 5 selected ISVD based GPC3 T-cell engager formats in Pichia.

| Sample ID | Titer (g/L) | Analytical SEC (% HMW) | RPC (% Post-peaks) | DSP yield (total %) |
|---|---|---|---|---|
| A022600412 | 3.9 | 5.4 | 3.3 | 26 |
| A022600424 | 4.9 | 1.8 | 1.7 | 45 |
| A022600425 | 5.6 | 6.3 | 2.7 | 24 |
| A022600426 | 5.4 | 2.4 | 3.3 | 32 |
| A022600427 | 4.7 | 5.1 | 1.4 | 32 |

Based on the best combination of GPC3 driven killing potency, reduced binding to pre-existing antibodies, and performance in *Pichia*, A022600424 was selected as development candidate.

6.11 Example 11: Binding and Affinity of A022600424 to GPC3, TCRab and Serum Albumin The affinity, expressed as the equilibrium dissociation constant ($K_D$), of A022600424 towards human and cyno GPC3 (R&D Systems, cat no 2119-GP and in house produced (accession number P51654, Q3-R358, 5359-H559), respectively), human and cyno TCRab (both in house produced, where alpha and beta chains extracellular domains are fused to a zipper peptide for dimerization; accession numbers: human alpha chain P01848, human beta chain P01850; predicted sequence of cyno alpha chain is identical to human, predicted sequence of cyno beta chain differs in 4 aa: A125V, E136V, V167M, S177F) and human, cyno and mouse serum albumin (Sigma cat no A8763, in house produced from animal tissue, DivBioScience cat no IMSA, respectively) was quantified by surface plasmon resonance (SPR) using a ProteOn XPR36.

Recombinant GPC3 proteins were captured on a GLC Sensor Chip (Biorad) immobilized with THE anti-His antibody (Genscript, cat no ABIN387699) via amine coupling, using EDC and NHS chemistry (running buffer: HBS-EP+, pH7.4). Purified ISVDs were injected for 2 minutes (flow rate 45 μL/min) at different concentrations (between 0.3 nM and 1000 nM) and dissociation was followed for 900 s. Regeneration was performed by injecting 10 mM Glycine-HCl (pH 1.5) for 1 minute (flow rate 45 μL/min). Data was double referenced by subtracting a reference ligand lane and a blank buffer injection. Processed sensorgrams were analyzed based on the 1:1 interaction model (Langmuir binding model) using ProteOn Manager 3.1.0 (Version 3.1.0.6) software.

Recombinant TCR proteins were immobilized on a GLC Sensor Chip (Biorad) via amine coupling, using EDC and NHS chemistry (running buffer: HBS-EP+, pH 7.4). Purified ISVDs were injected for 2 minutes (flow rate 45 μL/min) at different concentrations (between 0.2 nM and 200 nM) and dissociation was followed for 900 s. Regeneration was performed by injecting 3 M MgCl$_2$ for 3 minutes (flow rate 90 μL/min). Data was double referenced by subtracting a reference ligand lane and a blank buffer injection. Processed sensorgrams were analyzed based on the 1:1 interaction model (Langmuir binding model) using ProteOn Manager 3.1.0 (Version 3.1.0.6) software.

Serum albumin proteins were immobilized on a GLC Sensor Chip (Biorad) via amine coupling, using EDC and NHS chemistry (running buffer: HBS-EP+, pH 7.4). Purified ISVDs were injected for 2 minutes (flow rate 45 μL/min) at different concentrations (between 0.24 nM and 500 nM) and dissociation was followed for 900 s. Regeneration was performed by injecting 10 mM Glycine-HCl (pH 1.5) for 47 seconds (flow rate 100 μL/min). Data was double referenced by subtracting a reference ligand lane and a blank buffer injection. Processed sensorgrams were analyzed based on the 1:1 interaction model (Langmuir binding model) using ProteOn Manager 3.1.0 (Version 3.1.0.6) software.

The results (Table 20) demonstrate that A022600424 binds human and cyno GPC3 with high affinity.

TABLE 20

Binding affinities to human and cyno GPC3, human and cyno TCRab and human, cyno and mouse serum albumin.

| Antigen | Sample ID | KD (M) human | KD (M) cynomolgus | KD mouse |
|---|---|---|---|---|
| GPC3 | A022600424 | <5.6E−12 | <5.9E−12 | n.a. |
|  | Ab2 | 1.8E−09 | 1.7E−09 | n.a. |
| TCRab | A022600424 | 6.3E−09 | 5.4E−09 | n.a. |
|  | T017000698 | 8.5E−09 | 1.1E−08 | n.a. |
| Serum albumin | A022600424 | 8.3E−10 | 3.3E−10 | 6.9E−09 |
|  | ALB223 | 8.8E−10 | 5.7E−10 | 5.3E−09 | n.a. = not available

Binding of A022600424 to cell expressed human and cyno GPC3 was assessed by flow cytometry for CHO-Flp-In cells overexpressing human and cyno GPC3, as well as Huh-7 cells, yielding EC50 values between 1 and 2 nM (Table 21).

A022600424 was evaluated for binding to human and cyno T cells in competition with TCRab binding monovalent ISVDs T017000624 and T017000623 (T0170056G05 variants) respectively, at EC30 concentrations. T cells (human T cells obtained as described in Example 3 and cyno T cells purchased from LPT laboratory, Germany) were thawed and counted on the day of the assay and diluted to a concentration of 1E+06 cells/mL, before adding 75 μL to the wells of a V-bottom 96-well plate (Greiner, cat no 651180). Cells were washed once with cold FACS buffer, before adding 25 μL Nb and 25 μL competitor to the wells. T017000624 was diluted to a 2× concentration of 4E-08 M (2E-08 M in well), T017000623 was diluted to a 2× concentration of 1E-07 M (5E-08 M in well) and A022600424 was diluted to final concentrations in the wells ranging between 8 μM and 7.8 nM. Cells were resuspended and plates were incubated at 4° C. for 90 minutes, after which plates were washed twice in cold FACS buffer. Cells were resuspended in 50 μL 1/1000 diluted Monoclonal ANTI-FLAG® M2 (Sigma Aldrich, cat no F1804) in FACS buffer and incubated at 4° C. for 30 minutes. Plates were washed twice in cold FACS buffer. Cells were resuspended in 50 μL 1/100 diluted Allophycocyanin-conjugated AffiniPure Goat Anti-Mouse IgG (subclasses 1+2a+2b+3), Fc Fragment Specific (Jackson Immunoresearch, cat no 115-135-164) in FACS buffer and incubated at 4° C. for 30 minutes. Plates were washed twice in cold FACS buffer. Cells were resuspended in 55 μL 1/1000 diluted Propidium Iodide (Sigma-Aldrich, cat no P4170) in FACS buffer before acquiring data on the MACSQuant X (Miltenyi biotec).

The results are shown in Table 21. A022600424 binds with approx. 200 nM affinity to both, human and cyno T-cells.

TABLE 21

Binding assessment of A022600424 to cell expressed human and cyno GPC3 and human and cyno TCRab.

| Antigen | Sample ID | CHO huGPC3 EC50 (M) | CHO cyGPC3 EC50 (M) | Huh-7 EC50 (M) |
|---|---|---|---|---|
| GPC3 (binding FACS) | A022600424 | 1.82E−09 | 1.11E−09 | 1.25E−09 |
|  | Ab2 | 1.69E−08 | 5.4E−09 | 5.2E−09 |

| | | Primary hu T cells IC50 (M) | Primary cy T cells IC50 (M) |
|---|---|---|---|
| TCRab (competition FACS) | A022600424 | 1.7E−07 | 2.5E−07 |
|  | T017000698 | 1.9E−07 | 2.5E−07 |

To assess A022600424 functionality with cyno T-cells, a xCELLigence based TDC assay on Huh-7 was performed using cyno T-cells (LPT laboratory, Germany), as described in Example 8. IC50 values for cyno and human T cells were found to be comparable (Table 22).

TABLE 22

Functionality of A022600424 using cynomolgus T-cells in the xCELLigence based TDC assay on Huh-7, with an effector to target ratio of 15:1 and analyzed at 60 h.

| Sample ID | Primary hu T cells IC50 (M) | Primary cy T cells IC50 (M) |
|---|---|---|
| A022600424 | 7.59E−11 | 2.29E−10 |
| Ab2 | 7.88E−11 | 3.57E−11 |

6.12 Example 12: Selectivity of A022600424 for Binding to GPC3

Absence of A022600424 binding to family members of GPC3, namely GPC1, GPC2, GPC5 and GPC6, was assessed by ELISA and to GPC4 by SPR (Proteon XPR36).

Human GPC1 (R&D systems, cat no 4519-GP), human GPC2 (R&D systems, cat no 2304-GP), human GPC3 (R&D systems, cat no 2119-GP), human Glypican-5 (R&D systems, cat no 2607-G5) and human Glypican-6 (R&D systems, cat no 2845-GP) were directly coated overnight at 4° C. (2 μg/mL, 1×PBS buffer) on a 384-well HB SpectraPlate (PerkinElmer). The following day the plate was washed 6 times (AquaMax microplate washer, Molecular devices) and blocked with 1×PBS+1% Casein for 2 hours at room temperature. After an additional 6 wash steps A022600424 (1×PBS, 0.1% casein, 0.05% TWEEN 20) was added to the plate and incubated at room temperature for 1 hour. Next, the samples were removed, followed by 6 wash steps and anti-ISVD mAb ABH0077 was added at 17 nM final concentration (1×PBS, 0.1% casein, 0.05% TWEEN 20) during 1 hour at room temperature. The plate was washed again 6 times and goat anti-mouse IgG polyclonal antibody conjugated to HRP (Abcam, cat no ab97040) (1/1250 dilution;

1×PBS, 0.1% casein, 0.05% TWEEN 20) was applied to the plate for 1 hour at room temperature. After 6 final wash steps the es(HS)TMB substrate (SDT) was added and the reaction stopped by addition of 1 M HCl after 10 minutes. The absorbance of the plate was measured at wavelengths 450 and 620 nm on the Clariostar instrument (BMG LABTECH) and the $OD_{450}$-$OD_{620}$ calculated and plotted for data analysis.

Recombinant human GPC4/hFc (R&D Systems, cat no 9195-GP) was captured on a GLC Sensor Chip (Biorad) immobilized with mouse anti-human IgG1 (GE Healthcare, cat no BR-1008-39) via amine coupling, using EDC and NHS chemistry (running buffer used: HBS-EP+, pH7.4). Purified ISVDs were injected for 2 minutes (flow rate 45 µL/min) at different concentrations (between 4 nM and 1000 nM) and dissociation was followed for 900 s. Regeneration was performed by injecting 10 mM Glycine-HCl (pH1.5) for 1 minute (flow rate 45 µL/min). Data was double referenced by subtracting a reference ligand lane and a blank buffer injection. Processed sensorgrams were analysed based on the 1:1 interaction model (Langmuir binding model) using ProteOn Manager 3.1.0 (Version 3.1.0.6) software.

No binding was detected of A022600424 to any of the GPC3 family members tested.

6.13 Example 13: Reactivity of Human Pre-Existing Antibodies for A022600424

Binding of pre-existing antibodies to A022600424 was assessed for normal human serum (n=96) using the ProteOn XPR36 (Bio-Rad Laboratories, Inc.). PBS/Tween (phosphate buffered saline, pH 7.4, 0.005% Tween20) was used as running buffer and the experiments were performed at 25° C.

A022600424 was captured on the sensor chip via binding of the ALB23002 building block to HSA immobilized on the chip. To immobilize HSA, the ligand lanes of a ProteOn GLC Sensor Chip were activated with EDC/NHS (flow rate 30 µL/min) and HSA was injected at 100 µL/mL in ProteOn Acetate buffer pH4.5 to render immobilization levels of approximately 2900 RU. After immobilization, surfaces were deactivated with ethanolamine HCl (flow rate 30 µL/min).

Subsequently, A022600424 was injected for 2 min at 45 pl/min over the HSA surface to render an ISVD capture level of approximately 800 RU. The samples containing pre-existing antibodies were centrifuged for 2 minutes at 14,000 rpm and supernatants were diluted 1:10 in PBS-Tween20 (0.005%) before being injected for 2 minutes at 45 pl/min followed by a subsequent 400 seconds dissociation step. After each cycle (i.e. before a new ISVD capture and blood sample injection step) the HSA surfaces were regenerated via a 2 minute injection of HCl (100 mM) at 45 µL/min. Sensorgrams showing pre-existing antibody binding were obtained after double referencing by subtracting 1) ISVD-HSA dissociation and 2) non-specific binding to reference ligand lane. Binding levels of pre-existing antibodies were determined by setting report points at 125 seconds (5 seconds after end of association). Percentage reduction in pre-existing antibody binding is calculated relative to the binding levels at 125 seconds of a reference ISVD.

Tetravalent ISVD format A022600424, optimized for reduced pre-existing antibody binding by introduction of mutations L11V and V89A for the anti-TCR building block, mutations L11V and V89L in each GPC3 and the serum albumin binding building block and a C-terminal alanine, shows substantially less binding to pre-existing antibodies compared to a control non-optimized tetravalent ISVD format F027301099 (FIG. 11A).

6.14 Example 14: Assessment of T-Cell Activation Induction by A022600424 in the Presence of Soluble GPC3

T-cell activation induction by A022600424 in the presence of soluble GPC3 was assessed as described in Example 6. A022600424 showed the same behaviour as its wild-type variant A022600168 (FIG. 7).

6.15 Example 15: In Vivo Proof-of-Concept for A022600424 in Huh-7 Tumor Bearing NOG Mice Engrafted with In Vitro Expanded T Cells In an in vivo efficacy study in tumor bearing NOG mouse, Hepatocellular Carcinoma Huh-7 tumor cells were injected subcutaneously, and tumors were allowed to grow until a mean tumor volume of ~150 mm³ was reached. At this point, in vitro expanded T cells were injected intraperitoneally into the mice. Tumor cell killing by ISVD-mediated recruitment of T cells was evaluated by measuring the tumor volume and analyzing the tumor growth kinetics. The in vivo efficacy of A022600424 on tumor cell killing was evaluated and compared with the control T-cell engager T017000698 (SEQ ID NO: 74, Table A-6) lacking the GPC3 specificity.

In detail, $2 \times 10^6$ Huh-7 tumor cells resuspended in 100 µL of HBSS were subcutaneously injected in NOG mice. The tumors grew until the mean tumor volume of approximately 150 mm³ was reached. At this point, $10^7$ in vitro expanded T cells resuspended in 200 µL of PBS were injected into each mouse intraperitoneally (D0). This injection of T cells took place 24 hours after mice were randomized into different groups. The treatment with A022600424 injected intravenously started on D0, 3 h after T cell injection and continued D3, D6, D9 and D12 (q3d; FIG. 12). Four dose levels of the TCR/GPC3 binding polypeptides were tested (0.1 mg/kg, 0.2 mg/kg, 0.7 mg/kg and 2 mg/kg). T017000698 was injected in a control group at 2 mg/kg on D0, D3, D6, D9 and D12 (q3d). Survival blood sampling in heparin containing tubes was done on D6 and D12 to measure antibody exposure. Mice were sacrificed on D15, and blood and tumor tissue were collected. Blood was used for the antibody exposure measurements and tumor tissue was used for analysis of target expression (GPC3) and T cell infiltration analysis.

Results for tumor growth kinetics are shown in FIG. 13. Mice treated with T017000698 were used as control group for analyses on D24, when all control mice were alive as they did not reach end point criteria (2000 mm³ tumor volume). A dose response pattern was seen in tumor growth profile for A022600424 versus the control T017000698 for inducing tumor stasis. The 0.7 mg/kg (**, p=0.0016) and 2 mg/kg (*, p=0.0415) dose levels for the A022600424 were significantly different from the control T017000698. The 0.1 mg/kg, 0.2 mg/kg doses had lower effects on controlling tumor growth and were not significantly different to the control group. Statistical analysis has been performed with one-way ANOVA, using the Dunnett's multiple comparisons test for analysis.

In conclusion, the results demonstrate that A022600424 can dose-dependently induce statistically significant tumor stasis in this model. This confirms the concept of polypeptide-induced T cell-mediated killing via a GPC3 ISVD T-cell engager by cross-linking T cells to GPC3 on Huh-7 tumor cells.

7 INDUSTRIAL APPLICABILITY

The polypeptides, nucleic acid molecules encoding the same, vectors comprising the nucleic acids and compositions described herein may be used for example in the treatment of subjects suffering from cancer.

The invention claimed is:

1. A polypeptide that comprises at least three immunoglobulin single variable domains (ISVDs), wherein each of said ISVDs comprises three complementarity determining regions (CDRs), CDR1 to CDR3, respectively, and wherein:
   a) a first ISVD specifically binds to the constant domain of a T cell receptor (TCR) on a T cell and comprises:
      i. a CDR1 comprising the amino acid sequence of SEQ ID NO: 6;
      ii. a CDR2 comprising the amino acid sequence of SEQ ID NO: 10; and
      iii. a CDR3 comprising the amino acid sequence of SEQ ID NO: 14;
   b) a second ISVD specifically binds to Glypican-3 (GPC3) and comprises:
      iv. a CDR1 comprising the amino acid sequence of SEQ ID NO: 7;
      v. a CDR2 comprising the amino acid sequence of SEQ ID NO: 11; and
      vi. a CDR3 comprising the amino acid sequence of SEQ ID NO: 15; and
   c) a third ISVD specifically binds to GPC3 and comprises:
      vii. a CDR1 comprising the amino acid sequence of SEQ ID NO: 8;
      viii. a CDR2 comprising the amino acid sequence of SEQ ID NO: 12; and
      ix. a CDR3 comprising the amino acid sequence of SEQ ID NO: 16,
   wherein the order of the ISVDs indicates their relative position to each other considered from the N-terminus to the C-terminus of said polypeptide.

2. The polypeptide according to claim 1, wherein the at least three ISVDs are linked via one or more peptidic linkers.

3. The polypeptide according to claim 1, wherein the first ISVD is located at the N-terminus of said polypeptide.

4. The polypeptide according to claim 1, wherein:
   a) said first ISVD comprises a CDR1 consisting of the amino acid sequence of SEQ ID NO: 6, a CDR2 consisting of the amino acid sequence of SEQ ID NO: 10 and a CDR3 consisting of the amino acid sequence of SEQ ID NO: 14;
   b) said second ISVD comprises a CDR1 consisting of the amino acid sequence of SEQ ID NO: 7, a CDR2 consisting of the amino acid sequence of SEQ ID NO: 11 and a CDR3 consisting of the amino acid sequence of SEQ ID NO: 15; and
   c) said third ISVD comprises a CDR1 consisting of the amino acid sequence of SEQ ID NO: 8, a CDR2 consisting of the amino acid sequence of SEQ ID NO: 12 and a CDR3 consisting of the amino acid sequence of SEQ ID NO: 16.

5. The polypeptide according to claim 1, wherein:
   a) said first ISVD comprises the amino acid sequence of SEQ ID NO: 2;
   b) said second ISVD comprises the amino acid sequence of SEQ ID NO: 3; and
   c) said third ISVD comprises the amino acid sequence of SEQ ID NO: 4.

6. The polypeptide according to claim 1, wherein:
   a) said first ISVD consists of the amino acid sequence of SEQ ID NO: 2;
   b) said second ISVD consists of the amino acid sequence of SEQ ID NO: 3; and
   c) said third ISVD consists of the amino acid sequence of SEQ ID NO: 4.

7. The polypeptide according to claim 1, wherein the first ISVD and the second ISVD are linked to each other via a linker consisting of less than 10 amino acids, a linker consisting of less than 6 amino acids, or a 5GS linker.

8. The polypeptide according to claim 1, wherein said polypeptide further comprises one or more other groups, residues, moieties or binding units, in which said one or more other groups, residues, moieties or binding units provide the polypeptide with increased half-life, compared to the corresponding polypeptide without said one or more other groups, residues, moieties or binding units.

9. The polypeptide according to claim 8, wherein the one or more other groups, residues, moieties or binding units are linked via one or more peptidic linkers.

10. The polypeptide according to claim 8, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

11. The polypeptide according to claim 10, wherein said one or more other groups, residues, moieties or binding units that provide the polypeptide with increased half-life comprise a binding unit that can bind to serum albumin or a serum immunoglobulin.

12. The polypeptide according to claim 10, in which said one or more other groups, residues, moieties or binding units that provide the polypeptide with increased half-life comprise an ISVD that binds to human serum albumin.

13. The polypeptide according to claim 12, wherein the ISVD binding to human serum albumin comprises a CDR1 consisting of the amino acid sequence of SEQ ID NO: 9, a CDR2 consisting of the amino acid sequence of SEQ ID NO: 13 and a CDR3 consisting of the amino acid sequence of SEQ ID NO: 17.

14. The polypeptide according to claim 12, wherein said ISVD binding to human serum albumin consists of the amino acid sequence of SEQ ID NO: 5.

15. The polypeptide according to claim 1, wherein the polypeptide comprises the amino acid sequence of SEQ ID NO: 1.

16. The polypeptide according to claim 1, wherein the polypeptide consists of the amino acid sequence of SEQ ID NO: 1.

17. A polypeptide that comprises at least one immunoglobulin single variable domain (ISVD) that specifically binds Glypican-3 (GPC3), wherein said ISVD comprises three complementarity determining regions (CDRs, CDR1 to CDR3, respectively, and wherein the at least one ISVD comprises:
  a) a CDR1 consisting of the amino acid sequence of SEQ ID NO: 7;
     a CDR2 consisting of the amino acid sequence of SEQ ID NO: 11; and
     a CDR3 consisting of the amino acid sequence of SEQ ID NO: 15; or
  b) a CDR1 consisting of the amino acid sequence of SEQ ID NO: 8;
     a CDR2 consisting of the amino acid sequence of SEQ ID NO: 12; and
     a CDR3 consisting of the amino acid sequence of SEQ ID NO: 16.

18. A polypeptide that comprises at least two immunoglobulin single variable domains (ISVDs), wherein each of said ISVDs comprises three complementarity determining regions (CDRs), CDR1 to CDR3, respectively, and wherein:
  a) each of a first and a second ISVD specifically binds to Glypican-3 (GPC3) and comprises:
    i. a CDR1 consisting of the amino acid sequence of SEQ ID NO: 7;
    ii. a CDR2 consisting of the amino acid sequence of SEQ ID NO: 11; and
    iii. a CDR3 consisting of the amino acid sequence of SEQ ID NO: 15;
  b) each of a first and a second ISVD specifically binds to GPC3 and comprises:
    i. a CDR1 consisting of the amino acid sequence of SEQ ID NO: 8;
    ii. a CDR2 consisting of the amino acid sequence of SEQ ID NO: 12; and
    iii. a CDR3 consisting of the amino acid sequence of SEQ ID NO: 16;
  c) a first ISVD specifically binds to GPC3 and comprises:
    i. a CDR1 consisting of the amino acid sequence of SEQ ID NO: 7;
    ii. a CDR2 consisting of the amino acid sequence of SEQ ID NO: 11; and
    iii. a CDR3 consisting of the amino acid sequence of SEQ ID NO: 15; and
    a second ISVD specifically binds to GPC3 and comprises:
    iv. a CDR1 consisting of the amino acid sequence of SEQ ID NO: 8;
    v. a CDR2 consisting of the amino acid sequence of SEQ ID NO: 12; and
    vi. a CDR3 consisting of the amino acid sequence of SEQ ID NO: 16;
  d) a first ISVD specifically binds to GPC3 and comprises:
    i. a CDR1 consisting of the amino acid sequence of SEQ ID NO: 8;
    ii. a CDR2 consisting of the amino acid sequence of SEQ ID NO: 12; and
    iii. a CDR3 consisting of the amino acid sequence of SEQ ID NO: 16; and
    a second ISVD specifically binds to GPC3 and comprises:
    iv. a CDR1 consisting of the amino acid sequence of SEQ ID NO: 7;
    v. a CDR2 consisting of the amino acid sequence of SEQ ID NO: 11; and
    vi. a CDR3 consisting of the amino acid sequence of SEQ ID NO: 15;
  e) a first ISVD specifically binds to the constant domain of a T cell receptor (TCR) on a T cell and comprises:
    i. a CDR1 consisting of the amino acid sequence of SEQ ID NO: 6;
    ii. a CDR2 consisting of the amino acid sequence of SEQ ID NO: 10; and
    iii. a CDR3 consisting of the amino acid sequence of SEQ ID NO: 14; and
    a second ISVD specifically binds to GPC3 and comprises:
    iv. a CDR1 consisting of the amino acid sequence of SEQ ID NO: 7;
    v. a CDR2 consisting of the amino acid sequence of SEQ ID NO: 11; and
    vi. a CDR3 consisting of the amino acid sequence of SEQ ID NO: 15;
  f) a first ISVD specifically binds to GPC3 and comprises:
    i. a CDR1 consisting of the amino acid sequence of SEQ ID NO: 7;
    ii. a CDR2 consisting of the amino acid sequence of SEQ ID NO: 11; and
    iii. a CDR3 consisting of the amino acid sequence of SEQ ID NO: 15; and
    a second ISVD specifically binds to the constant domain of a TCR on a T cell and comprises:
    iv. a CDR1 consisting of the amino acid sequence of SEQ ID NO: 6;
    v. a CDR2 consisting of the amino acid sequence of SEQ ID NO: 10; and
    vi. a CDR3 consisting of the amino acid sequence of SEQ ID NO: 14;
  g) a first ISVD specifically binds to the constant domain of a TCR on a T cell and comprises:
    i. a CDR1 consisting of the amino acid sequence of SEQ ID NO: 6;
    ii. a CDR2 consisting of the amino acid sequence of SEQ ID NO: 10; and iii. a CDR3 consisting of the amino acid sequence of SEQ ID NO: 14; and a second ISVD specifically binds to GPC3 and comprises:

iv. a CDR1 consisting of the amino acid sequence of SEQ ID NO: 8;

v. a CDR2 consisting of the amino acid sequence of SEQ ID NO: 12; and vi. a CDR3 consisting of the amino acid sequence of SEQ ID NO: 16; or h) a first ISVD specifically binds to GPC3 and comprises:

i. a CDR1 consisting of the amino acid sequence of SEQ ID NO: 8;

ii. a CDR2 consisting of the amino acid sequence of SEQ ID NO: 12; and iii. a CDR3 consisting of the amino acid sequence of SEQ ID NO: 16; and a second ISVD specifically binds to the constant domain of a TCR on a T cell and comprises:

iv. a CDR1 consisting of the amino acid sequence of SEQ ID NO: 6;

v. a CDR2 consisting of the amino acid sequence of SEQ ID NO: 10; and vi. a CDR3 consisting of the amino acid sequence of SEQ ID NO: 14 wherein the order of the ISVDs indicates their relative position to each other considered from the N-terminus to the C-terminus of said polypeptide.

19. The polypeptide according to claim 18, wherein the at least two ISVDs are linked via one or more peptidic linkers.

20. A nucleic acid comprising a nucleotide sequence that encodes a polypeptide according to claim 1.

21. A host or host cell comprising a nucleic acid according to claim 20.

22. A method for producing a polypeptide comprising: expressing, in a suitable host cell or host organism or in another suitable expression system, a nucleic acid according to claim 20.

23. The method according to claim 22, further comprising: isolating and/or purifying the polypeptide encoded by the nucleic acid.

24. A composition comprising at least one polypeptide according to claim 1.

25. The composition according to claim 24, which is a pharmaceutical composition which further comprises at least one pharmaceutically acceptable carrier, diluent or excipient and/or adjuvant.

26. The composition according to claim 25, wherein the composition comprises one or more further pharmaceutically active polypeptides and/or compounds.

27. A method of treating liver cancer or lung cancer, wherein said method comprises administering, to a subject in need thereof, a pharmaceutically active amount of a polypeptide according to claim 1.

28. The method according to claim 27, wherein the liver cancer is hepatocellular carcinoma.

* * * * *

UNITED STATES PATENT AND TRADEMARK OFFICE
CERTIFICATE OF CORRECTION

PATENT NO. : 11,932,702 B2
APPLICATION NO. : 17/553908
DATED : March 19, 2024
INVENTOR(S) : Daniel Janssen et al.

It is certified that error appears in the above-identified patent and that said Letters Patent is hereby corrected as shown below:

In the Claims

Claim 17, beginning at Column 231, Line 30, should read:
17. A polypeptide that comprises at least one immunoglobulin single variable domain (ISVD) that specifically binds Glypican-3 (GPC3), wherein said ISVD comprises three complementarity determining regions (CDRs), CDR1 to CDR3, respectively, and wherein the at least one ISVD comprises:
    a) a CDR1 consisting of the amino acid sequence of SEQ ID NO: 7;
        a CDR2 consisting of the amino acid sequence of SEQ ID NO: 11; and
        a CDR3 consisting of the amino acid sequence of SEQ ID NO: 15; or
    b) a CDR1 consisting of the amino acid sequence of SEQ ID NO: 8;
        a CDR2 consisting of the amino acid sequence of SEQ ID NO: 12; and
        a CDR3 consisting of the amino acid sequence of SEQ ID NO: 16.

Signed and Sealed this
Eleventh Day of June, 2024

Katherine Kelly Vidal
*Director of the United States Patent and Trademark Office*